United States Patent
Qiao et al.

(10) Patent No.: US 9,199,946 B2
(45) Date of Patent: Dec. 1, 2015

(54) PYRIMIDINONE CARBOXAMIDE INHIBITORS OF ENDOTHELIAL LIPASE

(71) Applicant: BRISTOL-MYERS SQUIBB COMPANY, Princeton, NJ (US)

(72) Inventors: Jennifer X. Qiao, Princeton, NJ (US); Carol Hui Hu, New Hope, PA (US); Tammy C. Wang, Lawrenceville, NJ (US); Ji Jiang, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/390,172

(22) PCT Filed: Mar. 29, 2013

(86) PCT No.: PCT/US2013/034529
§ 371 (c)(1),
(2) Date: Oct. 2, 2014

(87) PCT Pub. No.: WO2013/151877
PCT Pub. Date: Oct. 10, 2013

(65) Prior Publication Data
US 2015/0065505 A1  Mar. 5, 2015

Related U.S. Application Data

(60) Provisional application No. 61/619,453, filed on Apr. 3, 2012.

(51) Int. Cl.
| | |
|---|---|
| *C07D 403/12* | (2006.01) |
| *C07D 239/545* | (2006.01) |
| *A61K 31/505* | (2006.01) |
| *C07D 239/557* | (2006.01) |
| *A61K 31/4709* | (2006.01) |
| *C07D 401/14* | (2006.01) |
| *C07D 405/14* | (2006.01) |
| *C07D 401/12* | (2006.01) |
| *C07D 403/14* | (2006.01) |
| *C07D 405/12* | (2006.01) |
| *C07D 409/12* | (2006.01) |
| *C07D 239/60* | (2006.01) |
| *C07D 413/12* | (2006.01) |
| *C07D 417/12* | (2006.01) |
| *C07D 487/04* | (2006.01) |
| *C07D 495/04* | (2006.01) |

(52) U.S. Cl.
CPC ........ *C07D 239/557* (2013.01); *A61K 31/4709* (2013.01); *A61K 31/505* (2013.01); *C07D 239/60* (2013.01); *C07D 401/12* (2013.01); *C07D 401/14* (2013.01); *C07D 403/12* (2013.01); *C07D 403/14* (2013.01); *C07D 405/12* (2013.01); *C07D 405/14* (2013.01); *C07D 409/12* (2013.01); *C07D 413/12* (2013.01); *C07D 417/12* (2013.01); *C07D 487/04* (2013.01); *C07D 495/04* (2013.01)

(58) Field of Classification Search
CPC .. C07D 401/12; C07D 401/14; C07D 403/12; C07D 403/14; C07D 239/545; C07D 405/12; C07D 409/12; C07D 417/12; A61K 31/4709; A61K 31/505; A61K 31/352; A61K 31/381; A61K 31/506
USPC ................. 544/122, 250, 309, 310, 311, 314; 514/235.8, 267, 274
See application file for complete search history.

(56) References Cited

U.S. PATENT DOCUMENTS

| | | | |
|---|---|---|---|
| 4,920,126 A * | 4/1990 | Brewer | ......................... 514/274 |
| 7,217,727 B2 | 5/2007 | Eacho et al. | |
| 7,595,403 B2 | 9/2009 | Eacho et al. | |
| 2003/0100549 A1 * | 5/2003 | Salituro et al. | ........... 514/217.06 |
| 2005/0261322 A1 | 11/2005 | Naidu et al. | |
| 2006/0094737 A1 * | 5/2006 | Isobe et al. | ..................... 514/269 |
| 2006/0211755 A1 | 9/2006 | Eacho et al. | |
| 2008/0125437 A1 * | 5/2008 | Dong et al. | .............. 514/252.13 |
| 2008/0287448 A1 | 11/2008 | Zoller et al. | |
| 2009/0054478 A1 | 2/2009 | Zoller et al. | |
| 2009/0076068 A1 | 3/2009 | Zoller et al. | |

FOREIGN PATENT DOCUMENTS

| | | |
|---|---|---|
| WO | WO99/32611 A1 | 7/1999 |
| WO | WO2004/093872 A1 | 11/2004 |

(Continued)

OTHER PUBLICATIONS

Baraldi, P.G. et al., "Design, Synthesis, and Biological Activity of Hybrid Compounds between Uramustine and DNA Minor Groove Binder Distamycin A", J. Med. Chem., vol. 45, pp. 3630-3638 (2002).

(Continued)

*Primary Examiner* — Deepak Rao
(74) *Attorney, Agent, or Firm* — Barry H. Jacobsen

(57) ABSTRACT

The present invention provides compounds of Formula (I), as defined in the specification and compositions comprising any of such novel compounds. These compounds are endothelial lipase inhibitors which may be used as medicaments.

(I)

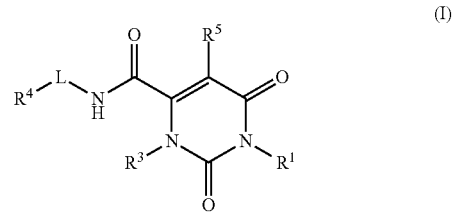

10 Claims, No Drawings

(56) References Cited

FOREIGN PATENT DOCUMENTS

| WO | WO2004/094393 A1 | 11/2004 |
|---|---|---|
| WO | WO2004/094394 A1 | 11/2004 |
| WO | WO2007/042178 A1 | 4/2007 |
| WO | WO2007/110215 A1 | 10/2007 |
| WO | WO2007/110216 A1 | 10/2007 |
| WO | WO2008/122352 A1 | 10/2008 |
| WO | WO2009/065406 A2 | 5/2009 |
| WO | WO2009/133834 A1 | 5/2009 |
| WO | WO2009/123164 A1 | 8/2009 |

OTHER PUBLICATIONS

Bevilacqua, M.P. et al., "Perspectives: Selectins", J. Clin. Invest., vol. 91, pp. 379-387 (1993).

Nielsen, N. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77(4), pp. 285-298 (1988).

Bundgaard, H., "Means to Enhance Penetration: Prodrugs as a means to improve the delivery of peptide drugs" Advanced Drug Delivery Reviews, vol. 8, pp. 1-38 (1992).

Culbertson, T.P., "Synthesis of 5,6-Dihydroxy-2-phenyl-4-pyrimidinecarboxylic Acid, Methyl Ester, a Corrected Structure", J. Heterocyclic Chem., vol. 16, p. 1423 (1979).

deLemos, A.S. et al., "Identification of Genetic Variants in Endothelial Lipase in Persons With Elevated High-Density Lipoprotein Cholesterol", Circulation, vol. 106, pp. 1321-1326 (2002).

Dreher, S.D. et al., "Highly selective synthesis of 2-substituted-5-hydroxy-6-oxo-1,6-dihydropyrimidine-4-carboxylic acid derivatives using a novel protected dihydroxyfumarate", Tetrahedron Letters, vol. 45, pp. 6023-6025 (2004).

Ellman, J.A., et al., "One-Pot Asymmetric Synthesis of Either Diastereomer of tert-Butanesulfinyl-protected Amines from Ketones", J. Org. Chemistry, vol. 72, pp. 626-629 (2007).

Elzein, E. et al., "Discovery of a Novel $A_{2B}$ Adenosine Receptor Antagonist as a Clinical Candidate for Chronic Inflammatory Airway Diseases", J. Med. Chem., vol. 51, pp. 2267-2278 (2008).

Folkman, J. et al., "Minireview: Angiogenesis", The Journal of Biological Chemistry, vol. 267(16), pp. 10931-10934 (1992).

Folkman, J. et al., "Angiogenic Factors", Science, vol. 235, pp. 442-447 (1987).

Gambacorta, A. et al., "HSAB-driven chemoselective $N^1$-alkylation of pyrimidine bases and their 4-methoxy- or 4-acetylamino-derivatives", Tetrahedron, vol. 62, pp. 6848-6854 (2006).

Gordon, D.J. et al., "High-density lipoprotein cholesterol and cardiovascular disease. Four prospective American studies", Circulation, vol. 79, pp. 8-15 (1989).

Gordon, D.J. et al., "High-Density Lipoprotein—The Clinical Implications of Recent Studies", New England Journal of Medicine, vol. 321(19), pp. 1311-1316 (1989).

Hirata, K. et al., "Cloning of a Unique Lipase from Endothelial Cells Extends the Lipase Gene Family", The Journal of Biological Chemistry, vol. 274(20), pp. 14170-14175 (1999).

Janssens, S.P. et al., "Cloning and Expression of a cDNA Encoding Human Endothelium-derived Relaxing Factor/Nitric Oxide Synthase", The Journal of Biological Chemistry, vol. 267(21), pp. 14519-14522—(1992).

Jaye, M. et al., "A novel endothelial-derived lipase that modulates HDL metabolism", Nature genetics, vol. 21, pp. 424-428 (1999).

Jin, W. et al., "Lipases and HDL metabolism", Trends in Endocrinology & Metabolism, vol. 13(4), pp. 174-178 (2002).

Kakeya, N. et al., "Studies on Prodrugs of Cephalosporins. I. Synthesis and Biological Properties of Glycyloxybenzoyloxymethyl and Glycylaminobenzoyloxmethyl Esters of 7β-[2-(2-Aminothiazol-4-yl)-(Z)-2-methoxyiminoacetamido]-3-methyl-3-cephem-4-carboxylic Acid", Chem. Pharm. Bulletin, vol. 32 (2), pp. 692-698 (1984).

Lamas, S. et al., "Endothelial nitric oxide synthase: Molecular cloning and characterization of a distinct constitutive enzyme isoform", Proc. Natl. Acad. Sci. USA., vol. 89, pp. 6348-6352 (1992).

Lukin, K. et al., "Practical Method for Asymmetric Addition of Arylboronic Acids to α,β-Unsaturated Carbonyl Compounds Utilizing an In Situ Prepared Rhodium Catalyst", J. Org. Chem., vol. 74, pp. 929-931 (2009).

Lüscher, T.F. et al., "Endothelium-derived contracting factors." Hypertension, vol. 19, pp. 117-130 (1992).

McCoy, M.G. et al., "Characterization of the lipolytic activity of endothelial lipase", Journal of Lipid Research, vol. 43, pp. 921-929 (2002).

Regiec, A. et al., "New Amides of 5-(4-Chlorobenzoyl)aminoorotic Acid: Their Synthesis and Biological Activity", Arch. Pharm. Chem. Life Sci., vol. 341, pp. 677-689 (2008).

Ross, Russell, The pathogenesis of atherosclerosis: a perspective for the 1990s, Nature, vol. 362, pp. 801-809 (1993).

Shimizu, M. et al., "Efficient and practical synthesis of both enantiomers of 3-phenylcyclopentanol derivatives", Tetrahedron, vol. 58, pp. 8729-8736 (2002).

Strauss, J.G. et al., "Endothelial cell-derived lipase mediates uptake and binding of high-density lipoprotein (HDL) particles and the selective uptake of HDL-associated cholesterol esters independent of its enzymic activity", Biochem, J., vol. 368, pp. 69-79 (2002).

Tao, L. et al., "A Mild and Efficient method for N-Arylnucleobase Synthesis via the Cross-Coupling Reactions of Nucleobases with Arylboronic Acids Catalyzed by Simple Copper Salts", Helvetica Chimica Acta, vol. 91(6), pp. 1008-1014 (2008).

Widder, K. et al., "Drug and Enzyme Targeting Part A", Methods in Enzymology, vol. 112 pp. 309-396 (1985).

Williams, T.J. et al., "3. Endothelial Cell Biology: Adhesion Molecules Involved in the Microvascular Inflammatory Response", Am Rev Respir Disease, vol. 146, pp. S45-S50 (1992).

Yamamoto, T. et al., "Addition reaction of arylboronic acids to aldehydes and α,β-unsaturated carbonyl compounds catalyzed by conventional palladium complexes in the presence of chloroform", Journal of Organometallic Chemistry, vol. 694, pp. 1325-1332 (2009).

Yanagisawa, M. et al., "A novel potent vasoconstrictor peptide produced by vascular endothelial cells", Nature, vol. 332, pp. 411-415 (1988).

Yue, Y. et al., "Copper-Catalyzed Cross-Coupling Reactions of Nucleobases with Arylboronic Acids: An Efficient Access to N-Arylnucleobases", Eur. J. Org. Chem., pp. 5154-5157 (2005).

Zajac, M.A. et al., "A Novel Method of Caffeine Synthesis from Uracil", Synthetic Communications, vol. 33(19), pp. 3291-3297 (2003).

Zhang, L. et al., "Microwave-assisted synthesis of 8-mercapto-3-methyl-7-alkyl xanthines—an improved method", Tetrahedron Letters, vol. 47, pp. 775-778 (2006).

Wong, H. et al., "The lipase gene family", Journal of Lipid Research, vol. 43, pp. 993-999 (2002).

* cited by examiner

PYRIMIDINONE CARBOXAMIDE INHIBITORS OF ENDOTHELIAL LIPASE

CROSS-REFERENCE TO RELATED APPLICATIONS

The present application is a 371 of International Application No. PCT/US2013/034529 filed Mar. 29, 2013, which claims priority benefit of U.S. provisional application Ser. No. 61/619,453, filed Apr. 3, 2012; each of which is fully incorporated by reference herein.

FIELD OF THE INVENTION

The present invention provides novel pyrimidinone carboxamide compounds and analogues, which are endothelial lipase (EL) inhibitors, compositions containing them, and methods of using them, for example, for the treatment and/or prophylaxis of dyslipidemias and the sequelae thereof.

BACKGROUND OF THE INVENTION

Cardiovascular disease is a major health risk throughout the industrialized world. Atherosclerosis, the most prevalent of cardiovascular diseases, is the principal cause of heart attack, and stroke, and thereby the principal cause of death in the United States.

Atherosclerosis is a complex disease involving many cell types and molecular factors (for a detailed review, see Ross, R., *Nature*, 362(6423):801-809 (1993)). Results from epidemiologic studies have clearly established an inverse relationship between levels of high density lipoprotein (HDL), which transports endogenous cholesterol from tissues to the liver as well as mediating selective cholesteryl ester delivery to steroidogenic tissues, and the risk for atherosclerosis (Gordon, D. J. et al., *N. Engl. J. Med.*, 321(19):1311-1316 (1989)).

The metabolism of HDL is influenced by several members of the triacylglycerol (TG) lipase family of proteins, which hydrolyze triglycerides, phospholipids, and cholesteryl esters, generating fatty acids to facilitate intestinal absorption, energy production, or storage. Of the TG lipases, lipoprotein lipase (LPL) influences the metabolism of HDL cholesterol by hydrolyzing triglycerides in triglyceride-rich lipoproteins, resulting in the transfer of lipids and apolipoproteins to HDL and is responsible for hydrolyzing chylomicron and very low density lipoprotein (VLDL) in muscle and adipose tissues. Hepatic lipase (HL) hydrolyzes HDL triglyceride and phospholipids, generating smaller, lipid-depleted HDL particles, and plays a role in the uptake of HDL cholesterol (Jin, W. et al., *Trends Endocrinol. Metab.*, 13(4):174-178 (2002); Wong, H. et al., *J. Lipid Res.*, 43:993-999 (2002)). Endothelial lipase (also known as EDL, EL, LIPG, endothelial-derived lipase, and endothelial cell-derived lipase) is synthesized in endothelial cells, a characteristic that distinguishes it from the other members of the family.

Recombinant endothelial lipase protein has substantial phospholipase activity but has been reported to have less hydrolytic activity toward triglyceride lipids (Hirata, K. et al., *J. Biol. Chem.*, 274(20):14170-14175 (1999); Jaye, M. et al., *Nat. Genet.*, 21:424-428 (1999)). However, endothelial lipase does exhibit triglyceride lipase activity ex vivo in addition to its HDL phospholipase activity, and endothelial lipase was found to hydrolyze HDL more efficiently than other lipoproteins (McCoy, M. G. et al., *J. Lipid Res.*, 43:921-929 (2002)). Overexpression of the human endothelial lipase gene in the livers of mice markedly reduces plasma concentrations of HDL cholesterol and its major protein apolipoprotein A-I (apoA-I) (Jaye, M. et al., *Nat. Genet.*, 21:424-428 (1999)).

Various types of compounds have been reported to modulate the expression of endothelial lipase, for example, 3-oxo-1,3-dihydro-indazole-2-carboxamides (WO 2004/093872, US 2006/0211755A1), 3-oxo-3-H-benzo[d]isoxazole-2-carboxamides (WO 2004/094393, U.S. Pat. No. 7,217,727), and benzisothiazol-3-one-2-carboxamides (WO 2004/094394, U.S. Pat. No. 7,595,403) by Eli Lilly & Co.; diacylindazole derivatives (WO 2007/042178, US 2008/0287448A1) and imidazopyridin-2-one derivatives (WO 2007/110215, US 2009/0076068A1), and azolopyridin-3-one derivatives (WO 2007/110216, US 2009/0054478A1) by Sanofi-Aventis; heterocyclic derivatives (WO 2009/123164) and keto-amide derivatives (WO 2009/133834) by Shionogi & Co., Ltd. However, because endothelial lipase is a relatively new member in the lipase gene family, a full understanding of the potential of endothelial lipase inhibitors to human health, as well as the inhibitors of other lipases in general, requires more studies.

Thus, there is a clear need for new types of compounds capable of inhibiting the activity of lipases, particularly endothelial lipase, that would constitute effective treatments to the diseases or disorders associated with the activity of such lipases.

SUMMARY OF THE INVENTION

The present disclosure provides novel pyrimidinone carboxamide compounds and their analogues, including stereoisomers, tautomers, pharmaceutically acceptable salts, or solvates thereof, which are useful as EL inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of dyslipidemias and the sequelae thereof.

The compounds of the invention may be used in therapy.

The compounds of the invention may be used for the manufacture of a medicament for the treatment and/or prophylaxis of dyslipidemias and the sequelae thereof.

The compounds of the invention can be used alone, in combination with other compounds of the present invention, or in combination with one or more, preferably one to two, and other agent.

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

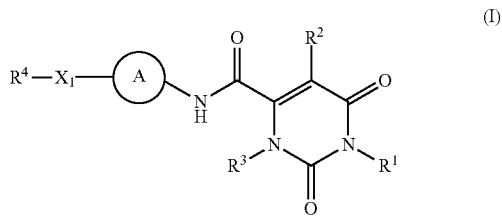

or a stereoisomer, a tautomer, a pharmaceutically acceptable salt, or a solvate thereof, wherein:

ring A is independently selected from the group consisting of: $C_{3-10}$ carbocycle and a 4- to 14-membered heterocycle comprising: carbon atoms and 1-4 heteroatoms selected from N, $NR^e$, O, and $S(O)_p$; wherein each said carbocycle and heterocycle are further substituted with 0-4 $R^5$;

$X_1$ is independently selected from the group consisting of: a bond, a hydrocarbon linker and a hydrocarbon-heteroatom linker; wherein said hydrocarbon linker and hydrocarbon-heteroatom linker may be substituted with 0-2 $R^g$; said hydrocarbon linker has one to six carbon atoms and may be saturated or unsaturated; and said hydrocarbon-heteroatom linker may be saturated or unsaturated and has zero to four carbon atoms and one group selected from O, —CO—, S, —SO—, —SO$_2$—, NH, N(C$_{1-4}$ alkyl), —NHCO—, —CONH—, —OCONH—, —NHCONH—, and —SO$_2$NH—;

$R^1$ and $R^3$ are each independently selected from the group consisting of: H, $C_{1-6}$ haloalkyl, $C_{1-6}$ alkyl substituted with 0-3 $R^a$, $C_{2-6}$ alkenyl substituted with 0-3 $R^a$,

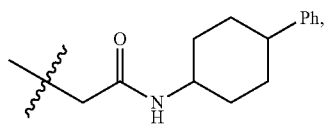 [SMILES: *CC(=O)NC1CCC(c2ccccc2)CC1]

and —(CH$_2$)$_n$—(C$_{3-10}$ carbocycle substituted with 0-3 $R^c$);

$R^2$ is independently selected from the group consisting of: $OR^6$ and $NHR^7$;

$R^4$ is independently selected from the group consisting of: H, =O, halogen, $C_{1-6}$ alkyl substituted with 0-1 OH, $C_{1-4}$ alkoxy, $C_{1-4}$ haloalkyl, $C_{1-4}$ haloalkoxy, CN, NO$_2$, NH$_2$, N(C$_{1-4}$ alkyl)$_2$, and a ring moiety substituted with 0-2 $R^h$ and selected from: $C_{3-10}$ carbocycle and a 5- to 10-membered heterocycle comprising: carbon atoms and 1-4 heteroatoms selected from N, $NR^e$, O, and $S(O)_p$;

$R^5$ is, independently at each occurrence, selected from the group consisting of: =O, OH, halogen, $C_{1-6}$ alkyl substituted with 0-1 OH, $C_{1-4}$ alkoxy, $C_{1-4}$ haloalkyl, $C_{1-4}$ haloalkoxy, SCF$_3$, CN, NH$_2$, NO$_2$, NH(C$_{1-4}$ alkyl), N(C$_{1-4}$ alkyl)$_2$, CO$_2$H, CO$_2$(C$_{1-4}$ alkyl), —CH$_2$CO$_2$(C$_{1-4}$ alkyl), CO(C$_{1-4}$ alkyl), CONH$_2$, CONH(C$_{1-4}$ alkyl), and CON(C$_{1-4}$ alkyl)$_2$;

$R^6$ is independently selected from the group consisting of: H and $C_{1-6}$ alkyl substituted with 0-1 $R^8$;

$R^7$ is independently selected from the group consisting of: H, COCF$_3$, $C_{1-6}$ haloalkyl, $C_{1-6}$ alkyl substituted with 0-1 $R^a$, —(CHR$^f$)$_n$—(C$_{3-10}$ carbocycle substituted with 0-3 $R^b$), and —(CHR$^f$)$_n$-(5- to 10-membered heterocycle comprising: carbon atoms and 1-4 heteroatoms selected from N, $NR^e$, O, and $S(O)_p$); and wherein said heterocycle is substituted with 0-3 $R^c$;

$R^8$ is independently selected from the group consisting of: CO$_2$H and OH;

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CN, NH$_2$, NO$_2$, NH(C$_{1-4}$ alkyl), N(C$_{1-4}$ alkyl)$_2$, CO$_2$H, CO$_2$(C$_{1-4}$ alkyl), NHCO(C$_{1-4}$ alkyl substituted with 0-1 NH$_2$), N(C$_{1-4}$ alkyl)CO(C$_{1-4}$ alkyl), NHCO$_2$(C$_{1-4}$ alkyl), CONHSO$_2$(C$_{1-4}$ alkyl), SO$_2$(C$_{1-4}$ alkyl), CONH$_2$, CONH(C$_{1-4}$ alkyl), NHSO$_2$(C$_{1-4}$ alkyl), N(C$_{1-4}$ alkyl)SO$_2$(C$_{1-4}$ alkyl), phenoxy, and —CONH(phenylcyclohexyl);

$R^b$ is, independently at each occurrence, selected from the group consisting of: halogen, OH, $C_{1-4}$ alkyl substituted with 0-1 OH, $C_{1-4}$ alkoxy, $C_{1-4}$ haloalkyl, $C_{1-4}$ haloalkoxy, CN, NH$_2$, NO$_2$, NH(C$_{1-4}$ alkyl), N(C$_{1-4}$ alkyl)$_2$, CO$_2$H, CO$_2$(C$_{1-4}$ alkyl), CONH$_2$, CONH(C$_{1-4}$ alkyl), CON(C$_{1-4}$ alkyl)$_2$, NHCO$_2$(C$_{1-4}$ alkyl), NHSO$_2$(C$_{1-4}$ alkyl), N(C$_{1-4}$ alkyl)SO$_2$(C$_{1-4}$ alkyl), SO$_2$(C$_{1-4}$ alkyl), SO$_2$NH$_2$, phenyl, benzyl, and phenoxy;

$R^c$ is, independently at each occurrence, selected from the group consisting of: =O and $R^b$;

$R^d$ is, independently at each occurrence, selected from the group consisting of: CONH$_2$, C$_{1-4}$ alkyl, —(CH$_2$)$_2$O(CH$_2$)$_2$O (C$_{1-4}$ alkyl), C$_{3-6}$-carbocycle substituted with 0-2 $R^h$, morpholin-1-yl, 1-C$_{1-4}$ alkyl-piperazin-4-yl, 1-CBz-piperazin-4-yl, pyridyl, indol-3-yl, and benzothiazol-2-yl;

$R^e$ is, independently at each occurrence, selected from the group consisting of: H, C$_{1-4}$ alkyl, CO(C$_{1-4}$ alkyl), CO$_2$(C$_{1-4}$ alkyl), CO$_2$(benzyl), CONH(C$_{1-4}$ alkyl), CONH(phenyl substituted with 0-2 halogens), SO$_2$(C$_{1-4}$ alkyl), and —(CH$_2$)$_n$ $R^d$;

$R^f$ is, independently at each occurrence, selected from the group consisting of: H and C$_{1-4}$ alkyl;

$R^g$ is, independently at each occurrence, selected from the group consisting of: halogen, OH, C$_{1-4}$ alkyl, C$_{2-4}$ alkenyl, C$_{1-4}$ haloalkyl, C$_{1-4}$ alkoxy, CO$_2$(C$_{1-4}$ alkyl), C$_{3-6}$ cycloalkyl, and phenyl;

$R^h$ is, independently at each occurrence, selected from the group consisting of: H, halogen, C$_{1-6}$ alkyl, C$_{1-6}$ alkoxy, C$_{1-4}$ haloalkyl, C$_{1-4}$ haloalkoxy, —(CH$_2$)$_2$O(C$_{1-4}$ alkyl), CF$_3$, NO$_2$, CONH$_2$, OBn, quinolinyl, 1-C$_{1-4}$ alkyl-pyrazolyl, 1-(CH$_2$CO$_2$(C$_{1-4}$ alkyl))-pyrazolyl, 1-C$_{1-4}$ alkyl-3-CF$_3$-pyrazolyl, 1-((CH$_2$)$_2$(morpholin-4-yl))-pyrazolyl, 1-(tetrahydro-2H-pyran-2-yl)-pyrazolyl, 1,2,5-triC$_{1-4}$ alkyl-pyrazolyl, 2-Ph-4-C$_{1-4}$ alkyl-thiazolyl, —NHSO$_2$(phenyl substituted with C$_{1-4}$ alkyl), and —(CH$_2$)$_{0-2}$-(phenyl substituted with zero to three substituents independently selected from the group consisting of: halogen, CH$_2$OH, C$_{1-4}$ alkyl, C$_{1-4}$ haloalkyl, C$_{1-4}$ alkoxy, C$_{1-4}$ haloalkoxy, N(C$_{1-4}$ alkyl)$_2$, CONH$_2$, and NHCO(C$_{1-4}$ alkyl));

n is, independently at each occurrence, selected from 0, 1, 2, 3, and 4; and p is, independently at each occurrence, selected from 0, 1, and 2.

In a second aspect, the present invention includes a compound of Formula (I), or a stereoisomer, a tautomer, a pharmaceutically acceptable salt, or a solvate thereof, within the scope of the first aspect, wherein:

ring A is independently selected from the group consisting of: $C_{3-10}$ carbocycle and a 4- to 13-membered heterocycle comprising: carbon atoms and 1-4 heteroatoms selected from N, $NR^e$, O, and $S(O)_p$; wherein each said carbocycle and heterocycle is substituted with 0-3 $R^5$;

$X_1$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to five carbon atoms; and said hydrocarbon-heteroatom linker may be saturated or unsaturated and has zero to four carbon atoms and one group selected from O, —CO—, S, —SO—, —SO$_2$—, NH, N(C$_{1-4}$ alkyl), —NHCO—, —CONH—, —OCONH—, —NHCONH—, and —SO$_2$NH—;

$R^1$ and $R^3$ are each independently selected from the group consisting of: H, $C_{1-6}$ haloalkyl, $C_{1-6}$ alkyl substituted with 0-3 $R^a$, $C_{1-6}$ haloalkyl,

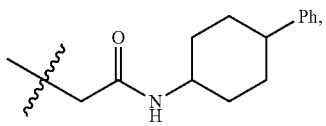 [SMILES: *CC(=O)NC1CCC(c2ccccc2)CC1]

and —(CH$_2$)$_n$-(phenyl substituted with 0-3 $R^c$C);

$R^2$ is independently selected from the group consisting of: $OR^6$ and $NHR^7$;

$R^4$ is independently selected from the group consisting of: H, $C_{1-4}$ alkyl, $C_{1-4}$ alkoxy, halogen, $C_{1-4}$ haloalkyl, $C_{1-4}$ haloalkoxy, and a ring moiety substituted with 0-2 $R^h$ and selected from: $C_{3-10}$ carbocycle and a 5- to 10-membered heterocycle comprising: carbon atoms and 1-4 heteroatoms selected from N, $NR^e$, O, and $S(O)_p$;

$R^5$ is, independently at each occurrence, selected from the group consisting of: OH, halogen, $C_{1-4}$ alkyl substituted with 0-1 OH, $C_{1-4}$ alkoxy, $C_{1-4}$ haloalkyl, $C_{1-4}$ haloalkoxy, CN, $NO_2$, $CO_2(C_{1-4}$ alkyl), $-CH_2CO_2(C_{1-4}$ alkyl), $NH_2$, $NH(C_{1-4}$ alkyl), and $N(C_{1-4}$ alkyl)$_2$; and $R^6$ is independently selected from the group consisting of: H and $C_{1-4}$ alkyl substituted with 0-1 $CO_2H$.

In a third aspect, the present invention includes a compound of Formula (I), or a stereoisomer, a tautomer, a pharmaceutically acceptable salt, or a solvate thereof, within the scope of the first or second aspect, wherein:

ring A is independently selected from the group consisting of: c,

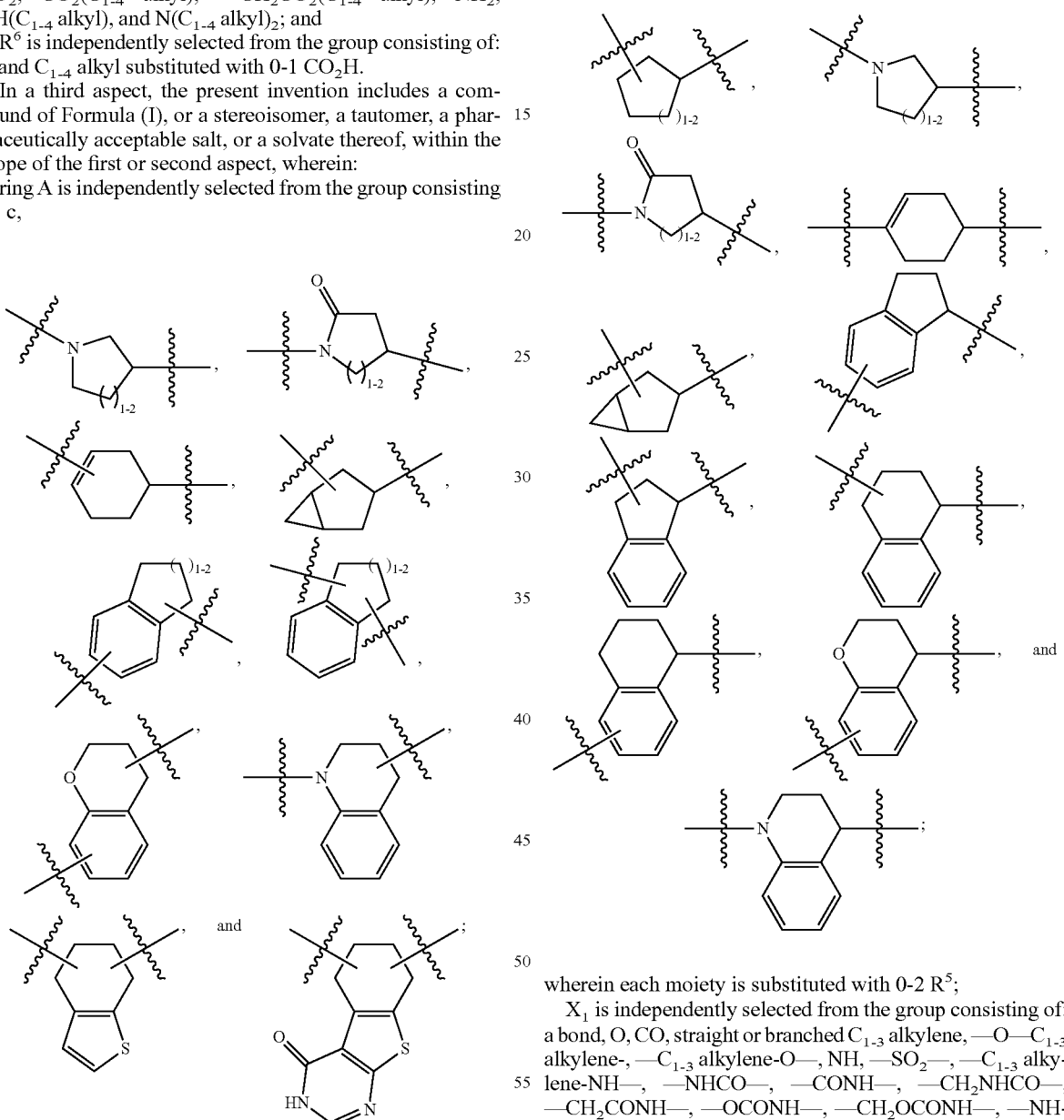

wherein each moiety is substituted with 0-2 $R^5$; and $X_1$ is independently selected from the group consisting of: a bond, a hydrocarbon linker and a hydrocarbon-heteroatom linker; wherein said hydrocarbon linker and hydrocarbon-heteroatom linker may be substituted with 0-1 $R^g$; said hydrocarbon linker may be saturated or unsaturated and has one to four carbon atoms; and said hydrocarbon-heteroatom linker may be saturated or unsaturated and has zero to three carbon atoms and one group selected from O, $-CO-$, S, $-SO-$, $-SO_2-$, NH, $N(C_{1-4}$ alkyl), $-NHCO-$, $-CONH-$, $-OCONH-$, $-NHCONH-$, and $-SO_2NH-$.

In a fourth aspect, the present invention includes a compound of Formula (I), or a stereoisomer, a tautomer, a pharmaceutically acceptable salt, or a solvate thereof, within the scope of any of the above aspects, wherein:

ring A is independently selected from the group consisting of:

wherein each moiety is substituted with 0-2 $R^5$;

$X_1$ is independently selected from the group consisting of: a bond, O, CO, straight or branched $C_{1-3}$ alkylene, $-O-C_{1-3}$ alkylene-, $-C_{1-3}$ alkylene-O—, NH, $-SO_2-$, $-C_{1-3}$ alkylene-NH—, $-NHCO-$, $-CONH-$, $-CH_2NHCO-$, $-CH_2CONH-$, $-OCONH-$, $-CH_2OCONH-$, $-NHCONH-$, and $-SO_2NH-$;

alternatively,

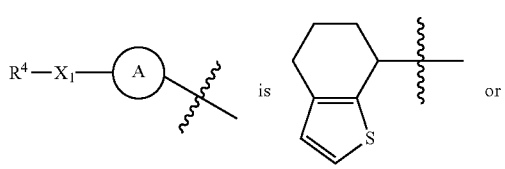

is or

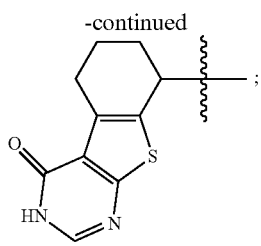

$R^1$ and $R^3$ are each independently selected from the group consisting of: H, $C_{1-6}$ alkyl, $C_{1-6}$ haloalkyl, —$(CH_2)_2OH$, —$CH_2CO_2H$, —$CH_2CO_2(C_{1-4}$ alkyl$)$, —$(CH_2)_{1-3}$Ph, 3-halo-4-halo-phenyl, 3-halo-5-$CF_3$-phenyl, and

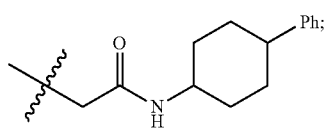

$R^2$ is independently selected from the group consisting of: OH and $NHR^7$;

$R^5$ is, independently at each occurrence, selected from the group consisting of: halogen, $C_{1-4}$ alkyl, $C_{1-4}$ alkoxy, $C_{1-4}$ haloalkyl, $C_{1-4}$ haloalkoxy, CN, $NO_2$, $CO_2(C_{1-4}$ alkyl$)$, —$CH_2CO_2(C_{1-4}$ alkyl$)$, $NH_2$, $NH(C_{1-4}$ alkyl$)$, and $N(C_{1-4}$ alkyl$)_2$;

$R^7$ is independently selected from the group consisting of: H, $C_{1-6}$ haloalkyl, $COCF_3$, —$(CH_2)_2O(C_{1-4}$ alkyl$)$, $C_{1-6}$ alkyl substituted with 0-1 OH, —$(CHR^f)_n$—$(C_{3-6}$ cycloalkyl substituted with 0-1 OH$)$, —$(CHR^f)_n$-(phenyl substituted with 0-2 $R^b$), 1-tetralinyl, 1-indanyl, tetrahydronaphthalenyl, 1-Bn-pyrrolidin-3-yl, —$(CH_2)_n$-(piperidin-1-yl), 1-$C_{1-4}$ alkyl-piperidiny-4-yl, 1-$CO_2(C_{1-4}$ alkyl$)$-piperidiny-4-yl, 1-(4-halo-phenyl)-piperidiny-4-yl, —$(CH_2)_n$(morpholin-4-yl), —$(CH_2)_n$-imidazolyl, —$(CH_2)_n$-pyridyl,

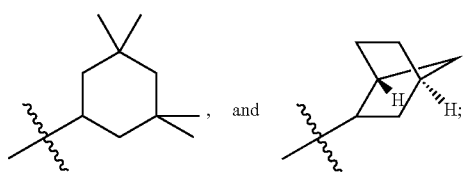

$R^b$ is, independently at each occurrence, selected from the group consisting of: halogen, OH, $C_{1-4}$ alkyl substituted with 0-1 OH, $C_{1-4}$ alkoxy, $C_{1-4}$ haloalkyl, $C_{1-4}$ haloalkoxy, CN, $NH_2$, $NO_2$, $NH(C_{1-4}$ alkyl$)$, $N(C_{1-4}$ alkyl$)_2$, $CO_2H$, $CO_2(C_{1-4}$ alkyl$)$, $CONH_2$, $CONH(C_{1-4}$ alkyl$)$, $CON(C_{1-4}$ alkyl$)_2$, $NHCO_2(C_{1-4}$ alkyl$)$, $SO_2(C_{1-4}$ alkyl$)$, and $SO_2NH_2$;

$R^f$ is, independently at each occurrence, selected from the group consisting of: H and methyl;

$R^h$ is, independently at each occurrence, selected from the group consisting of: H, halogen, $C_{1-6}$ alkyl, $C_{1-6}$ alkoxy, $C_{1-4}$ haloalkyl, $C_{1-4}$ haloalkoxy, —$(CH_2)_2O(C_{1-4}$ alkyl$)$, $CF_3$, $NO_2$, $CONH_2$, OBn, quinolinyl, 1-$C_{1-4}$ alkyl-pyrazolyl, 1-$(CH_2CO_2(C_{1-4}$ alkyl$))$-pyrazolyl, 1-$C_{1-4}$ alkyl-3-$CF_3$-pyrazolyl, 1-$((CH_2)_2$(morpholin-4-yl$))$-pyrazolyl, 1-(tetrahydro-2H-pyran-2-yl)-pyrazolyl, 1,2,5-tri$C_{1-4}$ alkyl-pyrazolyl, 2-Ph-4-$C_{1-4}$ alkyl-thiazolyl, —$NHSO_2$(phenyl substituted with $C_{1-4}$ alkyl), and —$(CH_2)_{0-2}$-(phenyl substituted with zero to three substituents independently selected from the group consisting of: halogen, $CH_2OH$, $C_{1-4}$ alkyl, $C_{1-4}$ haloalkyl, $C_{1-4}$ alkoxy, $C_{1-4}$ haloalkoxy, $N(C_{1-4}$ alkyl$)_2$, $CONH_2$, and $NHCO(C_{1-4}$ alkyl$)$); and n is, independently at each occurrence, selected from 0, 1, 2, and 3.

In a fifth aspect, the present invention includes a compound of Formula (I), or a stereoisomer, a tautomer, a pharmaceutically acceptable salt, or a solvate thereof, within the scope of any of the above aspects, wherein:

ring A is independently selected from the group consisting of:

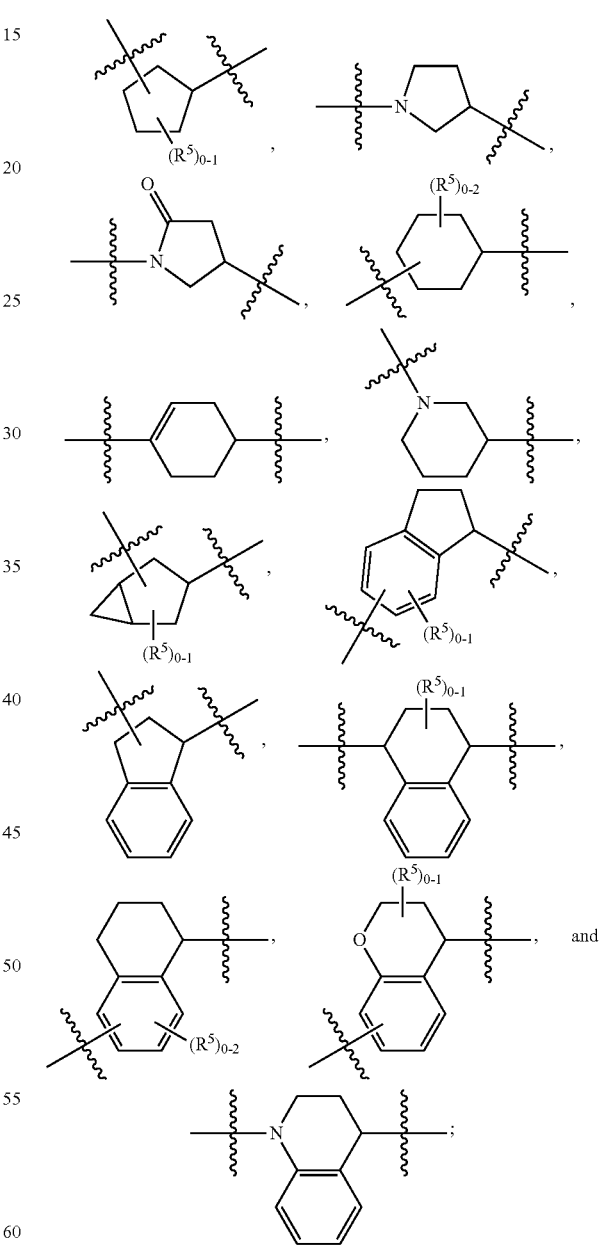

$X_1$ is independently selected from the group consisting of: a bond, O, $CH_2$, CO, —$SO_2$—, —$CH_2CH_2$—, —$CH_2O$—, —$OCH_2$—, NH, —$CH_2NH$—, —$NHCO$—, —$CONH$—, —$CH_2NHCO$—, —$CH_2CONH$—, —$OCONH$—, —$CH_2OCONH$—, —$NHCONH$—, and —$SO_2NH$—;

alternatively,

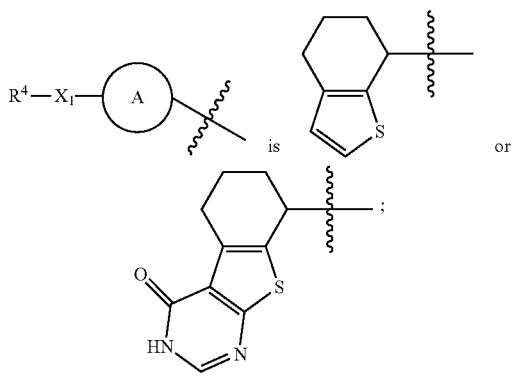

$R^1$ is independently selected from the group consisting of: H, $C_{1-4}$ alkyl, —$(CH_2)_2OH$, —$CH_2CO_2H$, $CH_2CF_3$, $CH_2CH_2CF_3$, —$(CH_2)_{1-3}Ph$, and

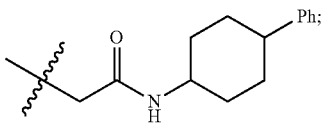

$R^3$ is independently selected from the group consisting of: H, $C_{1-4}$ alkyl, $CH_2CF_3$, —$(CH_2)_{1-3}Ph$, 3-halo-4-halo-phenyl, 3-halo-5-$CF_3$-phenyl, and benzyl;

$R^4$ is independently selected from the group consisting of: H, $C_{1-4}$ alkyl, $C_{1-4}$ alkoxy, halogen, $CF_3$,

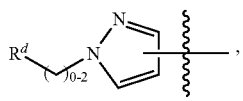

and a ring moiety substituted with 0-2 $R^h$ and selected from: $C_{3-6}$ cycloalkyl, phenyl, dihydroindenyl, tetrahydronaphthalenyl, pyrazolyl, oxadiazolyl, triazolyl, pyridyl, pyrimidinyl, benzothiazolyl, and 1H-pyrazolo[3,4-d]pyrimidinyl;

$R^5$ is, independently at each occurrence, selected from the group consisting of: halogen, $C_{1-4}$ alkyl, $C_{1-4}$ alkoxy, $CO_2$($C_{1-4}$ alkyl), and $NH_2$;

$R^7$ is independently selected from the group consisting of: H, $C_{1-6}$ alkyl substituted with 0-1 OH, $C_{1-6}$ haloalkyl, —$(CH_2)_2O(C_{1-4}$ alkyl), $C_{3-6}$ cycloalkyl, —$CH(CH_3)$(cyclohexyl), —$(CH_2)_{1-3}$-(phenyl substituted with 0-2 $R^b$), tetrahydronaphthalenyl, 1-Bn-pyrrolidin-3-yl, 1-$C_{1-4}$ alkyl-piperidin-4-yl, —$(CH_2)_2$(piperidin-1-yl), —$(CH_2)_2$(morpholin-4-yl), —$(CH_2)_3$(morpholin-4-yl), —$(CH_2)_2$(1H-imidazol-4-yl), —$(CH_2)_3$(imidazol-1-yl), —$CH_2$-pyridyl, and

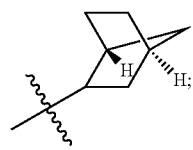

and
$R^h$ is, independently at each occurrence, selected from the group consisting of: H, halogen, $C_{1-6}$ alkyl, $C_{1-6}$ alkoxy, —$(CH_2)_2O(C_{1-4}$ alkyl), $CF_3$, $NO_2$, $CONH_2$, OBn, quinolinyl, 1-$C_{1-4}$ alkyl-pyrazolyl, 1-($CH_2CO_2(C_{1-4}$ alkyl))-pyrazolyl, 1-$C_{1-4}$ alkyl-3-$CF_3$-pyrazolyl, 1-Ph-5-$C_{1-4}$ alkyl-pyrazolyl, 1-(($CH_2)_2$(morpholin-4-yl))-pyrazolyl, 1-(tetrahydro-2H-pyran-2-yl)-pyrazolyl, 1,2,5-tri$C_{1-4}$ alkyl-pyrazolyl, 2-Ph-4-$C_{1-4}$ alkyl-thiazolyl, —$NHSO_2$(phenyl substituted with $C_{1-4}$ alkyl), and —$(CH_2)_{0-2}$-(phenyl substituted with zero to three substituents independently selected from the group consisting of: halogen, $CH_2OH$, $C_{1-4}$ alkyl, $C_{1-4}$ haloalkyl, $C_{1-4}$ alkoxy, $N(C_{1-4}$ alkyl)$_2$, $CONH_2$, and $NHCO(C_{1-4}$ alkyl)).

In a sixth aspect, the present invention includes a compound of Formula (I), wherein $R^2$ is $NHR^7$, further characterized by Formula (II):

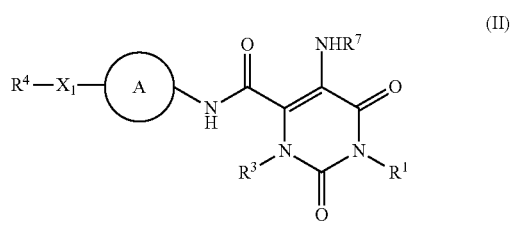

or a stereoisomer, a tautomer, a pharmaceutically acceptable salt, or a solvate thereof, within the scope of any of the above aspects.

In a seventh aspect, the present invention includes a compound of Formula (II), or a stereoisomer, a tautomer, a pharmaceutically acceptable salt, or a solvate thereof, within the scope of any of the above aspects, wherein:

ring A is independently selected from the group consisting of:

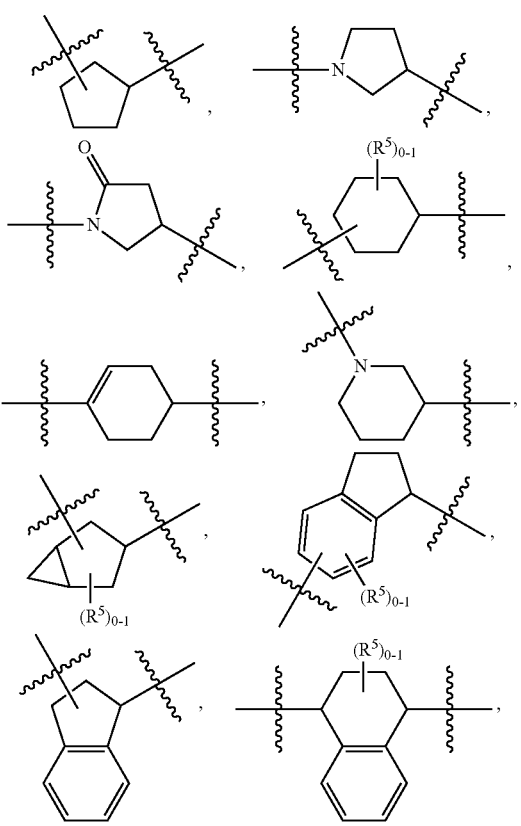

-continued

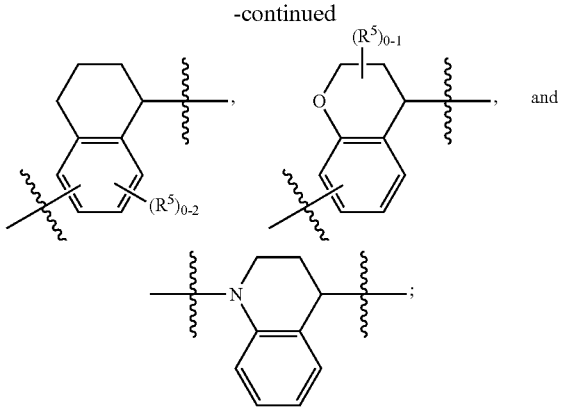

X₁ is independently selected from the group consisting of: a bond, O, $CH_2$, CO, $SO_2$, —$CH_2CH_2$—, —$CH_2O$—, —$OCH_2$—, NH, —$CH_2NH$—, —NHCO—, —CONH—, —$CH_2NHCO$—, —$CH_2CONH$—, —$CH_2OCONH$—, and —$SO_2NH$—;
alternatively,

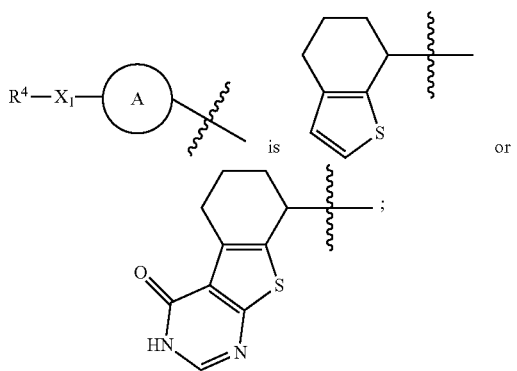

$R^1$ and $R^3$ are each independently selected from the group consisting of: H, $C_{1-4}$ alkyl, $CH_2CF_3$, and benzyl;
$R^4$ is independently selected from the group consisting of: H, $C_{1-4}$ alkyl, $C_{1-4}$ alkoxy, halogen, $CF_3$,

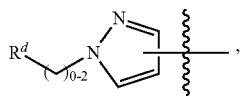

and a ring moiety substituted with 0-2 $R^h$ and selected from: $C_{3-6}$ cycloalkyl, phenyl, dihydroindenyl, tetrahydronaphthalenyl, pyrazolyl, oxadiazolyl, triazolyl, pyridyl, benzothiazolyl, and 1H-pyrazolo[3,4-d]pyrimidinyl;
$R^5$ is, independently at each occurrence, selected from the group consisting of: halogen, $C_{1-4}$ alkyl, $C_{1-4}$ alkoxy, and $CO_2(C_{1-4}$ alkyl);
$R^7$ is independently selected from the group consisting of: H, $C_{1-6}$ alkyl, $CH_2CF_3$, —$(CH_2)_2O(C_{1-4}$ alkyl), —$(CH_2)_2$OH, —$CH(CH_3)CH_2OH$, —$CH_2C(CH_3)_2OH$, $C_{3-6}$ cycloalkyl, —$CH(CH_3)$(cyclohexyl), —$(CH_2)_{1-3}$-(phenyl substituted with 0-2 $R^b$), tetrahydronaphthalenyl, 1-Bn-pyrrolidin-3-yl, 1-$C_{1-4}$ alkyl-piperidin-4-yl, —$(CH_2)_2$(piperidin-1-yl), —$(CH_2)_2$(morpholin-4-yl), —$(CH_2)_3$(morpholin-4-yl), —$(CH_2)_2$(1H-imidazol-4-yl), —$(CH_2)_3$(imidazol-1-yl), —$CH_2$(pyrid-3-yl), —$CH_2$(pyrid-4-yl), and

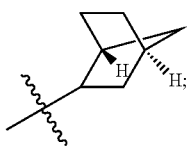

$R^b$ is, independently at each occurrence, selected from the group consisting of: halogen, $CH_2OH$, $CF_3$, and $SO_2NH_2$;
$R^d$ is, independently at each occurrence, selected from the group consisting of: $C_{1-4}$ alkyl and phenyl substituted with 0-2 $R^h$; and
$R^h$ is, independently at each occurrence, selected from the group consisting of: H, halogen, $C_{1-6}$ alkyl, $C_{1-6}$ alkoxy, $CF_3$, $NO_2$, $CONH_2$, OBn, quinolinyl, 1-$C_{1-4}$ alkyl-pyrazolyl, 1-($CH_2CO_2(C_{1-4}$ alkyl))-pyrazolyl, 1-$C_{1-4}$ alkyl-3-$CF_3$-pyrazolyl, 1-Ph-5-$C_{1-4}$ alkyl-pyrazolyl, 1-(($CH_2)_2$(morpholin-4-yl))-pyrazolyl, 1-(tetrahydro-2H-pyran-2-yl)-pyrazolyl, 1,2,5-tri$C_{1-4}$ alkyl-pyrazolyl, 2-Ph-4-$C_{1-4}$ alkyl-thiazolyl, —$NHSO_2$(phenyl substituted with $C_{1-4}$ alkyl), and —$(CH_2)_{0-2}$-(phenyl substituted with zero to three substituents independently selected from the group consisting of: halogen, $CH_2OH$, $C_{1-4}$ alkyl, $C_{1-4}$ haloalkyl, $C_{1-4}$ alkoxy, $N(C_{1-4}$ alkyl)$_2$, $CONH_2$, and $NHCO(C_{1-4}$ alkyl)).

In an eighth aspect, the present invention includes a compound of Formula (II), or a stereoisomer, a tautomer, a pharmaceutically acceptable salt, or a solvate thereof, within the scope of any of the above aspects, wherein:
ring A is independently selected from the group consisting of:

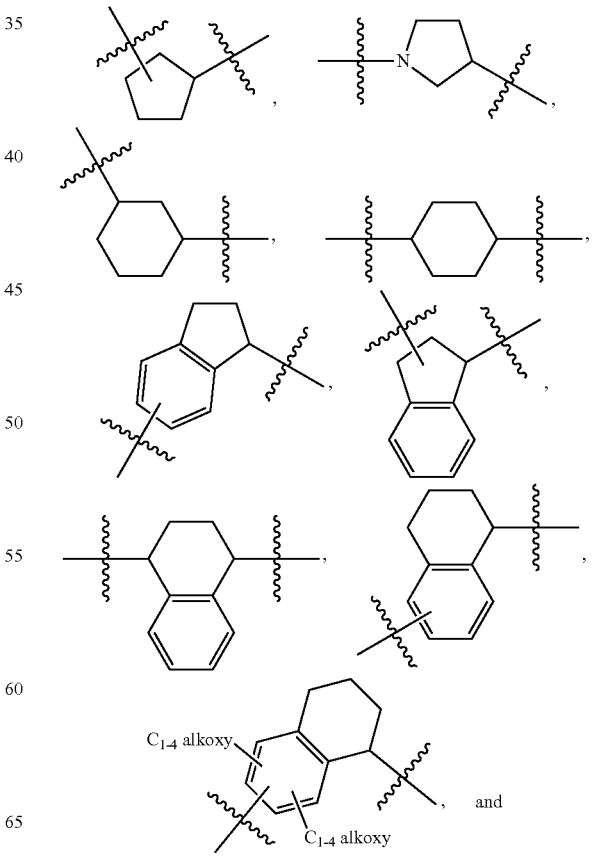

-continued

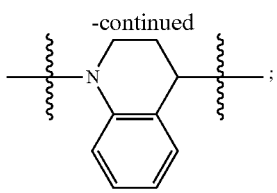

X₁ is independently selected from the group consisting of: a bond, O, CH₂, CO, SO₂, —CH₂CH₂—, —CH₂O—, —OCH₂—, NH, —CH₂NH—, —NHCO—, —CONH—, —CH₂NHCO—, —CH₂OCONH—, and —SO₂NH—;

$R^4$ is independently selected from the group consisting of: H, $C_{1-4}$ alkyl, $C_{1-4}$ alkoxy, halogen, $CF_3$,

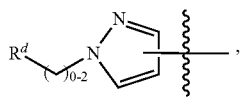

and a ring moiety substituted with 0-2 $R^h$ and selected from: $C_{3-6}$ cycloalkyl, phenyl, tetrahydronaphthalenyl, pyrazolyl, oxadiazolyl, triazolyl, pyridyl, benzothiazolyl, and 1H-pyrazolo[3,4-d]pyrimidinyl;

$R^7$ is independently selected from the group consisting of: H, —(CH₂)₂O(C₁₋₄ alkyl), —CH₂C(CH₃)₂OH, cyclopentyl, 4-halo-benzyl, 2-CH₂OH-benzyl, 3-CF₃-benzyl, 2-halo-phenethyl, 4-halo-phenethyl, —(CH₂)₃Ph, 1-Bn-pyrrolidin-3-yl, —(CH₂)₂(piperidin-1-yl), —(CH₂)₂(morpholin-4-yl), —(CH₂)₃(morpholin-4-yl), —(CH₂)₂(1H-imidazol-4-yl), and —CH₂(pyrid-3-yl); and $R^h$ is, independently at each occurrence, selected from the group consisting of: H, halogen, $C_{1-6}$ alkyl, $C_{1-6}$ alkoxy, $CF_3$, OBn, quinolinyl, 1-$C_{1-4}$ alkyl-pyrazolyl, 1-(CH₂CO₂($C_{1-4}$ alkyl))-pyrazolyl, 1-Ph-pyrazolyl, 1-$C_{1-4}$ alkyl-3-$CF_3$-pyrazolyl, 1-Ph-5-$C_{1-4}$ alkyl-pyrazolyl, 1-((CH₂)₂(morpholin-4-yl))-pyrazolyl, 1,2,5-tri$C_{1-4}$ alkyl-pyrazolyl, —NHSO₂(phenyl substituted with $C_{1-4}$ alkyl), and —(CH₂)₀₋₂-(phenyl substituted with zero to three substituents independently selected from the group consisting of: halogen, CH₂OH, CONH₂, $C_{1-4}$ alkyl, $C_{1-4}$ haloalkyl, $C_{1-4}$ alkoxy, and N($C_{1-4}$ alkyl)₂).

In a ninth aspect, the present invention includes a compound of Formula (II), or a stereoisomer, a tautomer, a pharmaceutically acceptable salt, or a solvate thereof, within the scope of any of the above aspects wherein:

$R^1$ and $R^3$ are each independently selected from the group consisting of: H, $C_{1-4}$ alkyl and benzyl;

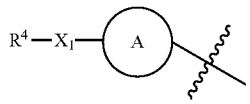

is independently selected from the group consisting of:

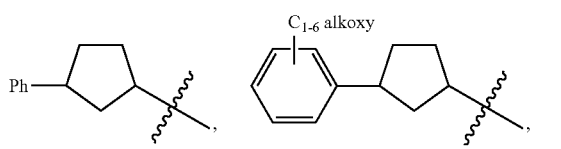

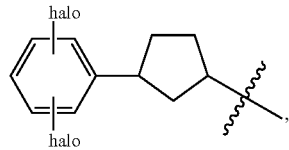

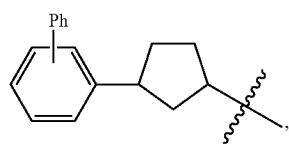

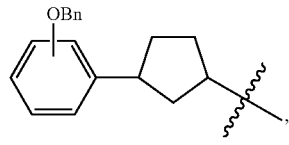

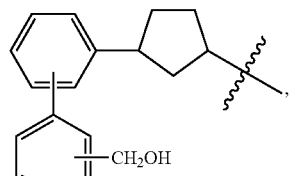

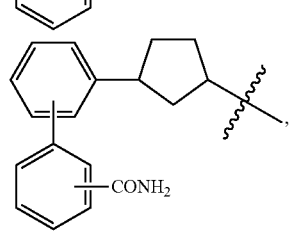

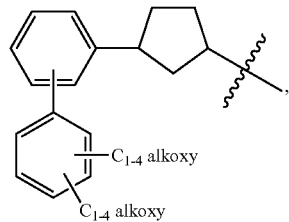

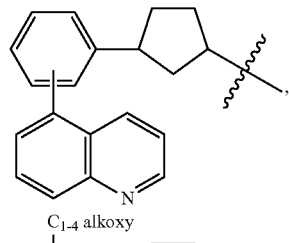

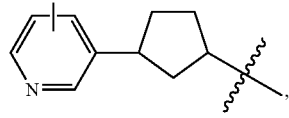

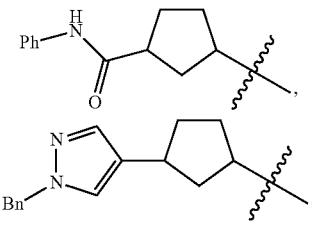

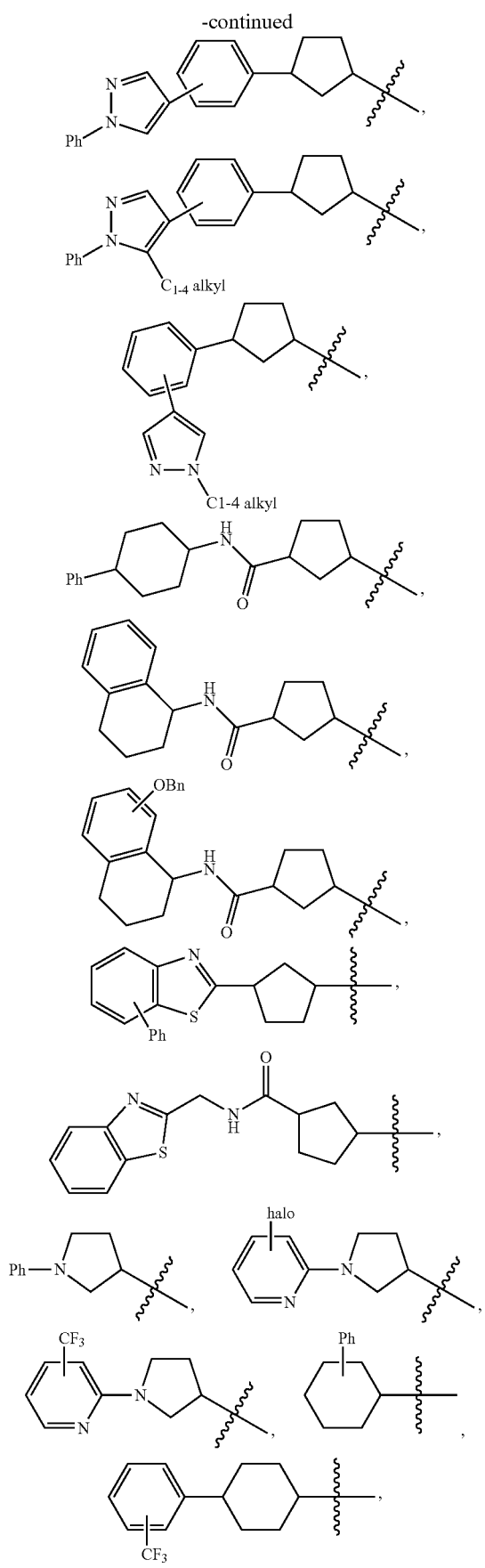
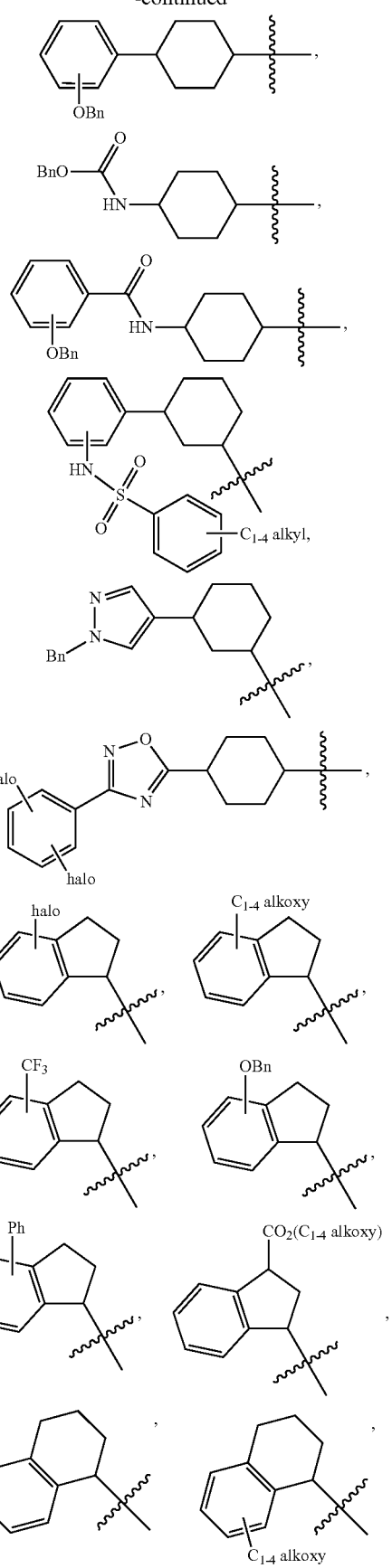

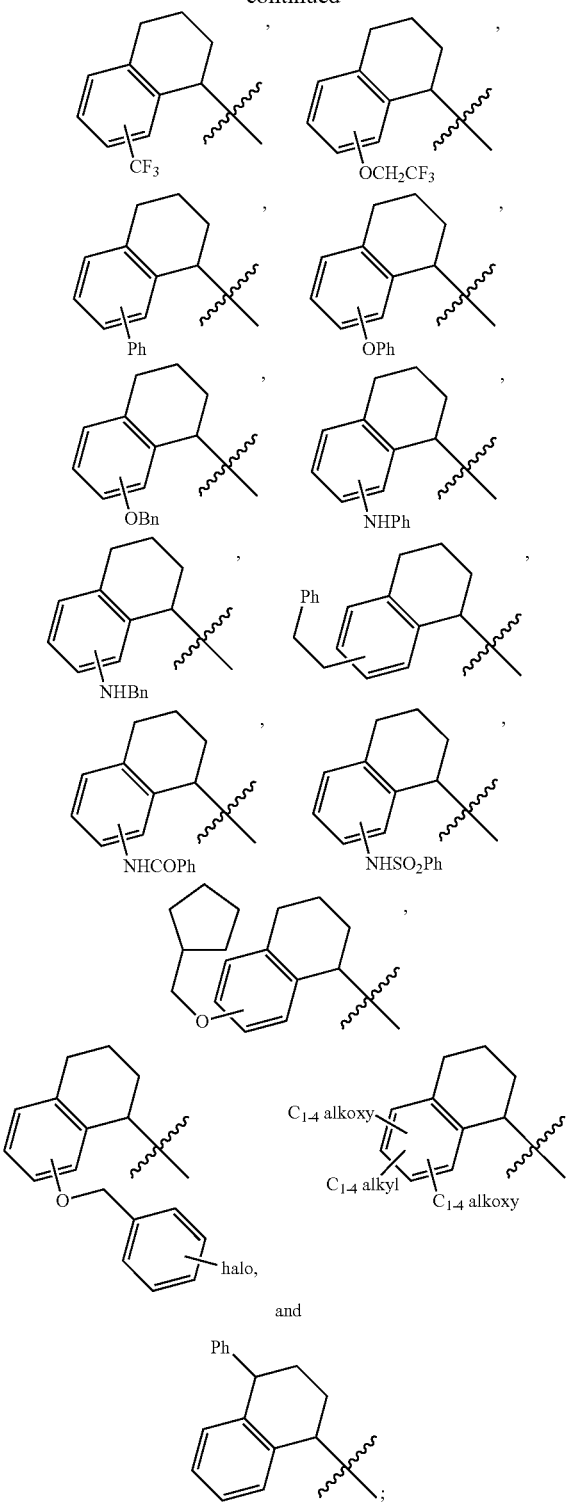

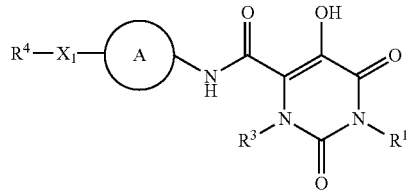

(III)

or a stereoisomer, a tautomer, a pharmaceutically acceptable salt, or a solvate thereof, within the scope of any of the first to fifth aspect.

In an eleventh aspect, the present invention includes a compound of Formula (III), or a stereoisomer, a tautomer, a pharmaceutically acceptable salt, or a solvate thereof, within the scope of any of the first to fifth or tenth aspect, wherein:

$R^1$ is independently selected from the group consisting of: H, $C_{1-4}$ alkyl, —$(CH_2)_2OH$, —$CH_2CO_2H$, $CH_2CF_3$, $CH_2CH_2CF_3$, —$(CH_2)_{1-3}$-Ph,

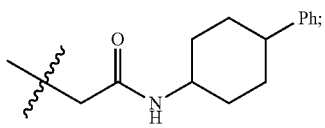 [SMILES: *CC(=O)NC1CCC(c2ccccc2)CC1]

$R^3$ is independently selected from the group consisting of: H, $C_{1-4}$ alkyl and benzyl; and

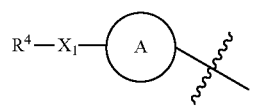

is independently selected from the group consisting of:

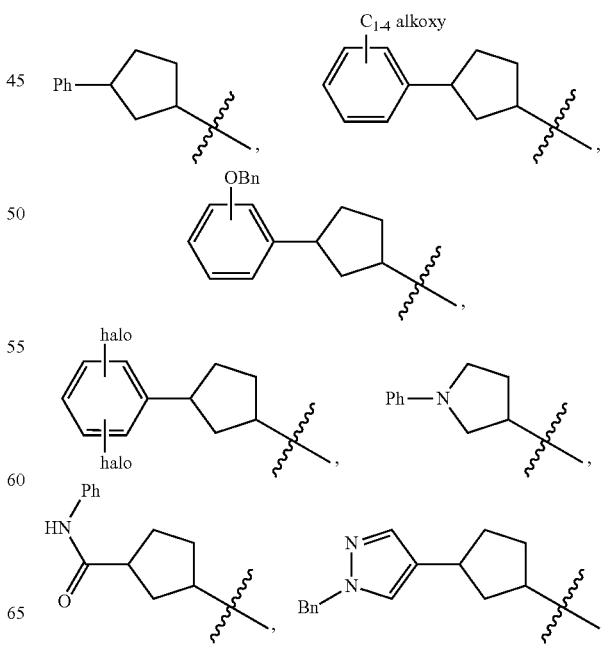

$R^7$ is independently selected from the group consisting of: H, —$(CH_2)_2O(C_{1-4}$ alkyl), —$CH_2C(CH_3)_2OH$, 4-halo-benzyl, 4-halo-phenethyl, —$(CH_2)_2$(morpholin-4-yl), and —$(CH_2)_3$(morpholin-4-yl).

In a tenth aspect, the present invention includes a compound of Formula (I), wherein $R^2$ is OH, further characterized by Formula (III):

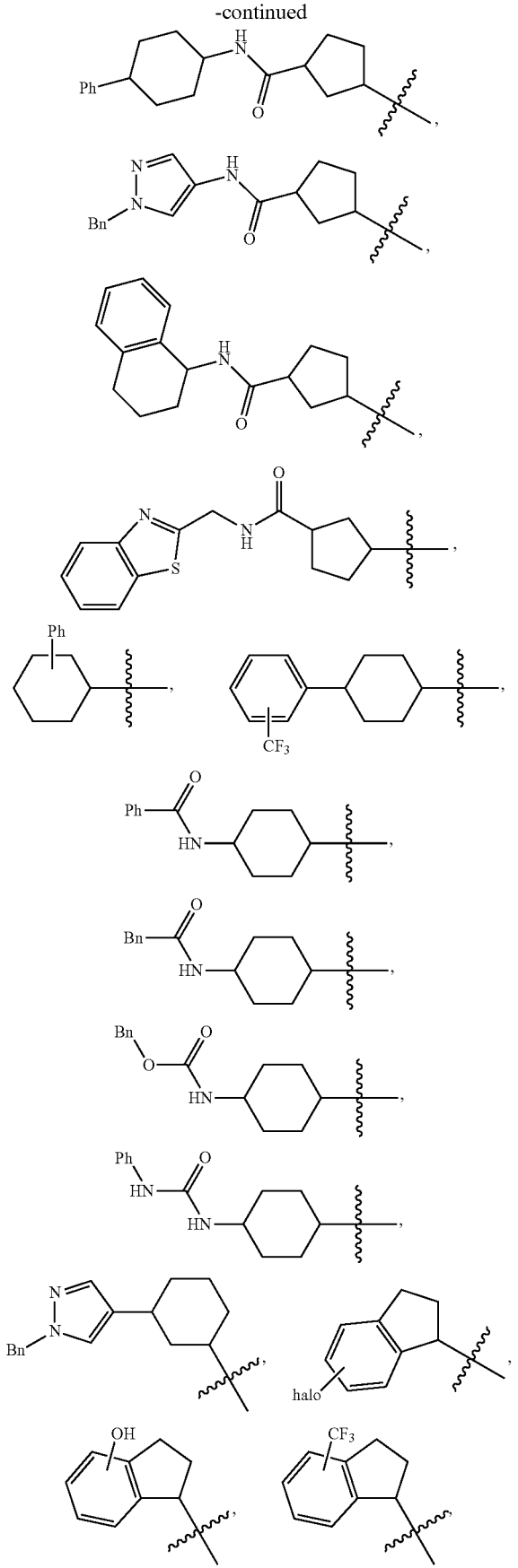
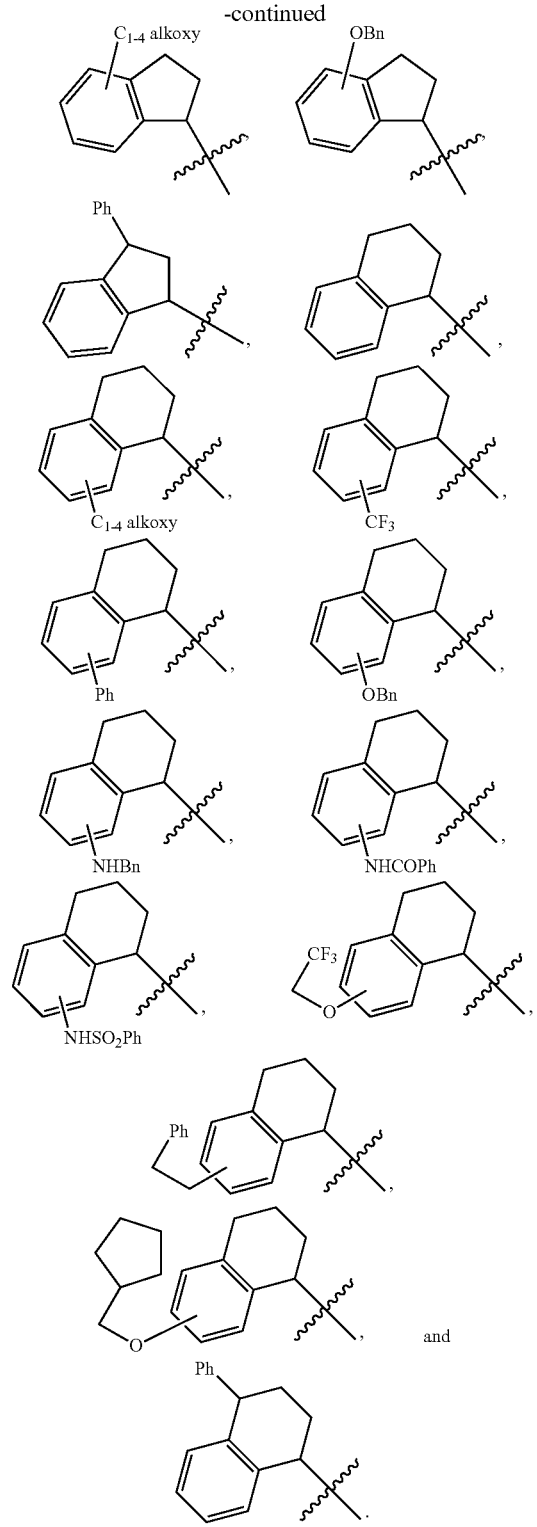
In a twelfth aspect, the present invention provides a compound selected from the exemplified examples or a stereoisomer, a tautomer, a pharmaceutically acceptable salt, or a solvate thereof.
In another aspect, the present invention provides a compound selected from any subset list of compounds within the scope of the twelfth aspect.

In another embodiment, the compounds of the present invention have EL $IC_{50}$ values ≤10 μM.

In another embodiment, the compounds of the present invention have EL $IC_{50}$ values ≤5 μM.

In another embodiment, the compounds of the present invention have EL $IC_{50}$ values ≤1 μM.

In another embodiment, the compounds of the present invention have EL $IC_{50}$ values ≤0.5 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising additional therapeutic agent(s).

In another embodiment, the present invention provides a method for the treatment and/or prophylaxis of dyslipidemias and the sequelae thereof comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of endothelial lipase that can be prevented, modulated, or treated according to the present invention include, but are not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

In one embodiment, the present invention provides a method for the treatment and/or prophylaxis of atherosclerosis, coronary heart disease, cerebrovascular disorders and dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of dyslipidemias and the sequelae thereof.

In another embodiment, the present invention also provides the use of a compound of the present invention for the manufacture of a medicament for the treatment and/or prophylaxis of dyslipidemias and the sequelae thereof.

In another embodiment, the present invention provides a method for the treatment and/or prophylaxis of dyslipidemias and the sequelae thereof, comprising: administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of dyslipidemias and the sequelae thereof.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin or fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, cyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl," "$C_{6-10}$ aryl," or "aromatic residue" may be unsubstituted or substituted with 1 to 5 groups, preferably 1 to 3 groups, selected from —OH, —OCH$_3$, —Cl, —F, —Br, —I, —CN, —NO$_2$, —NH$_2$, —N(CH$_3$)H, —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(═O)CH$_3$, SCH$_3$, S(═O)CH$_3$, S(═O)$_2$CH$_3$, CH$_3$, CH$_2$CH$_3$, CO$_2$H, and CO$_2$CH$_3$.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4 aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH), as shown in the following equation, wherein R=R$^4$—X$_1$-A:

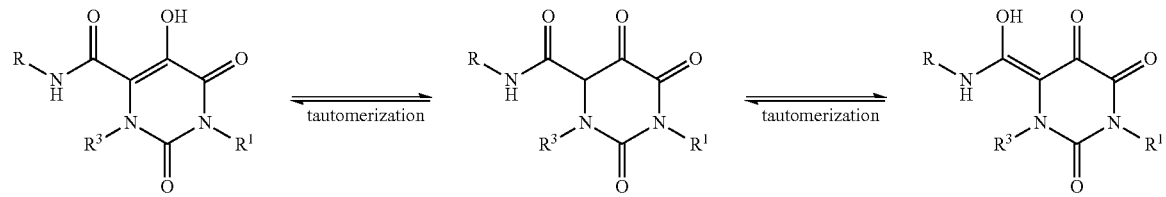

Likewise, an imine (—CH—C≡NHR) group in a molecule may tautomerize to its enamine form (—C≡C— NHR), as shown in the following equation for illustration purpose:

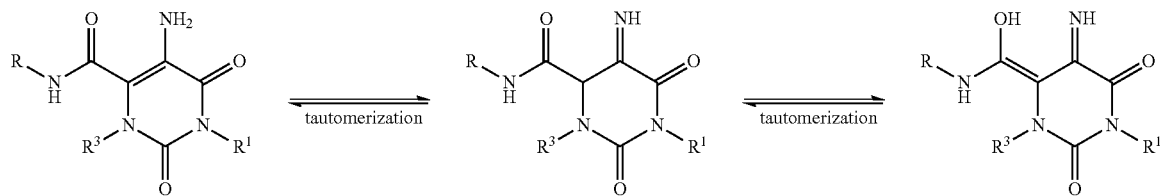

Various tautomerized forms may occur when both $R^1$ and $R^3$ are hydrogen, when $R^1$=H and $R^3$≠H, or when $R^1$≠H and $R^3$=H. For example, some possible tautomerized forms are shown for illustration purpose for the compounds when $R^2$ is OH and both $R^1$ and $R^3$ are hydrogen.

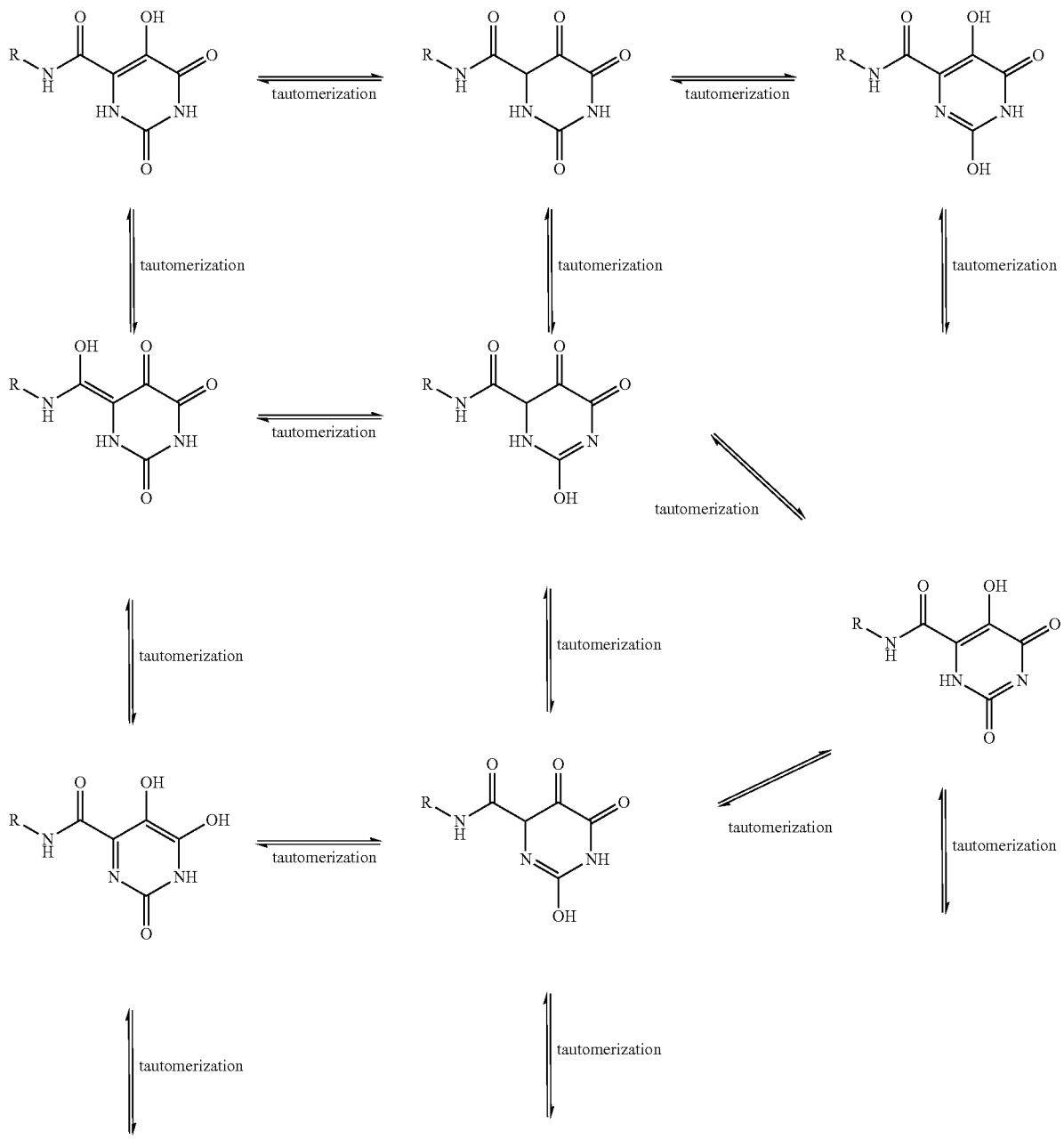

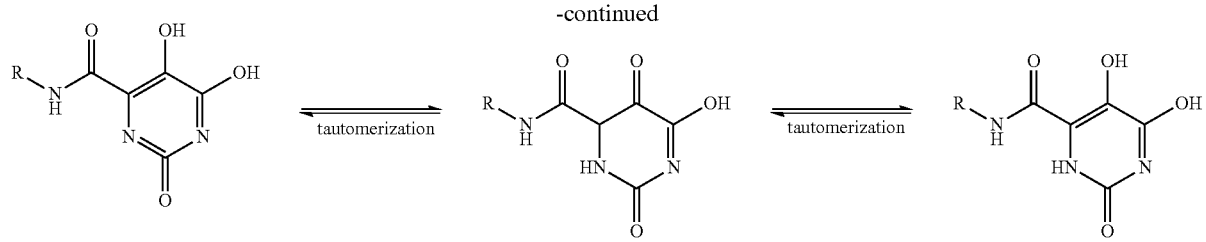
For example, some possible tautomerized forms are shown for illustration purpose for the compounds when $R^2$ is $NH_2$ and both $R^1$ and $R^3$ are hydrogen.
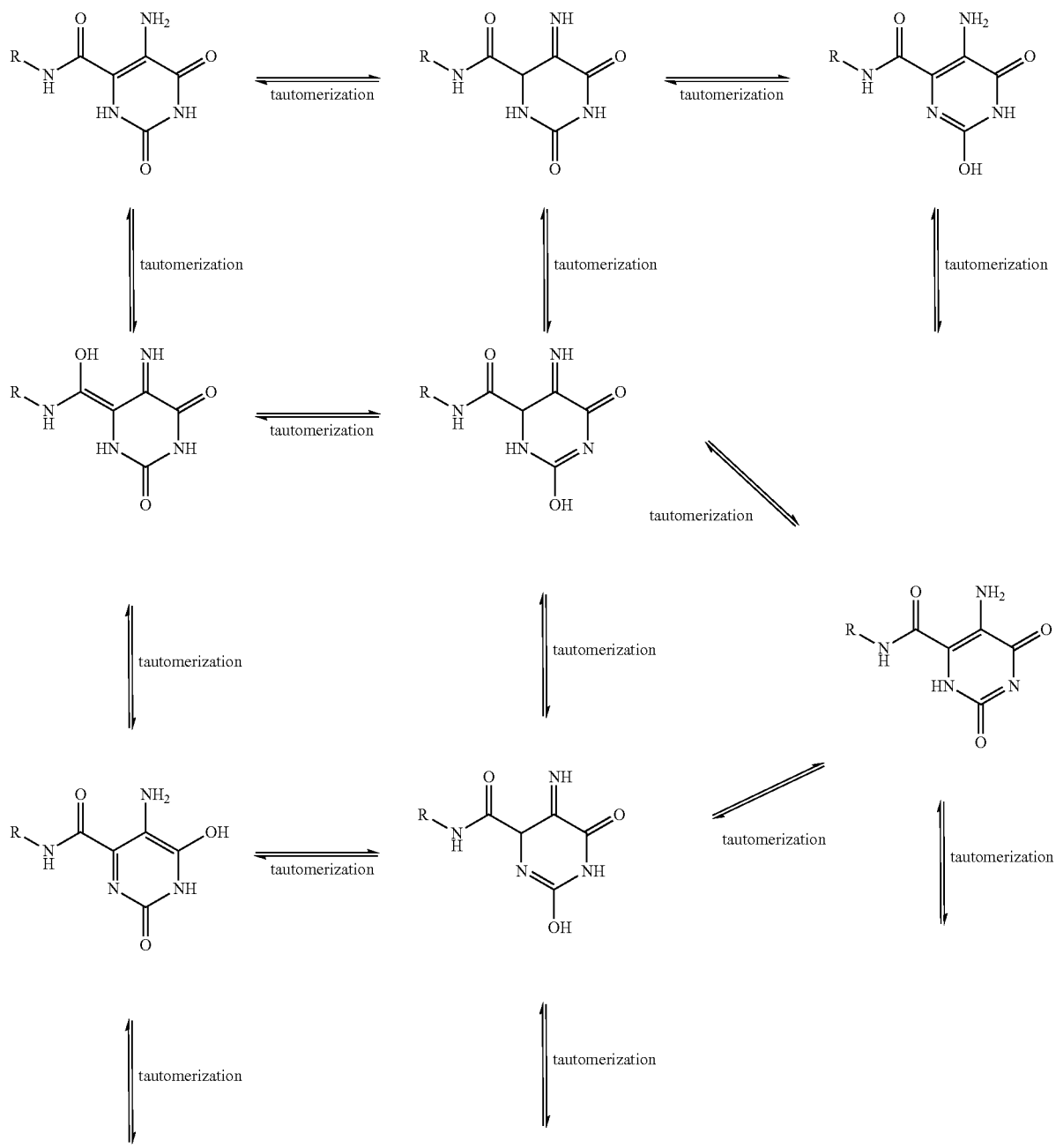

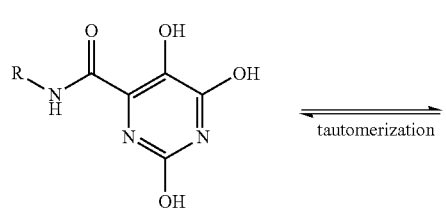 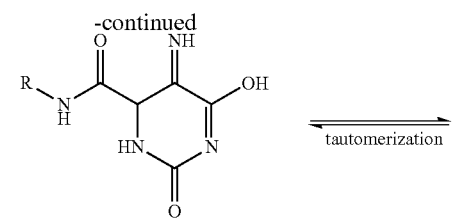

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of Formula (I), Formula (II), or Formula (III) may have prodrug forms. Any compound that will be converted in vivo to provide the bioactive agent (i.e., a compound of Formula (I), Formula (II) or Formula (III)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield Formula (I), Formula (II), Formula (III), or Formula (IV) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I), Formula (II), Formula (III), or Formula (IV) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyloxymethyl or ethoxycarbonyloxymethyl), glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
AlCl$_3$ aluminum chloride
BBr$_3$ boron tribromide
BCl$_3$ boron trichloride
BOP reagent benzotriazol-1-yloxytris(dimethylamino)phosphonium hexafluorophosphate
Cbz carbobenzyloxy
CH$_2$Cl$_2$ dichloromethane
CH$_3$CN or ACN acetonitrile
CDCl$_3$ deutero-chloroform
CDCl$_3$ chloroform
mCPBA or m-CPBA meta-chloroperbenzoic acid
Cs$_2$CO$_3$ cesium carbonate
Cu(OAc)$_2$ copper (II) acetate
DCE 1,2 dichloroethane
DCM dichloromethane
DEA diethylamine
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
EDC N-(3-dimthylaminopropyl)-N'-ethylcarbodiimide
EDTA ethylenediaminetetraacetic acid
Et$_3$N or TEA triethylamine
EtOAc ethyl acetate
Et$_2$O diethyl ether
EtOH ethanol
HCl hydrochloric acid
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NH$_3$ ammonia
NH$_4$Cl ammonium chloride
NH$_4$OH ammonium hydroxide
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_2$ [1,1'-bis(diphenylphosphino)-ferrocene]dichloropalladium(II)
Ph$_3$PCl$_2$ triphenylphosphine dichloride
PG protecting group
PMB p-methoxybenzyl
POCl$_3$ phosphorus oxychloride
i-PrOH or IPA isopropanol
PS polystyrene
PS-Pd(Ph$_3$)$_4$ tetrakis(triphenylphosphine)palladium (0) on polystyrene support
PyBOP (benzotriazol-1-yloxy)tripyrrolidinophosphonium hexafluorophosphate
SiO$_2$ silica oxide
SnCl$_2$ tin(II) chloride
TBAF tetra-n-butylammonium fluoride
TBAI tetra-n-butylammonium iodide
TEA triethylamine
TFA trifluoroacetic acid
THF tetrahydrofuran
TMSCHN$_2$ trimethylsilyldiazomethane
Xantphos 4,5-Bis(diphenylphosphino)-9,9-dimethylxanthene Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Wiley and Sons (1991)).

Schemes 1-21 describe synthetic routes for making intermediates and compounds of the present invention. Schemes 1-3 describe preparation of compounds of the present invention from key intermediates 2, 4 or 5. Schemes 4-6 illustrate several preparations for the hydroxypyrimidinedione esters from commercially available starting materials. Scheme 7 describes the preparation of aminopyrimidine dione ester 17 from commercially available starting materials. Schemes 8, 9 and 21 illustrate the synthesis of N–1 substituted or N–3 substituted hydroxypyrimidinedione analogs in the present invention. Schemes 10 and 11 exemplify the preparations of compounds of the present invention wherein $R^2$ is either an $NH_2$ group or a NHR group. Scheme 12 illustrates the selective N-arylation or N-alkenylation of the NH group at the 3 position of the pyrimidine dione core. Scheme 13 describes the general amine intermediates for the preparation of compounds of the present invention. Schemes 14-19 exemplify the preparation of examples of some of these amine intermediates. Scheme 20 describes the conversion of 5-amino to 5-hydroxy group under acidic conditions.

Scheme 1 describes a preparation of compounds of Formula (I) of the present invention from the key intermediate acid 2. The amine intermediates 3 ($R^4$—$X_1$-A-L-$NH_2$) or their HCl or TFA salts are either commercially available or can be readily prepared from commercially available materials by methods known to one skilled in the art of organic synthesis. Reaction of amine 3 with acid 2 can occur under standard amide coupling conditions at temperatures between 0° C. and 100° C. in a variety of solvents such as DMF or dichloromethane. The protocols include, but are not limited to, formation of the acid chloride of 2 using either oxalyl chloride and catalytic DMF in the presence of a suitable solvent such as dichloromethane or thionyl chloride, followed by addition of amine 3 in the presence of a base such as TEA, DIPEA or N-methylmorpholine, or formation of the active ester of intermediate 2 using EDC, HOBt, PyBOP and a base, such as TEA, DIPEA or N-methylmorpholine, in the presence of amine 3.

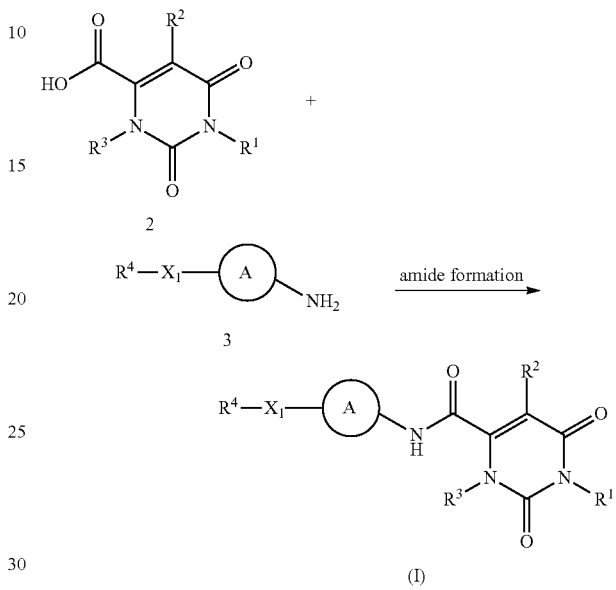

Scheme 1

Alternatively, compounds of Formula (I) of the present invention can be prepared by displacement of the methyl ester 4 with the amines 3 in polar solvents such as ethanol, DMF, or neat at elevated temperatures or under microwave irradiation as shown in Scheme 2.

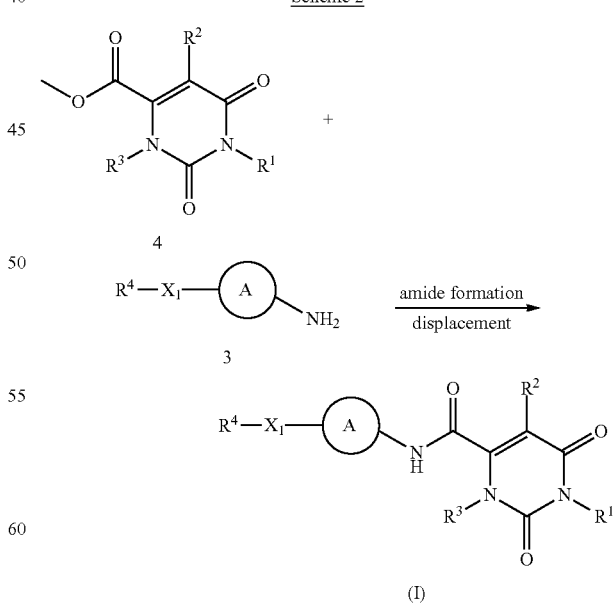

Scheme 2

Compounds of Formula (I) wherein $R^2$=OH can be made by the general methods described in Schemes 1 and 2. Alternatively, $R^2$ can be hydroxyl group protected as shown in intermediate 5 (Scheme 3), wherein the protecting group can be methyl, benzyl, allyl, or silyl-based groups. Amide formation between the ester or acid 5 and the amine 3, followed by deprotection to free the hydroxyl group in intermediate 6 can afford the compounds of Formula (I) (wherein $R^2$=OH). When the protecting group on the hydroxyl group is methyl, ethyl, isopropyl, or benzyl, deprotection can occur with $BBr_3$, $BCl_3$, $BBr_3.SMe$, $BCl_3.SMe$ $AlCl_3$, or $BCl_3$/TBAI at temperatures between −78° C. and refluxing in a solvent such as $CH_2Cl_2$. When heating is required, the reaction can also occur under microwave irradiation to shorten the reaction time. When the protecting group on the hydroxyl group is a benzyl group, debenzylation can also occur by hydrogenation (such as Pd/C, $H_2$) or by heating in TFA under microwave irradiation with or without a solvent, such as $CH_2Cl_2$, or by using $AlCl_3$ in $CH_2Cl_2$ in a variety of solvent such as methanol or EtOAc.

late using lithium bis(trimethylsilyl)amide or a similar base, followed by reacting with 2-methyl-2-thiopseudourea sulfate in one-pot to give the pyrimidinone intermediate 8 (US 2005/0261322A1 and Dreher, S. D. et al., *Tetrahedron Letters*, 45(31):6023-6025 (2004)). The intermediate methylsulfide 8 can then be oxidized to sulfone 9 by using standard oxidation reagents, such as mCPBA, hydrogen peroxide, or OXONE®. The resulting pyrimidinone sulfone 9 is stirred in the presence of an aqueous base, such as NaOH, KOH in solvent, such as dioxanes, to afford intermediate 7.

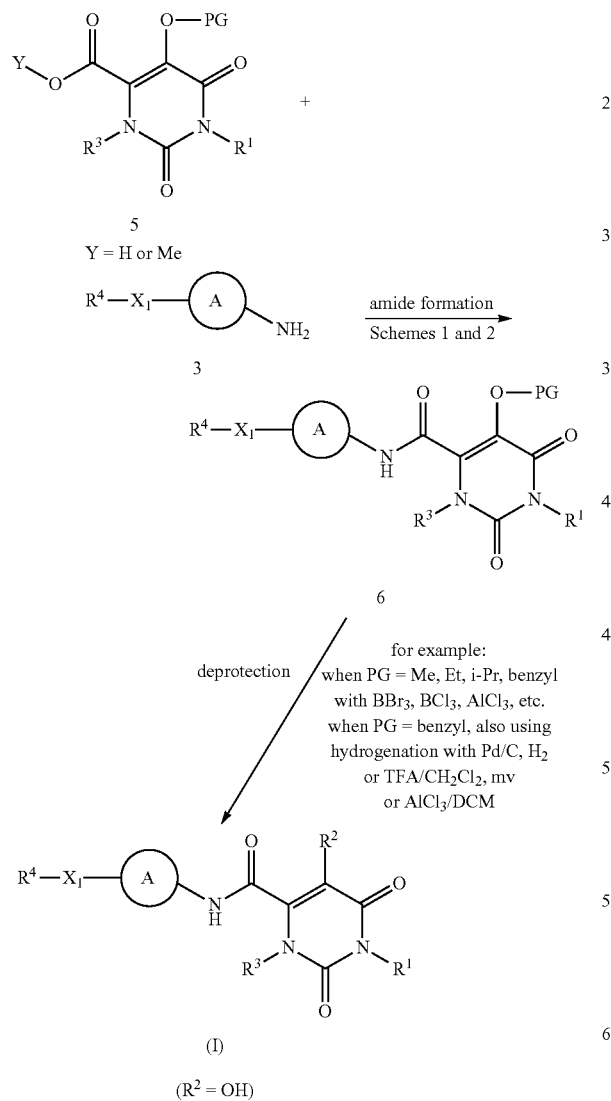

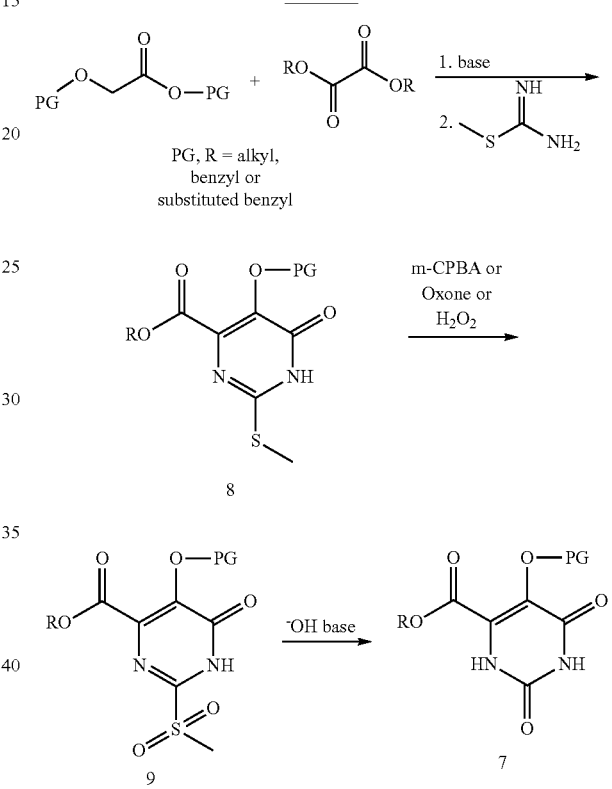

Alternatively, 2-oxo or 2-thioxo-tetrahydropyrimidinones 10 can be synthesized from the condensation of dihydroxyfumarate derivatives 11 with alkyl/aryl carbamimidates or alkyl/aryl carbamimidothioates 12, followed by deprotection to remove the alkyl or aryl groups on intermediate 13 and tautomerization as shown in Scheme 5.

Scheme 4 describes the preparation of 5-hydroxy pyrimidinone carboxylic acid intermediates 7 ($R^2$=OH) by ring construction. An oxalic acid diester is condensed with glyco-

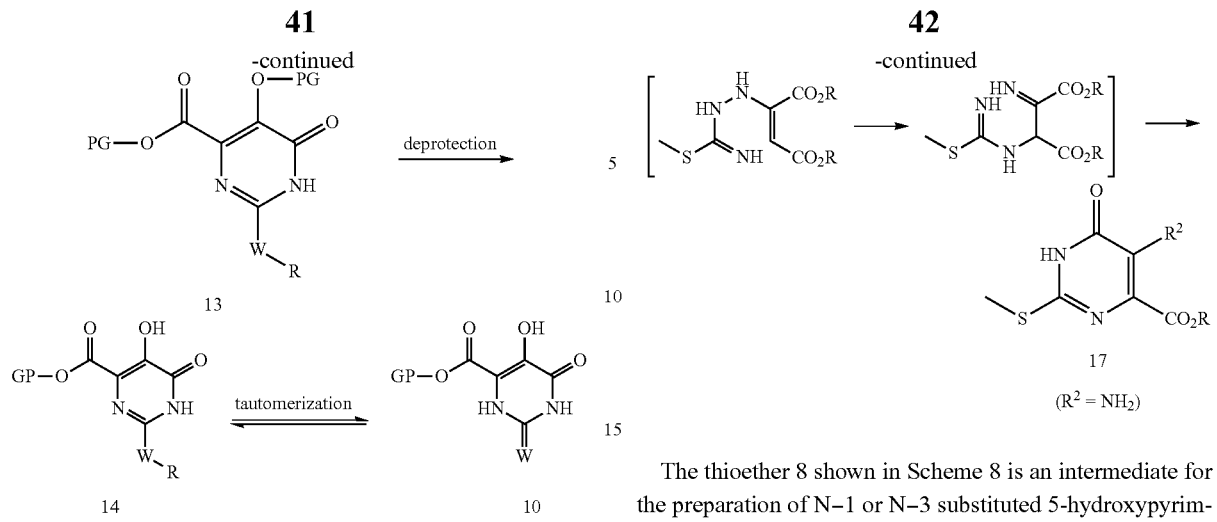

Alternatively, the pyrimidinone 13 can be synthesized as shown in Scheme 6 via Michael addition of N-hydroxy amidine 15 to acetylynic diesters 16, followed by thermal Claisen rearrangement and amide condensation (Culbertson, T. P., *J. Heterocycl. Chem.*, 16:1423-1424 (1979)).

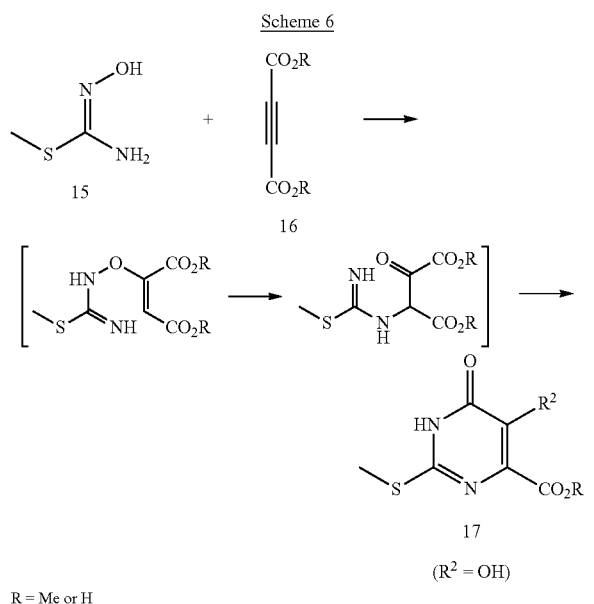

Similarly the corresponding 5-aminopyrimidinone 17 (R=Me or H) can be synthesized as shown in Scheme 7 using an aza-Claisen rearrangement, starting with (E)-methyl carbamohydrazonothioate 18.

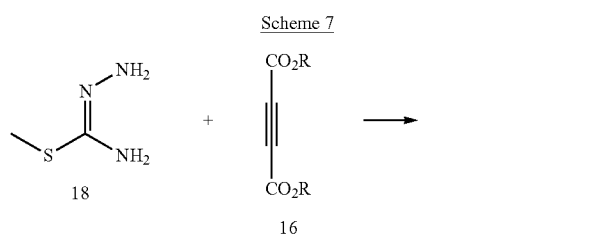

The thioether 8 shown in Scheme 8 is an intermediate for the preparation of N-1 or N-3 substituted 5-hydroxypyrimidinediones of Formula (I) of the present invention. Intermediate 8 can be N-1 alkylated with alkyl halides or benzyl halides (X=Br or Cl) in the presence of an inorganic or organic base (such as $K_2CO_3$, $Cs_2CO_3$, $Et_3N$, NaH, LiH). Alternatively, pyrimidinone 8 can be N-1 arylated using Ullmann-Goldberg reaction (CuI, base heating), or Buchwald modified Ullmann reaction (CuI, ligand, base, heating) or Pd C≡N cross-coupling reaction ($Pd(OAc)_2$, or other Pd(0) catalysts, base, ligand, heating) with aryl halides or copper-mediated cross-coupling reaction ($Cu(OAc)_2$, base (such as $Et_3N$, pyridine) with aryl boronic acids. Alternatively, pyrimidinone 8 can be alkylated by Mitsunobu protocol with a suitable alcohol. For example, alkylation of pyrimidinone 8 with alkyl halides or benzyl halides in the presence of an inorganic or organic base (such as $K_2CO_3$, $Cs_2CO_3$, $Et_3N$, NaH, LiH) can afford both the N-1 alkylated pyrimidinone intermediate 19 and the O-alkylated intermediate 20. Following similar sequences as shown in Scheme 4, the N-1 substituted acid 21 can be obtained. Formation of the amide of intermediate 21 followed by deprotection can provide N-1 substituted compound 22. Alternatively, O-alkylated pyrimidine 20 can be oxidized to the corresponding sulfone then hydrolyzed to pyrimidinone 23. Intermediate 23 can be further alkylated at the N-3 position followed by removal of the $R^1$ and PG groups to give the N-3 substituted ester 25. Hydrolysis of the ester in intermediate 25 followed by amide formation and then deprotection can provide the corresponding N-3 substituted compound 26.

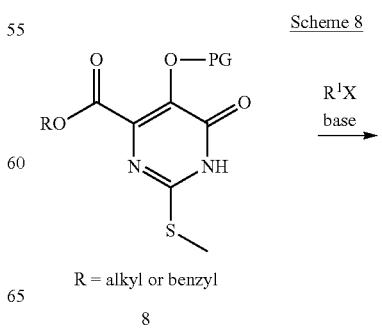

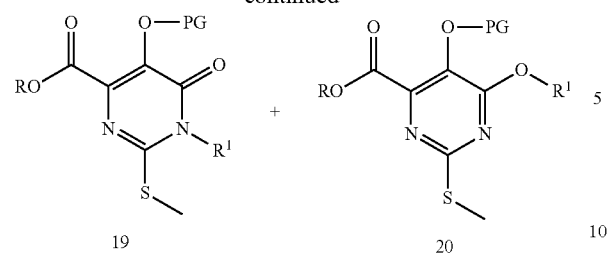
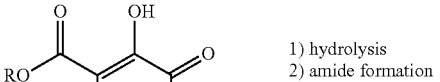
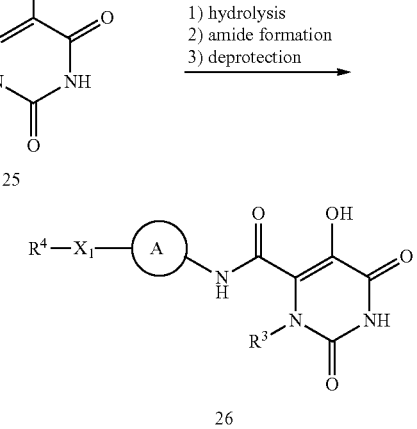
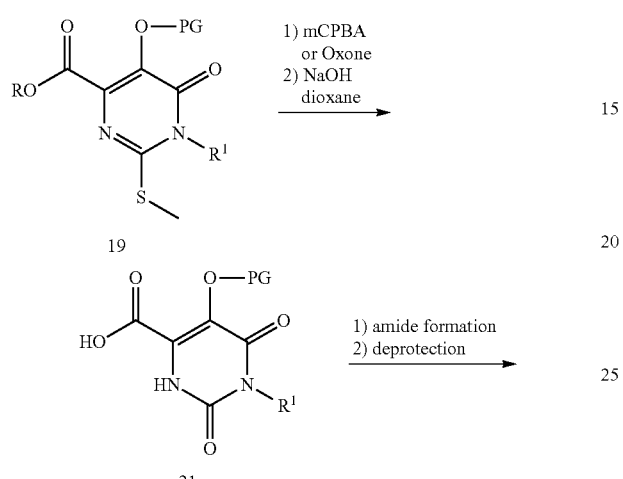
Similarly, the N-1 substituted compound 22 and the N-3 substituted compound 26 can also be prepared using the synthetic route shown in Scheme 9.
Scheme 9
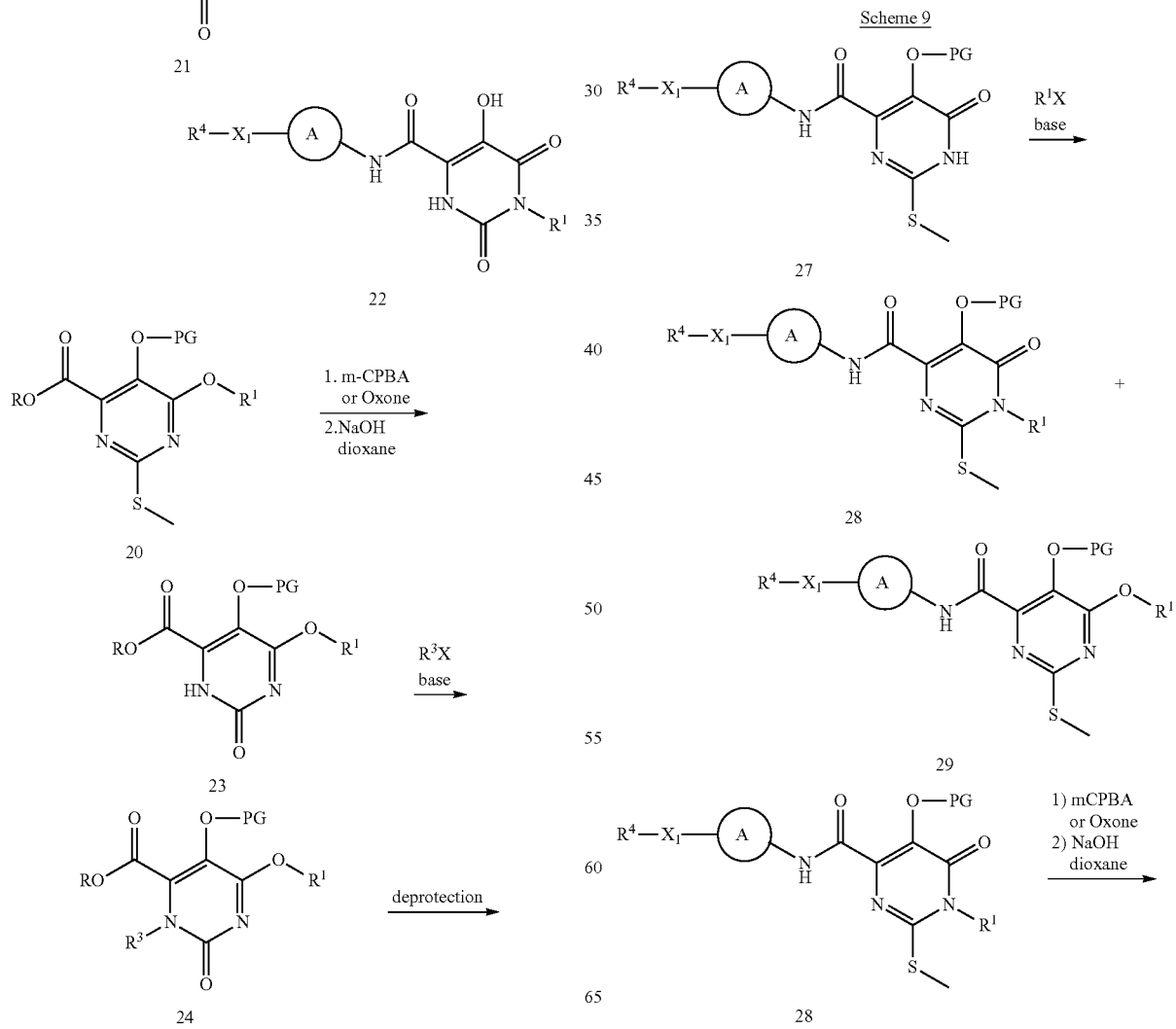

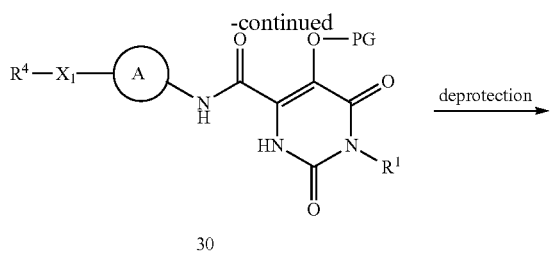

30

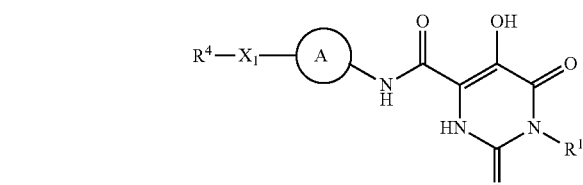

22

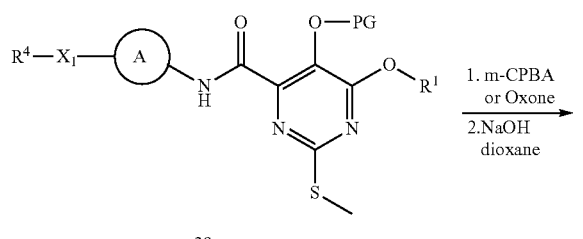

29

1. m-CPBA or Oxone
2. NaOH dioxane

30

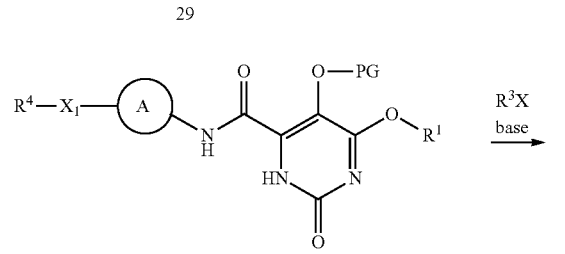

31

R³X base

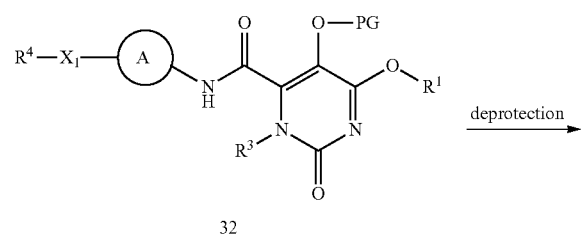

deprotection

32

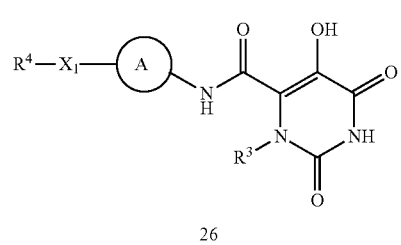

26

Scheme 10 illustrates one preparation of compounds of Formula (I) of the present invention wherein $R^2$ is either a $NH_2$ (Compound 33) or NHR group (Compound 34). The route involves the condensation of 2-oxosuccinic diesters 35 with amidines 12. The resulting 5-H pyrimidinone analog 36 can be oxidized to intermediate 5-H pyrimidine dione 37 which can then be brominated by standard bromination reagents, such as bromine or NBS. The 5-amino group can be introduced by displacement of the bromide 38 with p-methoxybenzyl amine in polar solvents such as ethanol, ethylene glycol, dioxanes, under microwave irradiation, followed by removal of PMB group with TFA. Compounds of Formula (I) of the present invention where in $R^2$ is NHR (Compound 34) can be prepared by displacement of the bromide 38 with amines $NH_2R$ in polar solvents such as ethanol, DMF, ethylene glycol or neat at elevated temperatures or under microwave irradiation as shown in Scheme 10. Alternatively, compound 34 can be prepared from the bromide 38 by using Ullmann coupling reactions (base such as $K_2CO_3$, Cu(I) catalyst such as CuCl or CuI, with or without ligand, solvent such as DMSO, DMF or ethylene glycol) or by using Pd catalyzed Buchwald-Hartwig reaction with suitable amines.

Scheme 10

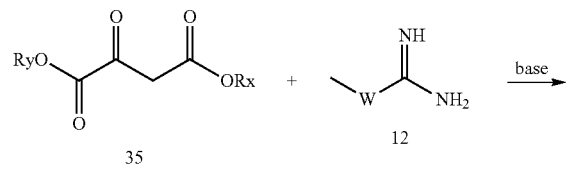

35    12

Rx, Ry = alkyl
W = S or O

1) amide formation
2) when W = O deprotection such as TFA; when W = S
   a) oxidation
   b) hydrolysis

36 bromination or chorination

37

1. PMBA
2. TFA

38

X = Br or Cl

33

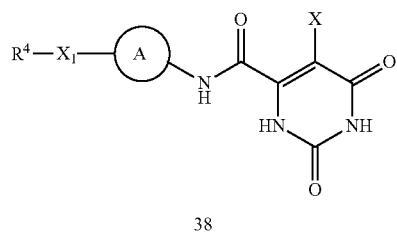

38 displacement
with NH₂R
neat or in polar
solvents such
as ethanol,
ethylene glycol
heating or under
microwave
irradiation or Ullmann
coupling with
NH₂R
using base
such as
K₂CO₃,
CuI or CuCl
DMSO, DMF
or ethylene
glycol,
heating or
under
microwave
irradiation

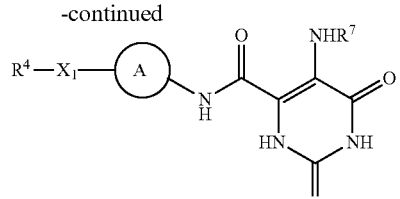

34

Scheme 11 depicts an alternate synthesis of 5-aminopyrimidinone 33 from 2,6-dioxo-1,2,3,6-tetrahydropyrimidine-4-carboxamide 37 by nitrosation with sodium nitrite in acetic acid followed by reduction of the nitroso group in 39 with sodium dithionite. (Elzein, E. et al., *J. Med. Chem.*, 51:2267-2278 (2008); Zhang, Y. J., *Tetrahedron Letters*, 47(5):775-778 (2006)). Alternatively 5-aminopyrimidinone can be synthesized from 2,6-dioxo-1,2,3,6-tetrahydropyrimidine-4-carboxamide by nitration using standard nitration condition followed by reduction of nitro group in 40 to the amino group with reducing agents, such as Fe/HCl, or hydrogenation condition, such as Pd/C/hydrogen (Baraldi, P. G. et al., *J. Med. Chem.*, 45(17):3630-3638 (2002); Zajac, M. A. et al., *Synthetic Communications*, 33(19):3291-3297 (2003)).

Scheme 11

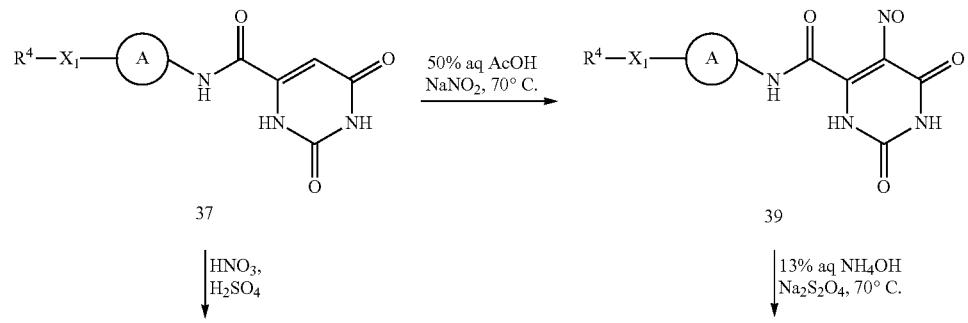

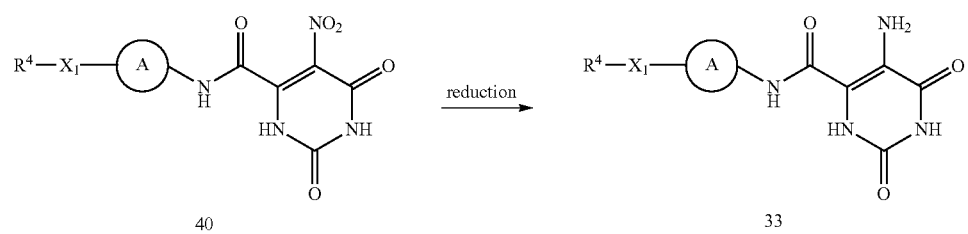

Scheme 12 illustrates one preparation of N-3 substituted analogs 41 from intermediate 42. Regioselective arylation or alkenlation of the N-3 NH group of intermediate 41 can be realized by using modified Chan-Lam Cu-prompted C═N cross-coupling reaction with $R^3$—$B(OH)_2$ and related boron reagents as described in Yang Yue et al., *Eur. J. Org. Chem.*, 5154-5157 (2005); Lan Tao et al., *Helvetica Chimica Acta* 91(6):1008-1014 (2008).

Scheme 12

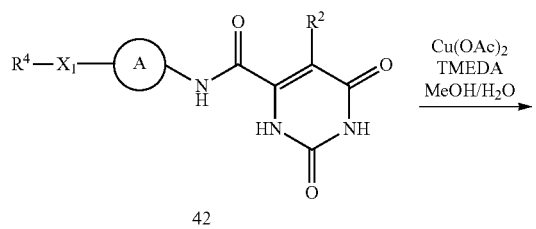

Scheme 13 illustrates examples of amine intermediates $NH_2$-A-$X_1$—$R^4$ (compound 3, Scheme 1) that can be used to prepare compounds of the present invention. These intermediates are either commercially available or can be prepared using methods, examples of which are shown in Schemes 14-19, known to those skilled in the art of organic synthesis.

Scheme 13

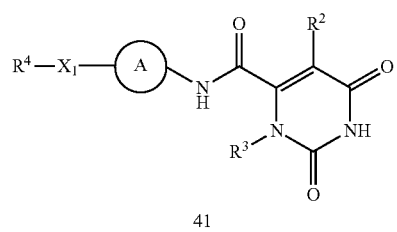

R = H, $C_{1-3}$ alkyl, or $C_{2-3}$ alkenyl

Scheme 14 outlines one possible preparation of amine intermediates 43, wherein L in Formula (I) is a cycloalkyl ring. Reductive amination of the cyclic ketone 44 with diphenylmethanamine followed by separation of the cis- and trans-isomers using silica gel chromatography and subsequent hydrogenation provided the desired cis or trans amines 43. Alternatively, amine 43 can be obtained from reduction of the oxime intermediate 44. Alternatively, the carbonyl in ketone 44 can be reduced to OH followed by activation and displacement with $NaN_3$ and reduction of the corresponding azide 47.

Scheme 14

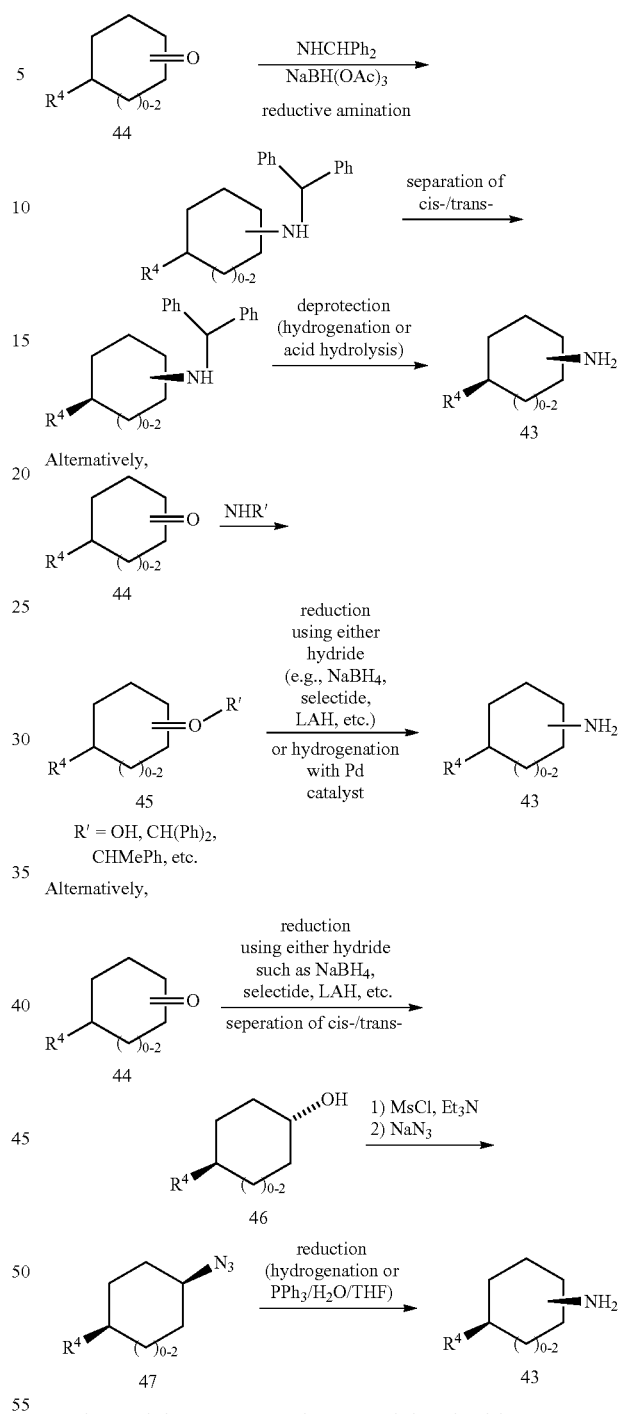

The cyclohexanone starting material 44 is either commercially available or can be readily prepared from commercially available materials by methods known to one skilled in the art of organic synthesis. For example, in Scheme 15, transformation of ketal 48 to vinyl OTf followed by C═C formation of $R^4$—$B(OH)_2$ with the vinyl triflate can afford the corresponding vinyl intermediate 49. Hydrogenation of intermediate 49 followed by deprotection of the ketal group under acidic condition can give the desired ketone 44. Alternatively, treatment of the ketal intermediate 48 with $R^4$—Li (generated by nBuLi with bromo or iodo $R^4$ species) can give the corresponding alcohol 50, which can be eliminated to give the vinyl intermediate and reduced and the acetal hydrolyzed to provide cyclohexane 44. Alternatively, alcohol 50 can be directly reduced with triethylsilane followed by deprotection of the ketal group of intermediate 51 under acidic condition can provide the desired ketone intermediate 44.

Scheme 15

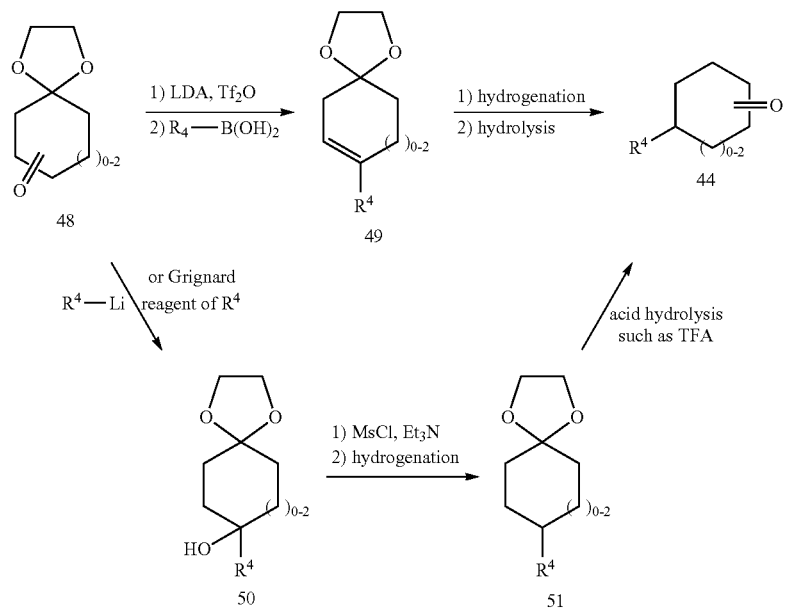

Scheme 16 illustrates bicyclic amines 52A and 52B ($R^4$—$X_1$-A-$NH_2$) wherein $R^4$—$X_1$-A is an indane or a tetralin or a 6,7,8,9-tetrahydro-5H-benzo[7]annulene ring. The ketone starting material 53 is either commercially available or can be readily prepared from commercially available materials by methods known to one skilled in the art of organic synthesis. For example, the ketone 53 can be prepared by Friedel-Crafts reaction of acid 54 or by intramolecular cyclization of halide 55 using nBuLi. The individual diastereomers can be obtained by using Ellman's t-butylsulfinamide methodology (Ellman, J. A., *J. Org. Chem.*, 72(2):626-629 (2007): reduction of sulfinamide 56 with either $NaBH_4$ or L-selectride at low temperature (for examples, −40 to −50° C.) in THF to give the diastereomers 57A and 57B after silica gel column chromatography or SFC separation. Intermediates 57A and 57B were hydrolyzed to give the desired enantiopure amines 52A and 52B, respectively.

Scheme 16

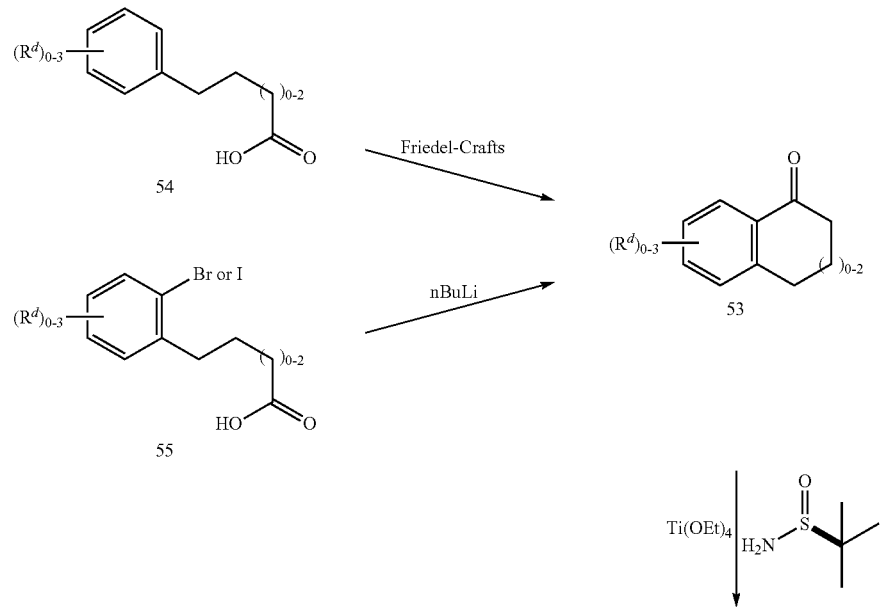

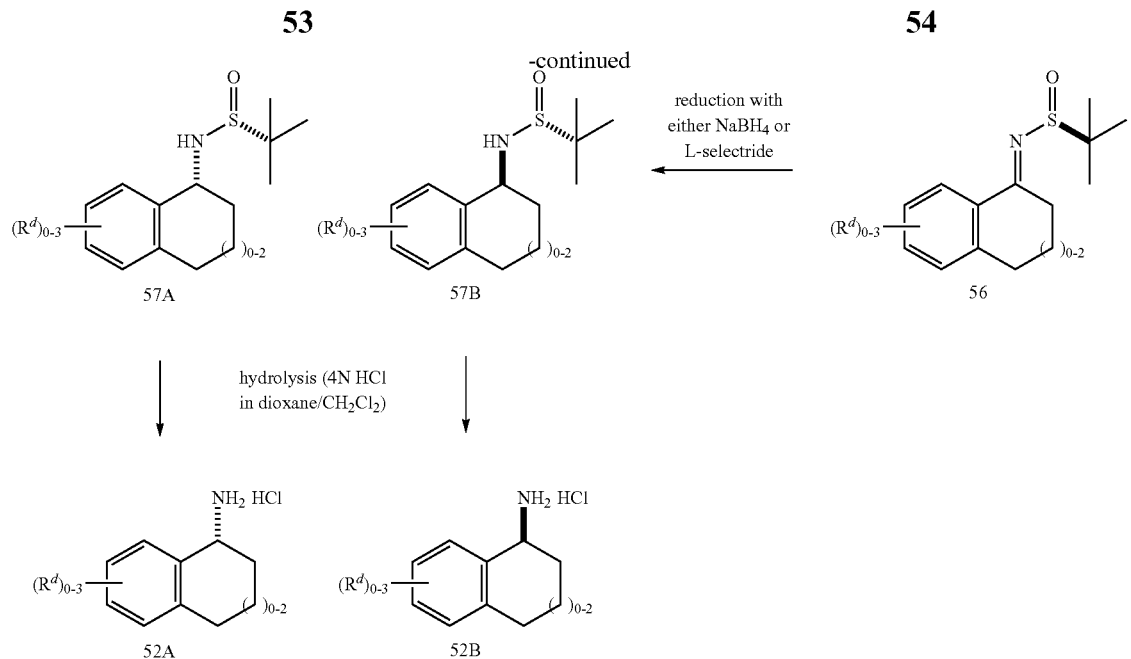

The 1,3-cycloalkylamines 58, such as 1,3-cyclohexylamines or 1,3-cyclopentylamines, can be readily prepared by using methods known to one skilled in the art of organic synthesis (Scheme 17). For example, transformation of diketone 59 to the corresponding vinyl halide or vinyl triflate intermediate 60, followed by C≡C bond formation with $R^4$—$B(OH)_2$ in the presence of a palladium source, such as $Pd(OAc)_2$, $Pd_2(dba)_3$, $Pd(PPh_3)_4$, and a base such as $Na_2CO_3$, $K_3PO_4$, in solvents such as toluene and water, can afford intermediate 61. Reductive amination of 61 followed by hydrogenation can give the racemic 1,3-cycloalkylamines 58. Alternatively, treatment of the ketal intermediate 62 with $R^4$—Li (generated by nBuLi with bromo or iodo $R^4$ species) can give the corresponding alcohol, which can be eliminated to give the vinyl intermediate 61.

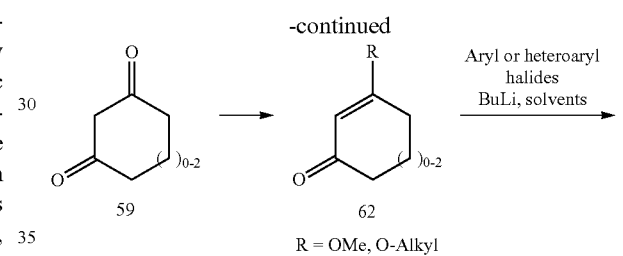

Scheme 17

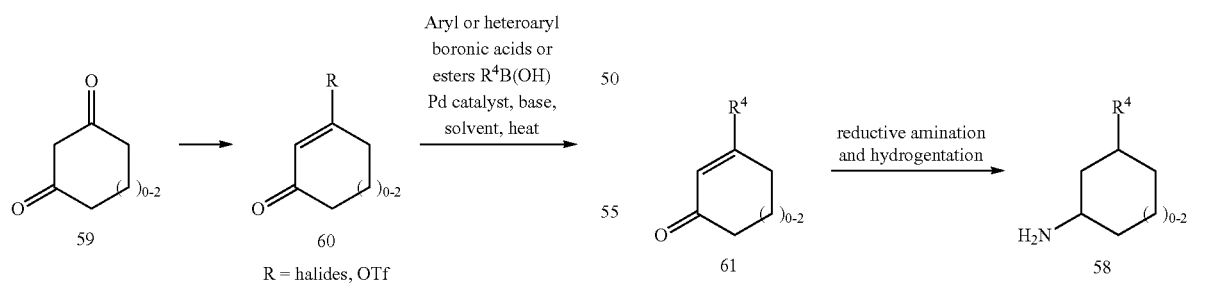

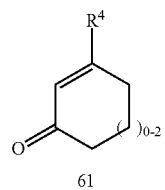

The 1,3-cycloalkylnone can be synthesized directly from 1,4-Michael addition of α,β-unsaturated carbonyl compounds with organoborons (Scheme 18). Arylboronic acids react with 64 in the presence of a base and a catalytic amount of a palladium(0) complex with chloroform, affording the corresponding addition products 63 in good yield (Yamamoto et al., *J. Organometallic Chemistry*, 694:1325-1332 (2009)).

Scheme 18

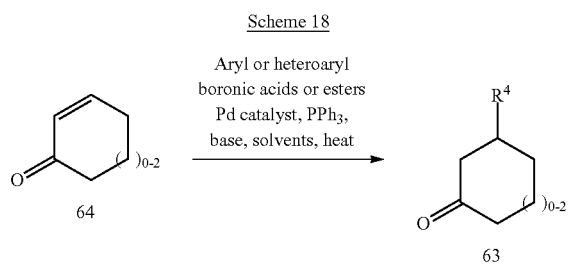

Asymmetric Michael addition of arylboronic acids to α,β-unsaturated carbonyl compounds utilizing in situ generated chiral rhodium-binap-based catalyst can give enantiopure cycloketones 65 in high levels of enantioselectivity (Kirill Lukin, *J. Org. Chem.*, 74:929-931 (2009)). The individual diastereomers can be obtained by using Ellman's t-butylsulfinamide methodology, followed by silica gel column chromatography or SFC separation, as described in Schemes 16 and 17. Alternatively, the separation of optical isomers of 1,3-alkylanols can be achieved by a lipase-catalyzed transesterification as indicated in Scheme 19 (Makoto Shimizu et al., Tetrahedron, 8729-8736 (2002); Fensholdt, J. et al., WO 2009/065406). The enantiopure alcohols then can be transformed to the corresponding amines by using the methods described in Scheme 14.

Scheme 20 illustrates that 5-aminoorotic amides can be transformed to 5-hydroxyorotic amides under acidic condition (such as 1 N HCl) with compatible solvents, such as dioxane, ethanol, etc. at reflux, and with or without a catalyst, such as $TiCl_4$.

Scheme 20

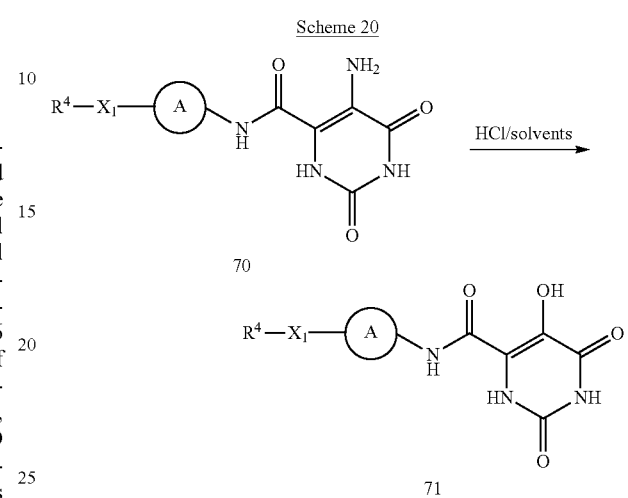

Scheme 19

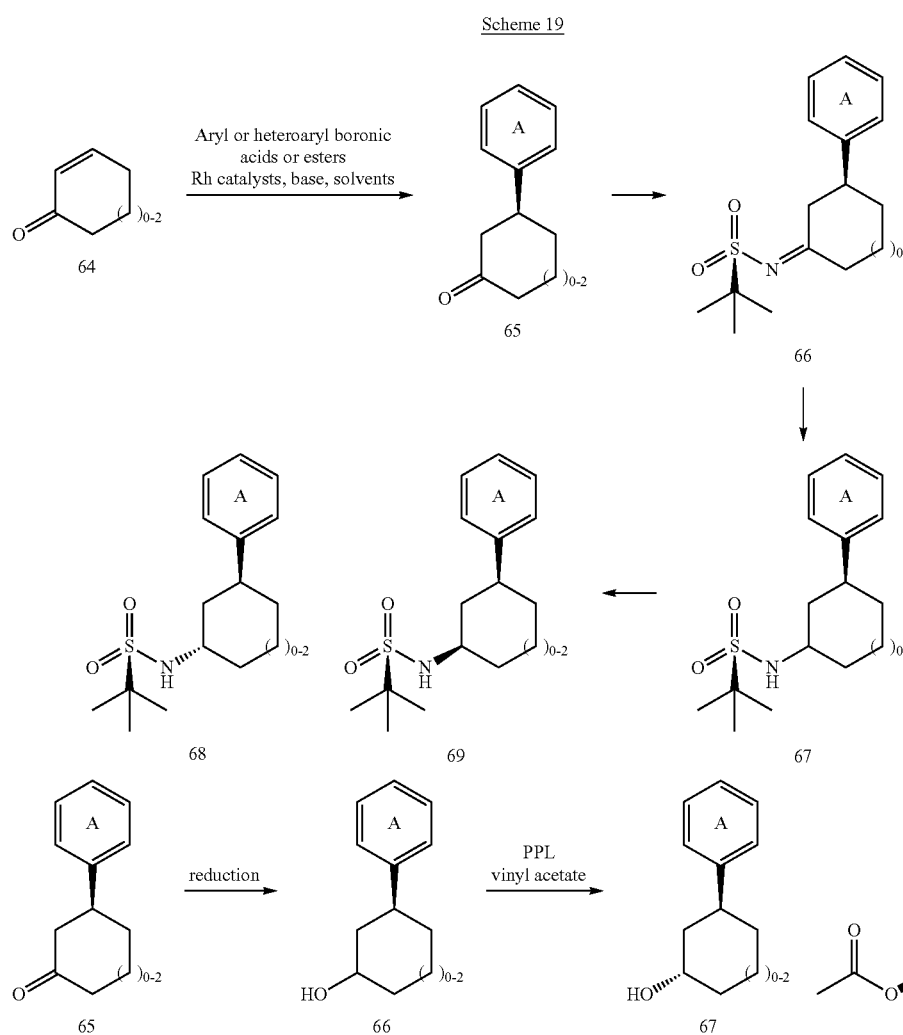

Scheme 21 describes the preparation of N-1 substituted 5-hydroxypyrimidinediones of Formula (I) of the present invention. Compound 13 (when W=O) can be N-alkylated and O-alkylated according to methods similar to Scheme 8. When NaH or LiH is used as the base with aprotic solvents, O-alkylation can be reduced to afford more favorable N-alkylated products (Gambacorta, A. et al., *Tetrahedron*, 62:6848-6854 (2006)). After removal of the protective group in compound, the resulting carboxylic acid 73 was then reacted with amines under standard amide coupling conditions to give 74, which is deprotected to give the N-1 alkylated 75. Alternatively, compound 13 can be selectively deprotected to give carboxylic acid 76. Amide formation of 76 with amines followed by N-1 alkylation and then deprotection can provide the N-1 substituted compound 75.

Products were analyzed by reverse phase analytical HPLC carried out on a Shimadzu Analytical HPLC system running Discovery VP software using Method A: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: PHENOMENEX® Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm) or Method C: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% $H_3PO_4$; B: 10% water, 89.9% methanol, 0.1% $H_3PO_4$, UV

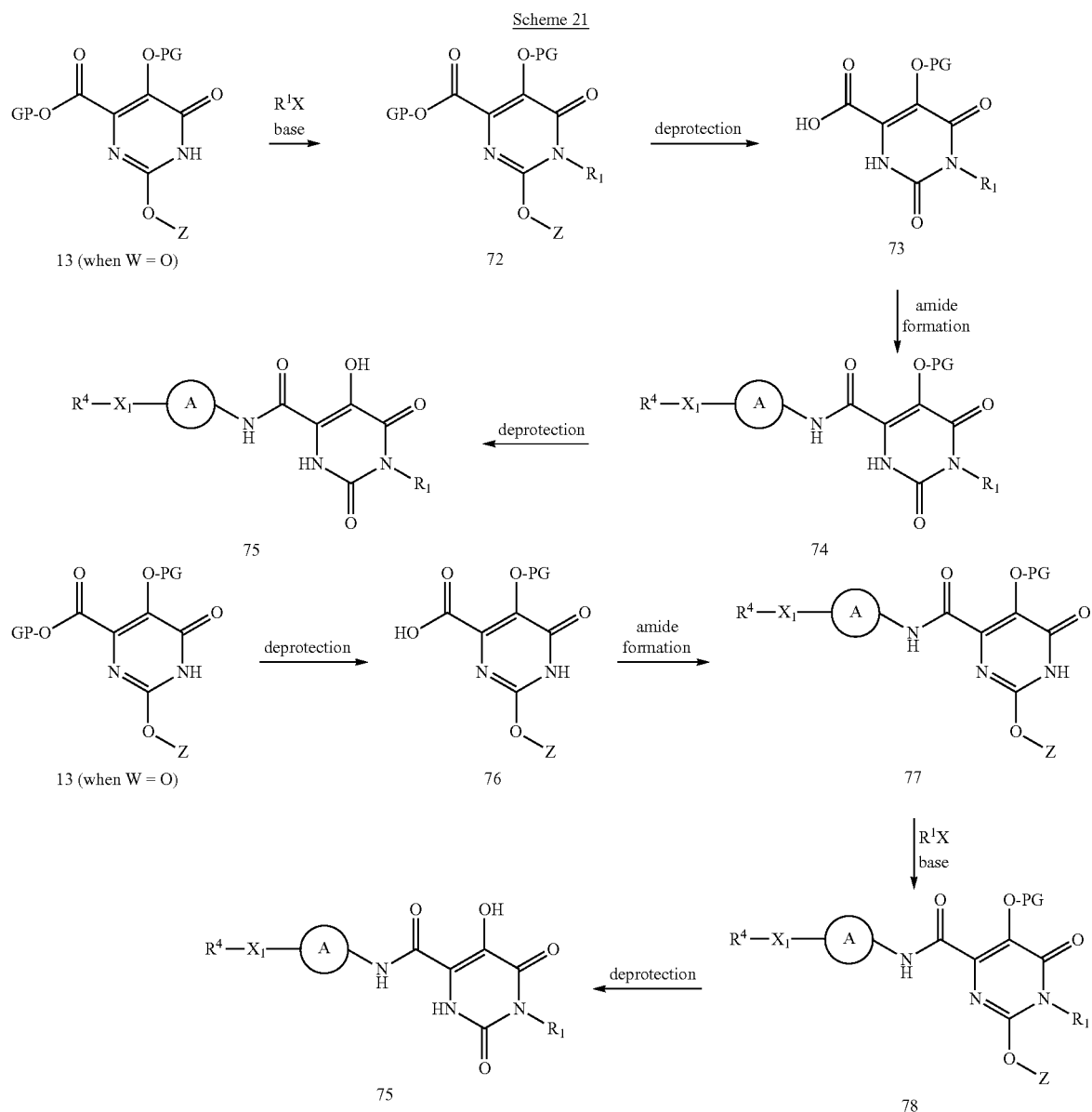

Scheme 21

General Methods

The following methods were used in the exemplified Examples, except where noted otherwise.

220 nm) or Method D: PHENOMENEX® Luna C18 column (4.6×50 mm or 4.6×75 mm) eluted at 4 mL/min with a 2, 4 or 8 min gradient from 100% A to 100% B (A: 10% methanol, 89.9% water, 0.1% NH$_4$OAc; B: 10% water, 89.9% methanol, 0.1% NH$_4$OAc, UV 220 nm).

Purification of intermediates and final products was carried out via either normal or reverse phase chromatography. Normal phase chromatography was carried out using prepacked SiO$_2$ cartridges eluted with gradients of hexanes and ethyl acetate or methylene chloride and methanol. Reverse phase preparative HPLC was carried out using a Shimadzu Preparative HPLC system running Discovery VP software using Method A: YMC Sunfire 5 m C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: PHENOMENEX® Luna Axia 5 m C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: PHENOMENEX® Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: PHENOMENEX® Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm).

Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm).

LCMS chromatograms were obtained on a Shimadzu HPLC system running Discovery VP software, coupled with a Waters ZQ mass spectrometer running MassLynx version 3.5 software and using the following respective methods. Unless specified otherwise, for each method, the LC column was maintained at room temperature and UV detection was set to 220 nm.

Method A: A linear gradient using solvent A (10% methanol, 90% water, 0.1% of TFA) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method B: A linear gradient using solvent A (10% methanol, 90% water, 0.1% of TFA) and solvent B (90% methanol, 10% water, 0.1% of TFA); 0-100% of solvent B over 2 min and then 100% of solvent B over 1 min. Column: PHENOMENEX® Luna 5 μm C18 (2.0×30 mm). Flow rate was 1 mL/min.

Method C: A linear gradient using solvent A (10% acetonitrile, 90% water, 10 mM NH$_4$OAc) and solvent B (90% acetonitrile, 10% water, 10 mM NH$_4$OAc); 0-100% of solvent B over 4 min and then 100% of solvent B over 1 min. Column: PHENOMENEX® Luna 5 μm C18 (4.5×50 mm). Flow rate was 4 mL/min.

Method D: A linear gradient using solvent A (10% acetonitrile, 90% water, 0.05% of TFA) and solvent B (90% acetonitrile, 10% water, 0.05% of TFA); 0-100% of solvent B over 2 min and then 100% of solvent B over 1 min. Column: Luna 5 m C18 (4.5×30 mm). Flow rate was 1 mL/min.

Method E: A linear gradient using solvent A (10% MeOH, 90% water, 10 mM NH$_4$OAc) and solvent B (90% MeOH, 10% water, 10 mM NH$_4$OAc); 0-100% of solvent B over 4 min and then 100% of solvent B over 1 min. Column: PHENOMENEX® Luna 5 μm C18 (4.5×50 mm). Flow rate was 4 mL/min.

Method F: A linear gradient using solvent A (10 mM ammonium acetate, 95% water, 5% ACN) and solvent B (10 mM ammonium acetate, 95% ACN, 5% water); 0-100% of solvent B over 4 min and then 100% of solvent B over 1 min. Column: Mac-Mod Halo (C18, 4.6×50 mm). Flow rate was 4 mL/min.

Method G: A linear gradient using solvent A (10% acetonitrile, 90% water, 0.1% TFA) and solvent B (90% acetonitrile, 10% water, 0.1% TFA); 0-100% of solvent B over 4 min and then 100% of solvent B over 1 min. Column: PHENOMENEX® Luna 3 μm C18 (2.0×50 mm). Flow rate was 4 mL/min.

Method H: A linear gradient using solvent A (10% methanol, 90% water, 0.1% of formic acid) and solvent B (90% methanol, 10% water, 0.1% of formic acid); 0-100% of solvent B over 2 min and then 100% of solvent B over 1 min. Column: PHENOMENEX® Luna 3 μm C18 (2.0×30 mm). Flow rate was 1 mL/min.

Method I: A linear gradient using solvent A (10% MeOH, 90% water, 10 mM NH$_4$OAc) and solvent B (90% MeOH, 10% water, 10 mM NH$_4$OAc); 0-100% of solvent B over 2 min and then 100% of solvent B over 1 min. Column: PHENOMENEX® Luna 3 μm C18 (2.0×30 mm). Flow rate was 1 mL/min.

Method J: A linear gradient using solvent A (10% methanol, 90% water, 0.1% of formic acid) and solvent B (90% methanol, 10% water, 0.1% of TFA); 0-100% of solvent B over 4 min and then 100% of solvent B over 1 min. Column: PHENOMENEX® Luna 5 μm C18 (4.5×50 mm). Flow rate was 4 mL/min.

Method K: A linear gradient using solvent A (10 mM ammonium acetate, 95% water, 5% ACN) and solvent B (10 mM ammonium acetate, 95% ACN, 5% water); 0-100% of solvent B over 5.5 min and then 100% of solvent B over 1.5 min. Column: SUPELCO® Ascentis 4.6×50 mm 2.7 μm C18. Flow rate was 4 mL/min.

Method L: A linear gradient using solvent A (5% methanol, 95% water, 0.05% of TFA) and solvent B (95% methanol, 5% water, 0.05% of TFA); 0-100% of solvent B over 4 min and then 100% of solvent B over 1 min. Column: Waters XBridge C18 (4.6×50 mm, 5 μm). Flow rate was 4 mL/min. The LC column was maintained at 35° C.

Method M: A linear gradient using of Solvent A (0.05% TFA, 100% water) and Solvent B (0.05% TFA, 100% ACN); 2 to 98% B over 1 min, with 0.5 min hold time at 98% B. Column: Waters BEH C18 (2.1×50 mm). Flow rate: 0.8 mL/min.

Preparative HPLC methods employed in the purification of products:

Method A: Linear gradient of 0 to 100% B over 10 min, with 5 min hold time at 100% B; Shimadzu LC-8A binary pumps Waters ZQ mass spectrometer using Waters Masslynx 4.0 SP4 MS software UV visualization at 220 nm Column: Waters XBridge 19×150 mm 5 m C18

Flow rate: 20 ml/min

Peak collection triggered by mass spectrometry

Solvent A: 0.1% TFA, 10% ACN, 90% water

Solvent B: 0.1% TFA, 90% ACN, 10% water

In addition, the following orthogonal HPLC conditions were used to check the purity of the compounds:

Method A: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Sunfire C18 3.5 µm (4.6×150 mm). Flow rate was 2 ml/min. and UV detection was set to 220 nm. The LC column was maintained at room temperature.

Method B: A linear gradient using solvent A (5% acetonitrile, 95% water, 0.05% TFA) and solvent B (95% acetonitrile, 5% water, 0.05% TFA); 10-100% of solvent B over 10 min and then 100% of solvent B over 5 min. Column: Xbridge Phenyl 3.5m (4.6×150 mm). Flow rate was 2 ml/min. and UV detection was set to 220 nm. The LC column was maintained at room temperature.

NMR Employed in Characterization of Examples $^1$H NMR spectra were obtained with Bruker or JEOL Fourier transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Biology

The endothelium occupies a pivotal position at the interface between the circulating humoral and cellular elements of the blood, and the solid tissues which constitute the various organs. In this unique position, endothelial cells regulate a large number of critical processes, including leukocyte adherence and transit through the blood vessel wall, local control of blood vessel tone, modulation of the immune response, the balance between thrombosis and thrombolysis, and new blood vessel development. Thus, endothelial cell dysfunction has been postulated as a central feature of vascular diseases such as hypertension and atherosclerosis. (WO 1999/032611 and references cited therein, e.g., Folkman, J. et al., *Science*, 235:442-447 (1987); Yanagisawa, M. et al., *Nature*, 332(6163):411-415 (1988); Folkman, J. et al., *J. Biol. Chem.*, 267(16):10931-10934 (1992); Janssens, S. P. et al., *J. Biol. Chem.*, 267(21):14519-14522 (1992); Lamas, S. et al., *Proc. Natl. Acad. Sci. U.S.A.*, 89(14):6348-6352 (1992); Luscher, T. F. et al., *Hypertension*, 19(2):117-130 (1992); Williams et al., *Am. Rev. Respir. Dis.*, 146:S45-S50 (1992); and Bevilacqua, M. P. et al., *J. Clin. Invest.*, 91(2):379-387 (1993)).

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated low density lipoprotein-cholesterol (LDL-C) may be the most recognized form of dyslipidemia, it is by no means the only significant lipid associated contributor to CHD. Low high density lipoprotein-cholesterol (HDL-C) is also a known risk factor for CHD (Gordon, D. J. et al., *Circulation*, 79(1): 8-15 (1989)).

High LDL-C and triglyceride levels are positively correlated, while high levels of HDL-C are negatively correlated with the risk for developing cardiovascular diseases. Thus, dyslipidemia is not a unitary risk profile for CHD but may be comprised of one or more, preferably one to three, lipid aberrations.

At least 50% of the variation in HDL cholesterol levels is genetically determined. The phenotype of elevated HDL cholesterol is often dominantly inherited, but homozygous deficiency of HL or of the cholesteryl ester transfer protein (CETP), which result in elevated HDL cholesterol, are recessive conditions. Recently, several genetic variations in the human endothelial lipase gene have been identified, six of which potentially produce functional variants of the protein, and the frequencies of these variants were found to be associated with elevated levels of HDL cholesterol in human subjects (deLemos, A. S. et al., *Circulation*, 106(11):1321-1326 (2002)). Notably, the endothelial lipase-mediated binding and uptake of HDL particles and the selective uptake of HDL-derived cholesterol esters have been reported to be independent of its enzymatic lipolytic activity (Strauss, J. G. et al., *Biochem. J.*, 368:69-79 (2002)).

Because of the beneficial effects widely associated with elevated HDL levels, an agent which inhibits EL activity in humans, by virtue of its HDL increasing ability, are expected to be useful for the treatment, prevention, the arrestment and/or regression of atherosclerosis, coronary heart disease, cerebrovascular disorders etc., especially those (but not restricted thereto) which are characterized by one or more of the following factors: (a) high plasma triglyceride concentrations, high postprandial plasma triglyceride concentrations; (b) low HDL cholesterol concentration; (c) low apoA lipoprotein concentrations; (d) high LDL cholesterol concentrations; (e) small dense LDL cholesterol particles; and (f) high apoB lipoprotein concentrations.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-atherosclerosis agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index.

As used herein, the term "patient" encompasses all mammalian species.

As used herein, the term "subject" refers to any human or non-human organism that could potentially benefit from treatment with an anti-atherosclerosis agent, e.g., an endothelial lipase inhibitor. Exemplary subjects include human beings of any age with risk factors for atherosclerosis and its associated coronary artery disease. Common risk factors include, but are not limited to, age, sex, weight, and family history.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit endothelial lipase and/or to prevent or treat the disorders listed herein. When applied to a combination, the term refers to combined amounts of the active ingredients that result in the preventive or therapeutic effect, whether administered in combination, serially, or simultaneously.

Biological Activity

Endothelial lipase activity was measured using a fluorescent substrate, A10070, (Invitrogen, CA) doped into an artificial vesicle containing DMPG (Avanti Polar Lipids) as the excipient. Vesicles were prepared by combining 285 µL of 1 mM DMPG in a 1:1 mixture of MeOH and CHCl$_3$ with 15 µL of 1 mM A10070 in a 1:1 mixture of MeOH and CHCl$_3$. The mixture was dried under nitrogen and resuspended in 150 µL of 50 mM HEPES pH 8.0 buffer containing 100 mM NaCl and 0.2 mM EDTA. The sample was allowed to sit at rt for 15 min and then was sonicated 3×4 mins on ice with a Branson Sonicator using duty cycle 1. This preparation provides vesicles with a mole fraction of 0.05 for the FRET substrate.

The enzymatic assay was measured using white, opaque 96-well half area plates. Each well contained 60 µL of assay buffer (50 mM HEPES pH 8.0, 50 mM NaCl and 1 mM CaCl$_2$) and 2 ul of a DMSO solution containing compound of interest. Conditioned media obtained from HT-1080 cells, which were transformed by RAGE technology (Athersys) to overexpress endogenous EL, was added and the reaction was allowed to incubate for 20 min at 37° C. with gentle agitation. The reaction was started by the addition of 20 µL of a 1:4 dilution of vesicles. The final total reaction volume was 100 µL. The reaction rates were measured on a Gemini plate reader with an excitation wavelength of 488 nm and an emission of 530 nm. Readings were taken every 20 seconds for 10 min with agitation between each reading. The slope of the linear portion of the readout was used to calculate the rate of the reaction.

The exemplified examples disclosed in the present invention were tested in the EL assay described above and found having EL inhibitory activity. A range of EL IC$_{50}$ values of ≤10 µM (10000 nM) was observed for Examples 1-14, 16-71 and 73-299. The EL IC$_{50}$ values measured for the following examples are listed in Table 1.

TABLE 1

| Ex. No. | EL IC$_{50}$ (nM) |
|---|---|
| 14 | 2779 |
| 15 | 12980 |
| 24 | 568 |
| 25 | 1058 |
| 26 | 9855 |
| 32 | 3738 |
| 45 | 3372 |
| 46 | 3317 |
| 48 | 447 |
| 53 | 18 |
| 54 | 7157 |
| 57 | 4890 |
| 72 | 22160 |
| 73 | 468 |
| 117 | 1190 |
| 125 | 329 |
| 127 | 30 |
| 128 | 13 |
| 135 | 3684 |
| 136 | 19 |
| 137 | 848 |
| 138 | 1724 |
| 139 | 28 |
| 142 | 39 |
| 158 | 525 |
| 163 | 2250 |
| 164 | 788 |
| 171 | 1477 |
| 175 | 496 |
| 176 | 1089 |
| 180 | 141 |
| 181 | 6440 |
| 184 | 5706 |
| 186 | 42 |
| 187 | 946 |
| 189 | 641 |
| 190 | 276 |
| 202 | 1905 |
| 203 | 6220 |
| 208 | 659 |
| 209 | 512 |
| 211 | 291 |
| 216 | 3483 |
| 218 | 296 |
| 225 | 5277 |
| 231 | 3841 |
| 234 | 439 |
| 240 | 24 |
| 243 | 967 |
| 258 | 10 |
| 259 | 10 |
| 267 | 1418 |
| 280 | 3140 |
| 281 | 875 |
| 289 | 10 |
| 299 | 9562 |

Accordingly, the compounds of the present invention can be administered to mammals, preferably humans, for the treatment of a variety of conditions and disorders, including, but not limited to, atherosclerosis, coronary heart disease, coronary artery disease, coronary vascular disease, cerebrovascular disorders, Alzheimer's disease, venous thrombosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia.

VI. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion.

Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors or other pharmaceutically active material.

The compounds of the present invention may be employed in combination with other EL inhibitors or one or more, preferably one to three, other suitable therapeutic agents useful in the treatment of the aforementioned disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease, treatment for malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), acyl-coenzyme A:cholesterol acyltransferase (ACAT) inhibitors, LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, (β-blockers, anti-diabetes agents, angiotensin II antagonists, angiotensin converting enzyme inhibitors, platelet aggregation inhibitors, fibrinogen receptor antagonists, aspirin or fibric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rivastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-SO$_4$); anti-glucocorticoids; TNFα inhibitors; α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, β$_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine H$_3$ receptors, dopamine D$_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the endothelial lipase. Such compounds may be provided in a commercial kit, for example, for use in pharmaceutical research involving endothelial lipase or HDL activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving endothelial lipase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of dyslipidemias and the sequelae thereof. In another embodiment, the package insert states that the pharmaceutical composition can be used in combination (as defined previously) with a second therapeutic agent for the treatment and/or prophylaxis of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

EXAMPLES

The following Examples have been prepared, isolated and characterized using the methods disclosed herein. The following examples demonstrate a partial scope of the invention and are not meant to be limiting of the scope of the invention.

Intermediate 1. Cis-4-phenylcyclohexanamine

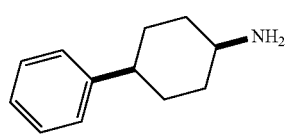

Intermediate 1A. Cis-N-benzhydryl-4-phenylcyclohexanamine: To a solution of 4-phenylcyclohexanone (500 mg, 2.87 mmol) and diphenylmethanamine (526 mg, 2.87 mmol) in DCE (4 mL) at 0° C. was added sodium triacetoxyborohydride (912 mg, 4.30 mmol) by portions slowly. A white suspension resulted and was stirred for 5 min before the ice-water bath was removed. The reaction was stirred at rt for 1.5 h. The reaction was quenched with water carefully, then saturated NaHCO$_3$ was added carefully and the aqueous portion was extracted with DCM (3×). The organic layers were combined, washed with brine, dried over Na$_2$SO$_4$, filtered and concentrated. The residue was purified by flash chromatography (0-100% hexane/EtOAc) to give Intermediate 1A (734 mg, 2.15 mmol, 74.9% yield) and trans-N-benzhydryl-4-phenylcyclohexanamine (191 mg, 0.559 mmol, 19.5% yield), LC-MS (ESI) m/z 342.1 (M+H), RT=1.76 min (Method B). $^1$H NMR (400 MHz, chloroform-d) δ ppm 7.37 (4H, d, J=7.33 Hz), 7.23-7.31 (6H, m), 7.11-7.23 (5H, m), 4.91 (1H, s), 2.80-2.88 (1H, m), 2.46-2.56 (1H, m), 1.74-1.90 (4H, m), 1.60-1.70 (2H, m), 1.47-1.59 (2H, m).

Intermediate 1

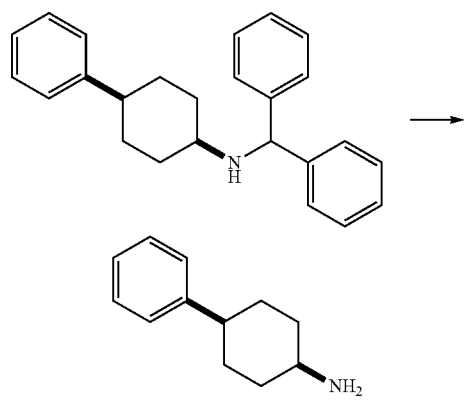

To a solution of Intermediate 1A (714 mg, 2.09 mmol) in MeOH (20 mL) and EtOAc (5 mL) were added 10% palladium on carbon (71.4 mg, 0.0670 mmol) and acetic acid (0.120 mL, 2.09 mmol). The reaction was stirred under H$_2$ balloon for 3 h. The reaction mixture was filtered through Celite® and rinsed with EtOAc. The filtrate was concentrated, re-dissolved in DCM, and the organic layer was extracted with 1 N HCl. The combined aqueous portions were made basic with 1 N NaOH and extracted with DCM (3×). The combined organic portions were washed with brine, dried over Na$_2$SO$_4$, decanted, and concentrated to give Intermediate 1 (321 mg, 1.83 mmol, 88.0% yield) as a colorless wax. LC-MS (ESI) m/z 176.1 (M+H), RT=1.43 min (Method B). $^1$H NMR (400 MHz, DMSO-d) δ ppm 7.24-7.30 (4H, m), 7.13-7.18 (1H, m), 3.10-3.16 (1H, m), 2.42-2.50 (1H, m), 1.80-1.93 (2H, m), 1.60-1.66 (4H, m), 1.44-1.54 (2H, m).

Intermediate 2.
Cis-4-amino-1-(4-fluorophenyl)cyclohexanol

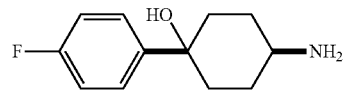

Intermediate 2 was prepared as a pink oil following the procedure described for Intermediate 1 by replacing 4-phenylcyclohexanone with 4-(4-fluorophenyl)-4-hydroxycyclohexanone. LC-MS (ESI) m/z 228.0 (M+H), RT=0.99 min (Method B).

Intermediate 3.
Cis-4-(3-(trifluoromethyl)phenyl)cyclohexanamine hydrochloride

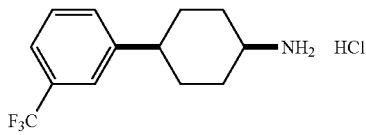

Intermediate 3A. 8-(3-(Trifluoromethyl)phenyl)-1,4-dioxaspiro[4.5]decan-8-ol

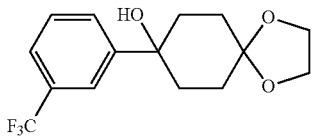

To a round bottom flask was added n-BuLi (3.84 mL, 9.60 mmol) at −78° C. under argon. THF (10 mL) was added followed by addition of 1-bromo-3-(trifluoromethyl)benzene (0.884 mL, 6.40 mmol) in THF (1 mL). The reaction mixture was stirred for 30 minutes at −78° C. A solution of 1,4-dioxaspiro[4.5]decan-8-one (1.00 g, 6.40 mmol) in THF (5 mL) was then added dropwise to the reaction mixture at −70° C. The reaction was stirred for 1 h at −70° C., and then quenched by the addition of 1 N HCl. The reaction mixture was extracted with EtOAc and the organic portions were separated and combined. The organic layer was dried over Na$_2$SO$_4$, filtered, and concentrated to give Intermediate 3A (1.87 g, 6.19 mmol, 97.0% yield). LCMS=325 [M+Na], RT=1.89 minutes (Method B).

Intermediate 3B. 8-(3-(Trifluoromethyl)phenyl)-1,4-dioxaspiro[4.5]dec-7-ene

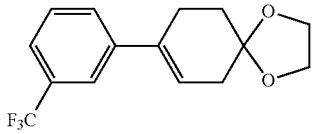 [SMILES: FC(F)(F)c1cccc(C2=CCC3(CC2)OCCO3)c1]

To a solution of Intermediate 3A (1.87 g, 6.19 mmol) and Et$_3$N (1.724 mL, 12.37 mmol) in DCM (30 mL) was added a solution of methanesulfonyl chloride (0.53 mL, 6.8 mmol) in DCM (10 mL) over 1 h at rt. The reaction mixture was stirred at rt for 2.5 h. Additional Et$_3$N (1.724 mL, 12.37 mmol) and methanesulfonyl chloride (0.53 mL, 6.8 mmol) were added and stirred for another 1 h. The reaction mixture was partitioned between 1 N HCl and DCM. The organic layer was dried over Na$_2$SO$_4$, filtered and the solvent was evaporated under reduced pressure to give Intermediate 3B (1.7 g, 5.9 mmol, 97% yield). LC-MS (ESI) m/z 285 (M+H), RT=3.43 min (Method C).

Intermediate 3C.
4-(3-(Trifluoromethyl)phenyl)cyclohex-3-enone

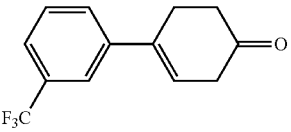

To a solution of Intermediate 3B (1.00 g, 3.52 mmol) in DCM (5 mL) was added TFA (2.5 mL, 32. mmol). The reaction was stirred at rt for 2 h. The reaction mixture was concentrated and purified on a 24 g silica gel column eluted from 0 to 100% EtOAc in hexanes over 15 minutes to Intermediate 3C (650 mg, 2.71 mmol, 77.0% yield). LCMS=241 [M+1], RT=3.59 min (Method A).

Intermediate 3D.
4-(3-(Trifluoromethyl)phenyl)cyclohexanone

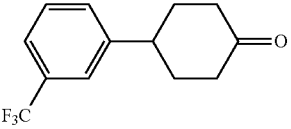

To a solution of Intermediate 3C (650 mg, 2.71 mmol) in EtOAc (10 mL) was added Pd/C (0.15 g, 0.27 mmol) in a pressure bottle. The mixture was stirred under 45 psi of hydrogen for 16 h. The catalyst was carefully filtered under nitrogen and the solvent was removed under vacuum. The residue was dissolved in DCM (10 mL) and Dess-Martin periodinane (1.26 g, 2.98 mmol) was added as one single portion. The reaction mixture was stirred at rt for 3 h. The reaction mixture was diluted with DCM, washed with brine, dried over Na$_2$SO$_4$, filtered and concentrated. The crude was purified by flash chromatography on a 24 g cartridge with 0 to 100% EtOAc in hexanes over 15 min to give Intermediate 3D (276 mg, 1.14 mmol, 42.1% yield). LCMS, RT=2.01 min (Method B).

Intermediate 3

Intermediate 3 was prepared as a pink oil following the procedure described for Intermediate 1 by replacing 4-phenylcyclohexanone with Intermediate 3D. The product was dissolved in Et$_2$O and 4N HCl in dioxane (100 μL) was added. The resulting precipitate was collected by filtration. The solid was pumped to dryness to give Intermediate 3 (88 mg, 75% yield). LC-MS (ESI) m/z 244 (M+H), RT=1.68 min (Method B).

Intermediate 4. (R)-6-(Trifluoromethyl)-2,3-dihydro-1H-inden-1-amine hydrochloride

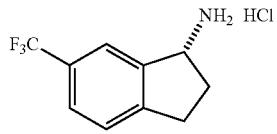 [SMILES: N[C@@H]1CCc2ccc(C(F)(F)F)cc21 ; Cl]

Intermediate 4A. (R)-2-Methyl-N-(6-(trifluoromethyl)-2,3-dihydro-1H-inden-1-ylidene)propane-2-sulfinamide

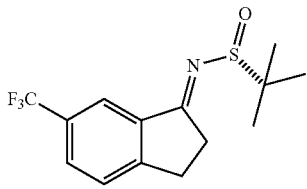 [SMILES: CC(C)(C)[S@@](=O)/N=C1\CCc2ccc(C(F)(F)F)cc21]

To a stirred solution of (R)-2-methylpropane-2-sulfinamide (578 mg, 4.77 mmol) and 6-(trifluoromethyl)-2,3-dihydro-1H-inden-1-one (1.00 g, 5.00 mmol) in THF (4 mL) at rt was added tetraethoxytitanium (1.88 mL, 9.08 mmol). The reaction mixture was heated at 75° C. for 16 h. The reaction mixture was allowed to cool and used directly in the next step. LC-MS (ESI) 304.0 (M+H), RT=2.20 min (Method B).

Intermediate 4B. (R)-2-Methyl-N—((R)-6-(trifluoromethyl)-2,3-dihydro-1H-inden-1-yl)propane-2-sulfinamide

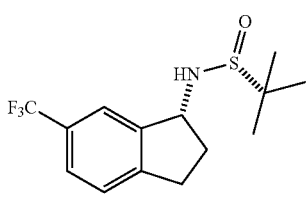 [SMILES: CC(C)(C)[S@@](=O)N[C@@H]1CCc2ccc(C(F)(F)F)cc21]

Sodium borohydride (756 mg, 20.0 mmol) was stirred in a round-bottomed flask under argon at −40 to −50° C. The reaction mixture of Intermediate 4A was added dropwise to the flask, and THF was added to the reaction mixture (ca. 0.6 M). The resulting mixture was allowed to warm up to 0° C. during 1.5 h period. The reaction mixture was cooled in dry ice and MeOH was added dropwise until gas evolution stopped. The mixture was stirred at rt for 20 min, filtered through Celite and rinsed with EtOAc then $CH_2Cl_2$. The filtrate was washed with brine (2×) and dried over $MgSO_4$, filtered and concentrated. The residue was purified by flash chromatography (hexanes/EtOAc) to give Intermediate 4B (370 mg, 1.21 mmol, 26.7% yield) as colorless crystals. LC-MS (ESI) 306.0 (M+H), RT=2.10 min (Method B).

Intermediate 4

Intermediate 4B (370 mg, 1.21 mmol) was stirred in MeOH (5 mL) at rt. 4 N HCl in dioxane (2 mL) was added. The resulting mixture was stirred at rt for 20 min. The solvents were evaporated and $CH_2Cl_2$(3×) was added and evaporated. The resulting white solids were vacuum dried for 1 h to give Intermediate 4 (84 mg, 0.35 mmol, 29% yield). The HCl salt was used directly in the next step. $^1$H NMR (400 MHz, MeOD) δ ppm 7.57 (1H, d, J=7.8 Hz), 7.47 (1H, d, J=7.6 Hz), 7.25 (1H, t, J=7.8 Hz), 4.88 (1H, dd, J=7.8, 4.8 Hz), 3.09-3.23 (1H, m), 2.90-3.08 (1H, m), 2.64 (1H, dddd, J=14.1, 8.5, 8.3, 5.7 Hz), 2.01-2.23 (1H, m, J=14.1, 8.7, 5.3, 5.3 Hz).

Intermediates 5-12 were prepared according to the procedures described in Intermediate 4 using the appropriate indanone or tetraline-1-one as the starting material.

| Intermediate No. | Structure | Name | LC-MS [M + 1]/RT |
|---|---|---|---|
| 5 | ![structure] | (R)-5-(trifluoromethyl)-2,3-dihydro-1H-inden-1-amine hydrochloride | 185.0 (M-$NH_3$ + H)/1.42 min (Method B) |
| 6 | ![structure] | (R)-4-(trifluoromethyl)-2,3-dihydro-1H-inden-1-amine hydrochloride | 185.0 (M-$NH_3$ + H)/1.38 min (Method B) |
| 7 | ![structure] | (R)-4,6-dichloro-2,3-dihydro-1H-inden-1-amine hydrochloride | 186.9 (M-$NH_3$ + H)/1.50 min (Method B) |
| 8 | ![structure] | (S)-6-(trifluoromethyl)-2,3-dihydro-1H-inden-1-amine hydrochloride | 185.0 (M-$NH_3$ + H)/1.32 min (Method B) |

| Intermediate No. | Structure | Name | LC-MS [M + 1]/RT |
|---|---|---|---|
| 9 | ![structure] | (R)-4-bromo-2,3-dihydro-1H-inden-1-amine hydrochloride | 196.9 (M-NH$_3$ + H)/1.34 min (Method B) |
| 10 | ![structure] | (R)-5-bromo-2,3-dihydro-1H-inden-1-amine hydrochloride | 196.9 (M-NH$_3$ + H)/1.30 min (Method B) |
| 11 | ![structure] | (R)-6-bromo-2,3-dihydro-1H-inden-1-amine hydrochloride | 196.9 (M-NH$_3$ + H)/1.25 min (Method B) |
| 12 | ![structure] | (R)-4,4-dimethyl-1,2,3,4-tetrahydronaphthalen-1-amine hydrochloride | 159.1 (M-NH$_3$ + H)/1.42 min (Method B) |

Intermediate 13. (S)-5-(2,2,2-Trifluoroethoxy)-1,2,3,4-tetrahydronaphthalen-1-amine

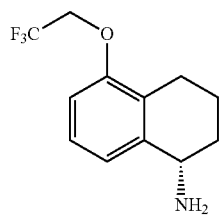 [SMILES: N[C@H]1CCCc2c(OCC(F)(F)F)cccc21]

Intermediate 13A. (R,Z)-2-Methyl-N-(5-(2,2,2-trifluoroethoxy)-3,4-dihydronaphthalen-1(2H)-ylidene)propane-2-sulfinamide

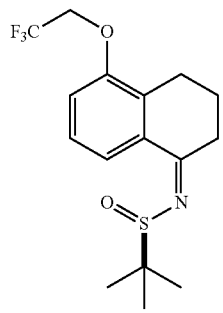 [SMILES: CC(C)(C)[S@@](=O)/N=C1/CCCc2c(OCC(F)(F)F)cccc21]

To a stirring solution of 2-methylpropane-2-sulfinamide (339 mg, 2.79 mmol) and 5-(2,2,2-trifluoroethoxy)-3,4-dihydronaphthalen-1(2H)-one (650 mg, 2.66 mmol) in THF (3 mL) was added tetraethoxytitanium (1.10 mL, 5.32 mmol) at rt. The reaction mixture was heated at 75° C. for 14 h. The reaction mixture was cooled to give Intermediate 13A which was used directly in the next step. LCMS=3.86 min [M+1]=347 (Method B).

Intermediate 13B. (R)-2-Methyl-N—((S)-5-(2,2,2-trifluoroethoxy)-1,2,3,4-tetrahydronaphthalen-1-yl)propane-2-sulfinamide

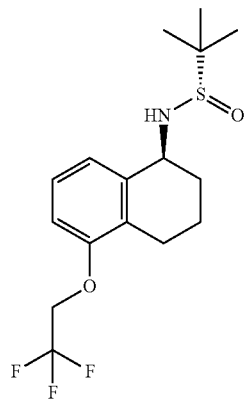

To a suspension of L-Selectride (3.90 mL, 3.90 mmol) in THF (1 mL) was added Intermediate 13A (0.45 g, 1.3 mmol)

in THF (1 mL) at −50° C. The reaction mixture was warmed up to rt until the reduction was complete. To the reaction mixture was added MeOH (2 mL) and brine (2 mL). The resulting reaction mixture was stirred for 5 minutes, filtered, and the filtrate was concentrated in vacuo. The crude product was dissolved in a small amount of DCM and loaded on a 4 g silica gel cartridge eluting from 0 to 100% EtOAc in hexanes over 15 minutes to give Intermediate 13B (196 mg, 0.561 mmol, 43.1% yield). LCMS=2.09 min [M+1]=350 (Method B).

Intermediate 13

To a solution of Intermediate 13B (245 mg, 0.701 mmol) in DCM (1 mL) was added 4 N HCl (175 µl, 0.701 mmol) in dioxane. The resulting mixture was stirred at rt for 0.5 h. The solvents were evaporated and DCM (3×) was added and evaporated. The resulting white solid was vacuum dried for 1 h to give Intermediate 13 (140 mg, 0.571 mmol, 81.0% yield) as a HCl salt which was used directly without further purification. LCMS=1.48 min [M+1-17]=229 (Method B).

Intermediate 14. (R)-5-(2,2,2-Trifluoroethoxy)-1,2,3,4-tetrahydronaphthalen-1-amine

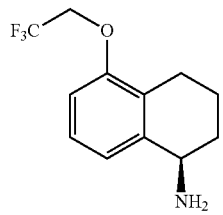 [SMILES: N[C@@H]1CCCc2c(OCC(F)(F)F)cccc21]

Intermediate 14A. (R)-2-Methyl-N—((R)-5-(2,2,2-trifluoroethoxy)-1,2,3,4-tetrahydronaphthalen-1-yl)propane-2-sulfinamide

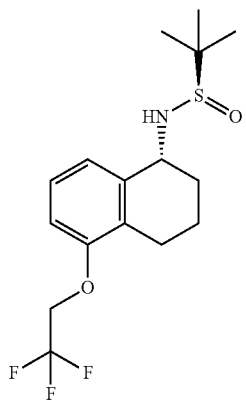 [SMILES: CC(C)(C)[S@@](=O)N[C@@H]1CCCc2c(OCC(F)(F)F)cccc21]

To a suspension of NaBH$_4$ (197 mg, 5.20 mmol) in THF was added Intermediate 21A (0.45 g, 1.3 mmol) in THF (1 mL) at −50° C. The reaction mixture was warm up to rt until the reduction was complete. The reaction mixture was added MeOH (1 mL) and equal amount of brine. The reaction was stirred for 5 minutes and filtered The filtrate was concentrated in vacuo. The crude product was dissolved in a small amount of DCM and loaded on a 4 g cartridge eluting from 0 to 100% EtOAc in hexanes over 15 minutes to give Intermediate 14A (245 mg, 0.701 mmol, 53.9% yield). LCMS=2.09 min [M+1]=350 (Method B).

Intermediate 14

To a solution of Intermediate 14A (206 mg, 0.590 mmol) in DCM (1 mL) was added 4 N HCl (147 µl, 0.590 mmol) in dioxane. The resulting mixture was stirred at rt for 0.5 h. The solvents were evaporated and DCM (3×) was added and evaporated. The resulting white solid was vacuum dried for 1 h to give Intermediate 14 (0.13 mg, 0.51 mmol, 86% yield) in HCl salt which was used directly without further purification. LCMS=1.55 min [M+1-17]=229 (Method B).

Intermediates 15-24HCl salts were prepared according to the procedures described in Intermediate 13-14 using the appropriate tetralin-1-one as the starting material.

| Intermediate No. | Structure | Name | LC-MS [M + 1]/RT |
|---|---|---|---|
| 15 | 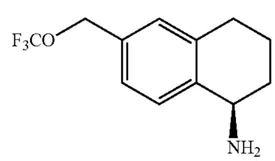 [SMILES: N[C@@H]1CCCc2cc(COC(F)(F)F)ccc21] | (R)-6-((trifluoromethoxy)methyl)-1,2,3,4-tetrahydronaphthalen-1-amine | 229.0 (M-NH$_3$ + H)/ 1.15 min (Method D) |
| 16 | 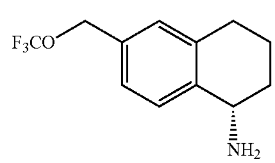 [SMILES: N[C@H]1CCCc2cc(COC(F)(F)F)ccc21] | (S)-6-((trifluoromethoxy)methyl)-1,2,3,4-tetrahydronaphthalen-1-amine | 229.0 (M-NH$_3$ + H)/ 1.17 min (Method D) |
| 17 | 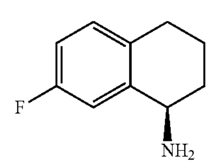 [SMILES: N[C@@H]1CCCc2ccc(F)cc21] | (R)-7-fluoro-1,2,3,4-tetrahydronaphthalen-1-amine | 149.0 (M-NH$_3$ + H)/ 1.20 min (Method B) |

-continued

| Intermediate No. | Structure | Name | LC-MS [M + 1]/RT |
|---|---|---|---|
| 18 | 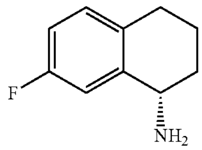 | (S)-7-fluoro-1,2,3,4-tetrahydronaphthalen-1-amine | 149.0 (M-NH₃ + H)/ 1.19 min (Method B) |
| 19 | 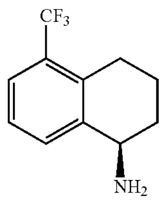 | (R)-5-(trifluoromethyl)-1,2,3,4-tetrahydronaphthalen-1-amine | 199.0 (M-NH₃ + H)/ 1.53 min (Method B) |
| 20 | 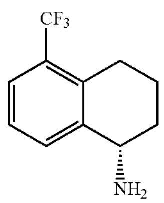 [SMILES: N[C@H]1CCCc2c1cccc2C(F)(F)F] | (S)-5-(trifluoromethyl)-1,2,3,4-tetrahydronaphthalen-1-amine | 199.0 (M-NH₃ + H)/ 1.53 min (Method B) |
| 21 | 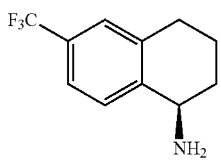 [SMILES: N[C@@H]1CCCc2cc(C(F)(F)F)ccc21] | (R)-6-(trifluoromethyl)-1,2,3,4-tetrahydronaphthalen-1-amine | 199.1 (M-NH₃ + H)/ 1.54 min (Method B) |
| 22 | 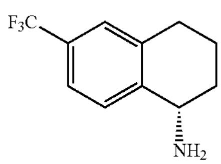 [SMILES: N[C@H]1CCCc2cc(C(F)(F)F)ccc21] | (S)-6-(trifluoromethyl)-1,2,3,4-tetrahydronaphthalen-1-amine | 199.1 (M-NH₃ + H)/ 1.54 min (Method B) |
| 23 | 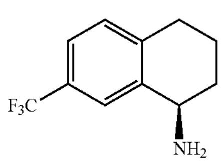 [SMILES: N[C@@H]1CCCc2ccc(C(F)(F)F)cc21] | (R)-7-(trifluoromethyl)-1,2,3,4-tetrahydronaphthalen-1-amine | 216.0 (M + H)/1.38 min (Method B) |
| 24 | 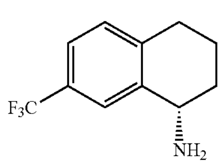 [SMILES: N[C@H]1CCCc2ccc(C(F)(F)F)cc21] | (S)-7-(trifluoromethyl)-1,2,3,4-tetrahydronaphthalen-1-amine | 216.1 (M + H)/1.37 min (Method B) |

Intermediate 25. (1R,4R)-4-Phenyl-1,2,3,4-tetrahydronaphthalen-1-amine

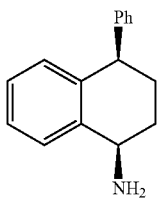 [SMILES: N[C@@H]1CC[C@H](c2ccccc2)c2ccccc21]

and

Intermediate 26. (1R,4S)-4-Phenyl-1,2,3,4-tetrahydronaphthalen-1-amine

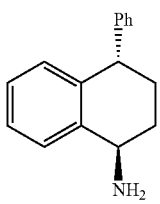 [SMILES: N[C@@H]1CC[C@@H](c2ccccc2)c2ccccc21]

Intermediate 25A. (R)-2-Methyl-N-((1R,4R)-4-phenyl-1,2,3,4-tetrahydronaphthalen-1-yl)propane-2-sulfinamide and Intermediate 26A. (R)-2-methyl-N-((1R,4S)-4-phenyl-1,2,3,4-tetrahydronaphthalen-1-yl)propane-2-sulfinamide Intermediate 25A

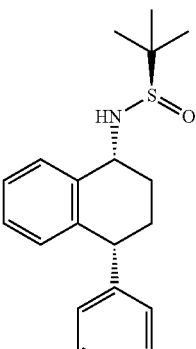

Intermediate 26A

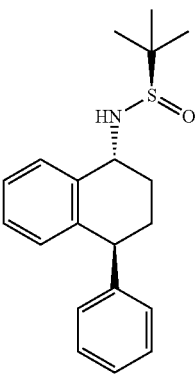

To a stirring solution of 2-methylpropane-2-sulfinamide (0.818 g, 6.75 mmol) and 4-phenyl-3,4-dihydronaphthalen-1 (2H)-one (1.5 g, 6.8 mmol) in THF (3.5 mL) at rt was added tetraethoxytitanium (2.80 mL, 13.5 mmol). The reaction mixture was heated at 75° C. for 14 h. The reaction mixture was cooled and used directly in the next step. Sodium borohydride (1.12 g, 29.7 mmol) was stirred in a round-bottomed flask under argon at −40 to −50° C. The reaction of (R)-2-methyl-N-(4-phenyl-3,4-dihydronaphthalen-1(2H)-ylidene)propane-2-sulfinamide was added dropwise to the reaction mixture. The resulting mixture was warmed up to 0° C. during 1.5 h period. It was cooled in dry ice and MeOH was added dropwise till gas evolution stopped, followed by the addition of brine. The white suspension was filtered through Celite, rinsed several times with EtOAc and DCM. The filtrate was concentrated and re-dissolved in DCM, washed with brine, dried over $Na_2SO_4$ and concentrated. The reaction mixture was purified by flash chromatography (0-50% EtOAc/hexanes) to give a pale yellow crystalline solid (1.1 g). This material was submitted for chiral separation on SFC (Instrument: Berger SFC MGII; Column: CHIRALCEL® OJ-H, 250×30 mm ID, 5 micron; Flow rate: 100 mL/min, 100 bar BP, 35° C.; Mobile Phase: 85/15 $CO_2$/Isopropanol-0.1 v/v % DEA; Detector Wavelength: 220 nm; Sample Solution: 1100 mg/21.6 mL (6 parts ACN:4 parts IPA) (51 mg/mL); Injection Size: 1.5 mL) to give Intermediate 25A (the fast eluent, 460 mg, 1.41 mmol, 20.8% yield) as a colorless viscous oil and Intermediate 26A (the slow eluent, 508 mg, 1.55 mmol, 23.0% yield) as a white solid.

Intermediate 25A: LC-MS (ESI) m/z 328.1 (M+H), RT=2.24 min (Method B). $^1$H NMR (500 MHz, chloroform-d) d ppm 7.46 (1H, d, J=6.88 Hz), 7.29-7.35 (2H, m), 7.21-7.27 (2H, m), 7.10-7.17 (3H, m), 6.86 (1H, d, J=7.70 Hz), 4.67 (1H, q, J=3.58 Hz), 4.02 (1H, dd, J=9.77, 5.91 Hz), 3.30 (1H, d, J=1.93 Hz), 2.08-2.20 (2H, m), 2.01-2.08 (1H, m), 1.92-2.01 (1H, m), 1.25 (9H, s).

Intermediate 26A: LC-MS (ESI) m/z 328.1 (M+H), RT=2.24 min (Method B). $^1$H NMR (500 MHz, chloroform-d) d ppm 7.58 (1H, d, J=7.43 Hz), 7.24-7.30 (3H, m), 7.14-7.22 (2H, m), 7.00 (2H, d, J=7.15 Hz), 6.93 (1H, d, J=7.98 Hz), 4.68 (1H, q, J=4.59 Hz), 4.20 (1H, t, J=5.50 Hz), 3.32 (1H, d, J=3.85 Hz), 2.32-2.42 (1H, m), 1.99-2.09 (1H, m), 1.79-1.89 (2H, m), 1.25 (9H, s).

Intermediate 25

Intermediate 25A (450 mg, 1.37 mmol) was stirred in MeOH (5 mL) at rt. 4 N HCl in dioxane (0.344 mL, 1.37 mmol) was added. The resulting mixture was stirred at rt for 0.5 h. The solvents were evaporated and $CH_2Cl_2$ (3×) was added and evaporated. The resulting white solids were vacuum dried for 1 h to give Intermediate 25 (409 mg, 1.57 mmol, 115% yield). LC-MS (ESI) m/z 207.1 (M−$NH_3$+H), RT=1.66 min (Method B). $^1$H NMR (400 MHz, MeOD) δ ppm 7.57 (1H, d, J=7.8 Hz), 7.47 (1H, d, J=7.6 Hz), 7.25 (1H, t, J=7.8 Hz), 4.88 (1H, dd, J=7.8, 4.8 Hz), 3.09-3.23 (1H, m), 2.90-3.08 (1H, m), 2.64 (1H, dddd, J=14.1, 8.5, 8.3, 5.7 Hz), 2.01-2.23 (1H, m, J=14.1, 8.7, 5.3, 5.3 Hz).

Intermediate 26

Intermediate 26 was prepared using the procedure described for Intermediate 25 from Intermediate 26A. LC-MS (ESI) m/z 207.1 (M−$NH_3$+H), RT=1.64 min (Method B).

Intermediates 27-30 were prepared according to the procedures described in Intermediate 25-26 using the appropriate tetralin-1-one as the starting material.

| Intermediate No. | Structure | Name | LC-MS [M + 1]/RT |
|---|---|---|---|
| 27 | 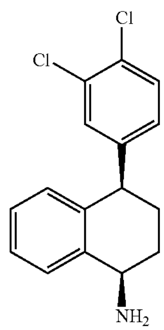 [SMILES: N[C@@H]1CC[C@H](c2ccc(Cl)c(Cl)c2)c2ccccc21] | (1R,4R)-4-(3,4-dichlorophenyl)-1,2,3,4-tetrahydronaphthalen-1-amine | 275.0 (M-NH$_3$ + H)/ 1.92 min (Method B) |
| 28 | 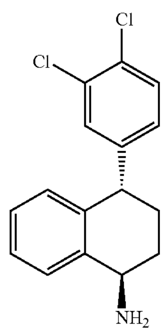 [SMILES: N[C@@H]1CC[C@@H](c2ccc(Cl)c(Cl)c2)c2ccccc21] | (1R,4S)-4-(3,4-dichlorophenyl)-1,2,3,4-tetrahydronaphthalen-1-amine | 275.0 (M-NH$_3$ + H)/ 1.92 min (Method B) |
| 29 | 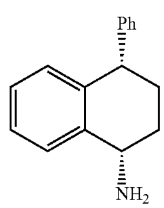 [SMILES: N[C@H]1CC[C@@H](c2ccccc2)c2ccccc21] | (1S,4S)-4-phenyl-1,2,3,4-tetrahydronaphthalen-1-amine | 207.1 (M-NH$_3$ + H)/ 1.67 min (Method B) |
| 30 | 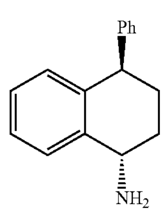 [SMILES: N[C@H]1CC[C@H](c2ccccc2)c2ccccc21] | (1S,4R)-4-phenyl-1,2,3,4-tetrahydronaphthalen-1-amine | 207.1 (M-NH$_3$ + H)/ 1.68 min (Method B) |

Intermediate 31.
(1S,3S)-3-Phenyl-2,3-dihydro-1H-inden-1-amine hydrochloride and

Intermediate 32.
(1R,3R)-3-Phenyl-2,3-dihydro-1H-inden-1-amine hydrochloride

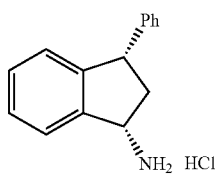

Intermediate 31

Intermediate 32

Intermediate 31A. (R)-2-Methyl-N-((1S,3S)-3-phenyl-2,3-dihydro-1H-inden-1-yl)propane-2-sulfinamide and

Intermediate 32A. (R)-2-Methyl-N-((1R,3R)-3-phenyl-2,3-dihydro-1H-inden-1-yl)propane-2-sulfinamide

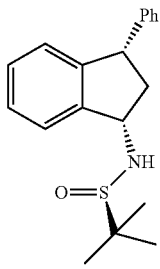

Intermediate 31A

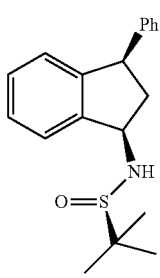

Intermediate 32A

The mixture of Intermediate 31A and 32A was prepared by using similar procedures as described for Intermediate 4B (0.55 g, 37%). LC-MS (ESI) 314.0. (M+H), RT=2.23 min (Method B). The mixture was submitted to chiral SFC separation (Instrument: Berger Multigram II SFC; Column: CHIRALPAK® AD-H, 250×21 mm ID, 5 μm; Flow rate: 60 mL/min, 100 bar BP, 35° C.; Mobile Phase: 15% Isopropanol/85% CO$_2$; Detector Wavelength: 220 nm (lambda max); Injection Volume: 1000 μL; Sample Preparation: 500 mg in 10 mL (6 mL of IPA and 4 mL of MeCN, ~50 mg/mL)) to give Intermediate 31A (0.2 g, the fast eluant) and Intermediate 32A (0.2 g, the slow eluant) as white solids. Both intermediates were crystallized in MeOH/hexanes.

Intermediate 31 and Intermediate 32

Intermediate 31 and 32 were prepared in a similar procedure described in Intermediate 4.
Intermediate 31: LC-MS (ESI) 193.0 (M−NH$_3$+H), RT=1.62 min (Method B).
Intermediate 32: LC-MS (ESI) 193.0 (M−NH$_3$+H), RT=1.62 min (Method B).

Intermediate 33. Cis-4-(3-(3,4-dichlorophenyl)-1,2,4-oxadiazol-5-yl)cyclohexanamine

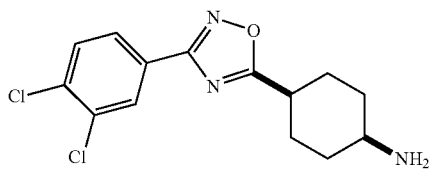

Intermediate 33A. (Z)-3,4-Dichloro-N'-hydroxybenzimidamide

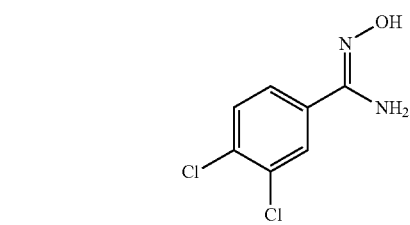 [SMILES: N/C(=N\O)c1ccc(Cl)c(Cl)c1]

A solution of 3,4-dichlorobenzonitrile (2.00 g, 11.6 mmol), hydroxylamine hydrochloride (1.65 mL, 12.8 mmol) and sodium hydroxide (4.15 mL, 12.4 mmol) in ethanol (40 mL) was stirred at rt for 1 h. The reaction mixture was concentrated and refluxed in hexanes for 30 min and concentrated in vacuo. The product, intermediate 33A was used directly without purification. HPLC/MS (Method C) retention time=1.24 min [M+H]$^+$204.9.

Intermediate 33B. tert-Butyl cis-4-(3-(3,4-dichlorophenyl)-1,2,4-oxadiazol-5-yl)cyclohexylcarbamate

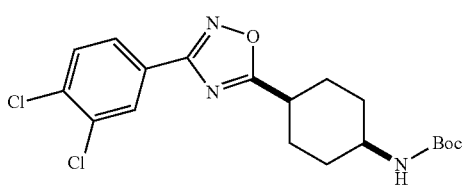

A microwave vial was charged with cis-4-(tert-butoxycarbonylamino)cyclohexanecarboxylic acid (0.24 g, 0.98 mmol), DMAP (0.12 g, 0.98 mmol) and Intermediate 33A (0.20 g, 0.98 mmol). The reactants were dissolved in DMF (1 mL) and DIC (0.15 mL, 0.98 mmol) was added. The reaction mixture was stirred at rt for 14 h. The reaction mixture was diluted in 3 mL of pyridine. The vial was capped and the reaction mixture was heated in the microwave at 145° C. for 20 minutes, allowed to cool to rt, diluted with EtOAc and washed with water and brine. The solution were concentrated under reduced pressure and purified by flash chromatography with EtOAc/hexanes to give Intermediate 33B (233 mg, 0.565 mmol, 57.9% yield) as a white solid. LCMS=434.1 [M+1], RT=2.43 min (Method B); $^1$H NMR (500 MHz, chloroform-d) δ ppm 8.19 (1H, d, J=1.93 Hz), 7.92 (1H, dd, J=8.53, 1.93 Hz), 7.56 (1H, d, J=8.25 Hz), 4.59 (1H, br. s.), 3.71 (1H, d, J=9.63 Hz), 3.14-3.22 (1H, m), 2.07-2.17 (2H, m), 1.92-2.02 (2H, m), 1.84 (2H, td, J=8.67, 4.13 Hz), 1.62-1.73 (2H, m), 1.44 (9H, s).

Intermediate 33

To Intermediate 33B (50 mg, 0.12 mmol) in $CH_2Cl_2$ (1 mL) was added TFA (2.00 mL, 26.0 mmol). The reaction was stirred at rt for 2 h. The reaction mixture was quenched with saturated $NaHCO_3$ and extracted with DCM. The organic portions were combined, dried over $Na_2SO_4$, and concentrated in vacuo to give Intermediate 33 which was used directly for the next step without any further purification. LCMS=312.0 [M+1], RT=1.86 min (Method B).

Intermediate 34.
5-Methoxy-1,2,3,4-tetrahydronaphthalen-1-amine

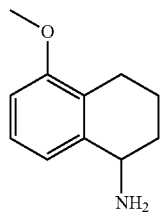

Intermediate 34A.
(Z)-5-Methoxy-3,4-dihydronaphthalen-1(2H)-one oxime

To a solution of 5-methoxy-3,4-dihydronaphthalen-1(2H)-one (200 mg, 1.14 mmol) and hydroxylamine methyl ether hydrochloride (284 mg, 3.40 mmol) in MeOH (5 mL) was added sodium acetate (279 mg, 3.40 mmol). The reaction mixture was heated at 60° C. for 1 h, cooled and partitioned between $H_2O$ and EtOAc. The organic layer was separated, dried over $Na_2SO_4$, filtered, and concentrated in vacuo to give Intermediate 34A (0.20 g, 1.1 mmol, 92% yield) which was used directly in the next step without further purification. LCMS=1.78 min [M+1]=192.1 (Method B).

Intermediate 34

To a stirred solution of Intermediate 34A (217 mg, 1.14 mmol) in THF (1 mL) was added borane dimethylamine complex (1.14 mL, 1.14 mmol). The reaction mixture was refluxed for 16 h. To this reaction mixture was added MeOH (1 mL), followed by 1N NaOH (1 mL) and the resulting solution stirred at 70° C. for 2 h. The reaction mixture was cooled and washed with saturated $NaHCO_3$. The organic layer was separated, dried over $Na_2SO_4$, filtered, and concentrated in vacuo to give Intermediate 34 (145 mg, 0.82 mmol, 72.1% yield) which was used directly in the next step. LCMS=1.24 min [M+1]=178.1 (Method B).

Intermediates 35-37 were prepared according to the procedures described in Intermediate 34 using the appropriate tetralin-1-one as the starting material.

| Intermediate No. | Structure | Name | LC-MS [M + 1]/RT |
|---|---|---|---|
| 35 | 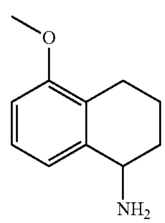 | 5-methoxy-1,2,3,4-tetrahydronaphthalen-1-amine | 178.1 (M + H)/1.24 min (Method B) |
| 36 | 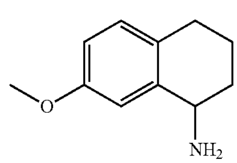 | 7-methoxy-1,2,3,4-tetrahydronaphthalen-1-amine | 178.0 (M + H)/1.21 min (Method B) |

| Intermediate No. | Structure | Name | LC-MS [M + 1]/RT |
|---|---|---|---|
| 37 | 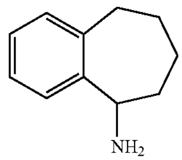 [SMILES: NC1CCCCc2ccccc21] | 6,7,8,9-tetrahydro-5H-benzo[7]annulen-5-amine | 145.0 (M-NH₃ + H)/ 1.28 min (Method B) |

Intermediate 38. Ethyl 4-amino-3,4-dihydroquinoline-1(2H)-carboxylate

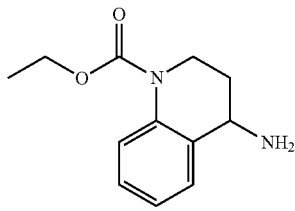 [SMILES: CCOC(=O)N1CCC(N)c2ccccc21]

Intermediate 38A. (Ethyl 4-(tert-butoxycarbonylamino)-3,4-dihydroquinoline-1(2H)-carboxylate

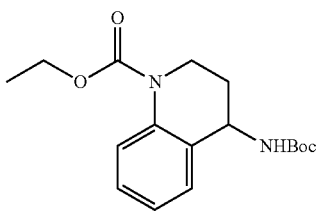 [SMILES: CCOC(=O)N1CCC(NC(=O)OC(C)(C)C)c2ccccc21]

To a solution of tert-butyl 1,2,3,4-tetrahydroquinolin-4-ylcarbamate (65 mg, 0.26 mmol) in DCM (1 mL) was added $Na_2CO_3$ (55.5 mg, 0.520 mmol), followed by ethyl carbonochloridate (0.028 mL, 0.29 mmol). The reaction mixture was stirred at rt for 2 h. The reaction mixture was diluted with DCM, washed with 1N HCl, dried over $Na_2SO_4$, filtered, and concentrated in vacuo to give Intermediate 38A (72 mg, 0.23 mmol, 86% yield). LCMS=1.97 min [M+Na]=342.9 (Method B).

Intermediate 38

To a solution of Intermediate 38A (30 mg, 0.094 mmol) in DCM (1 mL) was added 4N HCl in dioxane (0.023 mL, 0.094 mmol). The reaction was stirred at rt for 2 h. Organic solvents were evaporated under reduced pressure to give Intermediate 38 (20 mg, 0.091 mmol, 97% yield) which was used in next step without further purification. LCMS=1.19 min [M−NH₃+1]=204.1 (Method B).

Intermediates 39-40 were prepared according to the procedures described in Intermediate 38 using the appropriate coupling reagent as the starting material.

| Intermediate No. | Structure | Name | LC-MS [M + 1]/RT |
|---|---|---|---|
| 39 | 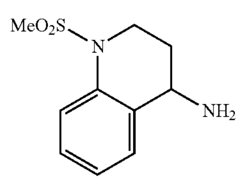 [SMILES: CS(=O)(=O)N1CCC(N)c2ccccc21] | 1-(methylsulfonyl)-1,2,3,4-tetrahydroquinolin-4-amine | 227.0 (M + H)/ 0.57 min (Method B) |
| 40 | 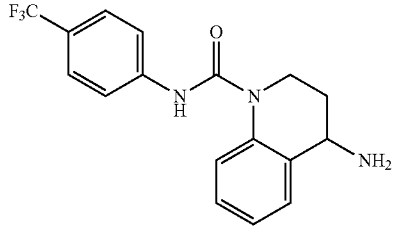 [SMILES: NC1CCN(C(=O)Nc2ccc(C(F)(F)F)cc2)c2ccccc21] | 7-methoxy-1,2,3,4-tetrahydronaphthalen-1-amine4-amino-N-(4-(trifluoromethyl)phenyl)-3,4-dihydroquinoline-1(2H)-carboxamide | 318.9 (M-NH₃ + H)/1.64 min (Method B) |

Intermediate 41.
(1R,3S)-3-(3,4-Dichlorophenyl)cyclopentanamine

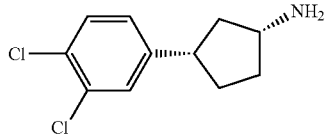 [SMILES: N[C@@H]1CC[C@H](c2ccc(Cl)c(Cl)c2)C1]

and

Intermediate 42.
(1S,3S)-3-(3,4-Dichlorophenyl)cyclopentanamine

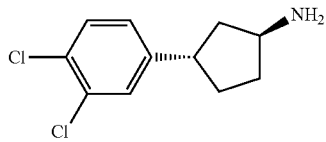 [SMILES: N[C@H]1CC[C@H](c2ccc(Cl)c(Cl)c2)C1]

Intermediate 41A.
(S)-3-(3,4-Dichlorophenyl)cyclopentanone

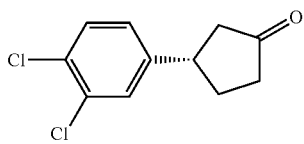 [SMILES: O=C1CC[C@H](c2ccc(Cl)c(Cl)c2)C1]

A mixture of 3,4-dichlorophenylboronic acid (488 mg, 2.56 mmol), bis(norbornadiene)rhodium tetrafluoroborate (14.6 mg, 0.0390 mmol) and S-2,2'-bis(diphenylphosphino)-1,1'-binaphthyl (25.8 mg, 0.0410 mmol) in dioxane (6.6 mL) was sparged with Ar three times and stirred at rt for 2 h. To the reaction mixture was added water (1.015 mL) followed by the addition of cyclopent-2-enone (200 mg, 2.44 mmol) and TEA (0.340 mL, 2.44 mmol). The reaction mixture was stirred at room for 18 h. The reaction mixture was diluted with DCM, washed with $H_2O$, dried over $MgSO_4$, filtered and concentrated. The residue was purified by flash chromatography 40 g using hexanes/EtOAc (0-100% over 15 min, flow rate 40 mL/min) to give Intermediate 41A (585 mg, 2.55 mmol, 100% yield) as a yellow oil. $^1$H NMR (400 MHz, chloroform-d) δ ppm 1.86-2.02 (1H, m), 2.18-2.38 (2H, m), 2.38-2.55 (2H, m), 2.67 (1H, dd, J=18.2, 7.4 Hz), 3.28-3.49 (1H, m), 7.09 (1H, dd, J=8.0, 2.5 Hz), 7.34 (1H, d, J=1.8 Hz), 7.41 (1H, d, J=8.3 Hz).

Intermediate 41B. N-((1R,3S)-3-(3,4-Dichlorophenyl)cyclopentyl)-2-methylpropane-2-sulfonamide

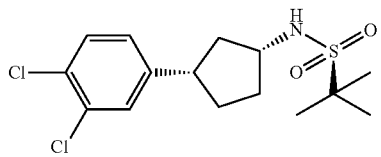

and

Intermediate 42B. N-((1S,3S)-3-(3,4-Dichlorophenyl)cyclopentyl)-2-methylpropane-2-sulfonamide

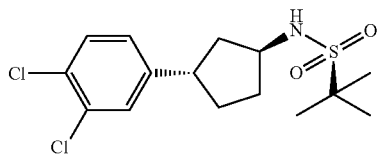

Intermediate 41B and 42B were prepared from Intermediate 41A and separated in a similar procedure described in Intermediate 31A and 32A. LC-MS (ESI) 334.0. (M+H), RT=1.10 min (Method M).

Intermediate 41 and 42

Intermediate 41 and 42 were prepared from Intermediate 41B and 42B in a similar procedure described in Intermediate 31 and 32.

Intermediate 41: LC-MS (ESI) 230.1 (M+H), RT=1.17 min (Method G).

Intermediate 42: LC-MS (ESI) 230.1 (M+H), RT=1.70 min (Method B).

Intermediates 43-44 were prepared according to the procedures described in Intermediate 41 and 42 using the appropriate starting material.

| Intermediate No. | Structure | Name | LC-MS [M + 1]/RT |
| --- | --- | --- | --- |
| 43 | ![structure] | (1S,3R)-3-(3,4-dichlorophenyl)cyclopentanamine | 230.1 (M + H)/1.68 min (Method B) |
| 44 | ![structure] | (1S,3R)-3-(3,4-dichlorophenyl)cyclopentanamine | 230.1 (M + H)/1.71 min (Method B) |

Intermediate 45.
3-(1-Benzyl-1H-pyrazol-4-yl)cyclohexanamine

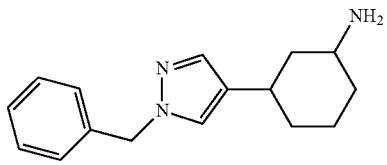 [SMILES: NC1CCCC(c2cnn(Cc3ccccc3)c2)C1]

Intermediate 45A.
3-(1-Benzyl-1H-pyrazol-4-yl)cyclohex-2-enone

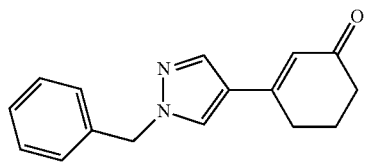 [SMILES: O=C1C=C(c2cnn(Cc3ccccc3)c2)CCC1]

To 1-benzyl-4-(4,4,5,5-tetramethyl-1,3,2-dioxaborolan-2-yl)-1H-pyrazole (406 mg, 1.43 mmol), 3-bromocyclohex-2-enone (200 mg, 1.14 mmol), and Pd(PPh$_3$)$_4$ (132 mg, 0.114 mmol) in toluene (2 mL) was added 2M Na$_2$CO$_3$ (1 mL). The reaction mixture was purged with nitrogen and heated at 110° C. for 16 h. The reaction was diluted with water (10 mL) and extracted DCM (3×15 mL), dried over Na$_2$SO$_4$ and purified by flash chromatography (24 g silica gel) using hexanes/EtOAc (0-50% over 15 min, flow rate 35 mL/min) to isolate Intermediate 45A (160 mg, 0.634 mmol, 55.5% yield) as a tan solid. LC-MS (ESI) 253.0 (M+H), RT=1.70 min (Method B).

Intermediate 45

A mixture of Intermediate 45A (160 mg, 0.634 mmol) and ammonium formate (800 mg, 12.7 mmol) in MeOH (5 mL)/water (0.5 mL) was stirred at rt for 45 min. The reaction was purged with nitrogen and treated with Pd/C Degussa wet type (100 mg, 0.634 mmol). After stirred for 16 h, additional amount of ammonium formate (800 mg, 12.7 mmol) was added. After 7 days, the reaction was filtered through Celite, concentrated, diluted in 1 N NaOH (50 mL), extracted with DCM (3×50 mL), dried over Na$_2$SO$_4$, concentrated, re-dissolved in methanol and purified using prep HPLC (0-100% B over 10 min, Column: PHENOMENEX® Luna Axia 5u C18 30×100 mm; Solvent A: 10% ACN–90% H$_2$O-0.1% TFA; Solvent B: 90% ACN–10% H$_2$O-0.1% TFA, flow rate=40 mL/min) to isolate Intermediate 45 (130 mg, 0.509 mmol, 80.0% yield) as a clear film. LC-MS (ESI) 256.1 (M+H), RT=1.43 min (Method B).

Intermediate 46. N-(4-(3-Aminocyclohexyl)phenyl)-4-methylbenzenesulfonamide

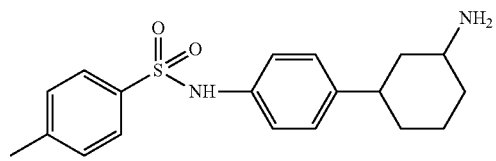 [SMILES: Cc1ccc(S(=O)(=O)Nc2ccc(C3CCCC(N)C3)cc2)cc1]

Intermediate 46 was prepared according to the procedures described in Intermediate 45 using the appropriate starting material. LC-MS (ESI) 345.1 (M+H)/1.54 min (Method B).

Intermediate 47.
3-(6-Phenylbenzo[d]thiazol-2-yl)cyclopentanamine

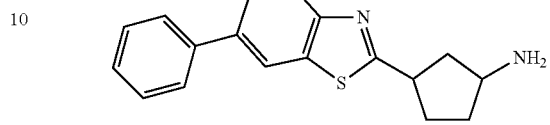

To a suspension of (1R,3R)-3-((tert-butoxycarbonyl)amino)cyclopentanecarboxylic acid (35.7 mg, 0.156 mmol) in DMF (1 mL) was added DIPEA (0.082 mL, 0.47 mmol), 3-((4-methoxybenzyl)thio)-[1,1'-biphenyl]-4-amine (50 mg, 0.16 mmol) and HATU (89 mg, 0.23 mmol). The reaction was stirred rt for 16 h. The mixture was concentrated, and the residue was dissolved in DCM and washed with 1 N HCl and water. The organics were combined and dried over Na$_2$SO$_4$ and concentrated. TFA (1 mL) was added to the residue and the solution was heated at 100° C. for 15 min in microwave. The reaction was heated at 60° C. for 16 h. The reaction was concentrated and dissolved in ACN and purified by Prep HPLC (5-90% B over 12 min, Column: PHENOMENEX® Luna Axia 5 u C18 30×100 mm; Solvent A: 10% ACN–90% H$_2$O-0.1% TFA; Solvent B: 90% ACN–10% H$_2$O-0.1% TFA, flow rate=40 mL/min) to give Intermediate 47 (22 mg, 48%) as a white solid. LC-MS (ESI) 295.0 (M+H), RT=1.86 min (Method B).

Intermediate 48. 1-(Pyridin-2-yl)pyrrolidin-3-amine

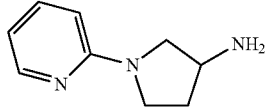

Intermediate 48A. tert-Butyl 1-(pyridin-2-yl)pyrrolidin-3-ylcarbamate

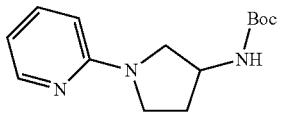 [SMILES: CC(C)(C)OC(=O)NC1CCN(c2ccccn2)C1]

A mixture of 2-fluoropyridine (58.3 mg, 0.600 mmol), tert-butyl pyrrolidin-3-ylcarbamate (55.9 mg, 0.300 mmol), and TEA (84.0 µL, 0.600 mmol) in EtOH (1 mL) was heated at 120° C. for 30 min. The reaction was concentrated and the crude was purified by flash chromatography (12 g silica gel) using hexanes/EtOAc (0-50% over 10 min, flow rate 30 mL/min) to give Intermediate 48A (15 mg, 0.057 mmol, 19% yield) as a white solid. LCMS=264.3 [M+1], RT=1.11 min (Method H). $^1$H NMR (400 MHz, chloroform-d) δ ppm 8.15 (1H, dd, J=5.05, 1.01 Hz), 7.44 (1H, ddd, J=8.59, 6.95, 1.89 Hz), 6.55 (1H, dd, J=6.44, 5.18 Hz), 6.35 (1H, d, J=8.34 Hz), 4.74 (1H, br. s.), 4.35 (1H, br. s.), 3.71 (1H, dd, J=10.61, 6.06 Hz), 3.46-3.64 (2H, m), 3.34 (1H, dd, J=10.61, 4.04 Hz), 2.27 (1H, td, J=13.20, 7.45 Hz), 1.96 (1H, td, J=12.51, 5.56 Hz), 1.45 (9H, s).

Intermediate 48

To a solution of Intermediate 48A (15 mg, 0.057 mmol) in DCM (0.2 mL) was added 4N HCl in dioxane (0.5 mL). The reaction was stirred at RT for 2 h. The solvents were removed and the residue as Intermediate 48 was dried and used directly in the next step. LCMS=164.1 [M+1], RT=0.24 min (Method B).

Example 1

(R)-5-Amino-2,6-dioxo-N-(6-(trifluoromethyl)-2,3-dihydro-1H-inden-1-yl)-1,2,3,6-tetrahydropyrimidine-4-carboxamide

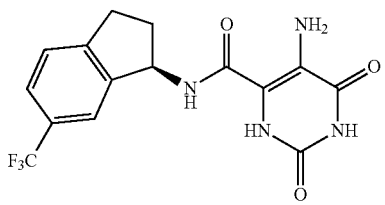 [SMILES: Nc1c(C(=O)N[C@@H]2CCc3ccc(C(F)(F)F)cc32)[nH]c(=O)[nH]c1=O]

To a 10-mL microwave reaction vial charged with 5-amino-2,6-dioxo-1,2,3,6-tetrahydropyrimidine-4-carboxylic acid (25 mg, 0.15 mmol) in DMF (1 mL) was added EDC (35 mg, 0.18 mmol), HOBt (28 mg, 0.18 mmol), and Intermediate 4 (35 mg, 0.15 mmol) followed by DIEA (0.13 mL, 0.73 mmol). The resulting solution was stirred at rt for 14 h. The reaction mixture was diluted with MeOH and purified by HPLC (0-75% B over 12 min, Column: PHENOMENEX® Luna Axia 5u C18 30×100 mm; Solvent A: 10% ACN–90% $H_2O$-0.1% TFA; Solvent B: 90% ACN–10% $H_2O$-0.1% TFA, flow rate=40 mL/min) to give Example 1 (20 mg, 0.056 mmol, 39% yield) as a white solid. LCMS=355.3 [M+1], RT=1.76 min (Method B); Orthogonal HPLC (150× 4.6 mm 3.5 um, 254 nm): Sunfire {RT=7.40 min, 99.7%, Method A}; Xbridge {RT=6.84 min, 99.8%, Method B}. $^1$H NMR (400 MHz, Acetone-$d_6$) δ ppm 8.02 (1H, br. s.), 7.72 (1H, s), 7.57 (1H, d, J=7.83 Hz), 7.44-7.53 (1H, m), 5.73 (2H, br. s.), 5.64 (1H, q, J=7.58 Hz), 3.08-3.22 (1H, m), 2.93-3.06 (1H, m), 2.58-2.71 (1H, m, J=16.67, 8.15, 4.01, 4.01 Hz), 2.08-2.19 (1H, m).

Examples 2-181 were prepared according the procedures described for Example 1 by using the appropriate intermediate amines and acids.

Examples 182-192 were prepared according the procedures described for Example 1 by using the appropriate intermediate amines and acids.

Example 193

Ethyl 4-(5-amino-2,6-dioxo-1,2,3,6-tetrahydropyrimidine-4-carboxamido)-3,4-dihydroquinoline-1(2H)-carboxylate (Enantiomer B)

Enantiomer B

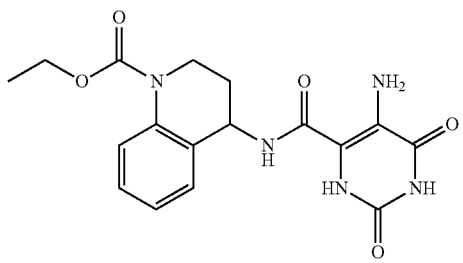

The racemates from Example 25 were separated by using preparative chromatographic SFC to give enantiomer A (fast eluting peak, RT=5.70 min) and enantiomer B as Example 193 (slow eluting peak, RT=6.33 min); Column: Regis Whelk-01(R, R), 250×4.6 mm ID, 5 μm; Flow rate: 3.0 mL/min; Mobile Phase: 70/30 $CO_2$/Methanol; Detector Wavelength: 220 nm). SFC conditions are: Instrument: Berger MGII SFC; Column: Regis Whelk-01(R, R), 250×21 mm ID; Flow rate: 60 mL/min; Mobile Phase: 75/25 $CO_2$/Methanol; Detector Wavelength: 240 nm; Sample Solution: 33 mg sample in 2 mL MeOH: Acetonitrile+40 μL DEA (~16 mg/mL); collected fractions in methanol. Example 193: LCMS=374 [M+1], RT=1.63 min (Method B); Orthogonal HPLC (150×4.6 mm 3.5 um, 254 nm): Sunfire {RT=6.31 min, 88.8%, Method A}; Xbridge {RT=5.98 min, 86.7%, Method B}.

Examples 194-201 were obtained according to the procedures described in Example 193 using the appropriate racemic starting material.

Example 202

5-Amino-N-(4-(3,4-difluorophenyl)cyclohex-3-enyl)-2,6-dioxo-1,2,3,6-tetrahydropyrimidine-4-carboxamide

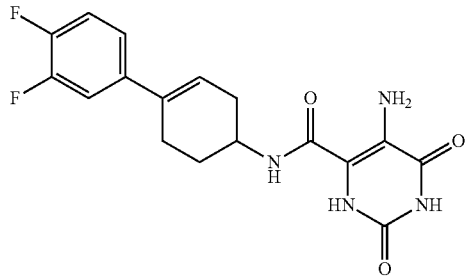 [SMILES: Nc1c(C(=O)NC2CC=C(c3ccc(F)c(F)c3)CC2)[nH]c(=O)[nH]c1=O]

Example 202A

5-Amino-N-(cis-4-(3,4-difluorophenyl)-4-hydroxycyclohexyl)-2,6-dioxo-1,2,3,6-tetrahydropyrimidine-4-carboxamide

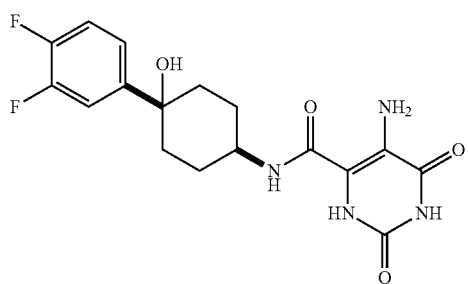 [SMILES: Nc1c(C(=O)N[C@H]2CC[C@@](O)(c3ccc(F)c(F)c3)CC2)[nH]c(=O)[nH]c1=O]

Example 202A was prepared according the procedures described for Example 1 by using Intermediate 10. LCMS=381.5 [M+1] RT=1.77 min (Method E); Orthogonal HPLC (150×4.6 mm 3.5 um, 254 nm): Sunfire {RT=5.48 min, 96.1%, Method A}; Xbridge {RT=5.10 min, 95.6%, Method B).

Example 202

To a solution of Example 202A (10 mg, 0.026 mmol) in DCM (0.50 mL) was added TFA (0.20 mL, 2.6 mmol). The resulting solution was stirred at rt for 30 min. The reaction was concentrated and titrated with MeOH to give Example 202 as a white solid (4.5 mg, 0.012 mmol, 47% yield). LCMS=363.1 [M+1] RT=2.47 min (Method G); Orthogonal HPLC (150×4.6 mm 3.5 um, 254 nm): Sunfire {RT=7.73 min, 85.8%, Method A}; Xbridge {RT=7.18 min, 84.7%, Method B). $^1$H NMR (400 MHz, DMSO-d$_6$) δ ppm 11.47 (1H, br. s.), 9.91 (1H, br. s.), 8.02 (1H, d, J=6.57 Hz), 7.49 (1H, dd, J=11.37, 8.84 Hz), 7.32-7.43 (1H, m), 7.29 (1H, br. s.), 6.17 (1H, br. s.), 5.95 (2H, br. s.), 4.00 (1H, br. s.), 2.52-2.67 (2H, m), 2.17 (1H, dd, J=15.79, 7.96 Hz), 1.89-2.09 (1H, m), 1.59-1.84 (1H, m), 1.15-1.36 (1H, m).

Example 203

5-Amino-3-(3-fluoro-5-(trifluoromethyl)phenyl)-2,6-dioxo-N-(cis-4-phenylcyclohexyl)-1,2,3,6-tetrahydropyrimidine-4-carboxamide

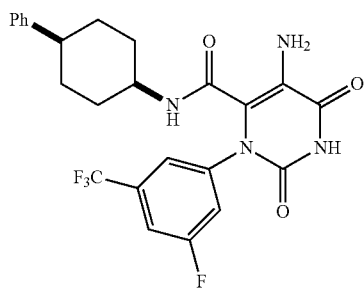 [SMILES: Nc1c(C(=O)N[C@H]2CC[C@@H](c3ccccc3)CC2)n(-c2cc(F)cc(C(F)(F)F)c2)c(=O)[nH]c1=O]

To a solution of Example 3 (25 mg, 0.076 mmol), 3-fluoro-5-(trifluoromethyl)phenylboronic acid (32 mg, 0.15 mmol) in MeOH (3045 μL) and water (761 μL) was added Cu(OAc)$_2$ (14 mg, 0.076 mmol) followed by addition of TMEDA (23.0 μL, 0.15 mmol). The reaction mixture was stirred at rt for 1.5 h. The reaction was concentrated and purified by HPLC (5-90% B over 12 min, Column: PHENOMENEX® Luna Axia 5u C18 30×100 mm; Solvent A: 10% ACN-90% H$_2$O-0.1% TFA; Solvent B: 90% ACN-10% H$_2$O-0.1% TFA, flow rate=40 mL/min) to give Example 203 (5.0 mg, 10 mol, 13% yield) as a white solid. LCMS=490.9 [M+1], RT=2.16 min (Method B); Orthogonal HPLC (150×4.6 mm 3.5 um, 254 nm): Sunfire {RT=9.95 min, 100%, Method A}; Xbridge {RT=8.93 min, 100%, Method B}.

Example 204 was prepared according the procedures described for Example 203 by using the appropriate intermediate boronic acid.

Example 205

5-(4-Fluorobenzylamino)-2,6-dioxo-N-(cis-4-phenylcyclohexyl)-1,2,3,6-tetrahydropyrimidine-4-carboxamide

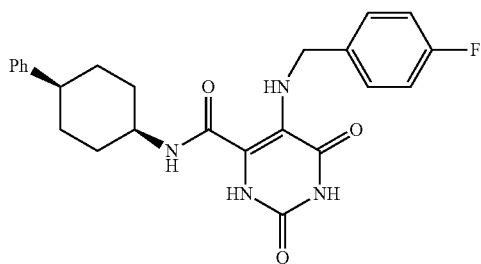 [SMILES: O=C(N[C@H]1CC[C@@H](c2ccccc2)CC1)c1[nH]c(=O)[nH]c(=O)c1NCc1ccc(F)cc1]

Example 205A 2,6-Dioxo-N-((1s,4s)-4-phenylcyclohexyl)-1,2,3,6-tetrahydropyrimidine-4-carboxamide

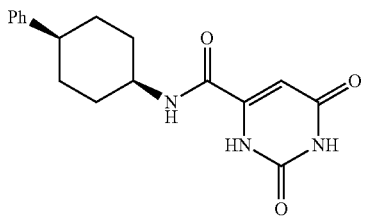 [SMILES: O=C(N[C@H]1CC[C@@H](c2ccccc2)CC1)c1cc(=O)[nH]c(=O)[nH]1]

To a 10 mL microwave reaction vial charged with 2,6-dioxo-1,2,3,6-tetrahydropyrimidine-4-carboxylic acid (3.00 g, 19.2 mmol) and DMF (10 mL) was added EDC (4.05 g, 21.1 mmol), HOBt (3.24 g, 21.1 mmol), and Intermediate 1, HCl salt (4.07 g, 19.2 mmol) followed by DIEA (10.1 mL, 57.7 mmol). The resulting solution was stirred at rt for 16 h. The reaction mixture then was heated at 55° C. for 2 h. The reaction was diluted with water and extracted with DCM (3×). The organics were combined and dried over MgSO$_4$ and concentrated. The crude was purified by flash chromatography (0-10% MeOH in DCM) to give Example 205A (4.5 g, 14 mmol, 75% yield) as a white solid. $^1$H NMR (500 MHz, DMSO-d$_6$) d ppm 11.23 (1H, br. s.), 10.86 (1H, br. s.), 8.48 (1H, d, J=7.15 Hz), 7.23-7.38 (4H, m), 7.13-7.23 (1H, m), 5.96-6.11 (1H, m), 4.08 (1H, ddd, J=7.02, 3.44, 3.30 Hz), 2.55-2.66 (1H, m), 1.77-1.97 (4H, m), 1.56-1.75 (4H, m). LCMS=314.1 [M+1], RT=3.44 min (Method A).

Example 205B

5-Bromo-2,6-dioxo-N-((1s,4s)-4-phenylcyclohexyl)-1,2,3,6-tetrahydropyrimidine-4-carboxamide

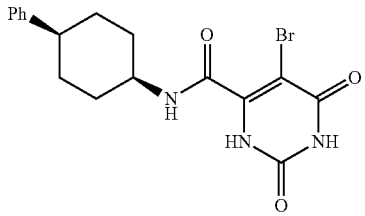 [SMILES: O=C(N[C@H]1CC[C@@H](c2ccccc2)CC1)c1[nH]c(=O)[nH]c(=O)c1Br]

To a vigorously stirred solution of Example 205A (0.27 g, 0.86 mmol) in acetic acid (15 mL) was added bromine (0.044 mL, 0.86 mmol) in acetic acid (5 mL) dropwise slowly over a 1 h period. The reaction was stirred at rt for 16 h. The reaction was diluted with water and filtered and rinsed with water to give Example 205B (289 mg, 0.737 mmol, 86.0% yield) as a white solid. LCMS=391.9 [M+1], 393.9 [M+3], RT=3.44 min (Method A).

Example 205

A mixture of (4-fluorophenyl)methanamine (63.8 mg, 0.510 mmol) and Example 205B (10 mg, 0.025 mmol) in dioxane (0.5 mL) was microwaved at 120° C. for 2 h. The reaction mixture was concentrated and purified by Prep-HPLC (0-100% MeOH/H$_2$O with 0.1% TFA as modifier over 10 min). Product was eluted at a retention time of 11.41 min, collected and concentrated to give Example 205 (6.0 mg, 0.014 mmol, 54% yield) as a colorless oil. LCMS=437.0 [M+1] RT=2.19 min (Method B); Orthogonal HPLC (150× 4.6 mm 3.5 um, 254 nm): Sunfire {RT=9.90 min, 100%, Method A}; Xbridge {RT=9.06 min, 100%, Method B}.

Examples 206-237 were prepared according the procedures described for Example 205 by using the appropriate intermediate amines and acids under microwave heating from 120 to 200° C. either neat or in solvents such as ethanol, dioxane, or ethylene glycol.

Example 238

Hydroxy-2,6-dioxo-N-(cis-4-phenylcyclohexyl)-1,2,3,6-tetrahydropyrimidine-4-carboxamide

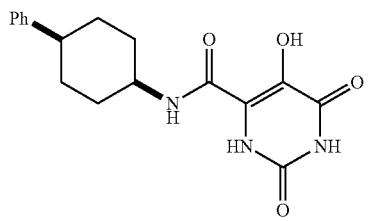

Example 238A

Ethyl 5-(benzyloxy)-2-(methylthio)-6-oxo-1,6-dihydropyrimidine-4-carboxylate

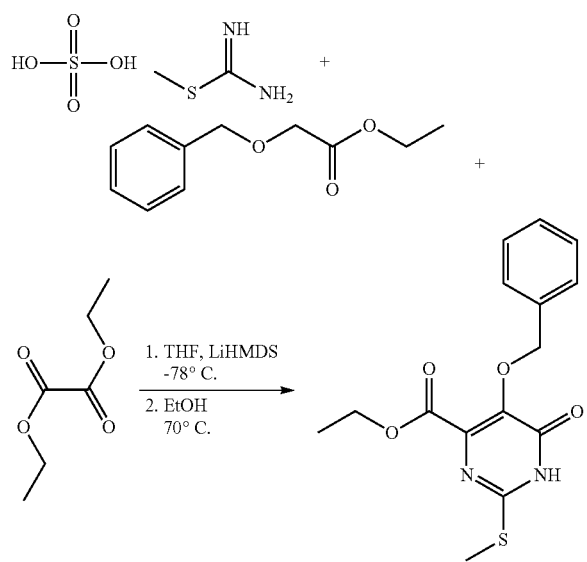

A solution of ethyl 2-(benzyloxy)acetate (24.9 g, 128 mmol) and diethyl oxalate (20.9 mL, 154 mmol) in THF (220 mL) was cooled to −78° C. under argon. Lithium bis(trimethylsilyl)amide (192 mL, 192 mmol) was added dropwise to this solution and the resulting mixture was stirred at −78° C. for 4 h. The reaction mixture was concentrated and the brown oily residue was dissolved in EtOH (450 mL). 2-Methyl-2-thiopseudourea sulfate (26.5 g, 141 mmol) was added and the mixture was stirred at 70° C. for 24 h. The reaction mixture was allowed to cool to rt and concentrated under reduced pressure. The residue was partitioned between EtOAc and 1N HCl. The organic layer was washed with brine, dried over Na₂SO₄, filtered and concentrated. The resulting brown oil was purified by flash chromatography eluting with EtOAc/hexanes (0-50%) to give a yellow residue that was crystallized from hot EtOAc/hexanes (1:4). The resulting white solid was collected by filtration to give Example 238A (6.01 g, 18.8 mmol, 14.6% yield). LC-MS (ESI) 321.2 (M+H), retention time=2.21 min (Method B). ¹H NMR (300 MHz, CDCl₃) δ: 12.03 (1H, bs), 7.45 (2H, dd, J=7.9, 1.6 Hz), 7.36-7.29 (3H, m), 5.22 (2H, s), 4.31 (2H, q, J=7.2 Hz), 2.56 (3H, s), 1.29 (3H, q, J=7.1 Hz).

Example 238B 5-(Benzyloxy)-2-(methylthio)-6-oxo-1,6-dihydropyrimidine-4-carboxylic acid

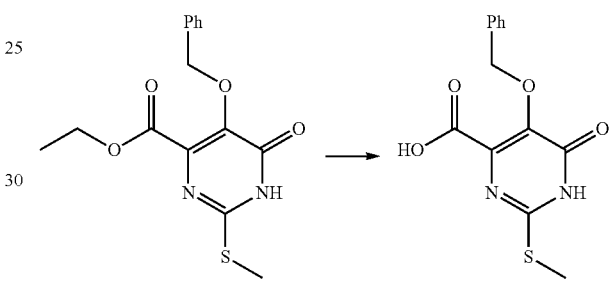

Example 238A (99 mg, 0.31 mmol) was stirred in ethanol (3 mL) at rt. 1 N NaOH (1.5 mL) was added. The reaction was stirred at 50° C. for 1 h. After cooling, the mixture was concentrated under reduced pressure and concentrated HCl was then added dropwise to the remaining mixture. The resulting white precipitate was filtered, and rinsed with H₂O, and then dried in vacuo to give Example 238B (70 mg, 0.24 mmol, 77% yield) as white solids. LC-MS (ESI) 292.9 (M+H), retention time=1.52 min (Method B).

Example 238C 5-(Benzyloxy)-2-(methylthio)-6-oxo-N-(cis-4-phenylcyclohexyl)-1,6-dihydropyrimidine-4-carboxamide

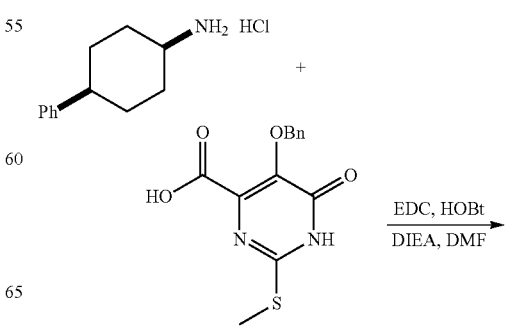

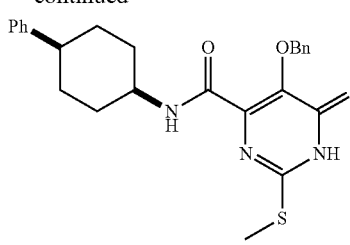

To a 1-dram vial charged with Example 238B (65 mg, 0.22 mmol), cis-4-phenylcyclohexanamine hydrochloride (57 mg, 0.27 mmol) and DMF (0.5 mL) was added EDC (53 mg, 0.28 mmol), HOBt (43 mg, 0.28 mmol) followed by DIEA (0.19 mL, 1.1 mmol). The resulting mixture was stirred at rt for 16 h. EtOAc was added. The solution was washed with H₂O, brine, dried over MgSO₄, filtered and concentrated under reduced pressure. The residue was dissolved in CH₂Cl₂ and purified by silica gel flash column chromatography (0-100% EtOAc/hexanes) to give Example 238C (70 mg, 0.16 mmol, 70% yield) as white solids. LC-MS (ESI) 449.9 (M+H), retention time=2.26 min (Method B).

Example 238D

5-Benzyloxy-2-methanesulfonyl-6-oxo-1,6-dihydro-pyrimidine-4-carboxylic acid (cis-4-phenyl-cyclo-hexyl)-amide

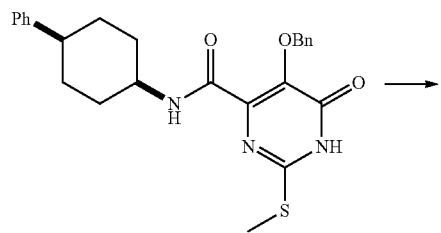

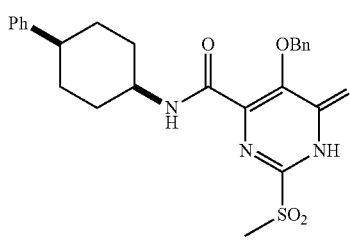

Example 238C (70 mg, 0.16 mmol) was stirred in CH₂Cl₂ (3 mL) at rt for 16 h. Additional CH₂Cl₂ (10 mL) was added. The reaction mixture was washed with aqueous Na₂CO₃, aqueous Na₂SO₃, H₂O, and then brine, dried over MgSO₄, filtered and concentrated to give Example 238D which was used directly in the next step without further purification. LC-MS (ESI) 481.9 (M+H), retention time=2.18 min (Method B).

Example 238E 5-(Benzyloxy)-2,6-dioxo-N-(cis-4-phenylcyclo-hexyl)-1,2,3,6-tetrahydropyrimidine-4-carboxamide

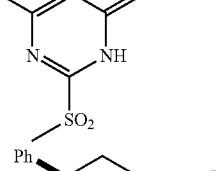

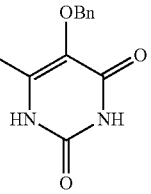

Example 238D (75 mg, 0.16 mmol) was dissolved in dioxane (3 mL). 1N NaOH (1 mL, 1.0 mmol) was added. The resulting solution was stirred at rt for 1 h. The reaction mixture was concentrated and made acidic by the addition of 1 N HCl. The resulting solution was concentrated under reduced pressure and the residue dissolved in MeOH, then purified by HPLC(CH₃CN/H₂O/TFA) to give Example 238E (23 mg, 0.060 mmol, 35% yield) as a white solid. LC-MS (ESI) 419.9 (M+H), retention time=2.19 min (Method B). ¹H NMR (400 MHz, acetone) δ ppm 10.37 (1H, br. s.), 8.34 (1H, br. s.), 7.50-7.65 (2H, m), 7.32-7.44 (3H, m), 7.22-7.31 (2H, m), 7.14-7.22 (1H, m), 7.07 (2H, d, J=7.1 Hz), 5.37 (2H, s), 4.17 (1H, dt, J=7.1, 3.6 Hz), 2.45-2.65 (1H, m), 1.77-1.89 (2H, m), 1.71 (2H, tt, J=13.4, 3.8 Hz), 1.60 (2H, d, J=13.9 Hz), 1.26-1.48 (2H, m).

Example 238

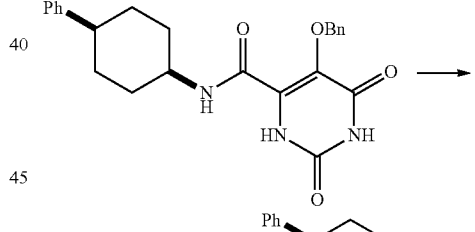

Example 238E (18 mg, 0.043 mmol) was stirred in CH₂Cl₂ (2.5 mL) and TFA (2.5 mL) under microwave irradiation at 120° C. for 20 min. The vial was then heated in an oil bath at 50° C. for 16 h. After cooling, the reaction mixture was concentrated under reduced pressure, dissolved in MeOH and purified by HPLC(CH₃CN/H₂O/TFA) to give Example 238 (5.0 mg, 0.020 mmol, 35% yield) as a white solid. LC-MS (ESI) 330.1 (M+H), retention time=1.93 min (Method B). Orthogonal HPLC (150×4.6 mm 3.5 um, 254 nm): RT=6.69 min, 100% (Method A); RT=6.21 min, 100% (Method B). ¹H NMR (400 MHz, MeOD) δ ppm 7.29-7.14 (5H, m), 4.31 (1H, m), 2.64 (1H, m), 1.98-1.94 (2H, m), 1.85-1.78 (4H, m), 1.74-1.67 (2H, m).

Example 239

1-Ethyl-5-hydroxy-2,6-dioxo-N-(cis-4-phenylcyclohexyl)-1,2,3,6-tetrahydropyrimidine-4-carboxamide

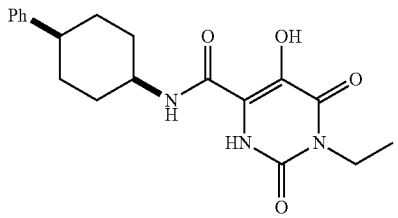 [SMILES: CCn1c(=O)[nH]c(C(=O)N[C@H]2CC[C@@H](c3ccccc3)CC2)c(O)c1=O]

and

Example 240

3-Benzyl-1-ethyl-5-hydroxy-2,6-dioxo-N-(cis-4-phenylcyclohexyl)-1,2,3,6-tetrahydropyrimidine-4-carboxamide

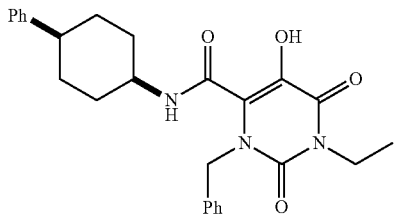 [SMILES: CCn1c(=O)c(O)c(C(=O)N[C@H]2CC[C@@H](c3ccccc3)CC2)n(Cc2ccccc2)c1=O]

Example 239A 5-(Benzyloxy)-6-ethoxy-2-(methylthio)-N-(cis-4-phenylcyclohexyl)pyrimidine-4-carboxamide

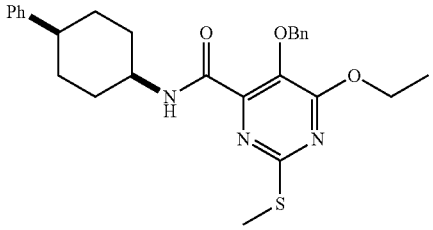 [SMILES: CCOc1nc(SC)nc(C(=O)N[C@H]2CC[C@@H](c3ccccc3)CC2)c1OCc1ccccc1]

and

Example 239B 5-(Benzyloxy)-1-ethyl-2-(methylthio)-6-oxo-N-(cis-4-phenylcyclohexyl)-1,6-dihydropyrimidine-4-carboxamide

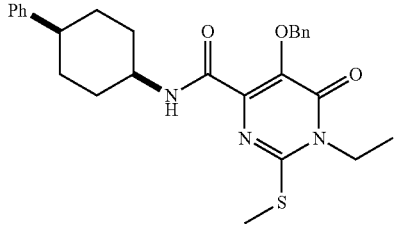 [SMILES: CCn1c(SC)nc(C(=O)N[C@H]2CC[C@@H](c3ccccc3)CC2)c(OCc2ccccc2)c1=O]

To a solution of Example 238C (75 mg, 0.17 mmol) in DMF (1 mL) was added cesium carbonate (82 mg, 0.25 mmol) and iodoethane (0.013 mL, 0.17 mmol) dropwise. The reaction was stirred at rt for 14 h. The reaction mixture was diluted with water and extracted with EtOAc (2×). The combined organic layers were dried over Na$_2$SO$_4$ and concentrated and purified by flash chromatography (0-30% EtOAc/hexanes over 10 min then 30-100% over 3 min on a 12 g silica gel column) to give Example 239A (faster eluant, 27 mg, 0.057 mmol, 34% yield) as a white solid and Example 239B (slower eluant, 27 mg, 0.057 mmol, 34% yield) as a colorless oil. Example 239A: LC-MS (ESI) 478.1 (M+H), retention time=4.56 min (Method A). $^1$H NMR (400 MHz, chloroform-d) δ ppm 8.01 (1H, d, J=8.24 Hz), 7.53 (2H, d, J=7.15 Hz), 7.26-7.37 (5H, m), 7.20 (1H, br. s.), 7.18 (2H, d, J=3.85 Hz), 5.10 (2H, s), 4.46 (2H, q, J=7.15 Hz), 4.35 (1H, dd, J=7.97, 3.57 Hz), 2.57-2.66 (1H, m), 2.55 (3H, s), 1.97 (2H, d, J=13.19 Hz), 1.69-1.87 (4H, m), 1.53-1.66 (2H, m), 1.42 (3H, t, J=6.87 Hz). Example 239B: LC-MS (ESI) 478.1 (M+H), retention time=4.35 min (Method A). $^1$H NMR (400 MHz, chloroform-d) δ ppm 7.86 (1H, d, J=7.70 Hz), 7.56 (2H, d, J=6.05 Hz), 7.30 (5H, m), 7.18-7.24 (1H, m), 7.14 (2H, d, J=7.15 Hz), 5.28 (2H, s), 4.32-4.40 (1H, m), 4.15 (2H, q, J=7.15 Hz), 2.65 (3H, s), 2.54-2.63 (1H, m), 1.92 (2H, d, J=11.54 Hz), 1.67-1.83 (4H, m), 1.42-1.58 (2H, m), 1.37 (3H, t, J=7.15 Hz).

Example 239C 5-(Benzyloxy)-1-ethyl-2,6-dioxo-N-(cis-4-phenylcyclohexyl)-1,2,3,6-tetrahydropyrimidine-4-carboxamide

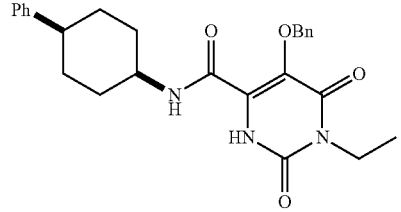 [SMILES: CCn1c(=O)[nH]c(C(=O)N[C@H]2CC[C@@H](c3ccccc3)CC2)c(OCc2ccccc2)c1=O]

A mixture of Example 239B (63 mg, 0.13 mmol) and mCPBA (114 mg, 0.462 mmol) was stirred in CH$_2$Cl$_2$ (1.5 mL) at rt for 14 h. Dioxane (1 mL) and 2.5 N NaOH (1 mL) was added and the resulting reaction mixture was stirred at rt for 1.5 h. Saturated Na$_2$S$_2$O$_3$ was added and the reaction mixture stirred for 5 min. A suspension was obtained and filtered. The filter cake was washed with water. The white solid was further dried under reduced vacuum to give Example 239C (47 mg, 0.11 mmol, 80% yield). LC-MS (ESI) 448.1 (M+H), retention time=2.33 min (Method B).

Example 239 and Example 240

Example 239C (18 mg, 0.040 mmol) was stirred in CH$_2$Cl$_2$ (2.5 mL) and TFA (2.5 mL) under microwave irradiation at 120° C. for 30 min. The vial was then heated in an oil bath at 50° C. for 14 h. After cooling, the mixture was concentrated and re-dissolved in MeOH and purified by prep HPLC (CH$_3$CN/H$_2$O/TFA) to give Example 239 (8.0 mg, 0.022 mmol, 56% yield) and Example 240 (2.0 mg, 4.5 mol, 11% yield).

Example 239: LC-MS (ESI) 358.1 (M+H), retention time=2.12 min (Method B). Orthogonal HPLC (150×4.6 mm 3.5 um, 254 nm): Sunfire {RT=8.46 min, 100%, Method A}; Xbridge {RT=7.56 min, 100%, Method B).

Example 240: LC-MS (ESI) 448.1 (M+H), retention time=2.39 min (Method B). Orthogonal HPLC (150×4.6 mm

Example 241

5-Hydroxy-3-methyl-2,6-dioxo-N-(cis-4-phenylcyclohexyl)-1,2,3,6-tetrahydropyrimidine-4-carboxamide

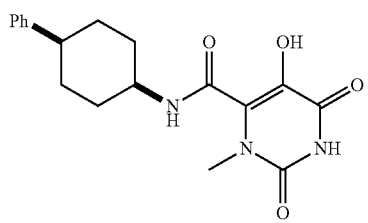 [SMILES: Cn1c(C(=O)N[C@H]2CC[C@@H](c3ccccc3)CC2)c(O)c(=O)[nH]c1=O]

Example 241A 5-(Benzyloxy)-6-ethoxy-2-oxo-N-(cis-4-phenylcyclohexyl)-2,3-dihydropyrimidine-4-carboxamide

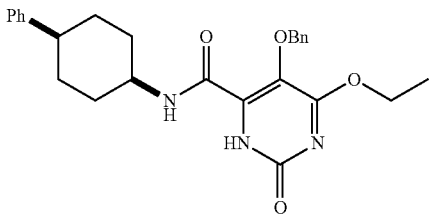 [SMILES: CCOc1nc(=O)[nH]c(C(=O)N[C@H]2CC[C@@H](c3ccccc3)CC2)c1OCc1ccccc1]

A mixture of Example 239A (75 mg, 0.16 mmol) and mCPBA (135 mg, 0.550 mmol) was stirred in CH$_2$Cl$_2$ (3 mL) at rt for 14 h. To the reaction was added sodium hydroxide (1 mL, 1 mmol) and the resulting solution stirred for 2 h. Additional CH$_2$Cl$_2$ (10 mL) was added. The reaction mixture was washed with aqueous Na$_2$CO$_3$, aqueous Na$_2$SO$_3$, H$_2$O and brine, then dried over MgSO$_4$, filtered and concentrated to give Example 241A (9.0 mg, 0.020 mmol, 13% yield). LC-MS (ESI) 448.2 (M+H), retention time=2.28 min (Method B).

Example 241B 5-(Benzyloxy)-6-ethoxy-3-methyl-2-oxo-N-(cis-4-phenylcyclohexyl)-2,3-dihydropyrimidine-4-carboxamide

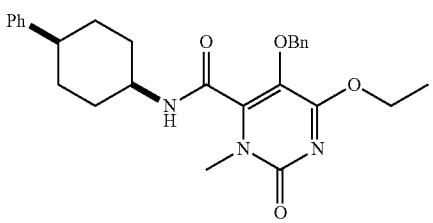 [SMILES: CCOc1nc(=O)n(C)c(C(=O)N[C@H]2CC[C@@H](c3ccccc3)CC2)c1OCc1ccccc1]

To a solution of Example 241A (15 mg, 0.034 mmol) in DMF (1 mL) was added iodomethane (2.0 µl, 0.034 mmol) dropwise. The reaction was stirred at rt for 14 h. The reaction mixture was diluted with water and extracted with EtOAc (2×). The combined organic layers were dried over Na$_2$SO$_4$ and concentrated and purified by flash chromatography (10% MeOH/DCM over 10 min on silica gel) followed by prep HPLC (ACN/water/TFA) to give Example 241B (6.0 mg, 0.013 mmol, 39% yield) as a white solid. LC-MS (ESI) 462.2 (M+H), retention time=2.23 min (Method B). $^1$H NMR (500 MHz, chloroform-d) δ ppm 7.31-7.40 (5H, m), 7.25 (2H, d, J=7.43 Hz), 7.16-7.20 (1H, m), 7.13 (2H, d, J=6.88 Hz), 7.00 (1H, d, J=6.60 Hz), 4.90 (2H, s), 4.44 (2H, q, J=6.97 Hz), 4.33 (1H, ddd, J=7.22, 3.51, 3.30 Hz), 3.44 (3H, s), 2.56 (1H, tt, J=11.14, 3.44 Hz), 1.93 (2H, d, J=2.20 Hz), 1.69-1.80 (5H, m, J=13.38, 13.38, 13.14, 3.58 Hz), 1.66 (2H, dd, J=13.62, 2.89 Hz), 1.36 (3H, t, J=7.02 Hz).

Example 241

Example 241B (6.0 mg, 0.013 mmol) was stirred in CH$_2$Cl$_2$ (2.5 mL) and TFA (2.5 mL) under microwave irradiation at 120° C. for 30 min. After cooling, the mixture was concentrated and redissolved in MeOH and purified by prep HPLC (CH$_3$CN/H$_2$O/TFA) to give Example 241 (2.0 mg, 5.8 µmol, 49% yield). LC-MS (ESI) 344.1 (M+H), retention time=1.82 min (Method B). PHENOMENEX® Luna C18; 30×2.0 mm; 2 min Grad}; Orthogonal HPLC (150×4.6 mm 3.5 um, 254 nm): Sunfire {RT=8.57 min, 100%, Method A}; Xbridge {RT=6.11 min, 100%, Method B). $^1$H NMR (400 MHz, acetone-d$_6$) δ ppm 7.07-7.31 (5H, m), 4.30 (1H, br. s.), 3.27 (3H, s), 2.54-2.72 (1H, m, J=11.68, 11.68, 3.85, 3.57 Hz), 1.99-2.03 (2H, m), 1.86-1.97 (2H, m), 1.69-1.84 (4H, m).

Examples 242-266 were prepared according the procedures described for Examples 239-241 by using the appropriate intermediate amines and acids.

Example 267

2-(5-Hydroxy-2,6-dioxo-4-((cis-4-phenylcyclohexyl)carbamoyl)-2,3-dihydropyrimidin-1(6H)-yl)acetic acid

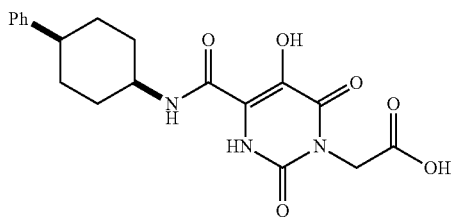

Example 267A tert-Butyl 5-(benzyloxy)-1-(2-methoxy-2-oxoethyl)-2,6-dioxo-1,2,3,6-tetrahydropyrimidine-4-carboxylate

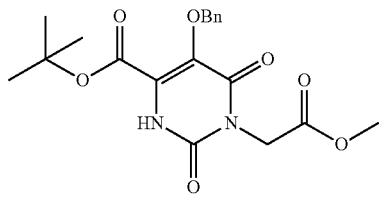 [SMILES: COC(=O)Cn1c(=O)[nH]c(C(=O)OC(C)(C)C)c(OCc2ccccc2)c1=O]

tert-Butyl 5-(benzyloxy)-2-methoxy-6-oxo-1,6-dihydropyrimidine-4-carboxylate (300 mg, 0.903 mmol) and sodium hydride (36.1 mg, 0.903 mmol) were stirred in anhydrous DMF (903 μl) at 0° C. under argon for 30 min. Methyl 2-bromoacetate (83 μl 0.90 mmol) was added and the mixture was stirred at rt for 3 h. The reaction was carefully quenched with water at 0° C. The reaction mixture was extracted with EtOAc (3×). The combined organic layers were washed with water, brine, dried over Na₂SO₄, concentrated and purified by flash chromatography (hexanes/EtOAc, eluted at ca. 30% EtOAc) to give tert-butyl 5-(benzyloxy)-2-methoxy-6-(2-methoxy-2-oxoethoxy)pyrimidine-4-carboxylate (109 mg, 0.270 mmol, 29.9% yield) as a colorless oil and Example 267A (117 mg, 0.289 mmol, 32.1% yield) as a colorless oil. $^1$H NMR (500 MHz, chloroform-d) δ 7.49-7.44 (m, 2H), 7.37-7.32 (m, 2H), 7.32-7.27 (m, 1H), 5.12 (s, 2H), 4.74 (s, 2H), 4.00 (s, 3H), 3.75 (s, 3H), 1.51 (s, 9H). LC-MS (ESI) 349.0 (M+H-t-Bu), retention time=2.07 min (Method B).

Example 267B 5-(Benzyloxy)-1-(2-methoxy-2-oxoethyl)-2,6-dioxo-1,2,3,6-tetrahydropyrimidine-4-carboxylic acid

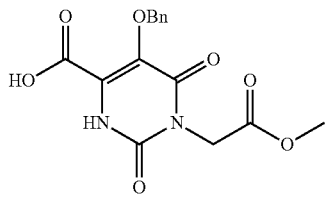 [SMILES: COC(=O)Cn1c(=O)[nH]c(C(=O)O)c(OCc2ccccc2)c1=O]

To a solution of Example 267A (117 mg, 0.289 mmol) in MeOH (2 mL) was added concentrated HCl (2.00 mL, 65.8 mmol). The reaction was stirred at rt for 48 h. The reaction was concentrated and filtered and rinsed with water. The filter cake was collected and dried under reduced vacuum to give Example 267B (97.0 mg, 0.290 mmol, 100% yield) as a white solid. LC-MS (ESI) 357.0 (M+Na), retention time=1.53 min (Method B).

Example 267C

Methyl 2-(5-(benzyloxy)-2,6-dioxo-4-((cis-4-phenylcyclohexyl)carbamoyl)-2,3-dihydropyrimidin-1(6H)-yl)acetate

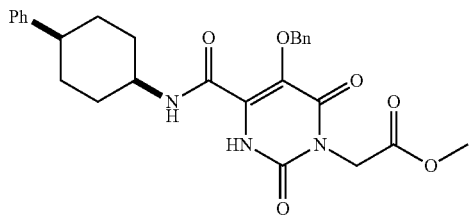

To a vial charged with Example 267B (34.8 mg, 0.165 mmol) in DMF (0.5 mL) was added EDC (35.8 mg, 0.187 mmol), HOBt (28.6 mg, 0.187 mmol) followed by DIEA (0.131 mL, 0.748 mmol) and Intermediate 9 (34.8 mg, 0.165 mmol). The resulting mixture was stirred at rt for 16 h. The mixture was diluted with EtOAc and washed with H₂O, brine, dried over MgSO₄, filtered and concentrated. The residue was dissolved in CH₂Cl₂ and purified by flash chromatography (0-100% EtOAc in hexanes) to give Example 267C (10 mg, 0.020 mmol, 14% yield) as a white solid. LC-MS (ESI) 492.1 (M+H), retention time=2.26 min (Method B).

Example 267D 2-(5-(Benzyloxy)-2,6-dioxo-4-((cis-4-phenylcyclohexyl)carbamoyl)-2,3-dihydropyrimidin-1(6H)-yl)acetic acid

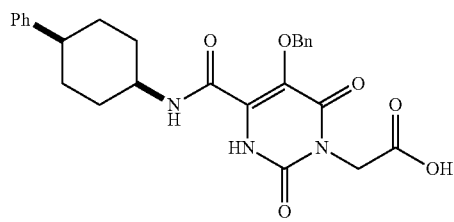

To Example 267C (40 mg, 0.081 mmol) in MeOH (1 mL) and THF (1 mL) was added LiOH (3.90 mg, 0.163 mmol) and the reaction was stirred for 3 h. The reaction was concentrated and dried under reduced vacuum to give Example 267D as a white solid. LC-MS (ESI) 478.2 (M+H), retention time=2.18 min (Method B).

Example 267

To Example 267D (10 mg, 0.021 mmol) in CH₂Cl₂(1 mL) was added TFA (0.2 mL). The resulting solution was heated at 120° C. for 15 min in microwave. The reaction was concentrated and dissolved in MeOH and purified by Prep HPLC (10-100% B over 10 min, ACN/H₂O/TFA) to give Example 267 (4.00 mg, 9.91 μmol, 47.3% yield) as a white solid. $^1$H NMR (500 MHz, MeOD) δ 7.32-7.23 (m, 4H), 7.20-7.14 (m, 1H), 4.66 (s, 2H), 4.34 (t, J=3.0 Hz, 1H), 2.71-2.59 (m, 1H), 2.03-1.94 (m, 2H), 1.89-1.78 (m, 4H), 1.75-1.63 (m, 2H). LCMS=388.1 [M+H] RT=1.91 min (Method B). Orthogonal HPLC (150×4.6 mm 3.5 um, 254 nm): Sunfire {RT=9.33 min, %, Method A}; Xbridge {RT=7.60 min, 96.0%, Method B}.

Example 268

5-Hydroxy-2,6-dioxo-1-(2-oxo-2-((cis-4-phenylcyclohexyl)amino)ethyl)-N-(cis-4-phenylcyclohexyl)-1,2,3,6-tetrahydropyrimidine-4-carboxamide

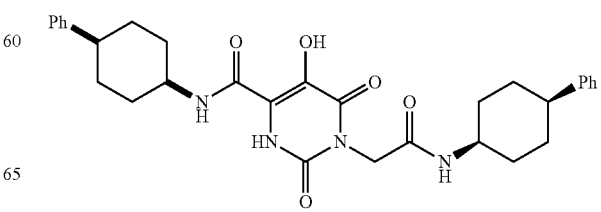

Example 268A 5-(Benzyloxy)-2,6-dioxo-1-(2-oxo-2-((cis-4-phenyl-cyclohexyl)amino)ethyl)-N-(cis-4-phenylcyclo-hexyl)-1,2,3,6-tetrahydropyrimidine-4-carboxamide

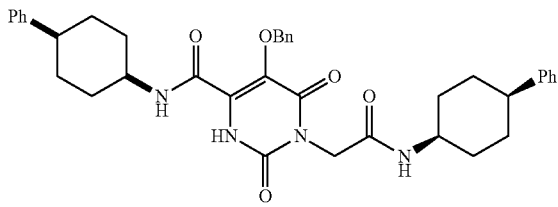

To a vial charged with Intermediate 1 (18 mg, 0.084 mmol) and Example 267D (20 mg, 0.042 mmol) in dioxane (0.5 mL) was added DIEA (0.037 mL, 0.21 mmol) and 2,4,6-tripropyl-1,3,5,2,4,6-trioxatriphosphinane 2,4,6-trioxide (0.037 mL, 0.063 mmol). The resulting mixture was stirred at rt for 1 h. DMF (0.3 mL) was added and the reaction was heated at 50° C. for 3 h then at rt for 3 days. The mixture was diluted with EtOAc and washed with $H_2O$, brine, dried over $MgSO_4$, filtered and concentrated. The residue was dissolved in $CH_2Cl_2$ and purified by flash chromatography (0-100% EtOAc/hexanes) to give Example 268A (10 mg, 0.016 mmol, 38% yield) as a white solid. LC-MS (ESI) 635.3 (M+H), retention time=2.47 min (Method B).

Example 268

To Example 268A (10 mg, 0.016 mmol) in $CH_2Cl_2$(1 mL) was added TFA (0.2 mL). The resulting solution was heated at 120° C. for 15 min in microwave. The reaction was concentrated and dissolved in MeOH and purified by Prep HPLC (10-100% B over 10 min, ACN/$H_2O$/0.1% TFA) to give Example 268 (4.00 mg, 7.27 mol, 46.2% yield) as a white solid. $^1$H NMR (500 MHz, MeOD) δ 8.26 (d, J=6.9 Hz, 1H), 7.38-7.21 (m, 9H), 7.21-7.08 (m, 2H), 4.69 (s, 2H), 4.38-4.26 (m, 1H), 4.20-4.02 (m, 1H), 2.73-2.50 (m, 2H), 2.03-1.95 (m, 2H), 1.95-1.88 (m, 2H), 1.88-1.76 (m, 6H), 1.76-1.61 (m, 6H). LCMS=545.3 [M+H] RT=2.29 min (Method B). Orthogonal HPLC (150×4.6 mm 3.5 um, 254 nm): Sunfire {RT=10.68 min, 99.0%, Method A}; Xbridge {RT=10.18 min, 99.3%, Method B).

Example 269

5-Hydroxy-1-(2-hydroxyethyl)-2,6-dioxo-N-(cis-4-phenylcyclohexyl)-1,2,3,6-tetrahydropyrimidine-4-carboxamide

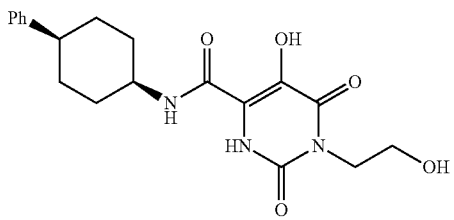 [SMILES: O=C(N[C@H]1CC[C@@H](c2ccccc2)CC1)c1[nH]c(=O)n(CCO)c(=O)c1O]

Example 269A 5-(Benzyloxy)-1-(2-hydroxyethyl)-2,6-dioxo-N-(cis-4-phenylcyclohexyl)-1,2,3,6-tetrahydropyrimidine-4-carboxamide

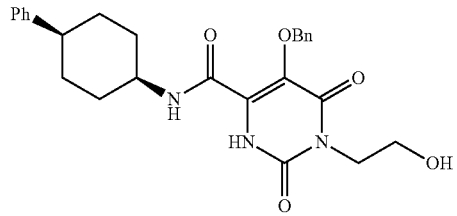 [SMILES: O=C(N[C@H]1CC[C@@H](c2ccccc2)CC1)c1[nH]c(=O)n(CCO)c(=O)c1OCc1ccccc1]

To a solution of Example 267C (25 mg, 0.051 mmol) in THF (1 mL) at 0° C. was added lithium borohydride (2M in THF) (38 μl, 0.076 mmol) slowly. The reaction was slowly warmed to room temperature where it was stirred at for 16 h. The mixture was slowly quenched with water. The organic layer was separated and the aqueous phase was extracted with EtOAc. The combined organic layers were dried ($MgSO_4$) and concentrated in vacuo. The crude material was purified by flash chromatography over 4 g of silica gel (20 min gradient with 0-100% ethyl acetate in hexanes) to afford Example 269A (22 mg, 0.047 mmol, 93% yield) as a white foam. LCMS=464.1 [M+H] RT=2.19 min (Method B).

Example 269

To a solution of Example 269A (22 mg, 0.047 mmol) in $CH_2Cl_2$(1 mL) was added Pd/C (5.1 mg, 0.047 mmol). The reaction mixture was stirred under $H_2$ for 2 h. The reaction mixture was filtered through the Celite and rinsed with MeOH. The filtrate was concentrated. The desired product was purified by prep HPLC using a 10 minutes gradient from 0 to 100% B (Column: PHENOMENEX® Luna Axia 100×20 mm 5u (10 min gradient). Solvent A: 10% ACN–90% $H_2O$-0.1% TFA. Solvent B: 90% ACN–10% $H_2O$-0.1% TFA) to give Example 269 (5.0 mg, 0.013 mmol, 27% yield). LCMS=1.92 minutes [M+H]=374.0 (Method B). Orthogonal HPLC (150×4.6 mm 3.5 um, 254 nm): Sunfire {RT=7.31 min, 96.2%, Method A}; Xbridge {RT=6.93 min, 100%, Method B}. $^1$H NMR (500 MHz, MeOD) δ 7.31-7.22 (m, 4H), 7.19-7.13 (m, 1H), 4.37-4.27 (m, 1H), 4.11 (t, J=6.1 Hz, 2H), 3.76 (t, J=6.1 Hz, 2H), 2.72-2.57 (m, 1H), 2.04-1.91 (m, 2H), 1.89-1.76 (m, 4H), 1.76-1.60 (m, 2H).

Example 270

5-Hydroxy-2,6-dioxo-N-(cis-4-phenylcyclohexyl)-1-(3-phenylpropyl)-1,2,3,6-tetrahydropyrimidine-4-carboxamide

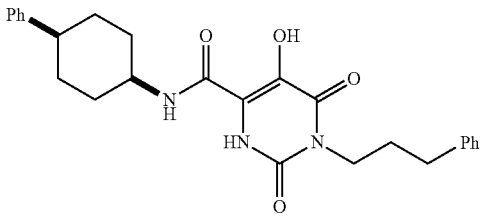

Example 270 was prepared in similar procedure described in Example 267. LC-MS (ESI) 448.2 (M+H), retention time=2.32 min (Method B).

Example 271

5-Hydroxy-2,6-dioxo-N-((1R,3S)-3-phenylcyclopentyl)-1,2,3,6-tetrahydropyrimidine-4-carboxamide

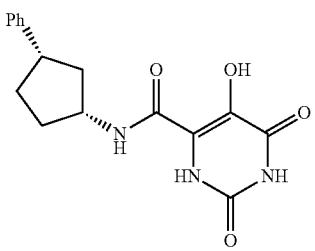 [SMILES: O=C(N[C@@H]1CC[C@H](c2ccccc2)C1)c1[nH]c(=O)[nH]c(=O)c1O]

To a reaction vial charged with Example 75 (10 mg, 0.032 mmol) in dioxane (0.8 mL) was added 1 N hydrogen chloride (0.795 mL, 0.795 mmol). The resulting mixture was stirred at 100° C. for 2 h. The reaction was cooled down to rt and the solvents were removed. The residue was dissolved in MeOH and DIEA (2 drops) and purified by Prep HPLC (0-100% B over 10 min, ACN/H$_2$O/0.1% TFA) to give Example 271 (9.0 mg, 0.028 mmol, 87% yield) as a white solid. LCMS=316.2 [M+H] RT=1.91 min (Method H); Orthogonal HPLC (150× 4.6 mm 3.5 um, 254 nm): Sunfire {RT=6.82 min, 98.8%, Method A}; Xbridge {RT=6.51 min, 96.8%, Method B).

Examples 272-298 were prepared according the procedures described for Example 271 by using the appropriate intermediates.

Example 299

(S)-5-(2-Hydroxyethoxy)-2,6-dioxo-N-(1,2,3,4-tetrahydronaphthalen-1-yl)-1,2,3,6-tetrahydropyrimidine-4-carboxamide

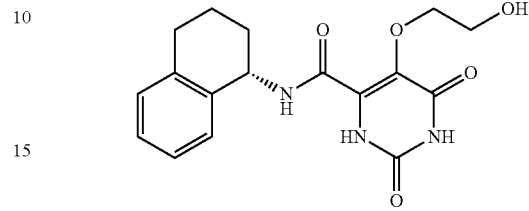

(S)-5-Fluoro-2,6-dioxo-N-(1,2,3,4-tetrahydronaphthalen-1-yl)-1,2,3,6-tetrahydropyrimidine-4-carboxamide (45.0 mg, 0.148 mmol) and potassium trimethylsilanolate (148 mg, 1.15 mmol) were stirred in diglyme (0.1 mL) at 120° C. for 16 h. After cooling, the reaction was quenched by adding 1 N HCl while cooling in an ice water bath. The mixture was purified by RP HPLC to give Example 299 (7.0 mg, 0.019 mmol, 13% yield). LC-MS (ESI) 346.2 (M+H), retention time=2.83 min (Method A).

The analytical data (mass, retention time, and conditions of LC-MS) of Examples 2-181, 182-192, 194-201, 204, 206-237, 242-266, and 272-298 are listed in Table 2.

TABLE 2

| Ex. No. | Structure | Name | LC-MS [M + 1]/RT | Purity (%) |
|---|---|---|---|---|
| 2 | 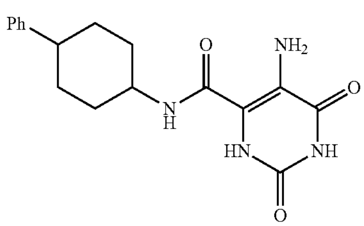 [SMILES: Nc1c(C(=O)NC2CCC(c3ccccc3)CC2)[nH]c(=O)[nH]c1=O] | 5-amino-2,6-dioxo-N-(4-phenylcyclohexyl)-1,2,3,6-tetrahydropyrimidine-4-carboxamide | 329.0/1.90 min (Method B) | RT = 7.50 min, 99.6% (Method A) RT = 6.99 min, 98.6% (Method B) |
| 3 | 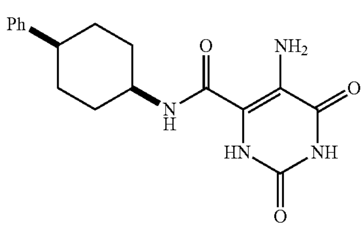 [SMILES: Nc1c(C(=O)N[C@H]2CC[C@@H](c3ccccc3)CC2)[nH]c(=O)[nH]c1=O] | 5-amino-2,6-dioxo-N-(cis-4-phenylcyclohexyl)-1,2,3,6-tetrahydropyrimidine-4-carboxamide | 329.3/1.86 min (Method B) | RT = 7.50 min, 100% (Method A) RT = 6.98 min, 100% (Method B) |
| 4 | 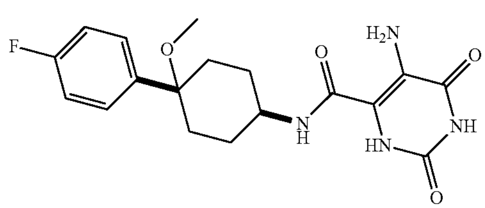 [SMILES: CO[C@]1(c2ccc(F)cc2)CC[C@@H](NC(=O)c2[nH]c(=O)[nH]c(=O)c2N)CC1] | 5-amino-N-(cis-4-(4-fluorophenyl)-4-methoxycyclohexyl)-2,6-dioxo-1,2,3,6-tetrahydropyrimidine-4-carboxamide | 377.3/1.77 min (Method B) | RT = 6.82 min, 99.2% (Method A) RT = 6.31 min, 99.0% (Method B) |

TABLE 2-continued

| Ex. No. | Structure | Name | LC-MS [M + 1]/RT | Purity (%) |
|---|---|---|---|---|
| 5 | 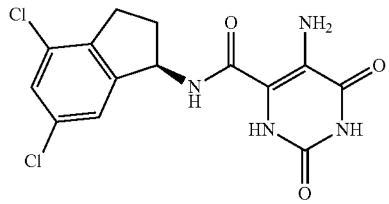 [SMILES: Nc1c(C(=O)N[C@@H]2CCc3c(Cl)cc(Cl)cc32)[nH]c(=O)[nH]c1=O] | (R)-5-amino-N-(4,6-dichloro-2,3-dihydro-1H-inden-1-yl)-2,6-dioxo-1,2,3,6-tetrahydropyrimidine-4-carboxamide | 355.0/2.49 min (Method G) | RT = 8.10 min, 98.8% (Method A) RT = 7.48 min, 96.6% (Method B) |
| 6 | 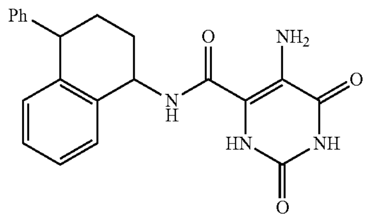 [SMILES: Nc1c(C(=O)NC2CCC(c3ccccc3)c3ccccc32)[nH]c(=O)[nH]c1=O] | 5-amino-2,6-dioxo-N-(4-phenyl-1,2,3,4-tetrahydronaphthalen-1-yl)-1,2,3,6-tetrahydropyrimidine-4-carboxamide | 377.1/2.03 min (Method B) | RT = 8.52 min, 100% (Method A) RT = 7.98 min, 100% (Method B) |
| 7 | 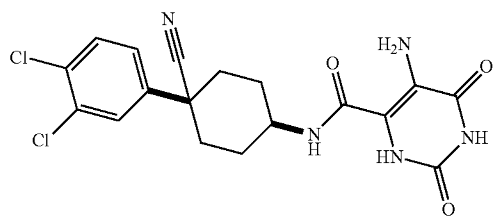 [SMILES: N#C[C@]1(c2ccc(Cl)c(Cl)c2)CC[C@@H](NC(=O)c2[nH]c(=O)[nH]c(=O)c2N)CC1] | 5-amino-N-(cis-4-cyano-4-(3,4-dichlorophenyl)cyclohexyl)-2,6-dioxo-1,2,3,6-tetrahydropyrimidine-4-carboxamide | 421.9/2.05 min (Method B) | RT = 8.29 min, 98.1% (Method A) RT = 7.80 min, 99.2% (Method B) |
| 8 | 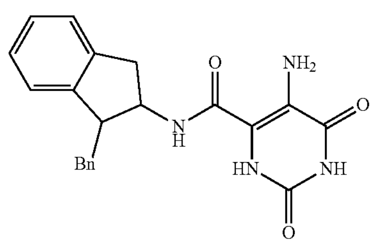 [SMILES: Nc1c(C(=O)NC2Cc3ccccc3C2Cc2ccccc2)[nH]c(=O)[nH]c1=O] | 5-amino-N-(1-benzyl-2,3-dihydro-1H-inden-2-yl)-2,6-dioxo-1,2,3,6-tetrahydropyrimidine-4-carboxamide | 377.1/2.03 min (Method F) | 98.2% |
| 9 | 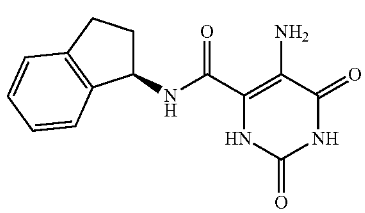 [SMILES: Nc1c(C(=O)N[C@@H]2CCc3ccccc32)[nH]c(=O)[nH]c1=O] | (R)-5-amino-N-(2,3-dihydro-1H-inden-1-yl)-2,6-dioxo-1,2,3,6-tetrahydropyrimidine-4-carboxamide | 287.1/1.32 min (Method F) | 97.7% |
| 10 | 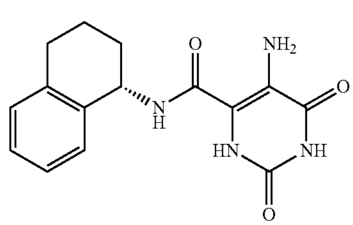 [SMILES: Nc1c(C(=O)N[C@H]2CCCc3ccccc32)[nH]c(=O)[nH]c1=O] | (S)-5-amino-2,6-dioxo-N-(1,2,3,4-tetrahydronaphthalen-1-yl)-1,2,3,6-tetrahydropyrimidine-4-carboxamide | 301.1/1.52 min (Method F) | 97.4% |
| 11 | 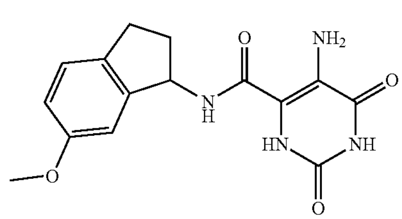 [SMILES: COc1ccc2c(c1)C(NC(=O)c1[nH]c(=O)[nH]c(=O)c1N)CC2] | 5-amino-N-(6-methoxy-2,3-dihydro-1H-inden-1-yl)-2,6-dioxo-1,2,3,6-tetrahydropyrimidine-4-carboxamide | 317.0/1.43 min (Method F) | 100% |

TABLE 2-continued

| Ex. No. | Structure | Name | LC-MS [M + 1]/RT | Purity (%) |
|---|---|---|---|---|
| 12 | 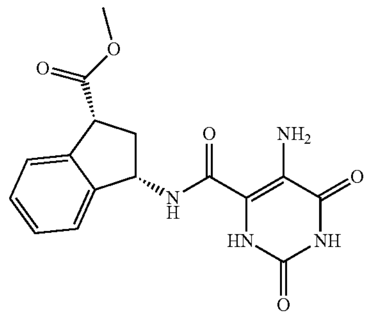 [SMILES: COC(=O)[C@@H]1C[C@H](NC(=O)c2[nH]c(=O)[nH]c(=O)c2N)c2ccccc21] | (1R,3S)-methyl 3-(5-amino-2,6-dioxo-1,2,3,6-tetrahydropyrimidine-4-carboxamido)-2,3-dihydro-1H-indene-1-carboxylate | 345.1/1.34 min (Method F) | 100% |
| 13 | 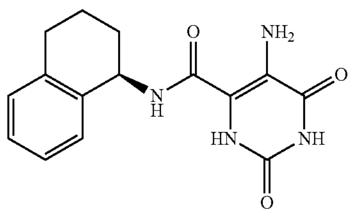 [SMILES: Nc1c(C(=O)N[C@@H]2CCCc3ccccc32)[nH]c(=O)[nH]c1=O] | (R)-5-amino-2,6-dioxo-N-(1,2,3,4-tetrahydronaphthalen-1-yl)-1,2,3,6-tetrahydropyrimidine-4-carboxamide | 301.1/1.51 min (Method F) | 100% |
| 14 | 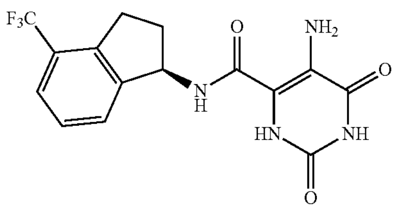 [SMILES: Nc1c(C(=O)N[C@@H]2CCc3c2cccc3C(F)(F)F)[nH]c(=O)[nH]c1=O] | (R)-5-amino-2,6-dioxo-N-(4-(trifluoromethyl)-2,3-dihydro-1H-inden-1-yl)-1,2,3,6-tetrahydropyrimidine-4-carboxamide | 355.1/2.36 min (Method G) | RT = 7.62 min, 98.2% (Method A) RT = 7.07 min, 99.2% (Method B) |
| 15 | 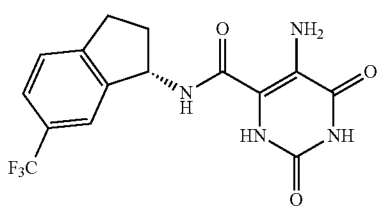 [SMILES: Nc1c(C(=O)N[C@H]2CCc3ccc(C(F)(F)F)cc32)[nH]c(=O)[nH]c1=O] | (S)-5-amino-2,6-dioxo-N-(6-(trifluoromethyl)-2,3-dihydro-1H-inden-1-yl)-1,2,3,6-tetrahydropyrimidine-4-carboxamide | 355.1/2.33 min (Method G) | RT = 7.52 min, 98.0% (Method A) RT = 6.96 min, 98.9% (Method B) |
| 16 | 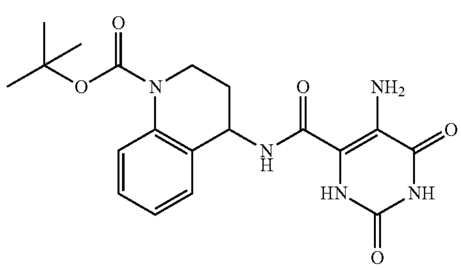 [SMILES: CC(C)(C)OC(=O)N1CCC(NC(=O)c2[nH]c(=O)[nH]c(=O)c2N)c2ccccc21] | tert-butyl 4-(5-amino-2,6-dioxo-1,2,3,6-tetrahydropyrimidine-4-carboxamido)-3,4-dihydroquinoline-1(2H)-carboxylate | 345.9 (M-tBu + H)/1.91 min (Method B) | RT = 4.12 min, 97.1% (Method A) RT = 4.83 min, 98.8% (Method B) |
| 17 | 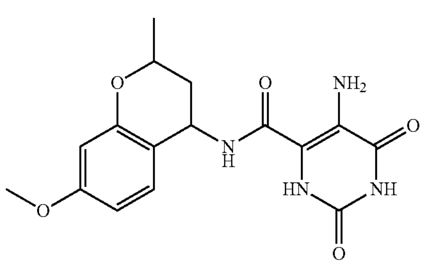 [SMILES: COc1ccc2c(c1)OC(C)CC2NC(=O)c1[nH]c(=O)[nH]c(=O)c1N] | 5-amino-N-(7-methoxy-2-methylchroman-4-yl)-2,6-dioxo-1,2,3,6-tetrahydropyrimidine-4-carboxamide | 347.1/1.92 min (Method G) | RT = 6.34 min, 97.6% (Method A) RT = 5.99 min, 99.3% (Method B) |

TABLE 2-continued

| Ex. No. | Structure | Name | LC-MS [M + 1]/RT | Purity (%) |
|---|---|---|---|---|
| 18 | (1:1 cis isomers) | 5-amino-2,6-dioxo-N-(cis-3-phenyl-2,3-dihydro-1H-inden-1-yl)-1,2,3,6-tetrahydropyrimidine-4-carboxamide | 363.3/1.97 min (Method B) | RT = 8.29 min, 97.7% (Method A) RT = 7.82 min, 99.0% (Method B) |
| 19 | 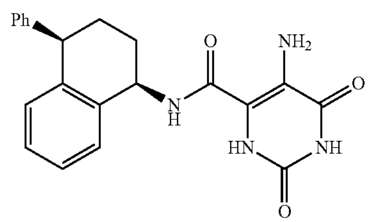 [SMILES: Nc1c(C(=O)N[C@@H]2CC[C@H](c3ccccc3)c3ccccc32)[nH]c(=O)[nH]c1=O] | 5-amino-2,6-dioxo-N-((1R,4R)-4-phenyl-1,2,3,4-tetrahydronaphthalen-1-yl)-1,2,3,6-tetrahydropyrimidine-4-carboxamide | 376/2.10 min (Method B) | RT = 8.62 min, 100% (Method A) RT = 8.10 min, 100% (Method B) |
| 20 | 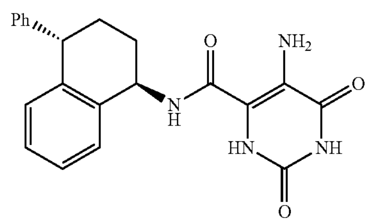 [SMILES: Nc1c(C(=O)N[C@@H]2CC[C@@H](c3ccccc3)c3ccccc32)[nH]c(=O)[nH]c1=O] | 5-amino-2,6-dioxo-N-((1R,4S)-4-phenyl-1,2,3,4-tetrahydronaphthalen-1-yl)-1,2,3,6-tetrahydropyrimidine-4-carboxamide | 399.3/2.01 min (M + Na, Method H) | RT = 8.50 min, 100% (Method A) RT = 8.04 min, 100% (Method B) |
| 21 | 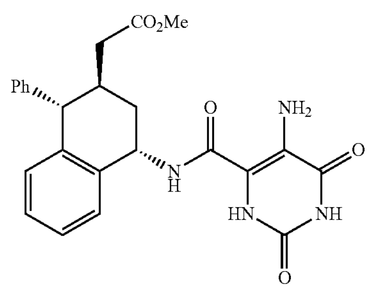 [SMILES: COC(=O)C[C@H]1C[C@H](NC(=O)c2[nH]c(=O)[nH]c(=O)c2N)c2ccccc2[C@@H]1c1ccccc1] | methyl 2-((1S,2R,4S)-4-(5-amino-2,6-dioxo-1,2,3,6-tetrahydropyrimidine-4-carboxamido)-1-phenyl-1,2,3,4-tetrahydronaphthalen-2-yl)acetate | 449.3/2.56 min (Method G) | RT = 8.50 min, 98.7% (Method A) RT = 8.05 min, 98% (Method B) |
| 22 | 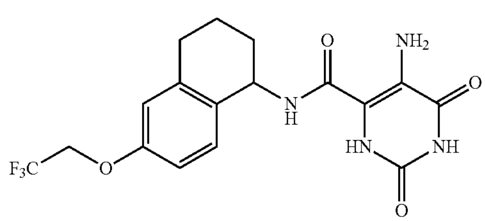 [SMILES: Nc1c(C(=O)NC2CCCc3cc(OCC(F)(F)F)ccc32)[nH]c(=O)[nH]c1=O] | 5-amino-2,6-dioxo-N-(6-(2,2,2-trifluoroethoxy)-1,2,3,4-tetrahydronaphthalen-1-yl)-1,2,3,6-tetrahydropyrimidine-4-carboxamide | 399.1/1.91 min (Method A) | RT = 8.17 min, 97.9% (Method A) RT = 7.73 min, 97.6% (Method B) |
| 23 | 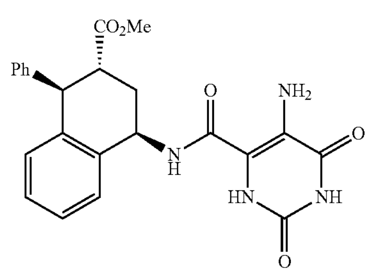 [SMILES: COC(=O)[C@@H]1C[C@@H](NC(=O)c2[nH]c(=O)[nH]c(=O)c2N)c2ccccc2[C@H]1c1ccccc1] | (1R,2R,4R)-methyl 4-(5-amino-2,6-dioxo-1,2,3,6-tetrahydropyrimidine-4-carboxamido)-1-phenyl-1,2,3,4-tetrahydronaphthalene-2-carboxylate | 435.1/1.82 min (Method B) | RT = 8.17 min, 97.9% (Method A) RT = 7.73 min, 96.6% (Method B) |

TABLE 2-continued

| Ex. No. | Structure | Name | LC-MS [M + 1]/RT | Purity (%) |
|---|---|---|---|---|
| 24 | 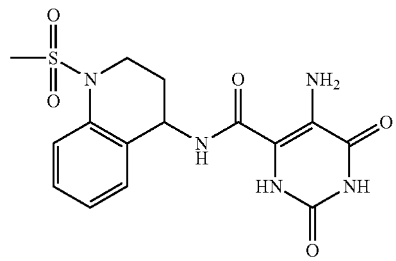 [SMILES: CS(=O)(=O)N1CCC(NC(=O)c2[nH]c(=O)[nH]c(=O)c2N)c2ccccc21] | 5-amino-N-(1-(methylsulfonyl)-1,2,3,4-tetrahydroquinolin-4-yl)-2,6-dioxo-1,2,3,6-tetrahydropyrimidine-4-carboxamide | 380.1/1.67 min (Method B) | RT = 5.48 min, 94.5% (Method A) RT = 5.31 min, 96.8% (Method B) |
| 25 | 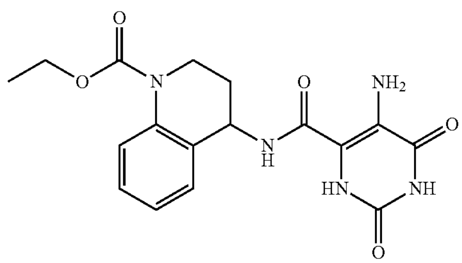 [SMILES: CCOC(=O)N1CCC(NC(=O)c2[nH]c(=O)[nH]c(=O)c2N)c2ccccc21] | ethyl 4-(5-amino-2,6-dioxo-1,2,3,6-tetrahydropyrimidine-4-carboxamido)-3,4-dihydroqiiinoline-1(2H)-carboxylate | 378/1.14 min (Method B) | RT = 6.28 min, 97.4% (Method A) RT = 5.93 min, 98.9% (Method B) |
| 26 | 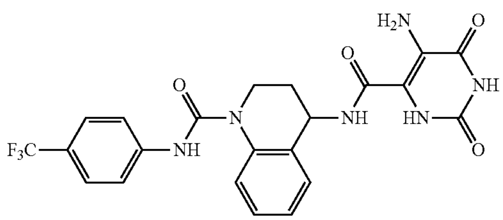 [SMILES: Nc1c(C(=O)NC2CCN(C(=O)Nc3ccc(C(F)(F)F)cc3)c3ccccc32)[nH]c(=O)[nH]c1=O] | 4-(5-amino-2,6-dioxo-1,2,3,6-tetrahydropyrimidine-4-carboxamido)-N-(4-(trifluoromethyl)phenyl)-3,4-dihydroquinoline-1(2H)-carboxamide | 449.1/1.43 min (Method B) | RT = 8.37 min, 94.3% (Method A) RT = 7.84 min, 92.5% (Method B) |
| 27 | 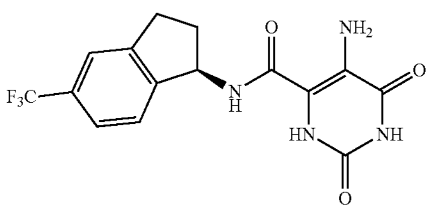 [SMILES: Nc1c(C(=O)N[C@@H]2CCc3cc(C(F)(F)F)ccc32)[nH]c(=O)[nH]c1=O] | (R)-5-amino-2,6-dioxo-N-(5-(trifluoromethyl)-2,3-dihydro-1H-inden-1-yl)-1,2,3,6-tetrahydropyrimidine-4-carboxamide | 355.1/2.39 min (Method B) | RT = 7.04 min, 100% (Method A) RT = 6.39 min, 99.5% (Method B) |
| 28 | 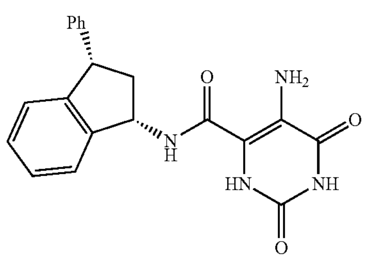 [SMILES: Nc1c(C(=O)N[C@H]2C[C@@H](c3ccccc3)c3ccccc32)[nH]c(=O)[nH]c1=O] | 5-amino-2,6-dioxo-N-((1S,3S)-3-phenyl-2,3-dihydro-1H-inden-1-yl)-1,2,3,6-tetrahydropyrimidine-4-carboxamide | 363.3/3.53 min (Method J) | RT = 7.93 min, 96.8% (Method A) RT = 7.21 min, 96.9% (Method B) |
| 29 | 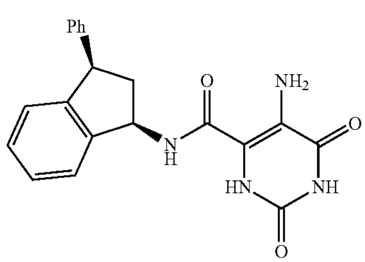 [SMILES: Nc1c(C(=O)N[C@@H]2C[C@H](c3ccccc3)c3ccccc32)[nH]c(=O)[nH]c1=O] | 5-amino-2,6-dioxo-N-((1R,3S)-3-phenyl-2,3-dihydro-1H-inden-1-yl)-1,2,3,6-tetrahydropyrimidine-4-carboxamide | 363.3/3.53 min (Method J) | RT = 7.93 min, 98.8% (Method A) RT = 7.18 min, 99.1% (Method B) |

TABLE 2-continued

| Ex. No. | Structure | Name | LC-MS [M + 1]/RT | Purity (%) |
|---|---|---|---|---|
| 30 | 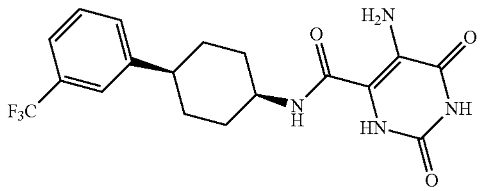 [SMILES: Nc1c(C(=O)N[C@H]2CC[C@@H](c3cccc(C(F)(F)F)c3)CC2)[nH]c(=O)[nH]c1=O] | 5-amino-2,6-dioxo-N-(cis-4-(3-(trifluoromethyl)phenyl)cyclohexyl)-1,2,3,6-tetrahydropyrimidine-4-carboxamide | 397/1.99 min (Method B) | RT = 8.82 min, 94.4% (Method A) RT = 8.10 min, 95.0% (Method B) |
| 31 | 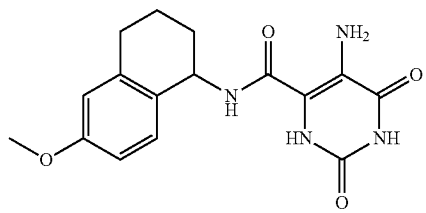 [SMILES: COc1ccc2c(c1)CCCC2NC(=O)c1[nH]c(=O)[nH]c(=O)c1N] | 5-amino-N-(6-methoxy-1,2,3,4-tetrahydronaphthalen-1-yl)-2,6-dioxo-1,2,3,6-tetrahydropyrimidine-4-carboxamide | 331/1.66 min (Method B) | RT = 6.55 min, 95.3% (Method A) RT = 6.16 min, 99.3% (Method B) |
| 32 | 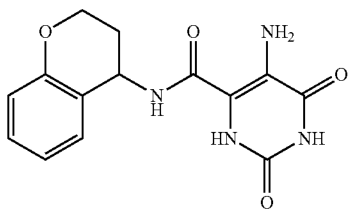 [SMILES: Nc1c(C(=O)NC2CCOc3ccccc32)[nH]c(=O)[nH]c1=O] | 5-amino-N-(chroman-4-yl)-2,6-dioxo-1,2,3,6-tetrahydropyrimidine-4-carboxamide | 303/1.46 min (Method B) | RT = 5.61 min, 89.2% (Method A) RT = 5.29 min, 99.5% (Method B) |
| 33 | 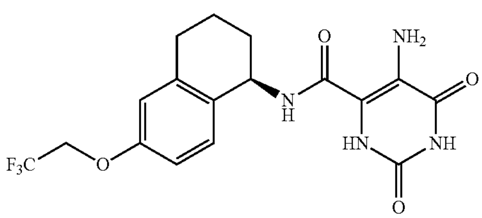 | (R)-5-amino-2,6-dioxo-N-(6-(2,2,2-trifluoroethoxy)-1,2,3,4-tetrahydronaphthalen-1-yl)-1,2,3,6-tetrahydropyrimidine-4-carboxamide | 399/3.34 min (Method G) | RT = 8.06 min, 99% (Method A) RT = 7.57 min, 100% (Method B) |
| 34 | 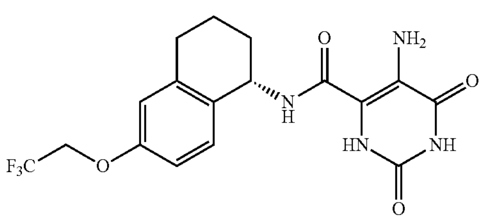 [SMILES: Nc1c(C(=O)N[C@H]2CCCc3cc(OCC(F)(F)F)ccc32)[nH]c(=O)[nH]c1=O] | (S)-5-amino-2,6-dioxo-N-(6-(2,2,2-trifluoroethoxy)-1,2,3,4-tetrahydronaphthalen-1-yl)-1,2,3,6-tetrahydropyrimidine-4-carboxamide | 399/1.90 min (Method B) | RT = 8.06 min, 98.5% (Method A) RT = 7.57 min, 100% (Method B) |
| 35 | 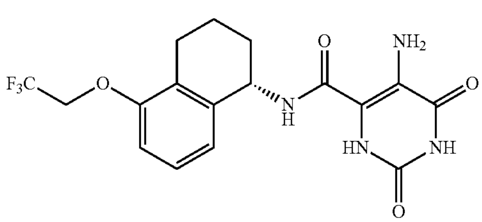 [SMILES: Nc1c(C(=O)N[C@H]2CCCc3c(OCC(F)(F)F)cccc32)[nH]c(=O)[nH]c1=O] | (S)-5-amino-2,6-dioxo-N-(5-(2,2,2-trifluoroethoxy)-1,2,3,4-tetrahydronaphthalen-1-yl)-1,2,3,6-tetrahydropyrimidine-4-carboxamide | 399/1.88 min (Method B) | RT = 8.11 min, 95.7% (Method A) RT = 7.59 min, 98.8% (Method B) |
| 36 | 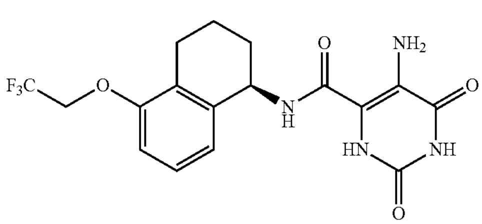 [SMILES: Nc1c(C(=O)N[C@@H]2CCCc3c(OCC(F)(F)F)cccc32)[nH]c(=O)[nH]c1=O] | (R)-5-amino-2,6-dioxo-N-(5-(2,2,2-trifluoroethoxy)-1,2,3,4-tetrahydronaphthalen-1-yl)-1,2,3,6-tetrahydropyrimidine-4-carboxamide | 399/1.90 min (Method B) | RT = 8.08 min, 95.7% (Method A) RT = 7.58 min, 98.8% (Method B) |

TABLE 2-continued

| Ex. No. | Structure | Name | LC-MS [M + 1]/RT | Purity (%) |
|---|---|---|---|---|
| 37 | Isomer A | 5-amino-N-((1R)-4-(3,4-dichlorophenyl)-1,2,3,4-tetrahydronaphthalen-1-yl)-2,6-dioxo-1,2,3,6-tetrahydropyrimidine-carboxamide | 445.0/3.09 min (Method G) | RT = 10.02 min, 100% (Method A) RT = 9.20 min, 99.5% (Method B) |
| 38 | Isomer B | 5-amino-N-((1R)-4-(3,4-dichlorophenyl)-1,2,3,4-tetrahydronaphthalen-1-yl)-2,6-dioxo-1,2,3,6-tetrahydropyrimidine-carboxamide | 467.2 (M + Na)/ 2.15 min (Method B) | RT = 10.21 min, 91.7% (Method A) RT = 9.29 min, 93.8% (Method B) |
| 39 | 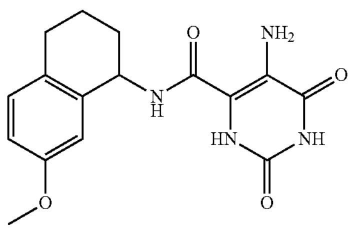 [SMILES: COc1ccc2c(c1)C(NC(=O)c1[nH]c(=O)[nH]c(=O)c1N)CCC2] | 5-amino-N-(7-methoxy-1,2,3,4-tetrahydronaphthalen-1-yl)-2,6-dioxo-1,2,3,6-tetrahydropyrimidine-4-carboxamide | 331/1.67 min (Method B) | RT = 9.81 min, 97.2% (Method A) RT = 8.92 min, 95.2% (Method B) |
| 40 | 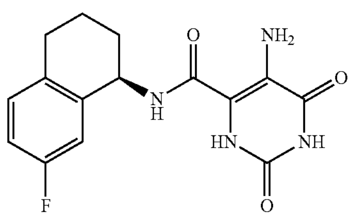 [SMILES: Nc1c(C(=O)N[C@@H]2CCCc3ccc(F)cc32)[nH]c(=O)[nH]c1=O] | (R)-5-amino-N-(7-fluoro-1,2,3,4-tetrahydronaphthalen-1-yl)-2,6-dioxo-1,2,3,6-tetrahydropyrimidine-4-carboxamide | 319/1.71 min (Method B) | RT = 6.85 min, 96% (Method A) RT = 6.41 min, 99% (Method B) |
| 41 | 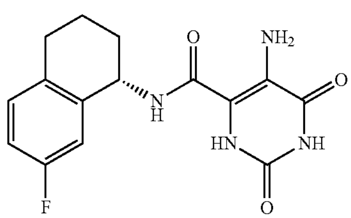 [SMILES: Nc1c(C(=O)N[C@H]2CCCc3ccc(F)cc32)[nH]c(=O)[nH]c1=O] | (S)-5-amino-N-(7-fluoro-1,2,3,4-tetrahydronaphthalen-1-yl)-2,6-dioxo-1,2,3,6-tetrahydropyrimidine-4-carboxamide | 319/1.71 min (Method B) | RT = 6.85 min, 99% (Method A) RT = 6.41 min, 99% (Method B) |
| 42 | 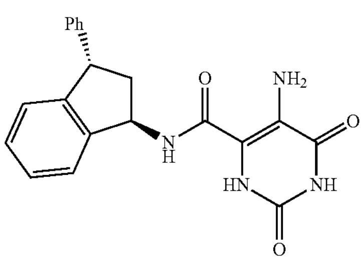 [SMILES: Nc1c(C(=O)N[C@@H]2C[C@@H](c3ccccc3)c3ccccc32)[nH]c(=O)[nH]c1=O] | 5-amino-2,6-dioxo-N-((1R,3S)-3-phenyl-2,3-dihydro-1H-inden-1-yl)-1,2,3,6-tetrahydropyrimidine-4-carboxamide | 363.3/1.99 min (Method B) | RT = 8.06 min, 99.2% (Method A) RT = 7.65 min, 99.1% (Method B) |

TABLE 2-continued

| Ex. No. | Structure | Name | LC-MS [M + 1]/RT | Purity (%) |
|---|---|---|---|---|
| 43 | 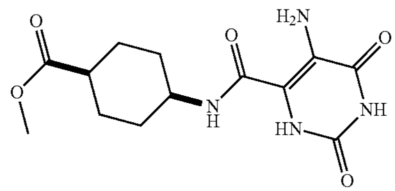 [SMILES: COC(=O)[C@H]1CC[C@@H](NC(=O)c2[nH]c(=O)[nH]c(=O)c2N)CC1] | cis-methyl 4-(5-amino-2,6-dioxo-1,2,3,6-tetrahydropyrimidine-4-carboxamido)cyclohexanecarboxylate | 311.2/1.04 min (Method B) | RT = 4.64 min, 100% (Method A) RT = 4.32 min, 100% (Method B) |
| 44 | 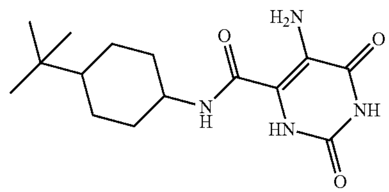 [SMILES: CC(C)(C)C1CCC(NC(=O)c2[nH]c(=O)[nH]c(=O)c2N)CC1] | 5-amino-N-(4-tert-butylcyclohexyl)-2,6-dioxo-1,2,3,6-tetrahydropyrimidine-4-carboxamide | 309.3/1.49 min (Method D) | RT = 8.22 min, 91.5% (Method A) RT = 7.33 min, 97.5% (Method B) |
| 45 | 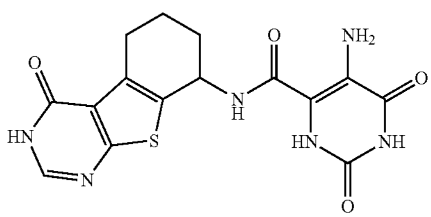 [SMILES: Nc1c(C(=O)NC2CCCc3c2sc2nc[nH]c(=O)c32)[nH]c(=O)[nH]c1=O] | 5-amino-2,6-dioxo-N-(4-oxo-1,4,5,6,7,8-hexahydro[1]benzothieno[2,3-d]pyrimidin-8-yl)-1,2,3,6-tetrahydro-4-pyrimidinecarboxamide | 375.0/1.50 min (Method D) | 94.9 |
| 46 | 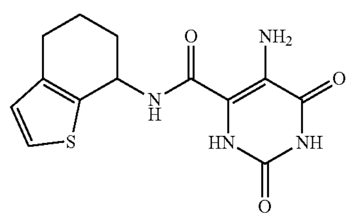 [SMILES: Nc1c(C(=O)NC2CCCc3ccsc32)[nH]c(=O)[nH]c1=O] | 5-amino-2,6-dioxo-N-(4,5,6,7-tetrahydrobenzo[b]thiophen-7-yl)-1,2,3,6-tetrahydropyrimidine-4-carboxamide | 307.2/2.98 min (Method J) | 97.6 |
| 47 | 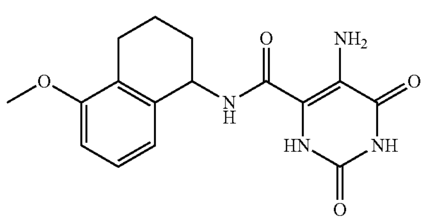 [SMILES: COc1cccc2c1CCCC2NC(=O)c1[nH]c(=O)[nH]c(=O)c1N] | 5-amino-N-(5-methoxy-1,2,3,4-tetrahydronaphthalen-1-yl)-2,6-dioxo 1,2,3,6-tetrahydropyrimidine-4-carboxamide | 331/1.74 min (Method B) | RT = 6.85 min, 96% (Method A) RT = 6.41 min, 99% (Method B) |
| 48 | 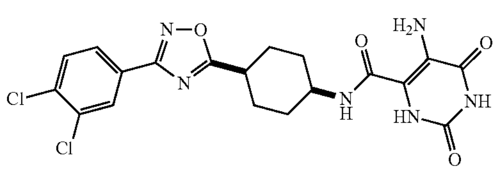 [SMILES: Nc1c(C(=O)N[C@H]2CC[C@@H](c3nc(-c4ccc(Cl)c(Cl)c4)no3)CC2)[nH]c(=O)[nH]c1=O] | 5-amino-N-(cis-4-(3-(3,4-dichlorophenyl)-1,2,4-oxadiazol-5-yl)cyclohexyl)-2,6-dioxo-1,2,3,6-tetrahydropyrimidine-4-carboxamide | 465.2/2.13 min (Method B) | RT = 9.11 min, 86% (Method A) RT = 8.11 min, 83.9% (Method B) |
| 49 | 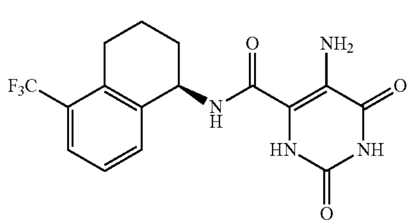 | (R)-5-amino-2,6-dioxo-N-(5-(trifluoromethyl)-1,2,3,4-tetrahydronaphthalen-1-yl)-1,2,3,6-tetrahydropyrimidine-4-carboxamide | 369/1.95 min (Method B) | RT = 8.00 min, 99% (Method A) RT = 7.40 min, 97% (Method B) |

TABLE 2-continued

| Ex. No. | Structure | Name | LC-MS [M + 1]/RT | Purity (%) |
|---|---|---|---|---|
| 50 | 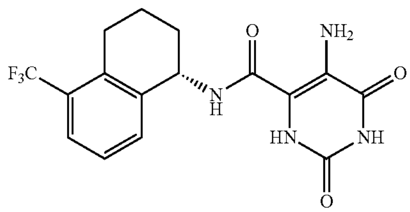 | (S)-5-amino-2,6-dioxo-N-(5-(trifluoromethyl)-1,2,3,4-tetrahydronaphthalen-1-yl)-1,2,3,6-tetrahydropyrimidine-4-carboxamide | 369/1.95 min (Method B) | RT = 8.01 min, 99% (Method A) RT = 7.42 min, 96% (Method B) |
| 51 | 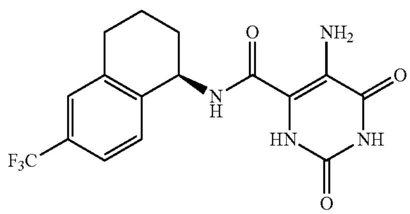 [SMILES: Nc1c(C(=O)N[C@@H]2CCCc3cc(C(F)(F)F)ccc32)[nH]c(=O)[nH]c1=O] | (R)-5-amino-2,6-dioxo-N-(6-(trifluoromethyl)-1,2,3,4-tetrahydronaphthalen-1-yl)-1,2,3,6-tetrahydropyrimidine-4-carboxamide | 369.1/2.48 min (Method G) | RT = 8.11 min, 99.1% (Method A) RT = 7.52 min, 99.6% (Method B) |
| 52 | 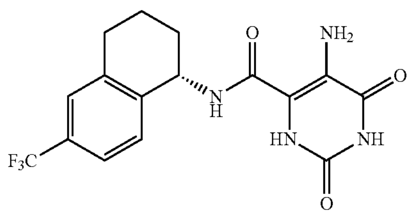 [SMILES: Nc1c(C(=O)N[C@H]2CCCc3cc(C(F)(F)F)ccc32)[nH]c(=O)[nH]c1=O] | (S)-5-amino-2,6-dioxo-N-(6-(trifluoromethyl)-1,2,3,4-tetrahydronaphthalen-1-yl)-1,2,3,6-tetrahydropyrimidine-4-carboxamide | 369.2/2.48 min (Method G) | RT = 8.11 min, 99.1% (Method A) RT = 7.52 min, 99.7% (Method B) |
| 53 | 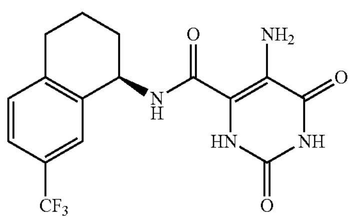 [SMILES: Nc1c(C(=O)N[C@@H]2CCCc3ccc(C(F)(F)F)cc32)[nH]c(=O)[nH]c1=O] | (R)-5-amino-2,6-dioxo-N-(7-(trifluoromethyl)-1,2,3,4-tetrahydronaphthalen-1-yl)-1,2,3,6-tetrahydropyrimidine-4-carboxamide | 369/1.90 min (Method B) | RT = 7.74 min, 97% (Method A) RT = 7.16 min, 97% (Method B) |
| 54 | 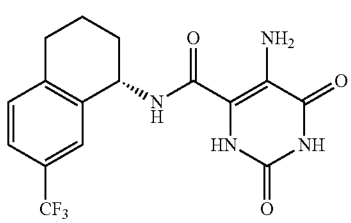 [SMILES: Nc1c(C(=O)N[C@H]2CCCc3ccc(C(F)(F)F)cc32)[nH]c(=O)[nH]c1=O] | (S)-5-amino-2,6-dioxo-N-(7-(trifluoromethyl)-1,2,3,4-tetrahydronaphthalen-1-yl)-1,2,3,6-tetrahydropyrimidine-4-carboxamide | 369/1.88 min (Method B) | RT = 7.72 min, 97% (Method A) RT = 7.14 min, 99% (Method B) |
| 55 | 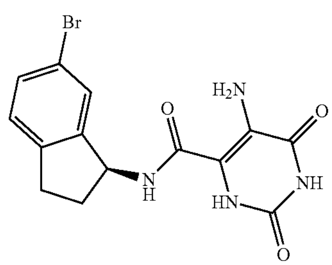 [SMILES: Nc1c(C(=O)N[C@H]2CCc3ccc(Br)cc32)[nH]c(=O)[nH]c1=O] | (S)-5-amino-N-(6-bromo-2,3-dihydro-1H-inden-1-yl)-2,6-dioxo-1,2,3,6-tetrahydropyrimidine-4-carboxamide | 364.9/1.93 (Method K) | 97.1 |
| 56 | 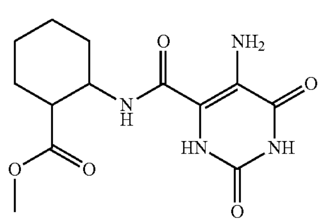 [SMILES: COC(=O)C1CCCCC1NC(=O)c1[nH]c(=O)[nH]c(=O)c1N] | methyl 2-(5-amino-2,6-dioxo-1,2,3,6-tetrahydropyrimidine-4-carboxamido)cyclohexanecarboxylate | 311.1/1.51 (Method K) | 95.5 |

TABLE 2-continued

| Ex. No. | Structure | Name | LC-MS [M + 1]/RT | Purity (%) |
|---|---|---|---|---|
| 57 | 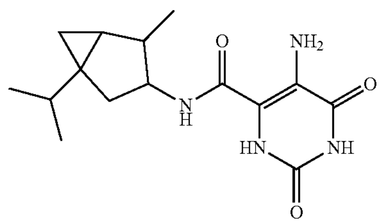 [SMILES: CC1C(NC(=O)c2[nH]c(=O)[nH]c(=O)c2N)CC2(C(C)C)CC12] | 5-amino-N-(1-isopropyl-4-methylbicyclo[3.1.0]hexan-3-yl)2,6-dioxo-1,2,3,6-tetrahydropyrimidine-4-carboxamide | 307.1./2.15 (Method K) | 97.2 |
| 58 | 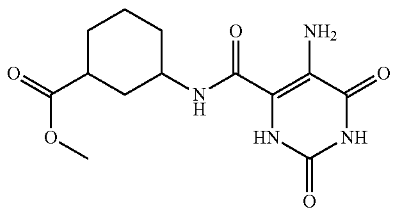 [SMILES: COC(=O)C1CCCC(NC(=O)c2[nH]c(=O)[nH]c(=O)c2N)C1] | methyl 3-(5-amino-2,6-dioxo-1,2,3,6-tetrahydropyrimidine-4-carboxamido)cyclohexanecarboxylate | 311.1/1.46 (Method K) | 98.7 |
| 59 | 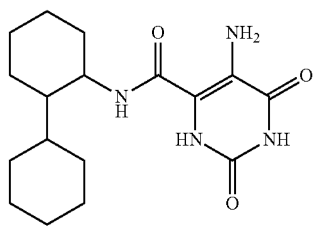 [SMILES: Nc1c(C(=O)NC2CCCCC2C2CCCCC2)[nH]c(=O)[nH]c1=O] | 5-amino-N-(bi(cyclohexan)-2-yl)-2,6-dioxo-1,2,3,6-tetrahydropyrimidine-4-carboxamide | 335.1/2.45 (Method K) | 100 |
| 60 | 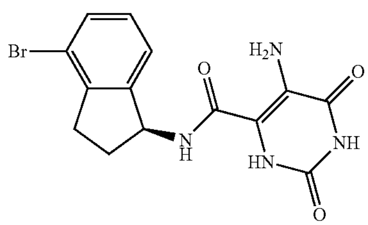 [SMILES: Nc1c(C(=O)N[C@H]2CCc3c(Br)cccc32)[nH]c(=O)[nH]c1=O] | (S)-5-amino-N-(4-bromo-2,3-dihydro-1H-inden-1-yl)-2,6-dioxo-1,2,3,6-tetrahydropyrimidine-4-carboxamide | 364.9/1.96 (Method K) | 100 |
| 61 | 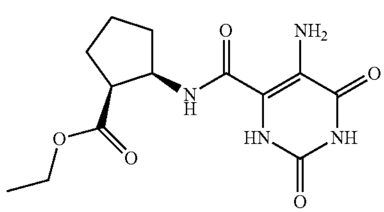 [SMILES: CCOC(=O)[C@H]1CCC[C@H]1NC(=O)c1[nH]c(=O)[nH]c(=O)c1N] | (1S,2R)-ethyl 2-(5-amino-2,6-dioxo-1,2,3,6-tetrahydropyrimidine-4-carboxamido)cyclopentanecarboxylate | 311.1/1.54 (Method K) | 96.2 |
| 62 | 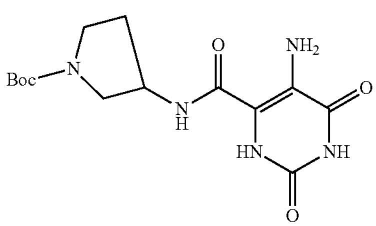 [SMILES: CC(C)(C)OC(=O)N1CCC(NC(=O)c2[nH]c(=O)[nH]c(=O)c2N)C1] | tert-butyl 3-(5-amino-2,6-dioxo-1,2,3,6-tetrahydropyrimidine-4-carboxamido)pyrrolidine-1-carboxylate | 240.2/1.66 (Method K) | 93.2 |
| 63 | 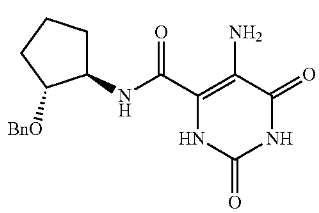 [SMILES: Nc1c(C(=O)N[C@@H]2CCC[C@H]2OCc2ccccc2)[nH]c(=O)[nH]c1=O] | 5-amino-N-((1R,2R)-2-(benzyloxy)cyclopentyl)-2,6-dioxo-1,2,3,6-tetrahydropyrimidine-4-carboxamide | 345.1/1.86 (Method K) | 95.4 |

TABLE 2-continued

| Ex. No. | Structure | Name | LC-MS [M + 1]/RT | Purity (%) |
|---|---|---|---|---|
| 64 | 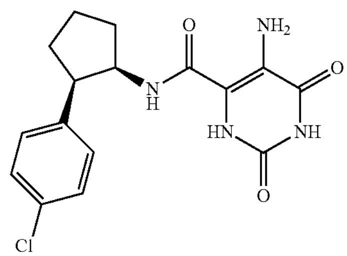 [SMILES: Nc1c(C(=O)N[C@@H]2CCC[C@@H]2c2ccc(Cl)cc2)[nH]c(=O)[nH]c1=O] | 5-amino-N-((1R,2R)-2-(4-chlorophenyl)cyclopentyl)-2,6-dioxo-1,2,3,6-tetrahydropyrimidine-carboxamide | 349.0/2.11 (Method K) | 92.2 |
| 65 | 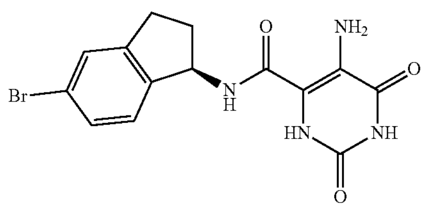 [SMILES: Nc1c(C(=O)N[C@@H]2CCc3cc(Br)ccc32)[nH]c(=O)[nH]c1=O] | (R)-5-amino-N-(5-bromo-2,3-dihydro-1H-inden-1-yl)-2,6-dioxo-1,2,3,6-tetrahydropyrimidine-4-carboxamide | 364.9/1.93 (Method K) | 92.6 |
| 66 | 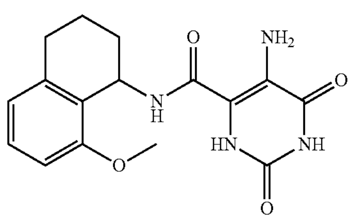 [SMILES: COc1cccc2c1C(NC(=O)c1[nH]c(=O)[nH]c(=O)c1N)CCC2] | 5-amino-N-(8-methoxy-1,2,3,4-tetrahydronaphthalen-1-yl)-2,6-dioxo-1,2,3,6-tetrahydropyrimidine-4-carboxamide | 331/1.15 (Method B) | RT = 5.98 min, 90% (Method A) RT = 5.76 min, 94% (Method B) |
| 67 | 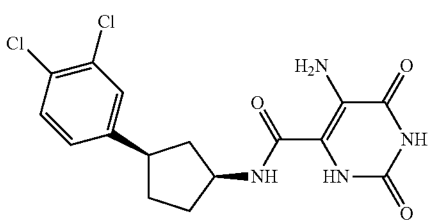 [SMILES: Nc1c(C(=O)N[C@H]2CC[C@@H](c3ccc(Cl)c(Cl)c3)C2)[nH]c(=O)[nH]c1=O] | 5-amino-N-((1S,3R)-3-(3,4-dichlorophenyl)cyclopentyl)-2,6-dioxo-1,2,3,6-tetrahydropyrimidine-4-carboxamide | 383.0/2.07 (Method B) | RT = 8.95 min, 99.5% (Method A) RT = 8.25 min, 100% (Method B) |
| 68 | 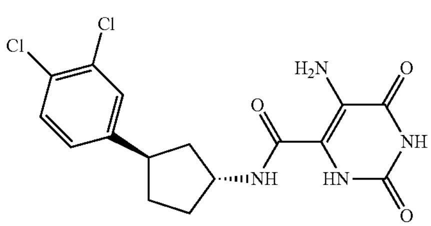 [SMILES: Nc1c(C(=O)N[C@@H]2CC[C@@H](c3ccc(Cl)c(Cl)c3)C2)[nH]c(=O)[nH]c1=O] | 5-amino-N-((1R,3R)-3-(3,4-dichlorophenyl)cyclopentyl)-2,6-dioxo-1,2,3,6-tetrahydropyrimidine-4-carboxamide | 383.0/2.03 (Method B) | RT = 9.00 min, 99.1% (Method A) RT = 8.28 min, 99.2% (Method B) |
| 69 | 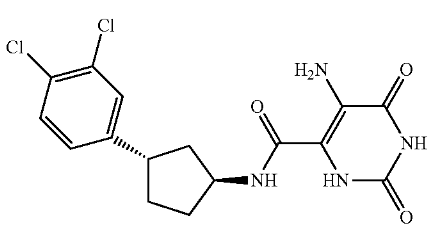 [SMILES: Nc1c(C(=O)N[C@H]2CC[C@H](c3ccc(Cl)c(Cl)c3)C2)[nH]c(=O)[nH]c1=O] | 5-amino-N-((1S,3S)-3-(3,4-dichlorophenyl)cyclopentyl)-2,6-dioxo-1,2,3,6-tetrahydropyrimidine-4-carboxamide | 383.1/2.03 (Method B) | RT = 8.96 min, 94.0% (Method A) RT = 8.26 min, 100% (Method B) |
| 70 | 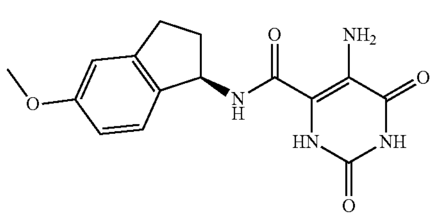 [SMILES: COc1ccc2c(c1)CC[C@H]2NC(=O)c1[nH]c(=O)[nH]c(=O)c1N] | (R)-5-amino-N-(5-methoxy-2,3-dihydro-1H-inden-1-yl)-2,6-dioxo-1,2,3,6-tetrahydropyrimidine-4-carboxamide | 317/1.55 (Method B) | RT = 5.87 min, 94% (Method A) RT = 5.50 min, 99% (Method B) |

TABLE 2-continued

| Ex. No. | Structure | Name | LC-MS [M + 1]/RT | Purity (%) |
|---|---|---|---|---|
| 71 | 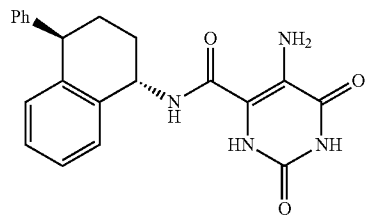 [SMILES: Nc1c(C(=O)N[C@H]2CC[C@H](c3ccccc3)c3ccccc32)[nH]c(=O)[nH]c1=O] | 5-amino-2,6-dioxo-N-((1S,4R)-4-phenyl-1,2,3,4-tetrahydronaphthalen-1-yl)-1,2,3,6-tetrahydropyrimidine-4-carboxamide | 399.2/2.05 (Method B) | RT = 8.34 min, 92.4% (Method A) RT = 7.84 min, 92.4% (Method B) |
| 72 | Isomer A | 5-amino-N-(6-methoxy-2,3-dihydro-1H-inden-1-yl)-2,6-dioxo-1,2,3,6-tetrahydropyrimidine-4-carboxamide | 317.1/1.65 (Method B) | RT = 6.05 min, 95.6% (Method A) RT = 5.71 min, 99.2% (Method B) |
| 73 | Isomer B | 5-amino-N-(6-methoxy-2,3-dihydro-1H-inden-1-yl)-2,6-dioxo-1,2,3,6-tetrahydropyrimidine-4-carboxamide | 317.1/1.65 (Method B) | RT = 6.04 min, 96.5% (Method A) RT = 5.71 min, 98.9% (Method B) |
| 74 | 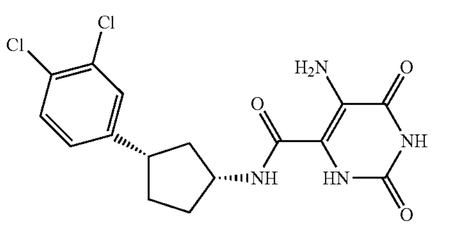 [SMILES: Nc1c(C(=O)N[C@@H]2CC[C@H](c3ccc(Cl)c(Cl)c3)C2)[nH]c(=O)[nH]c1=O] | 5-amino-N-((1R,3S)-3-(3,4-dichlorophenyl)cyclopentyl)-2,6-dioxo-1,2,3,6-tetrahydropyrimidine-4-carboxamide | 383.1/2.03 (Method B) | RT = 8.39 min, 99.4% (Method A) RT = 7.74 min, 99.6% (Method B) |
| 75 | 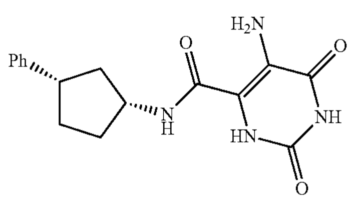 [SMILES: Nc1c(C(=O)N[C@@H]2CC[C@H](c3ccccc3)C2)[nH]c(=O)[nH]c1=O] | 5-amino-2,6-dioxo-N-((1R,3S)-3-phenylcyclopentyl)-1,2,3,6-tetrahydropyrimidine-4-carboxamide | 315.1/1.81 (Method H) | RT = 6.47 min, 99.5% (Method A) RT = 6.05 min, 100% (Method B) |
| 76 | 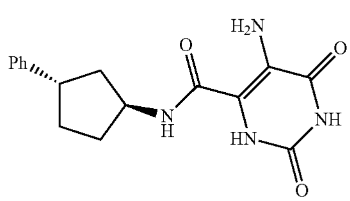 [SMILES: Nc1c(C(=O)N[C@H]2CC[C@H](c3ccccc3)C2)[nH]c(=O)[nH]c1=O] | 5-amino-2,6-dioxo-N-((1S,3S)-3-phenylcyclopentyl)-1,2,3,6-tetrahydropyrimidine-4-carboxamide | 315.1/1.79 (Method H) | RT = 6.44 min, 100% (Method A) RT = 6.03 min, 100% (Method B) |
| 77 | 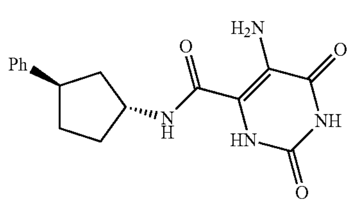 [SMILES: Nc1c(C(=O)N[C@@H]2CC[C@@H](c3ccccc3)C2)[nH]c(=O)[nH]c1=O] | 5-amino-2,6-dioxo-N-((1R,3R)-3-phenylcyclopentyl)-1,2,3,6-tetrahydropyrimidine-4-carboxamide | 315.1/3.18 (Method A) | RT = 10.41 min, 96.1% (Method A) RT = 11.01 min, 98.0% (Method B) |

TABLE 2-continued

| Ex. No. | Structure | Name | LC-MS [M + 1]/RT | Purity (%) |
|---|---|---|---|---|
| 78 | 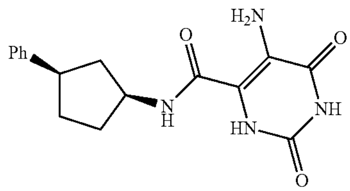 [SMILES: Nc1c(C(=O)N[C@H]2CC[C@@H](c3ccccc3)C2)[nH]c(=O)[nH]c1=O] | 5-amino-2,6-dioxo-N-((1S,3R)-3-phenylcyclopentyl)-1,2,3,6-tetrahydropyrimidine-4-carboxamide | 315.1/1.85 (Method H) | RT = 10.43 min, 99.3% (Method A) RT = 11.03 min, 99.4% (Method B) |
| 79 | 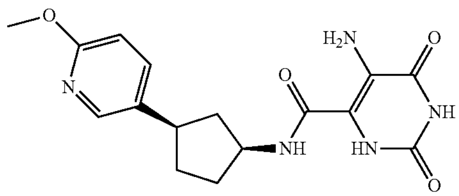 [SMILES: COc1ccc([C@@H]2CC[C@H](NC(=O)c3[nH]c(=O)[nH]c(=O)c3N)C2)cn1] | 5-amino-N-((1S,3R)-3-(6-methoxypyridin-3-yl)cyclopentyl)-2,6-dioxo-1,2,3,6-tetrahydropyrimidine-4-carboxamide | 346.2/1.23 (Method B) | RT = 4.57 min, 99.3% (Method A) RT = 5.23 min, 99.2% (Method B) |
| 80 | 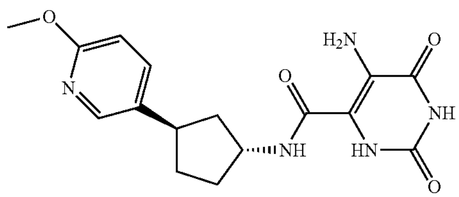 [SMILES: COc1ccc([C@@H]2CC[C@@H](NC(=O)c3[nH]c(=O)[nH]c(=O)c3N)C2)cn1] | 5-amino-N-((1R,3R)-3-(6-methoxypyridin-3-yl)cyclopentyl)-2,6-dioxo-1,2,3,6-tetrahydropyrimidine-4-carboxamide | 346.2/1.24 (Method B) | RT = 4.62 min, 99.4% (Method A) RT = 5.27 min, 99.8% (Method B) |
| 81 | 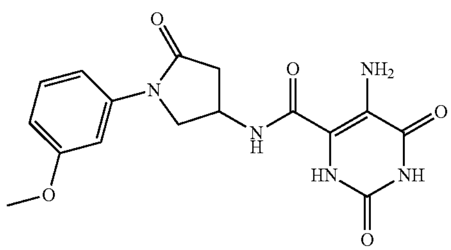 [SMILES: COc1cccc(N2CC(NC(=O)c3[nH]c(=O)[nH]c(=O)c3N)CC2=O)c1] | 5-amino-N-(1-(3-methoxyphenyl)-5-oxopyrrolidin-3-yl)-2,6-dioxo-1,2,3,6-tetrahydropyrimidine-4-carboxamide | 360.1/1.33 (Method A) | RT = 4.89 min, 94% (Method A) RT = 4.76 min, 96% (Method B) |
| 82 | 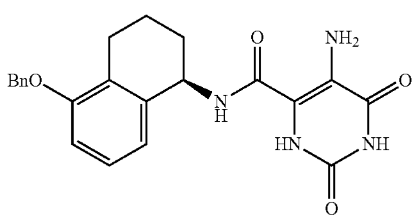 [SMILES: Nc1c(C(=O)N[C@@H]2CCCc3c(Oc4ccccc4)cccc32)[nH]c(=O)[nH]c1=O] | (R)-5-amino-N-(5-(benzyloxy)-1,2,3,4-tetrahydronaphthalen-1-yl)-2,6-dioxo-1,2,3,6-tetrahydropyrimidine-4-carboxamide | 407.1/2.34 (Method B) | RT = 8.82 min, 96% (Method A) RT = 8.18 min, 99% (Method B) |
| 83 | 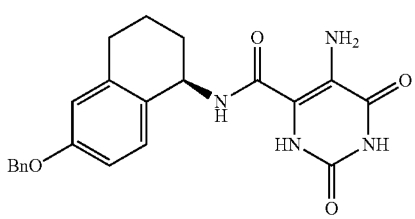 [SMILES: Nc1c(C(=O)N[C@@H]2CCCc3cc(Oc4ccccc4)ccc32)[nH]c(=O)[nH]c1=O] | (R)-5-amino-N-(6-(benzyloxy)-1,2,3,4-tetrahydronaphthalen-1-yl)-2,6-dioxo-1,2,3,6-tetrahydropyrimidine-4-carboxamide | 407.1/2.01 (Method B) | RT = 9.01 min, 94% (Method A) RT = 8.39 min, 93% (Method B) |
| 84 | 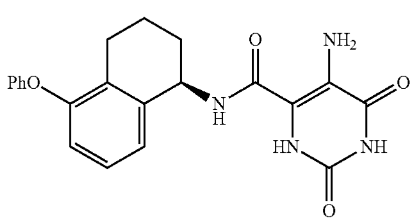 | (R)-5-amino-2,6-dioxo-N-(5-phenoxy-1,2,3,4-tetrahydronaphthalen-1-yl)-1,2,3,6-tetrahydropyrimidine-4-carboxamide | 393.1/2.04 (Method B) | RT = 8.8 min, 94% (Method A) RT = 8.2 min, 97% (Method B) |

TABLE 2-continued

| Ex. No. | Structure | Name | LC-MS [M + 1]/RT | Purity (%) |
|---|---|---|---|---|
| 85 | 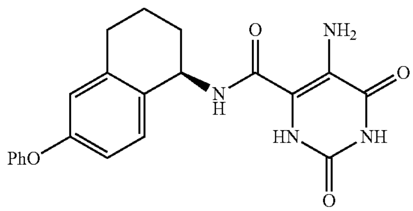 | (R)-5-amino-2,6-dioxo-N-(6-phenoxy-1,2,3,4-tetrahydronaphthalen-1-yl)-1,2,3,6-tetrahydropyrimidine-4-carboxamide | 393.1/3.75 (Method A) | RT = 8.73 min, 92% (Method A) RT = 8.16 min, 96% (Method B) |
| 86 | 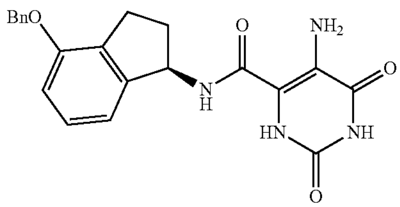 [SMILES: Nc1c(C(=O)N[C@@H]2CCc3c(OCc4ccccc4)cccc32)[nH]c(=O)[nH]c1=O] | (R)-5-amino-N-(4-(benzyloxy)-2,3-dihydro-1H-inden-1-yl)-2,6-dioxo-1,2,3,6-tetrahydropyrimidine-4-carboxamide | 393.1/1.97 (Method B) | RT = 8.35 min, 95.4% (Method A) RT = 7.88 min, 95.2% (Method B) |
| 87 | 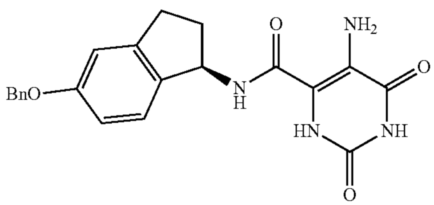 [SMILES: Nc1c(C(=O)N[C@@H]2CCc3cc(OCc4ccccc4)ccc32)[nH]c(=O)[nH]c1=O] | (R)-5-amino-N-(5-(benzyloxy)-2,3-dihydro-1H-inden-1-yl)-2,6-dioxo-1,2,3,6-tetrahydropyrimidine-4-carboxamide | 393.1/1.96 (Method B) | RT = 8.29 min, 95% (Method A) RT = 7.81 min, 99% (Method B) |
| 88 | 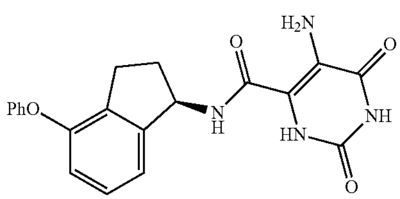 [SMILES: Nc1c(C(=O)N[C@@H]2CCc3c(Oc4ccccc4)cccc32)[nH]c(=O)[nH]c1=O] | (R)-5-amino-2,6-dioxo-N-(4-phenoxy-2,3-dihydro-1H-inden-1-yl)-1,2,3,6-tetrahydropyrimidine-4-carboxamide | 379.1/1.99 (Method B) | RT = 8.30 min, 95.9% (Method A) RT = 7.79 min, 99.3% (Method B) |
| 89 | 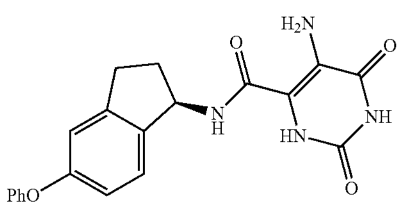 [SMILES: Nc1c(C(=O)N[C@@H]2CCc3cc(Oc4ccccc4)ccc32)[nH]c(=O)[nH]c1=O] | (R)-5-amino-2,6-dioxo-N-(5-phenoxy-2,3-dihydro-1H-inden-1-yl)-1,2,3,6-tetrahydropyrimidine-4-carboxamide | 379.1/1.99 (Method B) | RT = 8.27 min, 96.4% (Method A) RT = 7.75 min, 98.8% (Method B) |
| 90 | 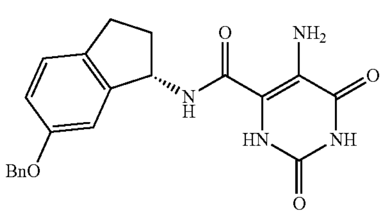 [SMILES: Nc1c(C(=O)N[C@H]2CCc3ccc(OCc4ccccc4)cc32)[nH]c(=O)[nH]c1=O] | (S)-5-amino-N-(6-(benzyloxy)-2,3-dihydro-1H-inden-1-yl)-2,6-dioxo-1,2,3,6-tetrahydropyrimidine-4-carboxamide | 393.1/1.93 (Method B) | RT = 8.10 min, 98% (Method A) RT = 7.74 min, 100% (Method B) |
| 91 | 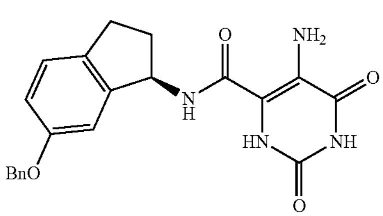 | (R)-5-amino-N-(6-(benzyloxy)-2,3-dihydro-1H-inden-1-yl)-2,6-dioxo-1,2,3,6-tetrahydropyrimidine-4-carboxamide | 393.1/1.82 (Method B) | RT = 8.21 min, 98% (Method A) RT = 7.73 min, 95% (Method B) |

TABLE 2-continued

| Ex. No. | Structure | Name | LC-MS [M + 1]/RT | Purity (%) |
|---|---|---|---|---|
| 92 | 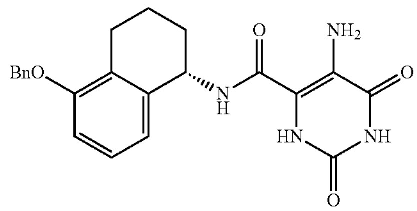 [SMILES: Nc1c(C(=O)N[C@H]2CCCc3c(OCc4ccccc4)cccc32)[nH]c(=O)[nH]c1=O] | (S)-5-amino-N-(5-(benzyloxy)-1,2,3,4-tetrahydronaphthalen-1-yl)-2,6-dioxo-1,2,3,6-tetrahydropyrimidine-4-carboxamide | 407.1/2.02 (Method B) | RT = 8.89 min, 94% (Method A) RT = 8.33 min, 83% (Method B) |
| 93 | 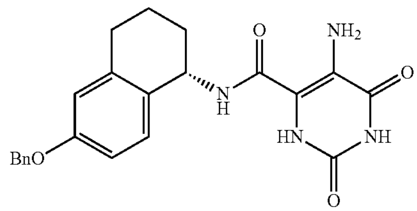 [SMILES: Nc1c(C(=O)N[C@H]2CCCc3cc(OCc4ccccc4)ccc32)[nH]c(=O)[nH]c1=O] | (S)-5-amino-N-(6-(benzyloxy)-1,2,3,4-tetrahydronaphthalen-1-yl)-2,6-dioxo-1,2,3,6-tetrahydropyrimidine-4-carboxamide | 407.1/2.02 (Method B) | RT = 8.68 min, 91% (Method A) RT = 8.15 min, 83% (Method B) |
| 94 | 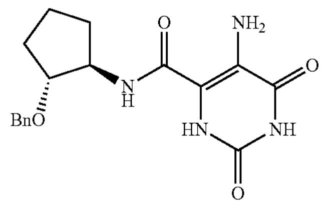 [SMILES: Nc1c(C(=O)N[C@@H]2CCC[C@H]2OCc2ccccc2)[nH]c(=O)[nH]c1=O] | 5-amino-N-((1R,2R)-2-(benzyloxy)cyclopentyl)-2,6-dioxo-1,2,3,6-tetrahydropyrimidine-4-carboxamide | 245.1/1.67 (Method B) | RT = 6.65 min, 92.8% (Method A) RT = 6.08 min, 97% (Method B) |
| 95 | 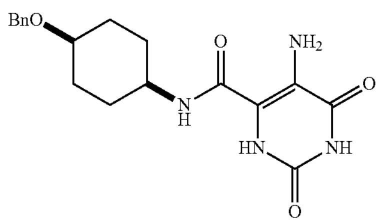 | 5-amino-N-(cis-4-(benzyloxy)cyclohexyl)-2,6-dioxo-1,2,3,6-tetrahydropyrimidine-4-carboxamide | 359.2/1.82 (Method B) | RT = 7.98 min, 94.7% (Method A) RT = 7.77 min, 95.3% (Method B) |
| 96 | 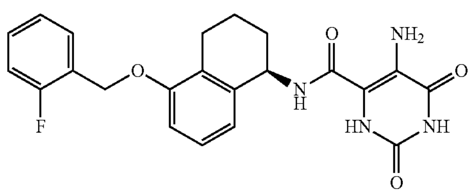 [SMILES: Nc1c(C(=O)N[C@@H]2CCCc3c(OCc4ccccc4F)cccc32)[nH]c(=O)[nH]c1=O] | (R)-5-amino-N-(5-(2-fluorobenzyloxy)-1,2,3,4-tetrahydronaphthalen-1-yl)-2,6-dioxo-1,2,3,6-tetrahydropyrimidine-4-carboxamide | 424/2.12 (Method B) | RT = 8.74 min, 91.3% (Method B) |
| 97 | 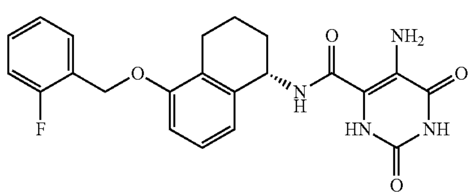 [SMILES: Nc1c(C(=O)N[C@H]2CCCc3c(OCc4ccccc4F)cccc32)[nH]c(=O)[nH]c1=O] | (S)-5-amino-N-(5-(2-fluorobenzyloxy)-1,2,3,4-tetrahydronaphthalen-1-yl)-2,6-dioxo-1,2,3,6-tetrahydropyrimidine-4-carboxamide | 424/2.19 (Method B) | RT = 9.43 min, 89.9% (Method A) RT = 8.73 min, 100% (Method B) |
| 98 | Diastereomer mixture | 5-amino-2,6-dioxo-N-(3-phenylcyclohexyl)-1,2,3,6-tetrahydropyrimidine-4-carboxamide | 329.2/1.97 (Method B) | RT = 9.31 min, 98.6% (Method A) RT = 9.10 min, 99.7% (Method B) |

TABLE 2-continued

| Ex. No. | Structure | Name | LC-MS [M + 1]/RT | Purity (%) |
|---|---|---|---|---|
| 99 | Isomer A | 5-amino-2,6-dioxo-N-(3-phenylcyclohexyl)-1,2,3,6-tetrahydropyrimidine-4-carboxamide | 329.2/1.95 (Method B) | RT = 8.72 min, 99.4% (Method A) RT = 8.54 min, 99.4% (Method B) |
| 100 | Isomer B | 5-amino-2,6-dioxo-N-(3-phenylcyclohexyl)-1,2,3,6-tetrahydropyrimidine-4-carboxamide | 329.1/1.91 (Method B) | RT = 8.65 min, 96.9% (Method A) RT = 8.46 min, 100% (Method B) |
| 101 | Isomer C | 5-amino-2,6-dioxo-N-(3-phenylcyclohexyl)-1,2,3,6-tetrahydropyrimidine-4-carboxamide | 329.1/1.91 (Method B) | RT = 8.70 min, 100% (Method A) RT = 8.54 min, 100% (Method B) |
| 102 | 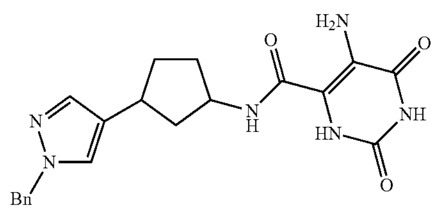 [SMILES: Nc1c(C(=O)NC2CCC(c3cnn(Cc4ccccc4)c3)C2)[nH]c(=O)[nH]c1=O] | 5-amino-N-(3-(1-benzyl-1H-pyrazol-4-yl)cyclopentyl)-2,6-dioxo-1,2,3,6-tetrahydropyrimidine-4-carboxamide | 395.0/0.72 (Method M) | RT = 6.61 min, 97% (Method A) RT = 6.49 min, 95% (Method B) |
| 103 | 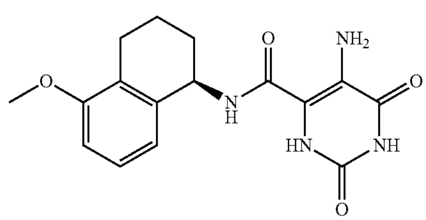 | (R)-5-amino-N-(5-methoxy-1,2,3,4-tetrahydronaphthalen-1-yl)-2,6-dioxo-1,2,3,6-tetrahydropyrimidine-4-carboxamide | 331.1/1.70 (Method B) | RT = 6.08 min, 95.3% (Method A) RT = 5.71 min, 100% (Method B) |
| 104 | 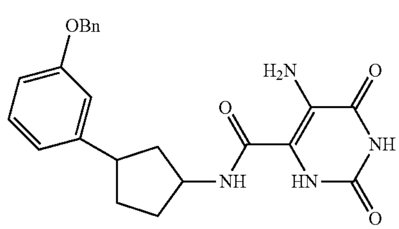 [SMILES: Nc1c(C(=O)NC2CCC(c3cccc(OCc4ccccc4)c3)C2)[nH]c(=O)[nH]c1=O] | 5-amino-N-(3-(3-(benzyloxy)phenyl)cyclopentyl)-2,6-dioxo-1,2,3,6-tetrahydropyrimidine-4-carboxamide | 421.0/0.91 (Method M) | RT = 9.27 min, 100% (Method A) RT = 8.75 min, 99% (Method B) |

TABLE 2-continued

| Ex. No. | Structure | Name | LC-MS [M + 1]/RT | Purity (%) |
|---|---|---|---|---|
| 105 | 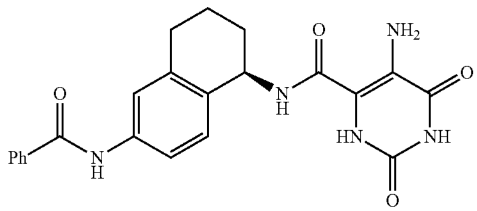 | (R)-5-amino-N-(6-benzamido-1,2,3,4-tetrahydronaphthalen-1-yl)-2,6-dioxo-1,2,3,6-tetrahydropyrimidine-4-carboxamide | 420.1/1.69 (Method B) | RT = 6.72 min, 94% (Method A) RT = 6.34 min, 94% (Method B) |
| 106 | 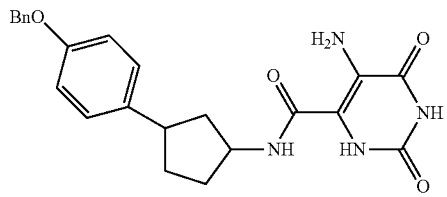 [SMILES: Nc1c(C(=O)NC2CCC(c3ccc(OCc4ccccc4)cc3)C2)[nH]c(=O)[nH]c1=O] | 5-amino-N-(3-(4-(benzyloxy)phenyl)cyclopentyl)-2,6-dioxo-1,2,3,6-tetrahydropyrimidine-4-carboxamide | 421.1/2.18 (Method B) | RT = 6.28 min, 100% (Method B) |
| 107 | 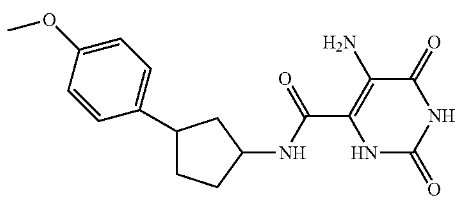 [SMILES: COc1ccc(C2CCC(NC(=O)c3[nH]c(=O)[nH]c(=O)c3N)C2)cc1] | 5-amino-N-(3-(4-methoxyphenyl)cyclopentyl)-2,6-dioxo-1,2,3,6-tetrahydropyrimidine-4-carboxamide | 345.0/1.75 (Method B) | RT = 8.0 min, 97.7% (Method A) RT = 7.9 min, 98.4% (Method B) |
| 108 | 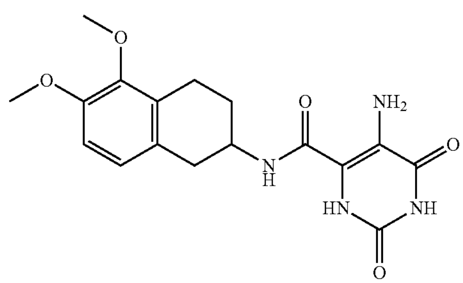 [SMILES: COc1ccc2c(c1OC)CCC(NC(=O)c1[nH]c(=O)[nH]c(=O)c1N)C2] | 5-amino-N-(5,6-dimethoxy-1,2,3,4-tetrahydronaphthalen-2-yl)-2,6-dioxo-1,2,3,6-tetrahydropyrimidine-4-carboxamide | 361.0/1.58 (Method B) | RT = 7.07 min, 90.8% (Method A) RT = 7.09 min, 100% (Method B) |
| 109 | 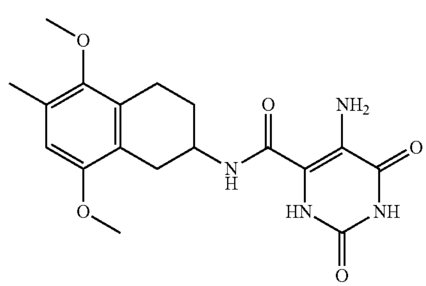 [SMILES: COc1cc(C)c(OC)c2c1CC(NC(=O)c1[nH]c(=O)[nH]c(=O)c1N)CC2] | 5-amino-N-(5,8-dimethoxy-6-methyl-1,2,3,4-tetrahydronaphthalen-2-yl)-2,6-dioxo-1,2,3,6-tetrahydropyrimidine-4-carboxamide | 375.2/1.99 (Method B) | RT = 8.14 min, 99.2% (Method A) RT = 7.99 min, 100% (Method B) |
| 110 | 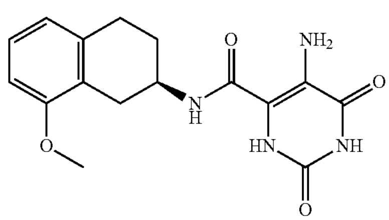 [SMILES: COc1cccc2c1C[C@H](NC(=O)c1[nH]c(=O)[nH]c(=O)c1N)CC2] | (R)-5-amino-N-(8-methoxy-1,2,3,4-tetrahydronaphthalen-2-yl)-2,6-dioxo-1,2,3,6-tetrahydropyrimidine-4-carboxamide | 331.0/1.72 (Method B) | RT = 7.86 min, 98.6% (Method A) RT = 7.83 min, 99.1% (Method B) |

TABLE 2-continued

| Ex. No. | Structure | Name | LC-MS [M + 1]/RT | Purity (%) |
|---|---|---|---|---|
| 111 | 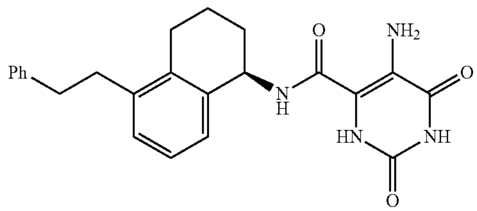 [SMILES: Nc1c(C(=O)N[C@@H]2CCCc3c(CCc4ccccc4)cccc32)[nH]c(=O)[nH]c1=O] | (R)-5-amino-2,6-dioxo-N-(5-phenethyl-1,2,3,4-tetrahydronaphthalen-1-yl)-1,2,3,6-tetrahydropyrimidine-4-carboxamide | 405.1/2.15 (Method B) | RT = 9.48 min, 98% (Method A) RT = 8.66 min, 99% (Method B) |
| 112 | 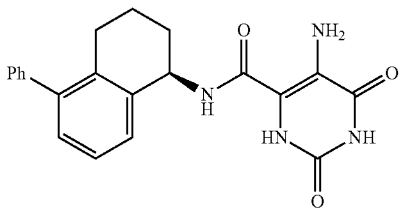 [SMILES: Nc1c(C(=O)N[C@@H]2CCCc3c(-c4ccccc4)cccc32)[nH]c(=O)[nH]c1=O] | (R)-5-amino-2,6-dioxo-N-(5-phenyl-1,2,3,4-tetrahydronaphthalen-1-yl)-1,2,3,6-tetrahydropyrimidine-4-carboxamide | 377.1/2.02 (Method B) | RT = 8.52 min, 97% (Method A) RT = 7.96 min, 99% (Method B) |
| 113 | 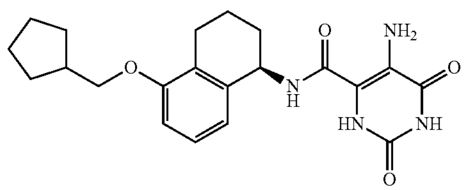 [SMILES: Nc1c(C(=O)N[C@@H]2CCCc3c(OCC4CCCC4)cccc32)[nH]c(=O)[nH]c1=O] | (R)-5-amino-N-(5-(cyclopentylmethoxy)-1,2,3,4-tetrahydronaphthalen-1-yl)-2,6-dioxo-1,2,3,6-tetrahydropyrimidine-4-carboxamide | 399.1/2.32 (Method B) | RT = 10.4 min, 91.2% (Method A) RT = 9.11 min, 99% (Method |
| 114 | 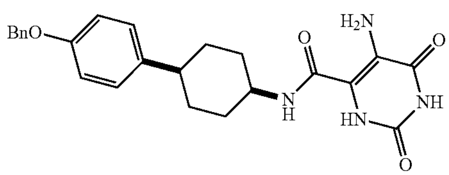 | 5-amino-N-(cis-4-(4-(benzyloxy)phenyl)cyclohexyl)-2,6-dioxo-1,2,3,6-tetrahydropyrimidine-4-carboxamide | 435.1/2.19 (Method B) | RT = 10.8 min, 99.2% (Method A) RT = 10.2 min, 98.3% (Method B) |
| 115 | 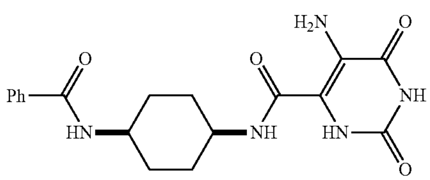 | 5-amino-N-(cis-4-benzamidocyclohexyl)-2,6-dioxo-1,2,3,6-tetrahydropyrimidine-4-carboxamide | 372.1/0.61 (Method M) | RT = 5.12 min, 93% (Method A) RT = 4.87 min, 91% (Method B) |
| 116 | 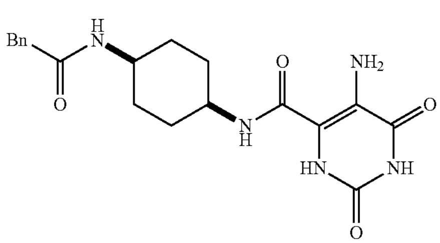 | 5-amino-2,6-dioxo-N-(cis-4-(2-phenylacetamido)cyclohexyl)-1,2,3,6-tetrahydropyrimidine-4-carboxamide | 386.0/0.62 (Method M) | RT = 5.27 min, 100% (Method A) RT = 5.06 min, 97% (Method B) |
| 117 | 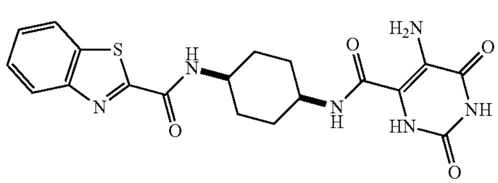 | N-(cis-4-(5-amino-2,6-dioxo-1,2,3,6-tetrahydropyrimidine-4-carboxamido)cyclohexyl)benzo[d]thiazole-2-carboxamide | 428.9/0.73 (Method M) | RT = 6.74 min, 95% (Method A) RT = 6.51 min, 99% (Method B) |

TABLE 2-continued

| Ex. No. | Structure | Name | LC-MS [M + 1]/RT | Purity (%) |
|---|---|---|---|---|
| 118 | 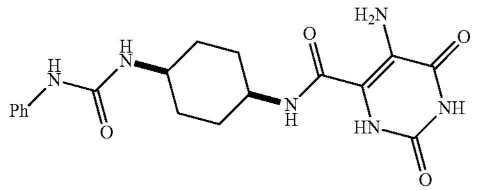 | 5-amino-2,6-dioxo-N-(cis-4-(3-phenylureido)cyclohexyl)-1,2,3,6-tetrahydropyrimidine-4-carboxamide | 387.0/0.64 (Method M) | RT = 5.72 min, 100% (Method A) RT = 5.47 min, 99% (Method B) |
| 119 | 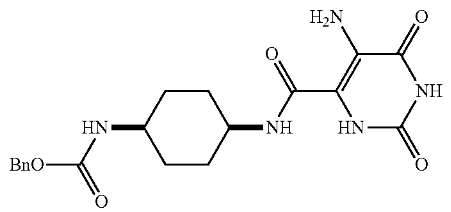 | benzyl cis-4-(5-amino-2,6-dioxo-1,2,3,6-tetrahydropyrimidine-4-carboxamido)cyclohexylcarbamate | 402.1/0.73 (Method M) | RT = 6.70 min, 100% (Method A) RT = 6.49 min, 99% (Method B) |
| 120 | 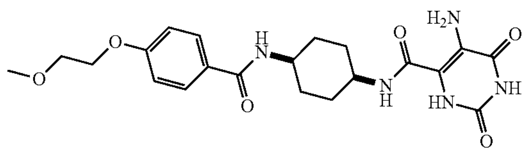 | 5-amino-N-(cis-4-(4-(2-methoxyethoxy)benzamido)cyclohexyl)-2,6-dioxo-1,2,3,6-tetrahydropyrimidine-4-carboxamide | 445.9/0.62 (Method M) | RT = 5.19 min, 97% (Method A) RT = 4.98 min, 95% (Method B) |
| 121 | 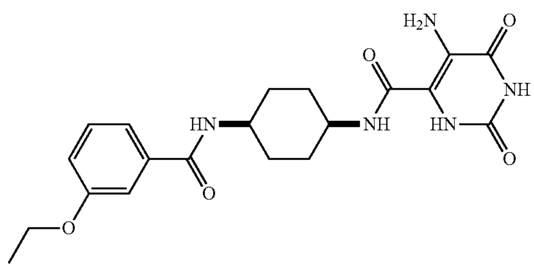 | 5-amino-N-(cis-4-(3-ethoxybenzamido)cyclohexyl)-2,6-dioxo-1,2,3,6-tetrahydropyrimidine-4-carboxamide | 416.0/0.68 (Method M) | RT = 6.10 min, 99% (Method A) RT = 5.86 min, 97% (Method B) |
| 122 | 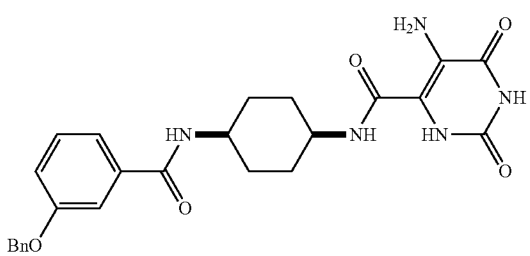 | 5-amino-N-(cis-4-(3-(benzyloxy)benzamido)cyclohexyl)-2,6-dioxo-1,2,3,6-tetrahydropyrimidine-4-carboxamide | 477.9/0.79 (Method M) | RT = 7.63 min, 94% (Method A) RT = 7.42 min, 94% (Method B) |
| 123 | 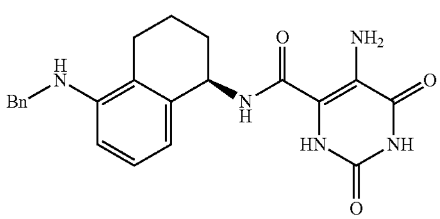 | (R)-5-amino-N-(5-(benzylamino)-1,2,3,4-tetrahydronaphthalen-1-yl)-2,6-dioxo-1,2,3,6-tetrahydropyrimidine-4-carboxamide | 405/1.68 (Method B) | RT = 6.81 min, 92.8% (Method A) RT = 6.41 min, 89.4% (Method B) |
| 124 | 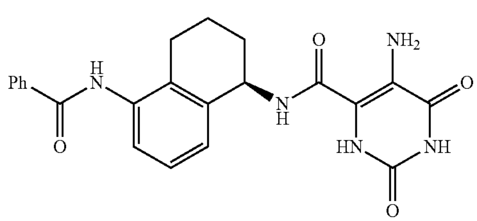 [SMILES: Nc1c(C(=O)N[C@@H]2CCCc3c(NC(=O)c4ccccc4)cccc32)[nH]c(=O)[nH]c1=O] | (R)-5-amino-N-(5-benzamido-1,2,3,4-tetrahydronaphthalen-1-yl)-2,6-dioxo-1,2,3,6-tetrahydropyrimidine-4-carboxamide | 420.1/1.58 (Method B) | RT = 6.24 min, 90% (Method A) RT = 5.91 min, 94% (Method B) |

TABLE 2-continued

| Ex. No. | Structure | Name | LC-MS [M + 1]/RT | Purity (%) |
|---|---|---|---|---|
| 125 | 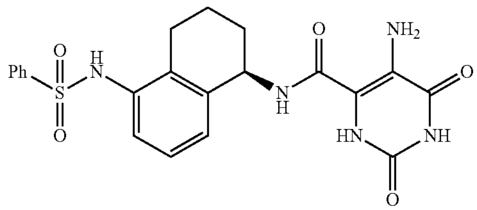 [SMILES: Nc1c(C(=O)N[C@@H]2CCCc3c(NS(=O)(=O)c4ccccc4)cccc32)[nH]c(=O)[nH]c1=O] | (R)-5-amino-2,6-dioxo-N-(5-(phenylsulfonamido)-1,2,3,4-tetrahydronaphthalen-1-yl)-1,2,3,6-tetrahydropyrimidine-4-carboxamide | 456.1/1.59 (Method B) | RT = 6.52 min, 93% (Method A) RT = 6.24 min, 89% (Method B) |
| 126 | 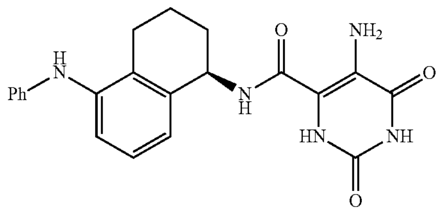 [SMILES: Nc1c(C(=O)N[C@@H]2CCCc3c(Nc4ccccc4)cccc32)[nH]c(=O)[nH]c1=O] | (R)-5-amino-2,6-dioxo-N-(5-(phenylamino)-1,2,3,4-tetrahydronaphthalen-1-yl)-1,2,3,6-tetrahydropyrimidine-4-carboxamide | 392.1/1.89 (Method B) | RT = 8.15 min, 89% (Method A) RT = 7.69 min, 92% (Method B) |
| 127 | 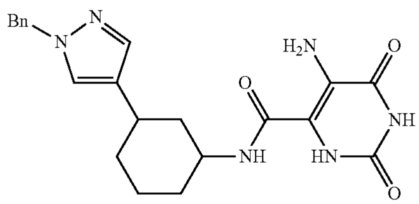 [SMILES: Nc1c(C(=O)NC2CCCC(c3cnn(Cc4ccccc4)c3)C2)[nH]c(=O)[nH]c1=O] | 5-amino-N-(3-(1-benzyl-1H-pyrazol-4-yl)cyclohexyl)-2,6-dioxo-1,2,3,6-tetrahydropyrimidine-4-carboxamide | 409.2/1.89 (Method B) | RT = 7.69 min, 96.8% (Method A) RT = 7.87 min, 96.2% (Method B) |
| 128 | 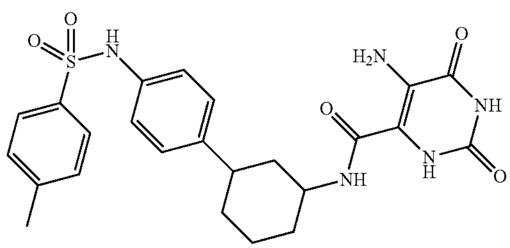 [SMILES: Cc1ccc(S(=O)(=O)Nc2ccc(C3CCCC(NC(=O)c4[nH]c(=O)[nH]c(=O)c4N)C3)cc2)cc1] | 5-amino-N-(3-(4-(4-methylphenylsulfonamido)phenyl)cyclohexyl)-2,6-dioxo-1,2,3,6-tetrahydropyrimidine-4-carboxamide | 498.1/1.86 (Method B) | RT = 9.43 min, 95.0% (Method A) RT = 9.49 min, 97.3% (Method B) |
| 129 | 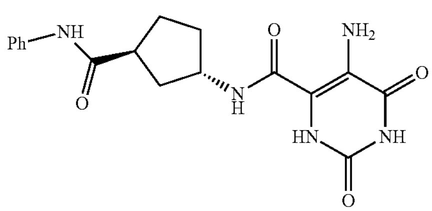 [SMILES: Nc1c(C(=O)N[C@H]2CC[C@H](C(=O)Nc3ccccc3)C2)[nH]c(=O)[nH]c1=O] | 5-amino-2,6-dioxo-N-((1S,3S)-3-(phenylcarbamoyl)cyclopentyl)-1,2,3,6-tetrahydropyrimidine-4-carboxamide | 358.1/1.42 (Method B) | RT = 6.47 min, 95% (Method A) RT = 6.54 min, 93% (Method B) |
| 130 | 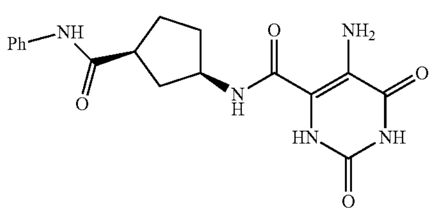 [SMILES: Nc1c(C(=O)N[C@@H]2CC[C@H](C(=O)Nc3ccccc3)C2)[nH]c(=O)[nH]c1=O] | 5-amino-2,6-dioxo-N-((1R,3S)-3-(phenylcarbamoyl)cyclopentyl)-1,2,3,6-tetrahydropyrimidine-4-carboxamide | 358.0/1.47 (Method B) | RT = 6.80 min, 85.3% (Method A) RT = 6.91 min, 91.6% (Method B) |
| 131 | Isomer A | 5-amino-N-(3-(1-benzyl-1H-pyrazol-4-yl)cyclopentyl)-2,6-dioxo-1,2,3,6-tetrahydropyrimidine-4-carboxamide | 394.9/0.72 (Method M) | RT = 6.61 min, 97% (Method A) RT = 6.49 min, 95% (Method B) |

TABLE 2-continued

| Ex. No. | Structure | Name | LC-MS [M + 1]/RT | Purity (%) |
|---|---|---|---|---|
| 132 | Isomer B | 5-amino-N-(3-(1-benzyl-1H-pyrazol-4-yl)cyclopentyl)-2,6-dioxo-1,2,3,6-tetrahydropyrimidine-4-carboxamide | 395.0/0.71 (Method M) | RT = 6.48 min, 100% (Method A) RT = 6.35 min, 99% (Method B) |
| 133 | Isomer C | 5-amino-N-(3-(1-benzyl-1H-pyrazol-4-yl)cyclopentyl)-2,6-dioxo-1,2,3,6-tetrahydropyrimidine-4-carboxamide | 395.0/0.71 (Method M) | RT = 6.55 min, 100% (Method A) RT = 6.41 min, 96% (Method B) |
| 134 | Isomer D | 5-amino-N-(3-(1-benzyl-1H-pyrazol-4-yl)cyclopentyl)-2,6-dioxo-1,2,3,6-tetrahydropyrimidine-4-carboxamide | 395.0/0.72 (Method M) | RT = 6.56 min, 100% (Method A) RT = 6.43 min, 100% (Method B) |
| 135 | 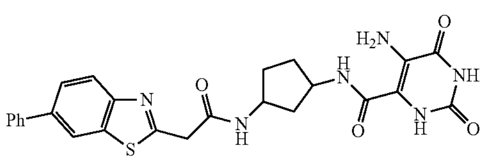 [SMILES: Nc1c(C(=O)NC2CCC(NC(=O)Cc3nc4ccc(-c5ccccc5)cc4s3)C2)[nH]c(=O)[nH]c1=O] | 5-amino-2,6-dioxo-N-(3-(2-(6-phenylbenzo[d]thiazol-2-yl)acetamido)cyclopentyl)-1,2,3,6-tetrahydropyrimidine-4-carboxamide | 505.1/1.88 (Method B) | RT = 8.29 min, 95% (Method A) RT = 8.41 min, 93% (Method B) |
| 136 | 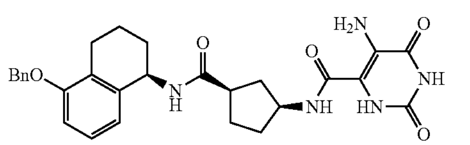 [SMILES: Nc1c(C(=O)N[C@H]2CC[C@@H](C(=O)N[C@@H]3CCCc4c(OCc5ccccc5)cccc43)C2)[nH]c(=O)[nH]c1=O] | 5-amino-N-((1S,3R)-3-((R)-5-(benzyloxy)-1,2,3,4-tetrahydronaphthalen-1-ylcarbamoyl)cyclopentyl)-2,6-dioxo-1,2,3,6-tetrahydropyrimidine-4-carboxamide | 540.3 [M + Na]/ 2.09 (Method B) | RT = 6.68 min, 99.1% (Method A) RT = 6.11 min, 99.3% (Method B) |
| 137 | 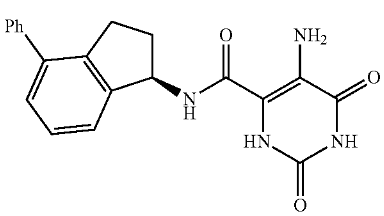 [SMILES: Nc1c(C(=O)N[C@@H]2CCc3c(-c4ccccc4)cccc32)[nH]c(=O)[nH]c1=O] | (R)-5-amino-2,6-dioxo-N-(4-phenyl-2,3-dihydro-1H-inden-1-yl)-1,2,3,6-tetrahydropyrimidine-4-carboxamide | 363.1/1.93 (Method B) | RT = 9.09 min, 89.8% (Method A) RT = 8.69 min, 91% (Method B) |
| 138 | 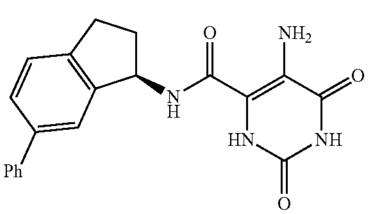 [SMILES: Nc1c(C(=O)N[C@@H]2CCc3ccc(-c4ccccc4)cc32)[nH]c(=O)[nH]c1=O] | (R)-5-amino-2,6-dioxo-N-(6-phenyl-2,3-dihydro-1H-inden-1-yl)-1,2,3,6-tetrahydropyrimidine-4-carboxamide | 363.1/1.95 (Method B) | RT = 9.12 min, 91% (Method A) RT = 8.72 min, 94% (Method B) |

TABLE 2-continued

| Ex. No. | Structure | Name | LC-MS [M + 1]/RT | Purity (%) |
|---|---|---|---|---|
| 139 | 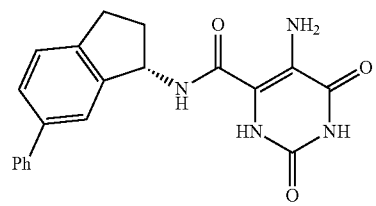 [SMILES: Nc1c(C(=O)N[C@H]2CCc3ccc(-c4ccccc4)cc32)[nH]c(=O)[nH]c1=O] | (S)-5-amino-2,6-dioxo-N-(6-phenyl-2,3-dihydro-1H-inden-1-yl)-1,2,3,6-tetrahydropyrimidine-4-carboxamide | 363.1/1.95 (Method B) | RT = 9.13 min, 91% (Method A) RT = 8.72 min, 94% (Method B) |
| 140 | 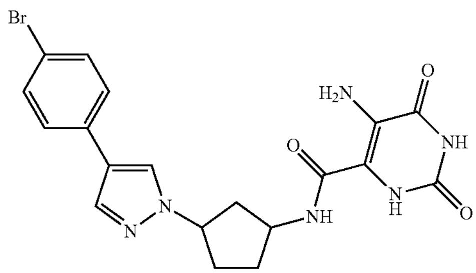 [SMILES: Nc1c(C(=O)NC2CCC(n3cc(-c4ccc(Br)cc4)cn3)C2)[nH]c(=O)[nH]c1=O] | 5-amino-N-(3-(4-(4-bromophenyl)-1H-pyrazol-1-yl)cyclopentyl)-2,6-dioxo-1,2,3,6-tetrahydropyrimidine-4-carboxamide | 461.0/1.96 (Method B) | RT = 9.34 min, 95% (Method A) |
| 141 | 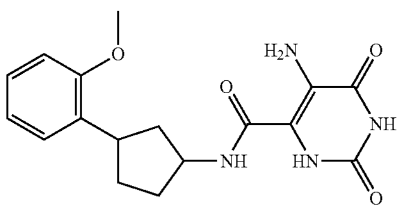 [SMILES: COc1ccccc1C1CCC(NC(=O)c2[nH]c(=O)[nH]c(=O)c2N)C1] | 5-amino-N-(3-(2-methoxyphenyl)cyclopentyl)-2,6-dioxo-1,2,3,6-tetrahydropyrimidine-4-carboxamide | 345.1/1.84 (Method B) | RT = 7.49 min, 96% (Method A) RT = 7.28 min, 96% (Method B) |
| 142 | 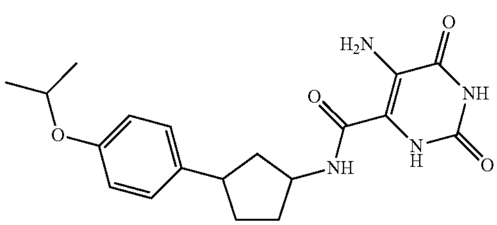 | 5-amino-N-(3-(4-isopropoxyphenyl)cyclopentyl)-2,6-dioxo-1,2,3,6-tetrahydropyrimidine-4-carboxamide | 373.2/1.98 (Method B) | RT = 8.66 min, 99% (Method B) |
| 143 | 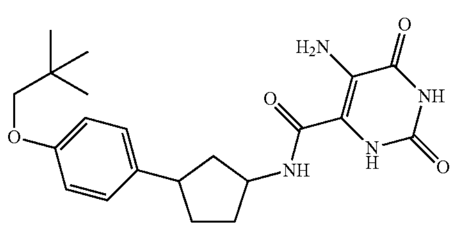 [SMILES: CC(C)(C)COc1ccc(C2CCC(NC(=O)c3[nH]c(=O)[nH]c(=O)c3N)C2)cc1] | 5-amino-N-(3-(4-(neopentyloxy)phenyl)cyclopentyl)-2,6-dioxo-1,2,3,6-tetrahydropyrimidine-4-carboxamide | 401.2/2.27 (Method B) | RT = 11.43 min, 93% (Method A) RT = 10.22 min, 92% (Method B) |
| 144 | 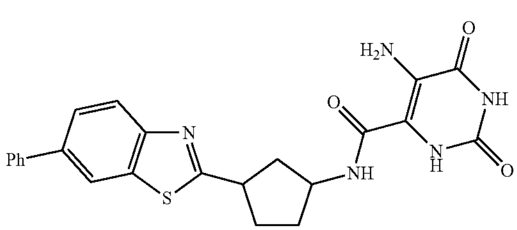 [SMILES: Nc1c(C(=O)NC2CCC(c3nc4ccc(-c5ccccc5)cc4s3)C2)[nH]c(=O)[nH]c1=O] | 5-amino-2,6-dioxo-N-(3-(6-phenylbenzo[d]thiazol-2-yl)cyclopentyl)-1,2,3,6-tetrahydropyrimidine-4-carboxamide | 448.2/2.23 (Method B) | RT = 9.70 min, 97% (Method A) RT = 9.29 min, 100% (Method B) |

TABLE 2-continued

| Ex. No. | Structure | Name | LC-MS [M + 1]/RT | Purity (%) |
|---|---|---|---|---|
| 145 | 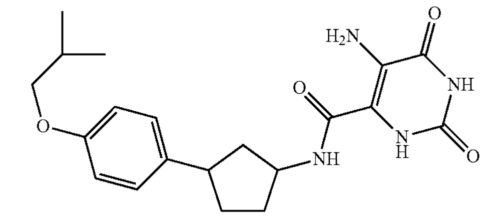 [SMILES: CC(C)COc1ccc(C2CCC(NC(=O)c3[nH]c(=O)[nH]c(=O)c3N)C2)cc1] | 5-amino-N-(3-(4-isobutoxyphenyl)cyclopentyl)-2,6-dioxo-1,2,3,6-tetrahydropyrimidine-4-carboxamide | 387.2/2.17 (Method B) | RT = 11.00 min, 100% (Method A) RT = 10.26 min, 100% (Method B) |
| 146 | 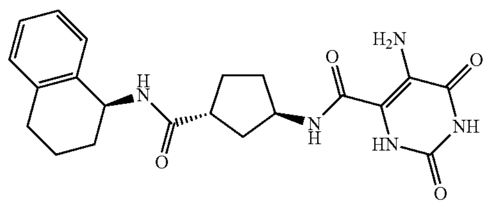 [SMILES: Nc1c(C(=O)N[C@@H]2CC[C@@H](C(=O)N[C@H]3CCCc4ccccc43)C2)[nH]c(=O)[nH]c1=O] | 5-amino-2,6-dioxo-N-((1R,3R)-3-((S)-1,2,3,4-tetrahydronaphthalen-1-ylcarbamoyl)cyclopentyl)-1,2,3,6-tetrahydropyrimidine-4-carboxamide | 412.1/1.67 (Method B) | RT = 6.94 min, 90% (Method A) RT = 6.89 min, 91% (Method B) |
| 147 | 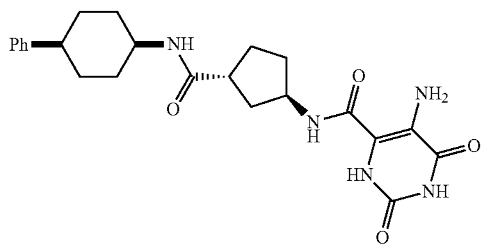 | 5-amino-2,6-dioxo-N-((1R,3R)-3-(cis-4-phenylcyclohexylcarbamoyl)cyclopentyl)-1,2,3,6-tetrahydropyrimidine-4-carboxamide | 440.1/1.85 (Method B) | RT = 7.9 min, 90% (Method A) RT = 7.7 min, 90% (Method B) |
| 148 | 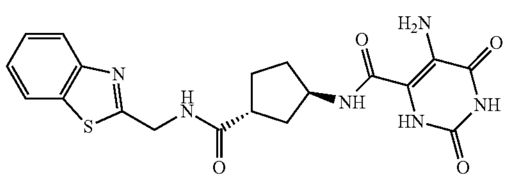 [SMILES: Nc1c(C(=O)N[C@@H]2CC[C@@H](C(=O)NCc3nc4ccccc4s3)C2)[nH]c(=O)[nH]c1=O] | 5-amino-N-((1R,3R)-3-(benzo[d]thiazol-2-ylmethylcarbamoyl)cyclopentyl)-2,6-dioxo-1,2,3,6-tetrahydropyrimidine-4-carboxamide | 429.1/1.56 (Method B) | RT = 5.91 min, 94% (Method A) RT = 5.88 min, 94% (Method B) |
| 149 | 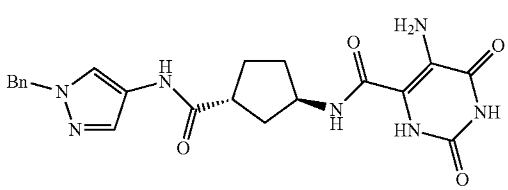 [SMILES: Nc1c(C(=O)N[C@@H]2CC[C@@H](C(=O)Nc3cnn(Cc4ccccc4)c3)C2)[nH]c(=O)[nH]c1=O] | 5-amino-N-((1R,3R)-3-(1-benzyl-1H-pyrazol-4-ylcarbamoyl)cyclopentyl)-2,6-dioxo-1,2,3,6-tetrahydropyrimidine-4-carboxamide | 438.1/1.62 (Method B) | RT = 9.92 min, 90% (Method A) RT = 9.46 min, 94% (Method B) |
| 150 | 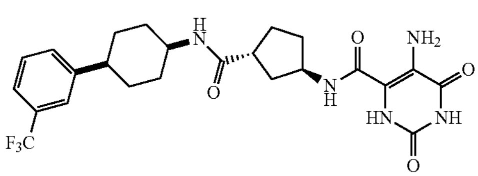 | 5-amino-2,6-dioxo-N-((1R,3R)-3-(cis-4-(3-(trifluoromethyl)phenyl)cyclohexylcarbamoyl)cyclopentyl)-1,2,3,6-tetrahydropyrimidine-4-carboxamide | 508.3/2.07 (Method B) | RT = 8.58 min, 88.5% (Method B) |
| 151 | Isomer A | 5-amino-N-(3-(4-(benzyloxy)phenyl)cyclopentyl)-2,6-dioxo-1,2,3,6-tetrahydropyrimidine-4-carboxamide | 421.1/2.12 (Method B) | RT = 10.95 min, 99.3% (Method A) RT = 10.50 min, 99.5% (Method B) |

TABLE 2-continued

| Ex. No. | Structure | Name | LC-MS [M + 1]/RT | Purity (%) |
|---|---|---|---|---|
| 152 | Isomer B | 5-amino-N-(3-(4-(benzyloxy) phenyl)cyclopentyl)-2,6-dioxo-1,2,3,6-tetrahydropyrimidine-4-carboxamide | 421.1/2.12 (Method B) | RT = 9.79 min, 98.4% (Method A) RT = 9.44 min, 100% (Method B) |
| 153 | Isomer C | 5-amino-N-(3-(4-(benzyloxy) phenyl)cyclopentyl)-2,6-dioxo-1,2,3,6-tetrahydropyrimidine-4-carboxamide | 421.1/2.14 (Method B) | RT = 9.87 min, 98.8% (Method A) RT- 9.47 min, 98.7% (Method B) |
| 154 | Isomer D | 5-amino-N-(3-(4-(benzyloxy) phenyl)cyclopentyl)-2,6-dioxo-1,2,3,6-tetrahydropyrimidine-4-carboxamide | 421.1/2.13 (Method B) | RT = 9.78 min, 97.9% (Method A) RT = 9.43 min, 97.5% (Method B) |
| 155 | Isomer A | 5-amino-N-(3-(3-(benzyloxy) phenyl)cyclopentyl)-2,6-dioxo-1,2,3,6-tetrahydropyrimidine-4-carboxamide | 421.0/0.91 (Method M) | RT = 9.23 min, 98% (Method A) RT = 8.78 min, 98% (Method B) |
| 156 | Isomer B | 5-amino-N-(3-(3-(benzyloxy) phenyl)cyclopentyl)-2,6-dioxo-1,2,3,6-tetrahydropyrimidine-4-carboxamide | 421.0/0.91 (Method M) | RT = 9.21 min, 96% (Method A) RT = 8.75 min, 95% (Method B) |
| 157 | Isomer C | 5-amino-N-(3-(3-(benzyloxy) phenyl)cyclopentyl)-2,6-dioxo-1,2,3,6-tetrahydropyrimidine-4-carboxamide | 421.0/0.91 (Method M) | RT = 9.20 min, 97% (Method A) RT = 8.73 min, 91% (Method B) |

TABLE 2-continued

| Ex. No. | Structure | Name | LC-MS [M + 1]/RT | Purity (%) |
|---|---|---|---|---|
| 158 | Isomer D | 5-amino-N-(3-(3-(benzyloxy) phenyl)cyclopentyl)-2,6-dioxo-1,2,3,6-tetrahydropyrimidine-4-carboxamide | 421.0/0.91 (Method M) | RT = 9.21 min, 91% (Method A) RT = 8.74 min, 93% (Method B) |
| 159 | 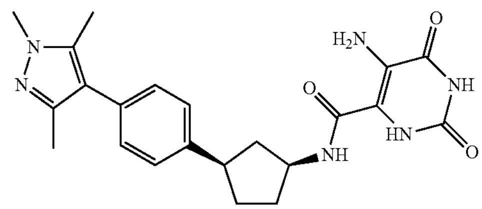 [SMILES: Cc1nn(C)c(C)c1-c1ccc([C@@H]2CC[C@H](NC(=O)c3[nH]c(=O)[nH]c(=O)c3N)C2)cc1] | 5-amino-2,6-dioxo-N-((1S,3R)-3-(4-(1,3,5-trimethyl-1H-pyrazol-4-yl)phenyl)cyclopentyl)-1,2,3,6-tetrahydropyrimidine-4-carboxamide | 423.0/1.03 (Method K) | 99.3 |
| 160 | 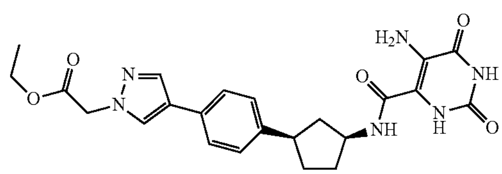 [SMILES: CCOC(=O)Cn1cc(-c2ccc([C@@H]3CC[C@H](NC(=O)c4[nH]c(=O)[nH]c(=O)c4N)C3)cc2)cn1] | ethyl 2-(4-(4-((1R,3S)-3-(5-amino-2,6-dioxo-1,2,3,6-tetrahydropyrimidine-4-carboxamido)cyclopentyl)phenyl)-1H-pyrazol-1-yl)acetate | 467.0/1.26 (Method K) | 99.6 |
| 161 | 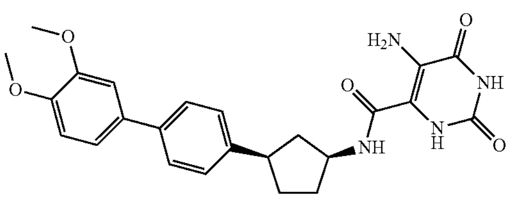 [SMILES: COc1ccc(-c2ccc([C@@H]3CC[C@H](NC(=O)c4[nH]c(=O)[nH]c(=O)c4N)C3)cc2)cc1OC] | 5-amino-N-((1S,3R)-3-(3',4'-dimethoxybiphenyl-4-yl) cyclopentyl)-2,6-dioxo-1,2,3,6-tetrahydropyrimidine-4-carboxamide | 451.0/1.50 (Method K) | 100 |
| 162 | 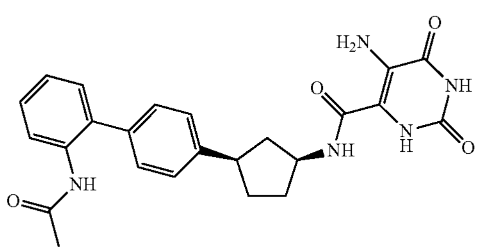 [SMILES: CC(=O)Nc1ccccc1-c1ccc([C@@H]2CC[C@H](NC(=O)c3[nH]c(=O)[nH]c(=O)c3N)C2)cc1] | N-((1S,3R)-3-(2'-acetamidobiphenyl-4-yl)cyclopentyl)-5-amino-2,6-dioxo-1,2,3,6-tetrahydropyrimidine-4-carboxamide | 448.0/1.24 (Method K) | 100 |
| 163 | 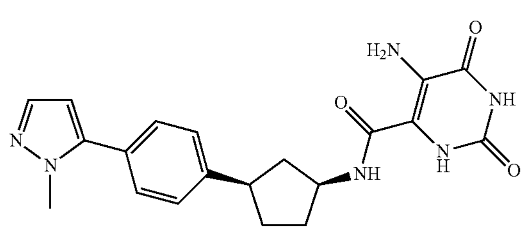 [SMILES: Cn1nccc1-c1ccc([C@@H]2CC[C@H](NC(=O)c3[nH]c(=O)[nH]c(=O)c3N)C2)cc1] | 5-amino-N-((1S,3R)-3-(4-(1-methyl-1H-pyrazol-5-yl)phenyl) cyclopentyl)-2,6-dioxo-1,2,3,6-tetrahydropyrimidine-4-carboxamide | 395.0/1.14 (Method K) | 100 |
| 164 | 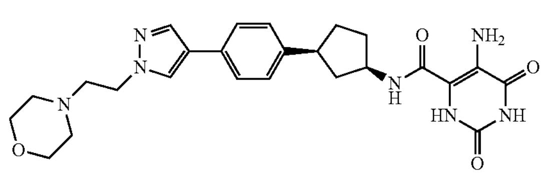 [SMILES: Nc1c(C(=O)N[C@@H]2CC[C@H](c3ccc(-c4cnn(CCN5CCOCC5)c4)cc3)C2)[nH]c(=O)[nH]c1=O] | 5-amino-N-((1R,3S)-3-(4-(1-(2-morpholinoethyl)-1H-pyrazol-4-yl)phenyl)cyclopentyl)-2,6-dioxo-1,2,3,6-tetrahydropyrimidine-4-carboxamide | 494.0/0.86 (Method K) | 100 |

TABLE 2-continued

| Ex. No. | Structure | Name | LC-MS [M + 1]/RT | Purity (%) |
|---|---|---|---|---|
| 165 | 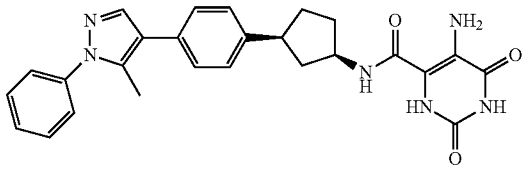 [SMILES: Cc1c(-c2ccc([C@H]3CC[C@@H](NC(=O)c4[nH]c(=O)[nH]c(=O)c4N)C3)cc2)cnn1-c1ccccc1] | 5-amino-N-((1R,3S)-3-(4-(5-methyl-1-phenyl-1H-pyrazol-4-yl)phenyl)cyclopentyl)-2,6-dioxo-1,2,3,6-tetrahydropyrimidine-4-carboxamide | 471.0/1.61 (Method K) | 100 |
| 166 | 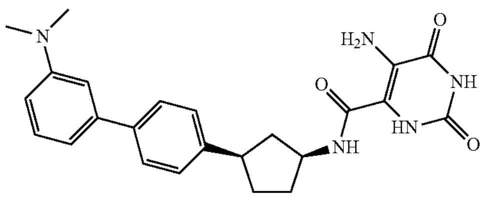 [SMILES: CN(C)c1cccc(-c2ccc([C@@H]3CC[C@H](NC(=O)c4[nH]c(=O)[nH]c(=O)c4N)C3)cc2)c1] | 5-amino-N-((1S,3R)-3-(3'-(dimethylamino)biphenyl-4-yl)cyclopentyl)-2,6-dioxo-1,2,3,6-tetrahydropyrimidine-4-carboxamide | 434.0/1.80 (Method K) | 100 |
| 167 | 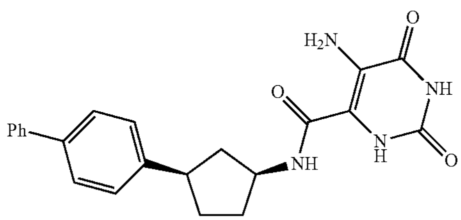 [SMILES: Nc1c(C(=O)N[C@H]2CC[C@@H](c3ccc(-c4ccccc4)cc3)C2)[nH]c(=O)[nH]c1=O] | 5-amino-N-((1S,3R)-3-(biphenyl-4-yl)cyclopentyl)-2,6-dioxo-1,2,3,6-tetrahydropyrimidine-4-carboxamide | 391.0/1.70 (Method K) | 100 |
| 168 | 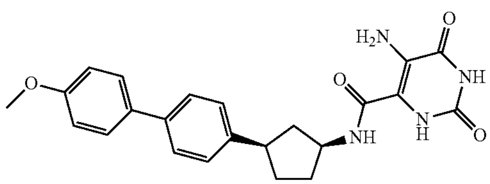 [SMILES: COc1ccc(-c2ccc([C@@H]3CC[C@H](NC(=O)c4[nH]c(=O)[nH]c(=O)c4N)C3)cc2)cc1] | 5-amino-N-((1S,3R)-3-(4'-methoxybiphenyl-4-yl)cyclopentyl)-2,6-dioxo-1,2,3,6-tetrahydropyrimidine-4-carboxamide | 421.0/1.65 (Method K) | 100 |
| 169 | 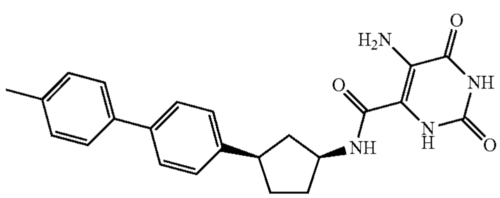 [SMILES: Cc1ccc(-c2ccc([C@@H]3CC[C@H](NC(=O)c4[nH]c(=O)[nH]c(=O)c4N)C3)cc2)cc1] | 5-amino-N-((1S,3R)-3-(4'-methylbiphenyl-4-yl)cyclopentyl)-2,6-dioxo-1,2,3,6-tetrahydropyrimidine-4-carboxamide | 405.0/1.87 (Method K) | 100 |
| 170 | 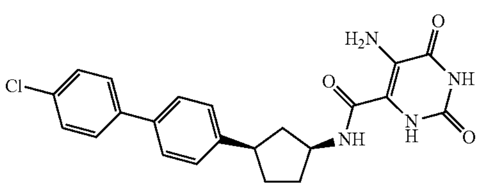 [SMILES: Nc1c(C(=O)N[C@H]2CC[C@@H](c3ccc(-c4ccc(Cl)cc4)cc3)C2)[nH]c(=O)[nH]c1=O] | 5-amino-N-((1S,3R)-3-(4'-chlorobiphenyl-4-yl)cyclopentyl)-2,6-dioxo-1,2,3,6-tetrahydropyrimidine-4-carboxamide | 424.9/1.92 (Method K) | 100 |
| 171 | 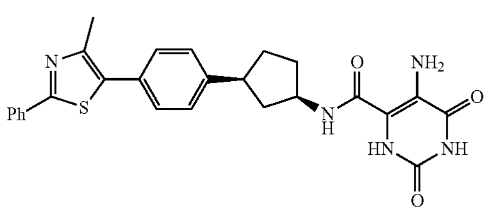 [SMILES: Cc1nc(-c2ccccc2)sc1-c1ccc([C@H]2CC[C@@H](NC(=O)c3[nH]c(=O)[nH]c(=O)c3N)C2)cc1] | 5-amino-N-((1S,3R)-3-(4-(4-methyl-2-phenylthiazol-5-yl)phenyl)cyclopentyl)-2,6-dioxo-1,2,3,6-tetrahydropyrimidine-4-carboxamide | 488.0/1.91 (Method K) | 99.4 |
| 172 | 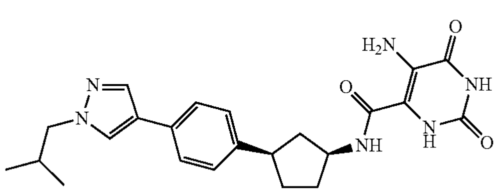 [SMILES: CC(C)Cn1cc(-c2ccc([C@@H]3CC[C@H](NC(=O)c4[nH]c(=O)[nH]c(=O)c4N)C3)cc2)cn1] | 5-amino-N-((1S,3R)-3-(4-(1-isobutyl-1H-pyrazol-4-yl)phenyl)cyclopentyl)-2,6-dioxo-1,2,3,6-tetrahydropyrimidine-4-carboxamide | 437.0/1.51 (Method K) | 100 |

TABLE 2-continued

| Ex. No. | Structure | Name | LC-MS [M + 1]/RT | Purity (%) |
|---|---|---|---|---|
| 173 | 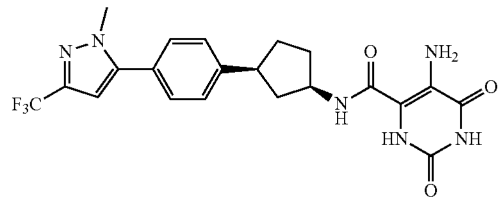 [SMILES: Cn1nc(C(F)(F)F)cc1-c1ccc([C@H]2CC[C@@H](NC(=O)c3[nH]c(=O)[nH]c(=O)c3N)C2)cc1] | 5-amino-N-((1R,3S)-3-(4-(1-methyl-3-(trifluoromethyl)-1H-pyrazol-5-yl)phenyl)cyclopentyl)-2,6-dioxo-1,2,3,6-tetrahydropyrimidine-4-carboxamide | 463.0/1.62 (Method K) | 99.3 |
| 174 | 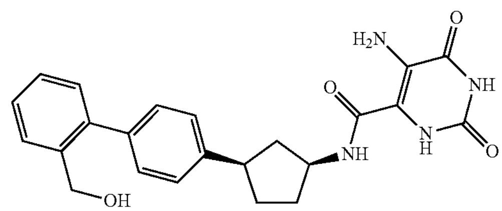 [SMILES: Nc1c(C(=O)N[C@H]2CC[C@@H](c3ccc(-c4ccccc4CO)cc3)C2)[nH]c(=O)[nH]c1=O] | 5-amino-N-((1S,3R)-3-(2'-(hydroxymethyl)biphenyl-4-yl)cyclopentyl)-2,6-dioxo-1,2,3,6-tetrahydropyrimidine-4-carboxamide | 421.0/1.35 (Method K) | 100 |
| 175 | 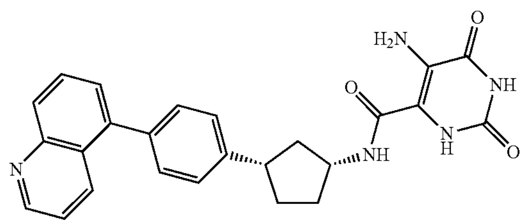 [SMILES: Nc1c(C(=O)N[C@@H]2CC[C@H](c3ccc(-c4cccc5ncccc45)cc3)C2)[nH]c(=O)[nH]c1=O] | 5-amino-2,6-dioxo-N-((1R,3S)-3-(4-(quinolin-5-yl)phenyl)cyclopentyl)-1,2,3,6-tetrahydropyrimidine-4-carboxamide | 442.0/1.44 (Method K) | 100 |
| 176 | 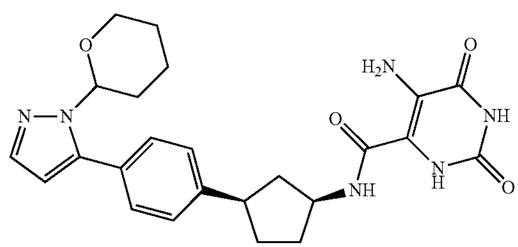 [SMILES: Nc1c(C(=O)N[C@H]2CC[C@@H](c3ccc(-c4ccnn4C4CCCCO4)cc3)C2)[nH]c(=O)[nH]c1=O] | 5-amino-2,6-dioxo-N-((1S,3R)-3-(4-(1-(tetrahydro-2H-pyran-2-yl)-1H-pyrazol-5-yl)phenyl)cyclopentyl)-1,2,3,6-tetrahydropyrimidine-4-carboxamide | 465.2/1.96 (Method K) | 100 |
| 177 | 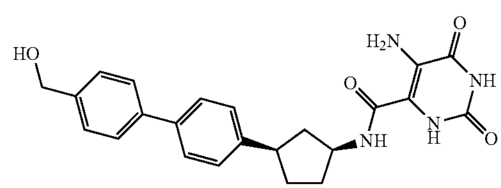 [SMILES: Nc1c(C(=O)N[C@H]2CC[C@@H](c3ccc(-c4ccc(CO)cc4)cc3)C2)[nH]c(=O)[nH]c1=O] | 5-amino-N-((1S,3R)-3-(4'-(hydroxymethyl)biphenyl-4-yl)cyclopentyl)-2,6-dioxo-1,2,3,6-tetrahydropyrimidine-4-carboxamide | 421.0/1.25 (Method K) | 100 |
| 178 | 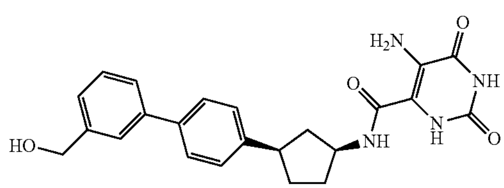 [SMILES: Nc1c(C(=O)N[C@H]2CC[C@@H](c3ccc(-c4cccc(CO)c4)cc3)C2)[nH]c(=O)[nH]c1=O] | 5-amino-N-((1S,3R)-3-(3'-(hydroxymethyl)biphenyl-4-yl)cyclopentyl)-2,6-dioxo-1,2,3,6-tetrahydropyrimidine-4-carboxamide | 421.0/1.30 (Method K) | 100 |
| 179 | 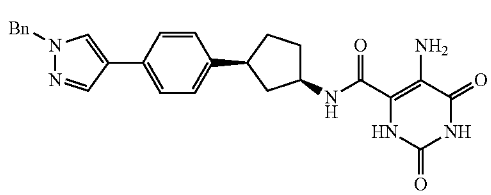 [SMILES: Nc1c(C(=O)N[C@@H]2CC[C@H](c3ccc(-c4cnn(Cc5ccccc5)c4)cc3)C2)[nH]c(=O)[nH]c1=O] | 5-amino-N-((1S,3R)-3-(4-(1-benzyl-1H-pyrazol-4-yl)phenyl)cyclopentyl)-2,6-dioxo-1,2,3,6-tetrahydropyrimidine-4-carboxamide | 471.0/1.52 (Method K) | 100 |

TABLE 2-continued

| Ex. No. | Structure | Name | LC-MS [M + 1]/RT | Purity (%) |
|---|---|---|---|---|
| 180 | 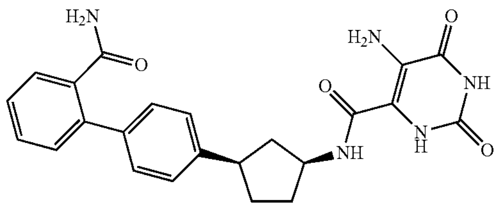 [SMILES: NC(=O)c1ccccc1-c1ccc([C@@H]2CC[C@H](NC(=O)c3[nH]c(=O)[nH]c(=O)c3N)C2)cc1] | 5-amino-N-((1S,3R)-3-(2'-carbamoyl-[1,1'-biphenyl]-4-yl)cyclopentyl)-2,6-dioxo-1,2,3,6-tetrahydropyrimidine-4-carboxamide | 434.1/1.58 (Method K) | 100 |
| 182 | 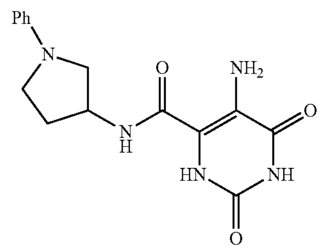 [SMILES: Nc1c(C(=O)NC2CCN(c3ccccc3)C2)[nH]c(=O)[nH]c1=O] | 5-amino-2,6-dioxo-N-(1-phenylpyrrolidin-3-yl)-1,2,3,6-tetrahydropyrimidine-4-carboxamide | 316.2/1.56 (Method B) | RT = 7.10 min, 98.9% (Method A) RT = 7.69 min, 97.1% (Method B) |
| 183 | 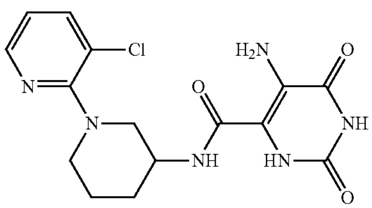 [SMILES: Nc1c(C(=O)NC2CCCN(c3ncccc3Cl)C2)[nH]c(=O)[nH]c1=O] | 5-amino-N-(1-(3-chloropyridin-2-yl)piperidin-3-yl)-2,6-dioxo-1,2,3,6-tetrahydropyrimidine-4-carboxamide | 365.1/1.41 (Method K) | 94.7 |
| 184 | 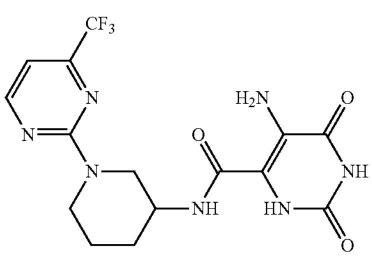 [SMILES: Nc1c(C(=O)NC2CCCN(c3nccc(C(F)(F)F)n3)C2)[nH]c(=O)[nH]c1=O] | 5-amino-2,6-dioxo-N-(1-(4-(trifluoromethyl)pyrimidin-2-yl)piperidin-3-yl)-1,2,3,6-tetrahydropyrimidine-4-carboxamide | 399.9/1.33 (Method K) | 100 |
| 185 | 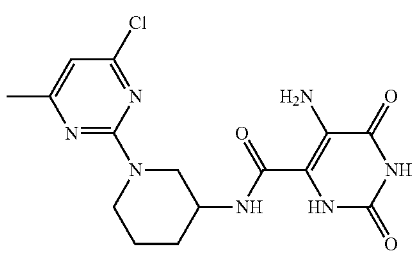 [SMILES: Cc1cc(Cl)nc(N2CCCC(NC(=O)c3[nH]c(=O)[nH]c(=O)c3N)C2)n1] | 5-amino-N-(1-(4-chloro-6-methylpyrimidin-2-yl)piperidin-3-yl)-2,6-dioxo-1,2,3,6-tetrahydropyrimidine-4-carboxamide | 380/0.92 (Method K) | 99.2 |
| 186 | 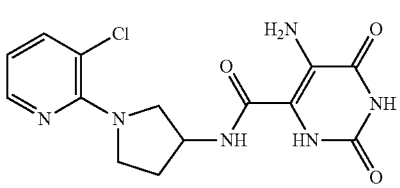 [SMILES: Nc1c(C(=O)NC2CCN(c3ncccc3Cl)C2)[nH]c(=O)[nH]c1=O] | 5-amino-N-(1-(3-chloropyridin-2-yl)pyrrolidin-3-yl)-2,6-dioxo-1,2,3,6-tetrahydropyrimidine-4-carboxamide | 350.9/1.06 (Method K) | 92.3 |
| 187 | 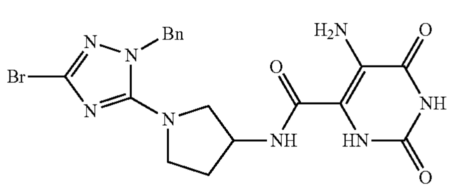 [SMILES: Nc1c(C(=O)NC2CCN(c3nc(Br)nn3Cc3ccccc3)C2)[nH]c(=O)[nH]c1=O] | 5-amino-N-(1-(1-benzyl-3-bromo-1H 1,2,4-triazol-5-yl)pyrrolidin-3-yl)-2,6 dioxo-1,2,3,6-tetrahydropyrimidine-4 carboxamide | 474.8/1.13 (Method K) | 96.4 |

TABLE 2-continued

| Ex. No. | Structure | Name | LC-MS [M + 1]/RT | Purity (%) |
|---|---|---|---|---|
| 188 | 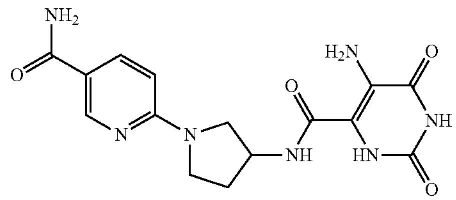 [SMILES: NC(=O)c1ccc(N2CCC(NC(=O)c3[nH]c(=O)[nH]c(=O)c3N)C2)nc1] | 5-amino-N-(1-(5-carbamoylpyridin-2-yl)pyrrolidin-3-yl)-2,6-dioxo-1,2,3,6-tetrahydropyrimidine-4-carboxamide | 359.9/0.53 (Method K) | 100 |
| 189 | 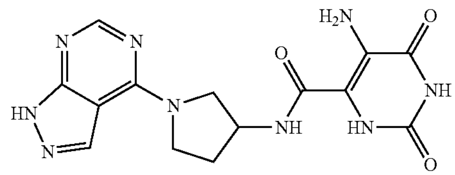 [SMILES: Nc1c(C(=O)NC2CCN(c3ncnc4[nH]ncc34)C2)[nH]c(=O)[nH]c1=O] | N-(1-(1H-pyrazolo[3,4-d]pyrimidin-4-yl)pyrrolidin-3-yl)-5-amino-2,6-dioxo-1,2,3,6-tetrahydropyrimidine-4-carboxamide | 358.0/0.51 (Method K) | 97.9 |
| 190 | 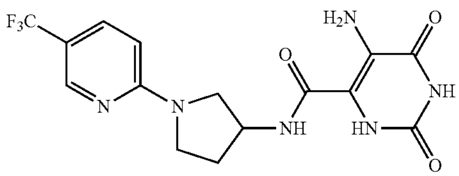 [SMILES: Nc1c(C(=O)NC2CCN(c3ccc(C(F)(F)F)cn3)C2)[nH]c(=O)[nH]c1=O] | 5-amino-2,6-dioxo-N-(1-(5-(trifluoromethyl)pyridin-2-yl)pyrrolidin-3-yl)-1,2,3,6-tetrahydropyrimidine-4-carboxamide | 385.0/1.67 (Method K) | 100 |
| 191 | 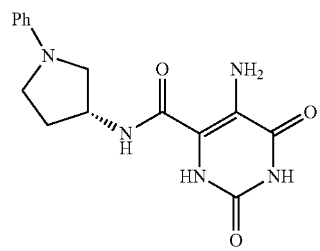 [SMILES: Nc1c(C(=O)N[C@@H]2CCN(c3ccccc3)C2)[nH]c(=O)[nH]c1=O] | (R)-5-amino-2,6-dioxo-N-(1-phenylpyrrolidin-3-yl)-1,2,3,6-tetrahydropyrimidine-4-carboxamide | 316.3/1.50 (Method H) | RT = 5.93 min, 99.4% (Method A) RT = 5.66 min, 98.7% (Method B) |
| 192 | 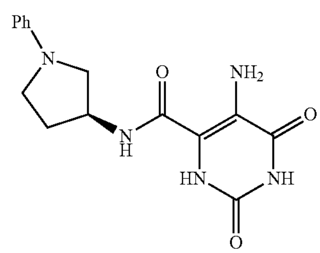 [SMILES: Nc1c(C(=O)N[C@H]2CCN(c3ccccc3)C2)[nH]c(=O)[nH]c1=O] | (S)-5-amino-2,6-dioxo-N-(1-phenylpyrrolidin-3-yl)-1,2,3,6-tetrahydropyrimidine-4-carboxamide | 316.2/1.77 (Method H) | RT = 5.93 min, 99.3% (Method A) RT = 5.66 min, 98.5% (Method B) |
| 194 | 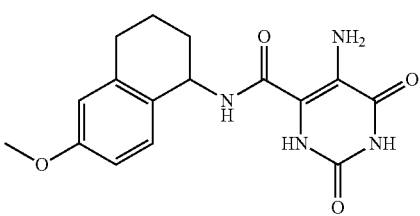 [SMILES: COc1ccc2c(c1)CCCC2NC(=O)c1[nH]c(=O)[nH]c(=O)c1N]<br>Enantiomer A | 5-amino-N-(6-methoxy-1,2,3,4-tetrahydronaphthalen-1-yl)-2,6-dioxo-1,2,3,6-tetrahydropyrimidine-4-carboxamide (Enantiomer A) | 331/1.66 min (Method B) | RT = 6.53 min, 96.3% (Method A) RT = 6.11 min, 99.6% (Method B) |
| 195 | 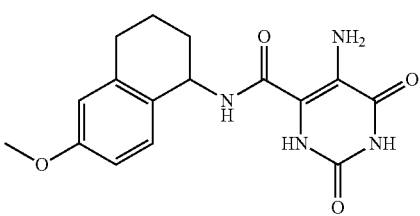 [SMILES: COc1ccc2c(c1)CCCC2NC(=O)c1[nH]c(=O)[nH]c(=O)c1N]<br>Enantiomer B | 5-amino-N-(6-methoxy-1,2,3,4-tetrahydronaphthalen-1-yl)-2,6-dioxo-1,2,3,6-tetrahydropyrimidine-4-carboxamide (Enantiomer B) | 331/1.66 min (Method B) | RT = 6.53 min, 94.3% (Method A) RT = 6.11 min, 99.2% (Method B) |

TABLE 2-continued

| Ex. No. | Structure | Name | LC-MS [M + 1]/RT | Purity (%) |
|---|---|---|---|---|
| 196 | Enantiomer B | 5-amino-N-(1-(methylsulfonyl)-1,2,3,4-tetrahydroquinolin-4-yl)-2,6-dioxo-1,2,3,6-tetrahydropyrimidine-4-carboxamide (Enantiomer B) | 380/1.67 min (Method G) | RT = 5.49 min, 97% (Method A) RT = 5.35 min, 98% (Method B) |
| 197 | Enantiomer B | 5-amino-N-(chroman-4-yl)-2,6-dioxo-1,2,3,6-tetrahydropyrimidine-4-carboxamide (Enantiomer B) | 303/1.47 min (Method B) | RT = 5.62 min, 99% (Method A) RT = 5.34 min, 100% (Method B) |
| 198 | Enantiomer A | 5-amino-N-(5-methoxy-1,2,3,4-tetrahydronaphthalen-1-yl)-2,6-dioxo 1,2,3,6-tetrahydropyrimidine-4-carboxamide (Enantiomer A) | 331.0 (M + H)/ 1.74 min (Method B) | RT = = 6.6 min, 95% (Method A) RT = 6.1 min, 98% (Method B) |
| 199 | Enantiomer B | 5-amino-N-(5-methoxy-1,2,3,4-tetrahydronaphthalen-1-yl)-2,6-dioxo 1,2,3,6-tetrahydropyrimidine-4-carboxamide (Enantiomer B) | 331.0 (M + H)/ 1.73 min (Method B) | RT = 6.6 min, 91% (Method A) RT = 6.1 min, 97% (Method B) |
| 200 | Enantiomer B | 5-amino-N-(7-methoxy-1,2,3,4-tetrahydronaphthalen-1-yl)-2,6-dioxo 1,2,3,6-tetrahydropyrimidine-4-carboxamide (Enantiomer B) | 331/1.66 min (Method B) | RT = 6.41 min, 95% (Method A) RT = 6.13 min, 97% (Method B) |

TABLE 2-continued

| Ex. No. | Structure | Name | LC-MS [M + 1]/RT | Purity (%) |
|---|---|---|---|---|
| 201 | Enantiomer A | 5-amino-N-(8-methoxy-1,2,3,4-tetrahydronaphthalen-1-yl)-2,6-dioxo-1,2,3,6-tetrahydropyrimidine-4-carboxamide (Enantiomer A) | 331/0.94min (Method G) | RT = 6.32 min, 96% (Method A) RT = 5.97 min, 94% (Method B) |
| 204 | 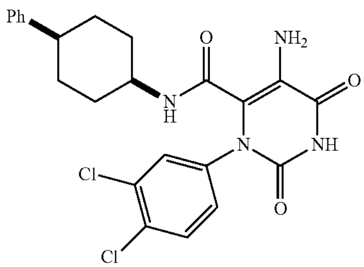 | 5-amino-3-(3,4-dichlorophenyl)-2,6-dioxo-N-(cis-4-phenylcyclohexyl)-1,2,3,6-tetrahydropyrimidine-4-carboxamide | 472.9/2.20 min (Method B) | RT = 9.71 min, 100% (Method A) RT = 8.76 min, 100% (Method B) |
| 206 | 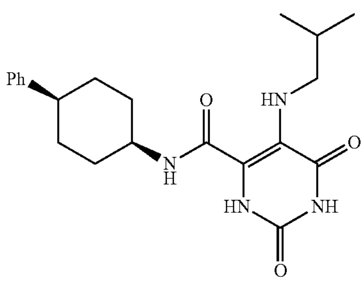 [SMILES: CC(C)CNc1c(C(=O)N[C@H]2CC[C@@H](c3ccccc3)CC2)[nH]c(=O)[nH]c1=O] | 5-(isobutylamino)-2,6-dioxo-N-(cis-4-phenylcyclohexyl)-1,2,3,6-tetrahydropyrimidine-4-carboxamide | 385.2/2.19 min (Method B) | RT = 8.92 min, 96.9% (Method A) RT = 8.82 min, 96.9% (Method B) |
| 207 | 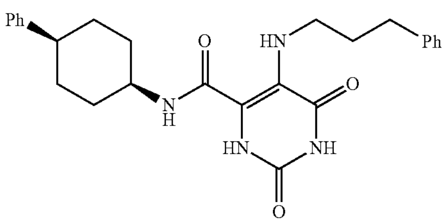 [SMILES: O=C(N[C@H]1CC[C@@H](c2ccccc2)CC1)c1[nH]c(=O)[nH]c(=O)c1NCCCc1ccccc1] | 2,6-dioxo-N-(cis-4-phenylcyclohexyl)-5-(3-phenylpropylamino)-1,2,3,6-tetrahydropyrimidine-4-carboxamide | 447.1/2.79 min (Method K) | 94.2 |
| 208 | 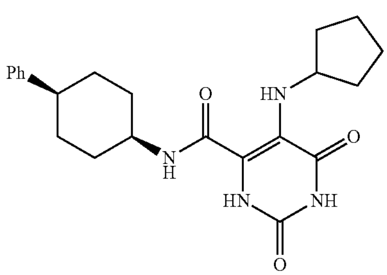 [SMILES: O=C(N[C@H]1CC[C@@H](c2ccccc2)CC1)c1[nH]c(=O)[nH]c(=O)c1NC1CCCC1] | 5-(cyclopentylamino)-2,6-dioxo-N-(cis-4-phenylcyclohexyl)-1,2,3,6-tetrahydropyrimidine-4-carboxamide | 397.1/2.55 min (Method K) | 94.8 |
| 209 | 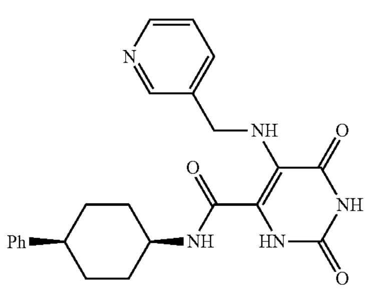 [SMILES: O=C(N[C@H]1CC[C@@H](c2ccccc2)CC1)c1[nH]c(=O)[nH]c(=O)c1NCc1cccnc1] | 2,6-dioxo-N-(cis-4-phenylcyclohexyl)-5-(pyridin-3-ylmethylamino)-1,2,3,6-tetrahydropyrimidine-4-carboxamide | 420.1/1.9 min (Method K) | 92.3 |

TABLE 2-continued

| Ex. No. | Structure | Name | LC-MS [M + 1]/RT | Purity (%) |
|---|---|---|---|---|
| 210 | 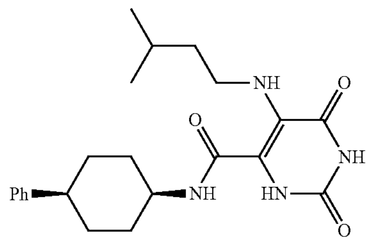 [SMILES: CC(C)CCNc1c(C(=O)N[C@H]2CC[C@@H](c3ccccc3)CC2)[nH]c(=O)[nH]c1=O] | 5-(isopentylamino)-2,6-dioxo-N-(cis-4-phenylcyclohexyl)-1,2,3,6-tetrahydropyrimidine-4-carboxamide | 399.1/2.7 min (Method K) | 93.2 |
| 211 | 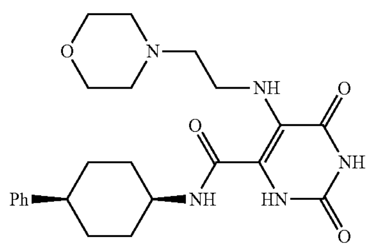 [SMILES: O=C(N[C@H]1CC[C@@H](c2ccccc2)CC1)c1[nH]c(=O)[nH]c(=O)c1NCCN1CCOCC1] | 5-(2-morpholinoethylamino)-2,6-dioxo-N-(cis-4-phenylcyclohexyl)-1,2,3,6-tetrahydropyrimidine-4-carboxamide | 442.1/2.05 min (Method K) | 92.6 |
| 212 | 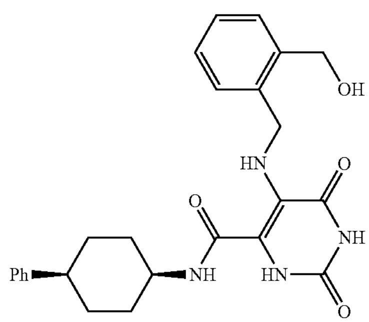 [SMILES: O=C(N[C@H]1CC[C@@H](c2ccccc2)CC1)c1[nH]c(=O)[nH]c(=O)c1NCc1ccccc1CO] | 5-(2-(hydroxymethyl)benzylamino)-2,6-dioxo-N-(cis-4-phenylcyclohexyl)-1,2,3,6-tetrahydropyrimidine-4-carboxamide | 449.0/2.2 min (Method K) | 91.9 |
| 213 | 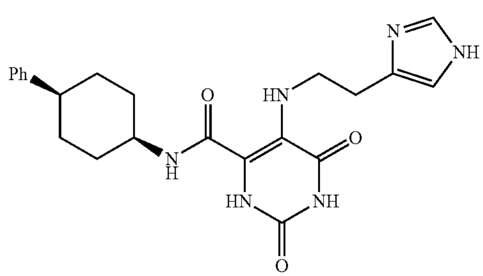 [SMILES: O=C(N[C@H]1CC[C@@H](c2ccccc2)CC1)c1[nH]c(=O)[nH]c(=O)c1NCCc1c[nH]cn1] | 5-(2-(1H-imidazol-4-yl)ethylamino)-2,6-dioxo-N-(cis-4-phenylcyclohexyl)-1,2,3,6-tetrahydropyrimidine-4-carboxamide | 423.1/1.7 min (Method K) | 99.1 |
| 214 | 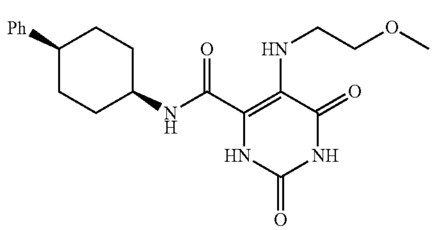 [SMILES: COCCNc1c(C(=O)N[C@H]2CC[C@@H](c3ccccc3)CC2)[nH]c(=O)[nH]c1=O] | 5-(2-methoxyethylamino)-2,6-dioxo-N-(cis-4-phenylcyclohexyl)-1,2,3,6-tetrahydropyrimidine-4-carboxamide | 387.1/2.1 min (Method K) | 95.8 |

TABLE 2-continued

| Ex. No. | Structure | Name | LC-MS [M + 1]/RT | Purity (%) |
|---|---|---|---|---|
| 215 | 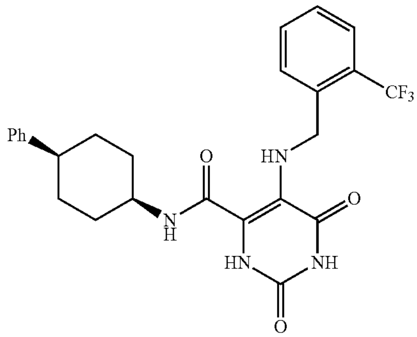 [SMILES: O=C(N[C@H]1CC[C@@H](c2ccccc2)CC1)c1[nH]c(=O)[nH]c(=O)c1NCc1ccccc1C(F)(F)F] | 2,6-dioxo-N-(cis-4-phenylcyclohexyl)-5-(2-(trifluoromethyl)benzylamino)-1,2,3,6-tetrahydropyrimidine-4-carboxamide | 487.0/2.71 min (Method K) | 92.6 |
| 216 | 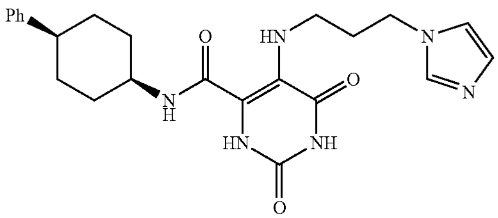 [SMILES: O=C(N[C@H]1CC[C@@H](c2ccccc2)CC1)c1[nH]c(=O)[nH]c(=O)c1NCCCn1ccnc1] | 5-(3-(1H-imidazol-1-yl)propylamino)-2,6-dioxo-N-(cis-4-phenylcyclohexyl)-1,2,3,6-tetrahydropyrimidine-4-carboxamide | 437.2/1.88 min (Method K) | 97.6 |
| 217 | 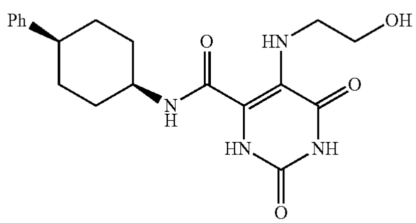 [SMILES: O=C(N[C@H]1CC[C@@H](c2ccccc2)CC1)c1[nH]c(=O)[nH]c(=O)c1NCCO] | 5-(2-hydroxyethylamino)-2,6-dioxo-N-(cis-4-phenylcyclohexyl)-1,2,3,6-tetrahydropyrimidine-4-carboxamide | 373.1/1.83 min (Method K) | 100 |
| 218 | 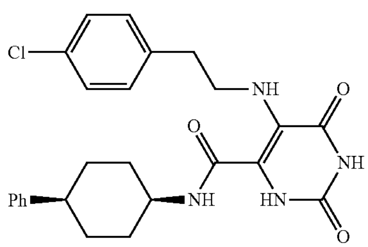 [SMILES: O=C(N[C@H]1CC[C@@H](c2ccccc2)CC1)c1[nH]c(=O)[nH]c(=O)c1NCCc1ccc(Cl)cc1] | 5-(4-chlorophenethylamino)-2,6-dioxo-N-(cis-4-phenylcyclohexyl)-1,2,3,6-tetrahydropyrimidine-4-carboxamide | 467.1/2.91 min (Method K) | 100 |
| 219 | 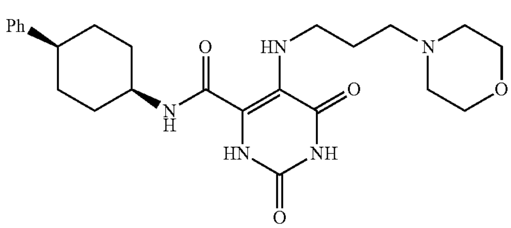 [SMILES: O=C(N[C@H]1CC[C@@H](c2ccccc2)CC1)c1[nH]c(=O)[nH]c(=O)c1NCCCN1CCOCC1] | 5-(3-morpholinopropylamino)-2,6-dioxo-N-(cis-4-phenylcyclohexyl)-1,2,3,6-tetrahydropyrimidine-4-carboxamide | 456.2/1.96 min (Method K) | 99.0 |
| 220 | 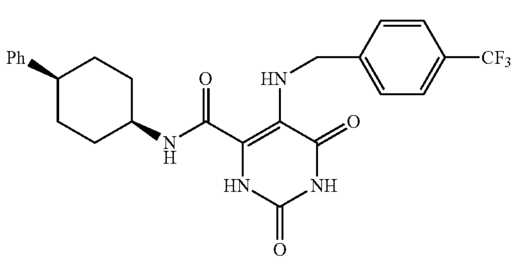 [SMILES: O=C(N[C@H]1CC[C@@H](c2ccccc2)CC1)c1[nH]c(=O)[nH]c(=O)c1NCc1ccc(C(F)(F)F)cc1] | 2,6-dioxo-N-(cis-4-phenylcyclohexyl)-5-(4-(trifluoromethyl)benzylamino)-1,2,3,6-tetrahydropyrimidine-4-carboxamide | 487.1/2.82 min (Method K) | 96.3 |

TABLE 2-continued

| Ex. No. | Structure | Name | LC-MS [M + 1]/RT | Purity (%) |
|---|---|---|---|---|
| 221 | 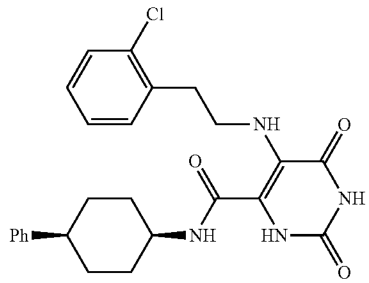 [SMILES: O=C(N[C@H]1CC[C@@H](c2ccccc2)CC1)c1[nH]c(=O)[nH]c(=O)c1NCCc1ccccc1Cl] | 5-(2-chlorophenethylamino)-2,6-dioxo-N-(cis-4-phenylcyclohexyl)-1,2,3,6-tetrahydropyrimidine-4-carboxamide | 467.1/2.84 min (Method K) | 100 |
| 222 | 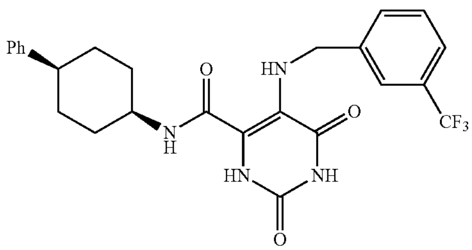 [SMILES: O=C(N[C@H]1CC[C@@H](c2ccccc2)CC1)c1[nH]c(=O)[nH]c(=O)c1NCc1cccc(C(F)(F)F)c1] | 2,6-dioxo-N-(cis-4-phenylcyclohexyl)-5-(3-(trifluoromethyl)benzylamino)-1,2,3,6-tetrahydropyrimidine-4-carboxamide | 487.1/2.8 min (Method K) | 95.5 |
| 223 | 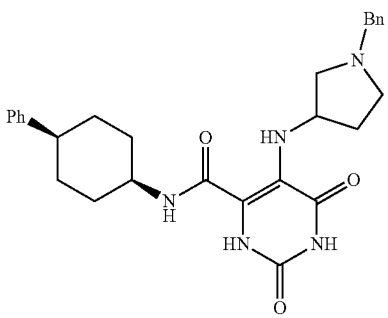 [SMILES: O=C(N[C@H]1CC[C@@H](c2ccccc2)CC1)c1[nH]c(=O)[nH]c(=O)c1NC1CCN(Cc2ccccc2)C1] | 5-(1-benzylpyrrolidin-3-ylamino)-2,6-dioxo-N-(cis-4-phenylcyclohexyl)-1,2,3,6-tetrahydropyrimidine-4-carboxamide | 488.2/2.47 min (Method K) | 98.7 |
| 224 | 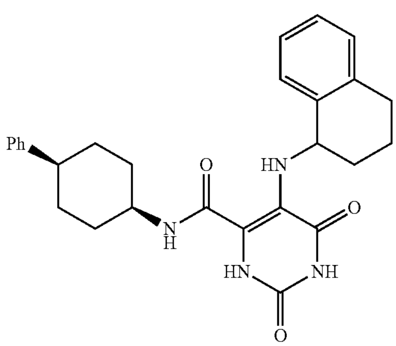 [SMILES: O=C(N[C@H]1CC[C@@H](c2ccccc2)CC1)c1[nH]c(=O)[nH]c(=O)c1NC1CCCc2ccccc21] | 2,6-dioxo-N-(cis-4-phenylcyclohexyl)-5-(1,2,3,4-tetrahydronaphthalen-1-ylamino)-1,2,3,6-tetrahydropyrimidine-4-carboxamide | 459.1/2.86 min (Method K) | 97.8 |
| 225 | 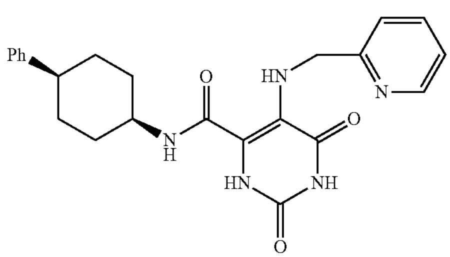 [SMILES: O=C(N[C@H]1CC[C@@H](c2ccccc2)CC1)c1[nH]c(=O)[nH]c(=O)c1NCc1ccccn1] | 2,6-dioxo-N-(cis-4-phenylcyclohexyl)-5-(pyridin-2-ylmethylamino)-1,2,3,6-tetrahydropyrimidine-4-carboxamide | 420.1/2.15 min (Method K) | 92.6 |

TABLE 2-continued

| Ex. No. | Structure | Name | LC-MS [M + 1]/RT | Purity (%) |
|---|---|---|---|---|
| 226 | 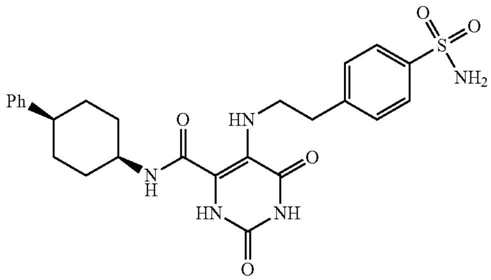 [SMILES: NS(=O)(=O)c1ccc(CCNc2c(C(=O)N[C@H]3CC[C@@H](c4ccccc4)CC3)[nH]c(=O)[nH]c2=O)cc1] | 2,6-dioxo-N-(cis-4-phenylcyclohexyl)-5-(4-sulfamoylphenethylamino)-1,2,3,6-tetrahydropyrimidine-4-carboxamide | 512.1/2.1 min (Method K) | 99.2 |
| 227 | 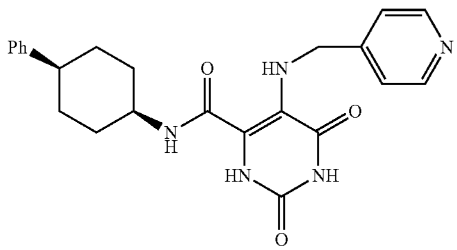 [SMILES: O=C(N[C@H]1CC[C@@H](c2ccccc2)CC1)c1[nH]c(=O)[nH]c(=O)c1NCc1ccncc1] | 2,6-dioxo-N-(cis-4-phenylcyclohexyl)-5-(pyridin-4-ylmethylamino)-1,2,3,6-tetrahydropyrimidine-4-carboxamide | 420.1/1.91 min (Method K) | 99.0 |
| 228 | 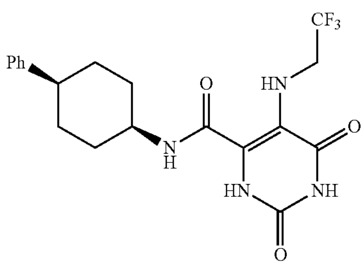 [SMILES: O=C(N[C@H]1CC[C@@H](c2ccccc2)CC1)c1[nH]c(=O)[nH]c(=O)c1NCC(F)(F)F] | 2,6-dioxo-N-(cis-4-phenylcyclohexyl)-5-(2,2,2-trifluoroethylamino)-1,2,3,6-tetrahydropyrimidine-4-carboxamide | 411.1/3.86 min (Method A) | RT = 8.84 min, 97.5% (Method A) RT = 8.02 min, 98.2% (Method B) |
| 229 | 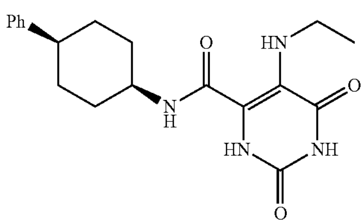 [SMILES: CCNc1c(C(=O)N[C@H]2CC[C@@H](c3ccccc3)CC2)[nH]c(=O)[nH]c1=O] | 5-(ethylamino)-2,6-dioxo-N-(cis-4-phenylcyclohexyl)-1,2,3,6-tetrahydropyrimidine-4-carboxamide | 357.2/2.25 min (Method K) | 91.1 |
| 230 | 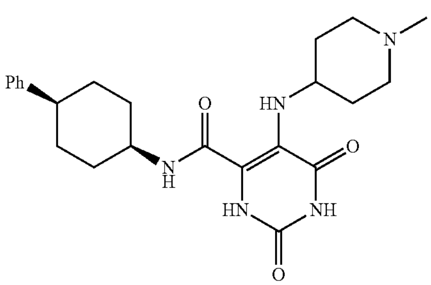 [SMILES: CN1CCC(Nc2c(C(=O)N[C@H]3CC[C@@H](c4ccccc4)CC3)[nH]c(=O)[nH]c2=O)CC1] | 5-(1-methylpiperidin-4-ylamino)-2,6-dioxo-N-(cis-4-phenylcyclohexyl)-1,2,3,6-tetrahydropyrimidine-4-carboxamide | 426.2/1.6 min (Method K) | 98.3 |
| 231 | 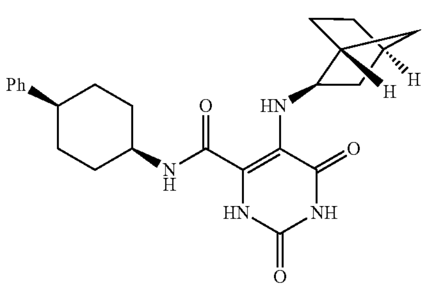 [SMILES: O=C(N[C@H]1CC[C@@H](c2ccccc2)CC1)c1[nH]c(=O)[nH]c(=O)c1N[C@@H]1C[C@H]2CC[C@@H]1C2] | 5-(((1R,2R,4S)-bicyclo[2.2.1]heptan-2-ylamino)-2,6-dioxo-N-(cis-4-phenylcyclohexyl)-1,2,3,6-tetrahydropyrimidine-4-carboxamide | 423.2/2.82 min (Method K) | 100 |

TABLE 2-continued

| Ex. No. | Structure | Name | LC-MS [M + 1]/RT | Purity (%) |
|---|---|---|---|---|
| 232 | 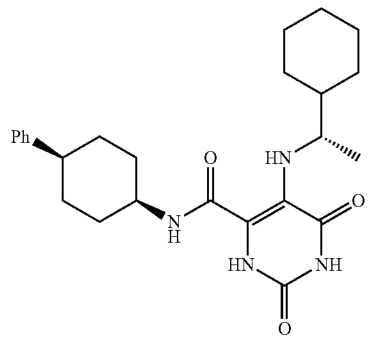 [SMILES: C[C@H](Nc1c(C(=O)N[C@H]2CC[C@@H](c3ccccc3)CC2)[nH]c(=O)[nH]c1=O)C1CCCCC1] | 5-((S)-1-cyclohexylethylamino)-2,6-dioxo-N-(cis-phenylcyclohexyl)-1,2,3,6-tetrahydropyrimidine-4-carboxamide | 439.2/3.11 min (Method K) | 100 |
| 233 | 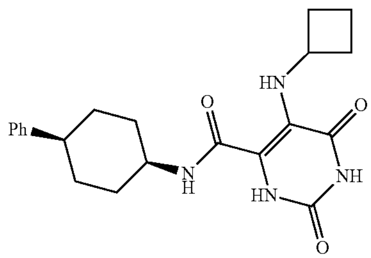 [SMILES: O=C(N[C@H]1CC[C@@H](c2ccccc2)CC1)c1[nH]c(=O)[nH]c(=O)c1NC1CCC1] | 5-(cyclobutylamino)-2,6-dioxo-N-(cis-4-phenylcyclohexyl)-1,2,3,6-tetrahydropyrimidine-4-carboxamide | 383.2/2.48 min (Method K) | 97.3 |
| 234 | 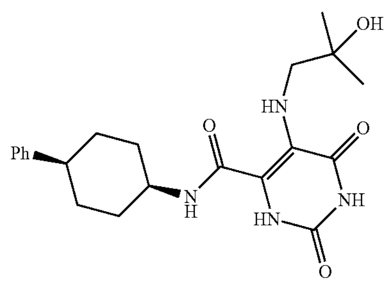 [SMILES: CC(C)(O)CNc1c(C(=O)N[C@H]2CC[C@@H](c3ccccc3)CC2)[nH]c(=O)[nH]c1=O] | 5-(2-hydroxy-2-methylpropylamino)-2,6-dioxo-N-(cis-4-phenylcyclohexyl)-1,2,3,6-tetrahydropyrimidine-4-carboxamide | 401.3/1.55 min (Method K) | 98.7 |
| 235 | 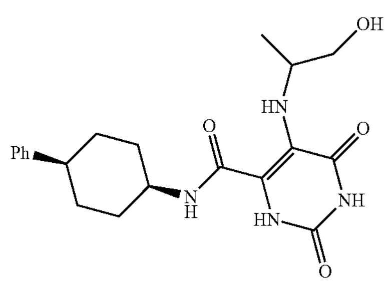 [SMILES: CC(CO)Nc1c(C(=O)N[C@H]2CC[C@@H](c3ccccc3)CC2)[nH]c(=O)[nH]c1=O] | 5-(1-hydroxypropan-2-ylamino)-2,6-dioxo-N-(cis-4-phenylcyclohexyl)-1,2,3,6-tetrahydropyrimidine-4-carboxamide | 387.4/1.4 min (Method K) | 87.3 |
| 236 | 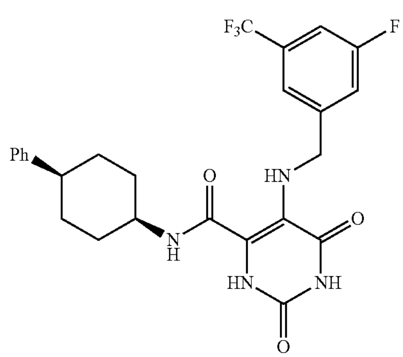 [SMILES: O=C(N[C@H]1CC[C@@H](c2ccccc2)CC1)c1[nH]c(=O)[nH]c(=O)c1NCc1cc(F)cc(C(F)(F)F)c1] | 5-(3-fluoro-5-(trifluoromethyl)benzylamino)-2,6-dioxo-N-((1s,4s)-4-phenylcyclohexyl)-1,2,3,6-tetrahydropyrimidine-4-carboxamide | 505.0/2.16 min (Method K) | 100 |

TABLE 2-continued

| Ex. No. | Structure | Name | LC-MS [M + 1]/RT | Purity (%) |
|---|---|---|---|---|
| 237 | 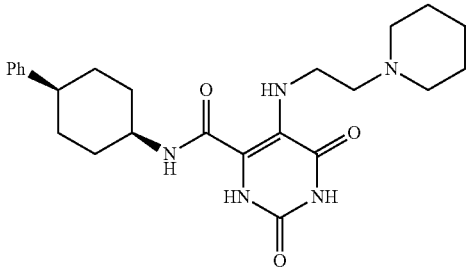 [SMILES: O=C(N[C@H]1CC[C@@H](c2ccccc2)CC1)c1[nH]c(=O)[nH]c(=O)c1NCCN1CCCCC1] | 2,6-dioxo-N-((1s,4s)-4-phenylcyclohexyl)-5-(2-(piperidin-1-yl)ethylamino)-1,2,3,6-tetrahydropyrimidine-4-carboxamide | 440.2/1.75 min (Method K) | 100 |
| 242 | 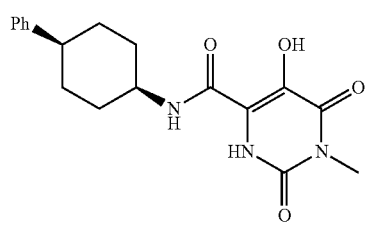 | 5-hydroxy-1-methyl-2,6-dioxo-N-(cis-4-phenylcyclohexyl)-1,2,3,6-tetrahydropyrimidine-4-carboxamide | 358.1/2.12 min (Method B) | RT = 8.46 min, 100% (Method A) RT = 7.56 min, 100% (Method B) |
| 243 | 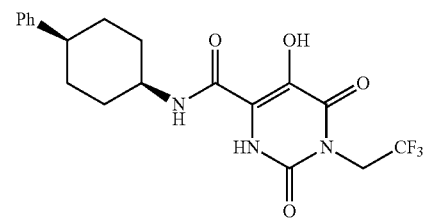 [SMILES: O=C(N[C@H]1CC[C@@H](c2ccccc2)CC1)c1[nH]c(=O)n(CC(F)(F)F)c(=O)c1O] | 5-hydroxy-2,6-dioxo-N-(cis-4-phenylcyclohexyl)-1-(2,2,2-trifluoroethyl)-1,2,3,6-tetrahydropyrimidine-4-carboxamide | 412/2.11 min (Method B) | RT = 9.22 min, 100% (Method A) RT = 8.20 min, 100% (Method B) |
| 244 | 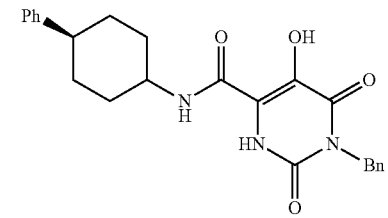 | 1-benzyl-5-hydroxy-2,6-dioxo-N-(4-phenylcyclohexyl)-1,2,3,6-tetrahydropyrimidine-4-carboxamide | 420.1/2.25 min (Method B) | RT = 10.09 min, 100% (Method A) RT = 9.02 min, 100% (Method B) |
| 245 | 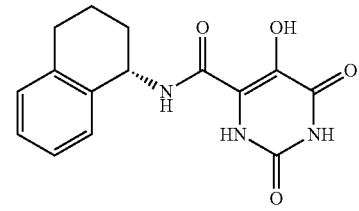 [SMILES: O=C(N[C@H]1CCCc2ccccc21)c1[nH]c(=O)[nH]c(=O)c1O] | (S)-5-hydroxy-2,6-dioxo-N-(1,2,3,4-tetrahydronaphthalen-1-yl)-1,2,3,6-tetrahydropyrimidine-4-carboxamide | 301/1.75 min (Method B) | RT = 6.03 min, 98.2% (Method A) RT = 5.64 min, 97.8% (Method B) |
| 246 | 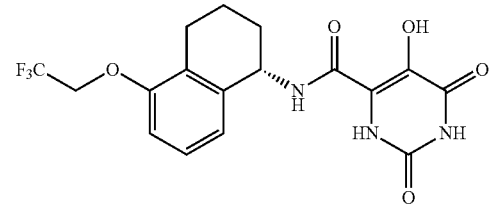 [SMILES: O=C(N[C@H]1CCCc2c(OCC(F)(F)F)cccc21)c1[nH]c(=O)[nH]c(=O)c1O] | (S)-5-hydroxy-2,6-dioxo-N-(5-(2,2,2-trifluoroethoxy)-1,2,3,4-tetrahydronaphthalen-1-yl)-1,2,3,6-tetrahydropyrimidine-4-carboxamide | 400.1/1.45 min (Method D) | RT = 7.76 min, 100% (Method A) RT = 7.29 min, 100% (Method B) |

TABLE 2-continued

| Ex. No. | Structure | Name | LC-MS [M + 1]/RT | Purity (%) |
|---|---|---|---|---|
| 247 | 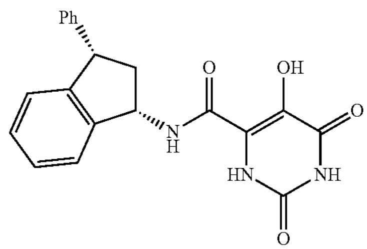 [SMILES: O=C(N[C@H]1C[C@@H](c2ccccc2)c2ccccc21)c1[nH]c(=O)[nH]c(=O)c1O] | 5-hydroxy-2,6-dioxo-N-((1S,3S)-3-phenyl-2,3-dihydro-1H-inden-1-yl)-1,2,3,6-tetrahydropyrimidine-4-carboxamide | 364.1/2.02 min (Method B) | RT = 7.97 min, 100% (Method A) RT = 7.51 min, 100% (Method B) |
| 248 | 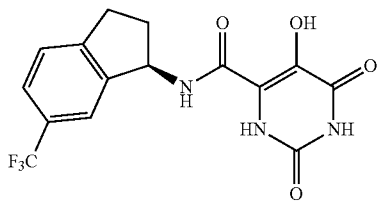 [SMILES: O=C(N[C@@H]1CCc2ccc(C(F)(F)F)cc21)c1[nH]c(=O)[nH]c(=O)c1O] | (R)-5-hydroxy-2,6-dioxo-N-(6-(trifluoromethyl)-2,3-dihydro-1H-inden-1-yl)-1,2,3,6-tetrahydropyrimidine-4-carboxamide | 356.1/1.86 min (Method B) | RT = 7.10 min, 93% (Method A) RT = 6.64 min, 90.5% (Method B) |
| 249 | 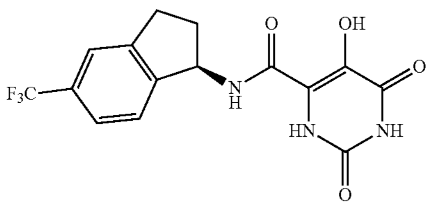 | (R)-5-hydroxy-2,6-dioxo-N-(5-(trifluoromethyl)-2,3-dihydro-1H-inden-1-yl)-1,2,3,6-tetrahydropyrimidine-4-carboxamide | 378.2 (M + Na)/ 3.39 min (Method J) | RT = 7.16 min, 100% (Method A) RT = 6.64 min, 89.7% (Method B) |
| 250 | 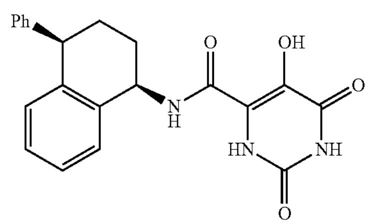 [SMILES: O=C(N[C@@H]1CC[C@H](c2ccccc2)c2ccccc21)c1[nH]c(=O)[nH]c(=O)c1O] | 5-hydroxy-2,6-dioxo-N-((1R,4R)-4-phenyl-1,2,3,4-tetrahydronaphthalen-1-yl)-1,2,3,6-tetrahydropyrimidine-4-carboxamide | 400.2/2.03 min (Method H) | RT = 7.80 min, 100% (Method A) RT = 7.25 min, 100% (Method B) |
| 251 | 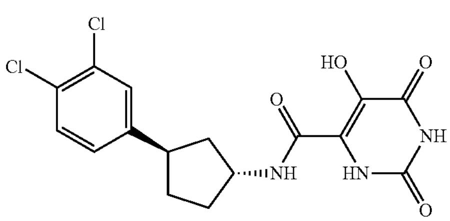 [SMILES: O=C(N[C@@H]1CC[C@@H](c2ccc(Cl)c(Cl)c2)C1)c1[nH]c(=O)[nH]c(=O)c1O] | N-((1R,3R)-3-(3,4-dichlorophenyl)cyclopentyl)-5-hydroxy-2,6-dioxo-1,2,3,6-tetrahydropyrimidine-4-carboxamide | 384.2/2.05 min (Method H) | RT = 8.32 min, 98.9% (Method A) RT = 7.72 min, 98.9% (Method B) |
| 252 | 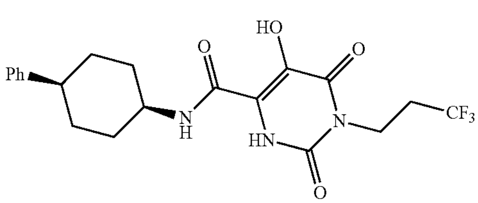 [SMILES: O=C(N[C@H]1CC[C@@H](c2ccccc2)CC1)c1[nH]c(=O)n(CCC(F)(F)F)c(=O)c1O] | 5-hydroxy-2,6-dioxo-N-((1s,4s)-4-phenylcyclohexyl)-1-(3,3,3-trifluoropropyl)-1,2,3,6-tetrahydropyrimidine-4-carboxamide | 426.2/2.16 min (Method B) | RT = 9.86 min, 100% (Method A) RT = 8.86 min, 100% (Method B) |
| 253 | 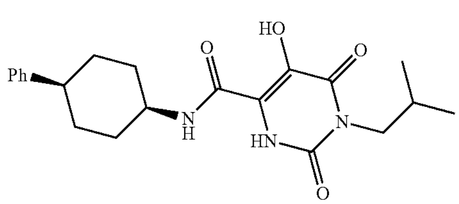 [SMILES: CC(C)Cn1c(=O)[nH]c(C(=O)N[C@H]2CC[C@@H](c3ccccc3)CC2)c(O)c1=O] | 5-hydroxy-1-isobutyl-2,6-dioxo-N-((1s,4s)-4-phenylcyclohexyl)-1,2,3,6-tetrahydropyrimidine-4-carboxamide | 386.3/2.25 min (Method B) | RT = 10.12 min, 98.9% (Method A) RT = 8.86 min, 98.8% (Method B) |

TABLE 2-continued

| Ex. No. | Structure | Name | LC-MS [M + 1]/RT | Purity (%) |
|---|---|---|---|---|
| 254 | 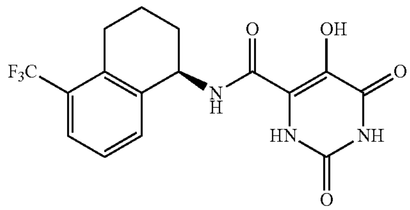 [SMILES: O=C(N[C@@H]1CCCc2c1cccc2C(F)(F)F)c1[nH]c(=O)[nH]c(=O)c1O] | (R)-5-hydroxy-2,6-dioxo-N-(5-(trifluoromethyl)-1,2,3,4-tetrahydronaphthalen-1-yl)-1,2,3,6-tetrahydropyrimidine-4-carboxamide | 370.1/1.94 min (Method B) | RT = 7.67 min, 97% (Method A) RT = 7.19 min, 98% (Method B) |
| 255 | 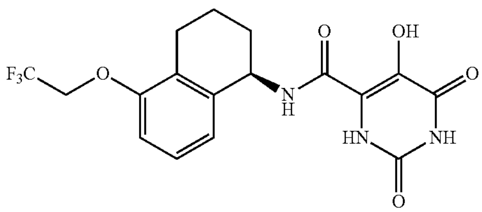 [SMILES: O=C(N[C@@H]1CCCc2c(OCC(F)(F)F)cccc21)c1[nH]c(=O)[nH]c(=O)c1O] | (R)-5-hydroxy-2,6-dioxo-N-(5-(2,2,2-trifluoroethoxy)-1,2,3,4-tetrahydronaphthalen-1-yl)-1,2,3,6-tetrahydropyrimidine-4-carboxamide | 400.2/1.95 min (Method B) | RT = 7.85 min, 99% (Method A) RT = 7.38 min, 99% (Method B) |
| 256 | 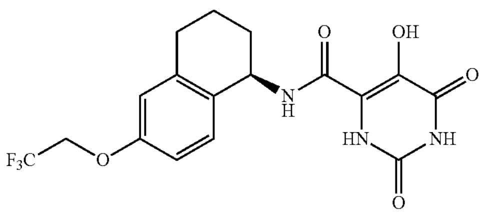 [SMILES: O=C(N[C@@H]1CCCc2cc(OCC(F)(F)F)ccc21)c1[nH]c(=O)[nH]c(=O)c1O] | (R)-5-hydroxy-2,6-dioxo-N-(6-(2,2,2-trifluoroethoxy)-1,2,3,4-tetrahydronaphthalen-1-yl)-1,2,3,6-tetrahydropyrimidine-4-carboxamide | 400.2/1.89 min (Method B) | RT = 7.76 min, 99% (Method A) RT = 7.32 min, 99% (Method B) |
| 257 | 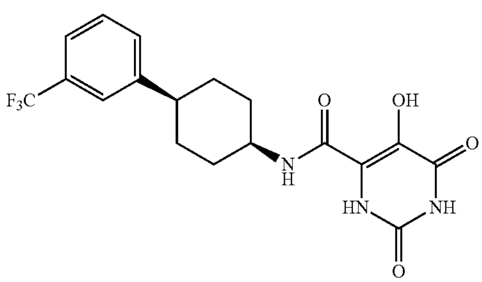 [SMILES: O=C(N[C@H]1CC[C@@H](c2cccc(C(F)(F)F)c2)CC1)c1[nH]c(=O)[nH]c(=O)c1O] | 5-hydroxy-2,6-dioxo-N-((1s,4s)-4-(3-(trifluoromethyl)phenyl)cyclohexyl)-1,2,3,6-tetrahydropyrimidine-4-carboxamide | 398.1/2.01 min (Method B) | RT = 8.36 min, 92.2% (Method A) RT = 7.79 min, 92.2% (Method B) |
| 258 | 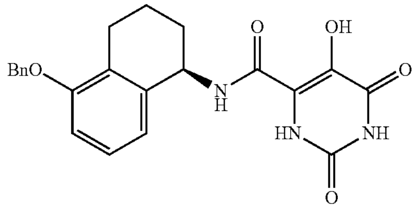 | (R)-N-(5-(benzyloxy)-1,2,3,4-tetrahydronaphthalen-1-yl)-5-hydroxy-2,6-dioxo-1,2,3,6-tetrahydropyrimidine-4-carboxamide | 407.1/2.02 min (Method B) | RT = 8.50 min, 93.8% (Method A) RT = 7.84 min, 96.7% (Method B) |
| 259 | 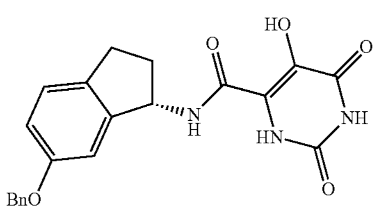 [SMILES: O=C(N[C@H]1CCc2ccc(OCc3ccccc3)cc21)c1[nH]c(=O)[nH]c(=O)c1O] | (S)-N-(6-(benzyloxy)-2,3-dihydro-1H-inden-1-yl)-5-hydroxy-2,6-dioxo-1,2,3,6-tetrahydropyrimidine-4-carboxamide | 394.1/1.98 min (Method B) | RT = 8.08 min, 94.5% (Method A) RT = 7.51 min, 99.3% (Method B) |
| 260 | 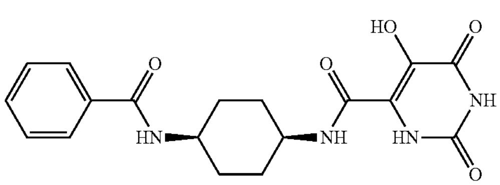 [SMILES: O=C(N[C@H]1CC[C@@H](NC(=O)c2[nH]c(=O)[nH]c(=O)c2O)CC1)c1ccccc1] | N-((1s,4s)-4-benzamidocyclohexyl)-5-hydroxy-2,6-dioxo-1,2,3,6-tetrahydropyrimidine-4-carboxamide | 373.1/0.61 min (Method M) | RT = 5.25 min, 100% (Method A) RT = 5.01 min, 95% (Method B) |

TABLE 2-continued

| Ex. No. | Structure | Name | LC-MS [M + 1]/RT | Purity (%) |
|---|---|---|---|---|
| 261 | 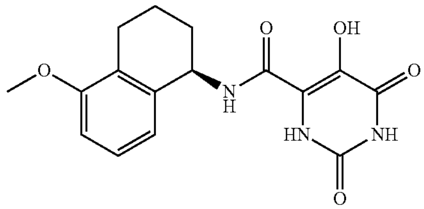 [SMILES: COc1cccc2c1CCC[C@H]2NC(=O)c1[nH]c(=O)[nH]c(=O)c1O] | (R)-5-hydroxy-N-(5-methoxy-1,2,3,4-tetrahydronaphthalen-1-yl)-2,6-dioxo-1,2,3,6-tetrahydropyrimidine-4-carboxamide | 332.1/1.76 min (Method B) | RT = 6.01 min, 99.3% (Method A) RT = 5.66 min, 100% (Method B) |
| 262 | 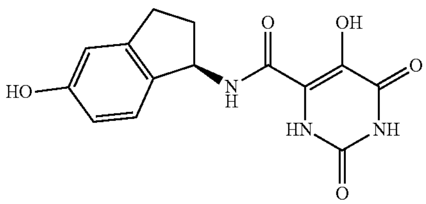 [SMILES: O=C(N[C@@H]1CCc2cc(O)ccc21)c1[nH]c(=O)[nH]c(=O)c1O] | (R)-5-hydroxy-N-(5-hydroxy-2,3-dihydro-1H-inden-1-yl)-2,6-dioxo-1,2,3,6-tetrahydropyrimidine-4-carboxamide | 304.1/1.32 min (Method B) | RT = 6.01 min, 93.1% (Method A) RT = 5.66 min, 100% (Method B) |
| 263 | 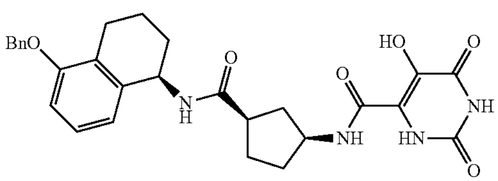 [SMILES: O=C(N[C@H]1CC[C@@H](C(=O)N[C@@H]2CCCc3c(OCc4ccccc4)cccc32)C1)c1[nH]c(=O)[nH]c(=O)c1O] | N-((1S,3R)-3-((R)-5-(benzyloxy)-1,2,3,4-tetrahydronaphthalen-1-ylcarbamoyl)cyclopentyl)-5-hydroxy-2,6-dioxo-1,2,3,6-tetrahydropyrimidine-4-carboxamide | 519.3/2.04 min (Method B) | RT = 13.99 min, 96.1% (Method A) RT = 14.3 min, 96.3% (Method B) |
| 264 | 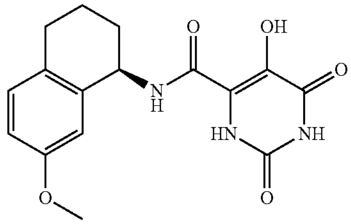 [SMILES: COc1ccc2c(c1)[C@H](NC(=O)c1[nH]c(=O)[nH]c(=O)c1O)CCC2] | (R)-5-hydroxy-N-(7-methoxy-1,2,3,4-tetrahydronaphthalen-1-yl)-2,6-dioxo-1,2,3,6-tetrahydropyrimidine-4-carboxamide | 332.1/1.75 min (Method B) | RT = 6.51 min, 91.4% (Method A) RT = 6.13 min, 96.1% (Method B) |
| 265 | 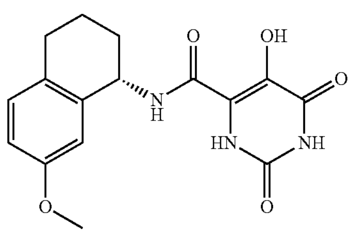 [SMILES: COc1ccc2c(c1)[C@@H](NC(=O)c1[nH]c(=O)[nH]c(=O)c1O)CCC2] | (S)-5-hydroxy-N-(7-methoxy-1,2,3,4-tetrahydronaphthalen-1-yl)-2,6-dioxo-1,2,3,6-tetrahydropyrimidine-4-carboxamide | 332.1/1.70 min (Method B) | RT = 6.5 min, 87.2% (Method A) RT = 6.1 min, 98.2% (Method B) |
| 266 | 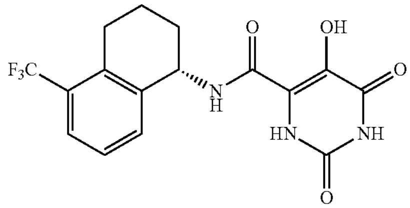 [SMILES: O=C(N[C@H]1CCCc2c1cccc2C(F)(F)F)c1[nH]c(=O)[nH]c(=O)c1O] | (S)-5-hydroxy-2,6-dioxo-N-(5-(trifluoromethyl)-1,2,3,4-tetrahydronaphthalen-1-yl)-1,2,3,6-tetrahydropyrimidine-4-carboxamide | 370.1/1.88 min (Method B) | NA |
| 272 | 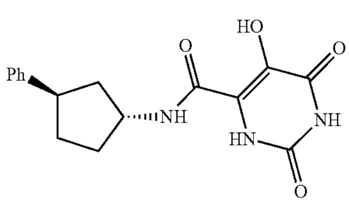 [SMILES: O=C(N[C@@H]1CC[C@@H](c2ccccc2)C1)c1[nH]c(=O)[nH]c(=O)c1O] | 5-hydroxy-2,6-dioxo-N-((1R,3R)-3-phenylcyclopentyl)-1,2,3,6-tetrahydropyrimidine-4-carboxamide | 316.2/1.91 min (Method B) | RT = 8.83 min, 97.0% (Method C) R= 8.35 min, 96.0% (Method D) |

TABLE 2-continued

| Ex. No. | Structure | Name | LC-MS [M + 1]/RT | Purity (%) |
|---|---|---|---|---|
| 273 | 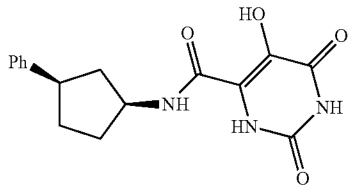 [SMILES: O=C(N[C@H]1CC[C@@H](c2ccccc2)C1)c1[nH]c(=O)[nH]c(=O)c1O] | 5-hydroxy-2,6-dioxo-N-((1S,3R)-3-phenylcyclopentyl)-1,2,3,6-tetrahydropyrimidine-4-carboxamide | 316.1/3.26 min (Method A) | RT = 8.83 min, 97.0% (Method A) RT = 8.35 min, 96.0% (Method B) |
| 274 | 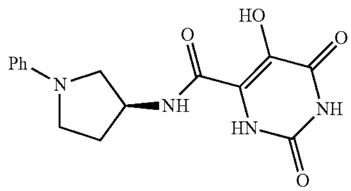 [SMILES: O=C(N[C@H]1CCN(c2ccccc2)C1)c1[nH]c(=O)[nH]c(=O)c1O] | (S)-5-hydroxy-2,6-dioxo-N-(1-phenylpyrrolidin-3-yl)-1,2,3,6-tetrahydropyrimidine-4-carboxamide | 317.2/1.58 min (Method B) | RT = 5.84 min, 99.4% (Method A) RT = 5.64 min, 99.4% (Method B) |
| 275 | 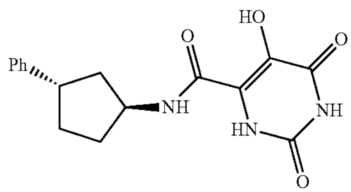 [SMILES: O=C(N[C@H]1CC[C@H](c2ccccc2)C1)c1[nH]c(=O)[nH]c(=O)c1O] | 5-hydroxy-2,6-dioxo-N-((1S,3S)-3-phenylcyclopentyl)-1,2,3,6-tetrahydropyrimidine-4-carboxamide | 316.2/1.91 min (Method B) | RT = 7.01 min, 96.8% (Method A) RT = 6.71 min, 96.2% (Method B) |
| 276 | 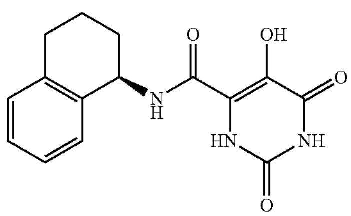 [SMILES: O=C(N[C@@H]1CCCc2ccccc21)c1[nH]c(=O)[nH]c(=O)c1O] | (R)-5-hydroxy-2,6-dioxo-N-(1,2,3,4-tetrahydronaphthalen-1-yl)-1,2,3,6-tetrahydropyrimidine-4-carboxamide | 302.1/1.83 min (Method B) | RT = 7.43 min, 98.3% (Method A) RT = 8.03 min, 100% (Method B) |
| 277 | 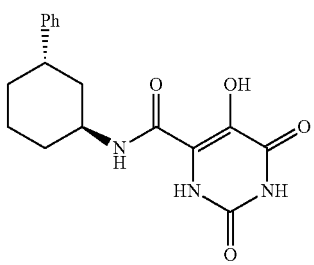 [SMILES: O=C(N[C@H]1CCC[C@H](c2ccccc2)C1)c1[nH]c(=O)[nH]c(=O)c1O] | 5-hydroxy-2,6-dioxo-N-((1S,3S)-3-phenylcyclohexyl)-1,2,3,6-tetrahydropyrimidine-4-carboxamide | 330.0/1.91 min (Method B) | RT = 6.01 min, 99.3% (Method A) RT = 5.66 min, 100% (Method B) |
| 278 | 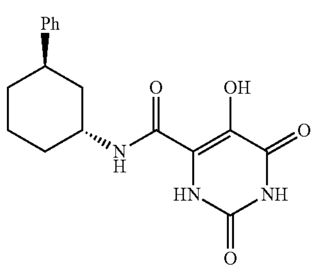 [SMILES: O=C(N[C@@H]1CCC[C@@H](c2ccccc2)C1)c1[nH]c(=O)[nH]c(=O)c1O] | 5-hydroxy-2,6-dioxo-N-((1R,3R)-3-phenylcyclohexyl)-1,2,3,6-tetrahydropyrimidine-4-carboxamide | 330.1/1.94 min (Method B) | RT = 7.14 min, 90.3% (Method A) RT = 6.72 min, 97.3% (Method B) |
| 279 | 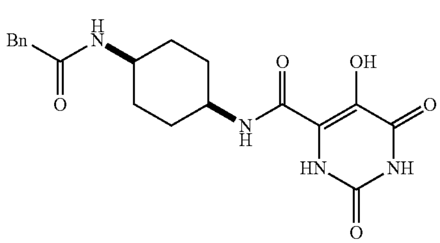 | 5-hydroxy-2,6-dioxo-N-(cis-4-(2-phenylacetamido)cyclohexyl)-1,2,3,6-tetrahydropyrimidine-4-carboxamide | 387.0/0.62 min (Method M) | RT = 5.30 min, 98% (Method A) RT = 5.07 min, 97% (Method B) |

TABLE 2-continued

| Ex. No. | Structure | Name | LC-MS [M + 1]/RT | Purity (%) |
|---|---|---|---|---|
| 280 | 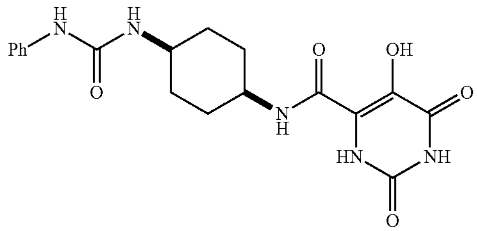 | 5-hydroxy-2,6-dioxo-N-(cis-4-(3-phenylureido)cyclohexyl)-1,2,3,6-tetrahydropyrimidine-4-carboxamide | 388.0/0.64 min (Method M) | RT = 5.66 min, 100% (Method A) RT = 5.41 min, 95% (Method B) |
| 281 | 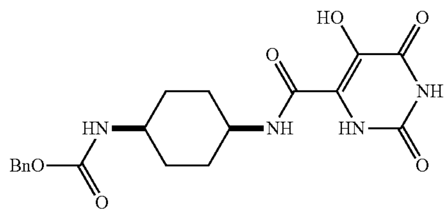 | benzyl cis-4-(5-hydroxy-2,6-dioxo-1,2,3,6-tetrahydropyrimidine-4-carboxamido)cyclohexylcarbamate | 402.9/0.73 min (Method M) | RT = 6.66 min, 97% (Method A) RT = 6.45 min, 95% (Method B) |
| 282 | 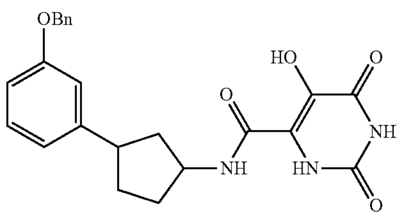 [SMILES: O=C(NC1CCC(c2cccc(OCc3ccccc3)c2)C1)c1[nH]c(=O)[nH]c(=O)c1O] | N-(3-(3-(benzyloxy)phenyl)cyclopentyl)-5-hydroxy-2,6-dioxo-1,2,3,6-tetrahydropyrimidine-4-carboxamide | 422.0/0.93 min (Method M) | RT = 9.18 min, 96% (Method A) RT = 8.70 min, 95% (Method B) |
| 283 | 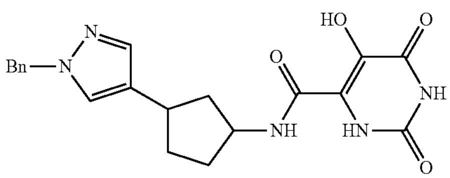 [SMILES: O=C(NC1CCC(c2cnn(Cc3ccccc3)c2)C1)c1[nH]c(=O)[nH]c(=O)c1O] | N-(3-(1-benzyl-1H-pyrazol-4-yl)cyclopentyl)-5-hydroxy-2,6-dioxo-1,2,3,6-tetrahydropyrimidine-4-carboxamide | 396.0/0.72 min (Method M) | RT = 6.54 min, 96% (Method A) RT = 6.43 min, 96% (Method B) |
| 284 | 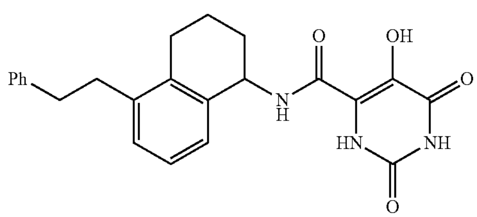 [SMILES: O=C(NC1CCCc2c(CCc3ccccc3)cccc21)c1[nH]c(=O)[nH]c(=O)c1O] | 5-hydroxy-2,6-dioxo-N-(5-phenethyl-1,2,3,4-tetrahydronaphthalen-1-yl)-1,2,3,6-tetrahydropyrimidine-4-carboxamide | 406.1/2.15 min (Method B) | RT = 9.51 min, 94% (Method A) RT = 8.72 min, 99.3% (Method B) |
| 285 | 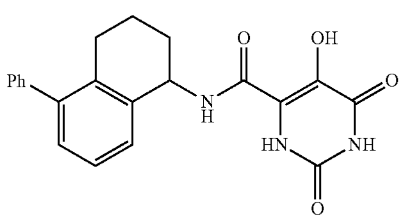 [SMILES: O=C(NC1CCCc2c(-c3ccccc3)cccc21)c1[nH]c(=O)[nH]c(=O)c1O] | 5-hydroxy-2,6-dioxo-N-(5-phenyl-1,2,3,4-tetrahydronaphthalen-1-yl)-1,2,3,6-tetrahydropyrimidine-4-carboxamide | 378.1/2.01 min (Method B) | RT = 8.58 min, 88% (Method A) RT = 8.02 min, 95% (Method B) |
| 286 | 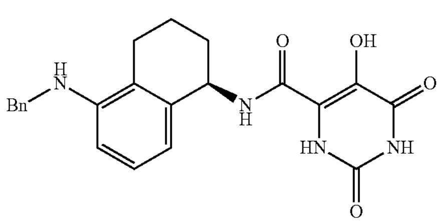 [SMILES: O=C(N[C@@H]1CCCc2c(NCc3ccccc3)cccc21)c1[nH]c(=O)[nH]c(=O)c1O] | (R)-N-(5-(benzylamino)-1,2,3,4-tetrahydronaphthalen-1-yl)-5-hydroxy-2,6-dioxo-1,2,3,6-tetrahydropyrimidine-4-carboxamide | 407.1/1.71 min (Method B) | RT = 6.79 min, 89% (Method A) RT = 6.38 min, 97% (Method B) |

TABLE 2-continued

| Ex. No. | Structure | Name | LC-MS [M + 1]/RT | Purity (%) |
|---|---|---|---|---|
| 287 | 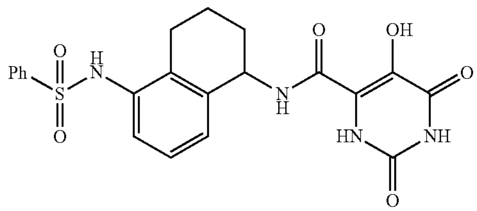 [SMILES: O=C(NC1CCCc2c(NS(=O)(=O)c3ccccc3)cccc21)c1[nH]c(=O)[nH]c(=O)c1O] | 5-hydroxy-2,6-dioxo-N-(5-(phenylsulfonamido)-1,2,3,4-tetrahydronaphthalen-1-yl)-1,2,3,6-tetrahydropyrimidine-4-carboxamide | 456/1.63 min (Method B) | RT = 6.23 min, 92.9% (Method A) RT = 5.99 min, 91.4% (Method B) |
| 288 | 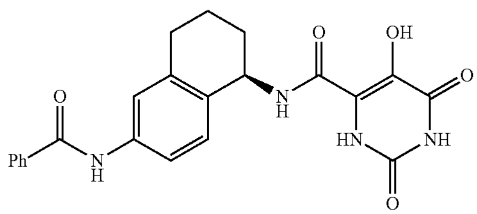 [SMILES: O=C(Nc1ccc2c(c1)CCC[C@H]2NC(=O)c1[nH]c(=O)[nH]c(=O)c1O)c1ccccc1] | (R)-N-(6-benzamido-1,2,3,4-tetrahydronaphthalen-1-yl)-5-hydroxy-2,6-dioxo-1,2,3,6-tetrahydropyrimidine-4-carboxamide | 420/1.75 min (Method B) | RT = 9.11 min, 100% (Method A) RT = 8.91 min, 100% (Method B) |
| 289 | 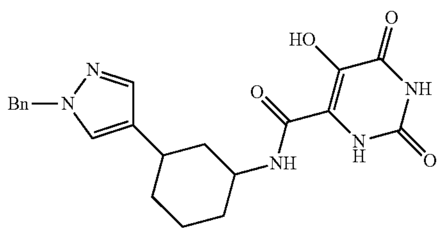 [SMILES: O=C(NC1CCCC(c2cnn(Cc3ccccc3)c2)C1)c1[nH]c(=O)[nH]c(=O)c1O] | N-(3-(1-benzyl-1H-pyrazol-4-yl)cyclohexyl)-5-hydroxy-2,6-dioxo-1,2,3,6-tetrahydropyrimidine-4-carboxamide | 410.1/1.79 min (Method B) | Racemic mixture |
| 290 | 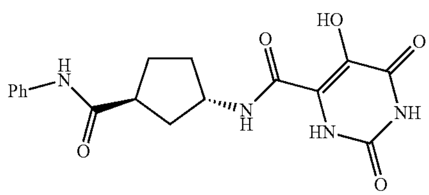 [SMILES: O=C(N[C@H]1CC[C@H](C(=O)Nc2ccccc2)C1)c1[nH]c(=O)[nH]c(=O)c1O] | 5-hydroxy-2,6-dioxo-N-((1S,3S)-3-(phenylcarbamoyl)cyclopentyl)-1,2,3,6-tetrahydropyrimidine-4-carboxamide | 359.1/1.42 min (Method B) | RT = 6.51 min, 93% (Method A) RT = 6.62 min, 93% (Method B) |
| 291 | 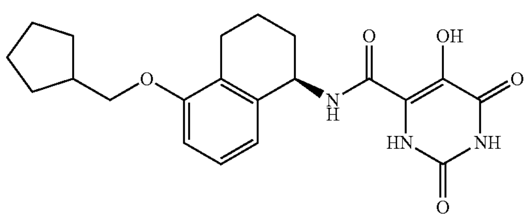 [SMILES: O=C(N[C@@H]1CCCc2c(OCC3CCCC3)cccc21)c1[nH]c(=O)[nH]c(=O)c1O] | (R)-N-(5-(cyclopentylmethoxy)-1,2,3,4-tetrahydronaphthalen-1-yl)-5-hydroxy-2,6-dioxo-1,2,3,6-tetrahydropyrimidine-4-carboxamide | 400.1/2.24 min (Method B) | RT = 10.99 min, 90% (Method A) RT = 10.78 min, 93% (Method B) |
| 292 | 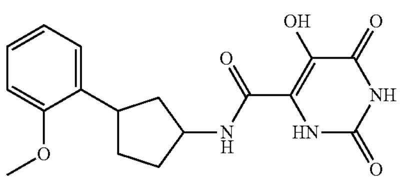 [SMILES: COc1ccccc1C1CCC(NC(=O)c2[nH]c(=O)[nH]c(=O)c2O)C1] | 5-hydroxy-N-(3-(2-methoxyphenyl)cyclopentyl)-2,6-dioxo-1,2,3,6-tetrahydropyrimidine-4 carboxamide | 346.1/2.09 min (Method B) | RT = 8.34 min, 97% (Method A) RT = 8.46 min, 97.5% (Method B) |
| 293 | 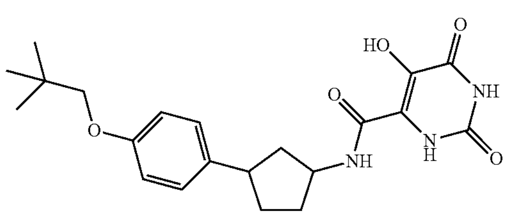 [SMILES: CC(C)(C)COc1ccc(C2CCC(NC(=O)c3[nH]c(=O)[nH]c(=O)c3O)C2)cc1] | 5-hydroxy-N-(3-(4-(neopentyloxy)phenyl)cyclopentyl)-2,6-dioxo-1,2,3,6-tetrahydropyrimidine-4-carboxamide | 402.2/2.28 min (Method B) | RT = 11.2 min, 87.8% (Method A) RT = 10.11 min, 100% (Method B) |

TABLE 2-continued

| Ex. No. | Structure | Name | LC-MS [M + 1]/RT | Purity (%) |
|---|---|---|---|---|
| 294 | 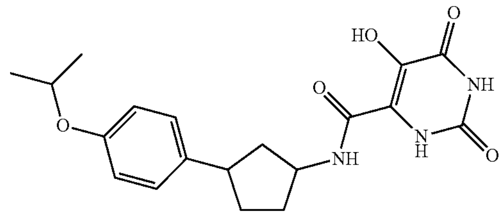 [SMILES: CC(C)Oc1ccc(C2CCC(NC(=O)c3[nH]c(=O)[nH]c(=O)c3O)C2)cc1] | 5-hydroxy-N-(3-(4-isopropoxyphenyl)cyclopentyl)-2,6-dioxo-1,2,3,6-tetrahydropyrimidine-4 carboxamide | 374.2/2.01 min (Method B) | RT = 8.97 min, 92.6% (Method A) RT = 8.68 min, 93.9% (Method B) |
| 295 | 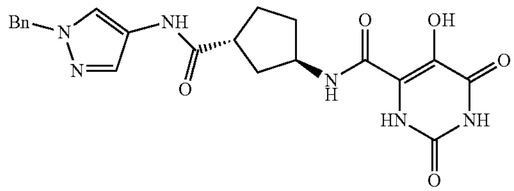 [SMILES: O=C(N[C@@H]1CC[C@@H](C(=O)Nc2cnn(Cc3ccccc3)c2)C1)c1[nH]c(=O)[nH]c(=O)c1O] | N-((1R,3R)-3-(1-benzyl-1H-pyrazol-4-ylcarbamoyl)cyclopentyl)-5-hydroxy-2,6-dioxo-1,2,3,6-tetrahydropyrimidine-4-carboxamide | 439.1/1.53 min (Method B) | RT = 6.08 min, 90.6% (Method A) RT = 6.09 min, 94.6% (Method B) |
| 296 | 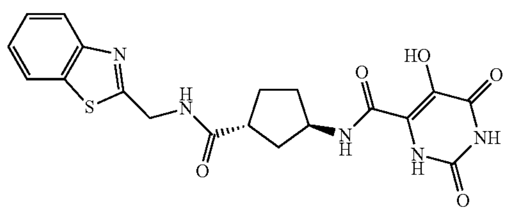 [SMILES: O=C(N[C@@H]1CC[C@@H](C(=O)NCc2nc3ccccc3s2)C1)c1[nH]c(=O)[nH]c(=O)c1O] | N-((1R,3R)-3-(benzo[d]thiazol-2-ylmethylcarbamoyl)cyclopentyl)-5-hydroxy-2,6-dioxo-1,2,3,6-tetrahydropyrimidine-4-carboxamide | 430/1.51 min (Method B) | RT = 5.77 min, 93.9% (Method A) RT = 5.77 min, 91.8% (Method B) |
| 297 | 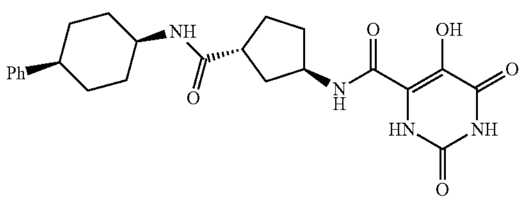 [SMILES: O=C(N[C@@H]1CC[C@@H](C(=O)N[C@H]2CC[C@@H](c3ccccc3)CC2)C1)c1[nH]c(=O)[nH]c(=O)c1O] | 5-hydroxy-2,6-dioxo-N-((1R,3R)-3-((1s,4S)-4-phenylcyclohexylcarbamoyl)cyclopentyl)-1,2,3,6-tetrahydropyrimidine-4-carboxamide | 441.1/1.87 min (Method B) | RT = 7.87 min, 98.6% (Method A) RT = 7.75 min, 89.8% (Method B) |
| 298 | 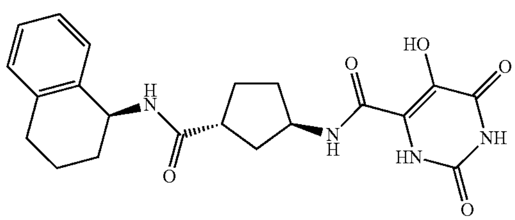 [SMILES: O=C(N[C@@H]1CC[C@@H](C(=O)N[C@H]2CCCc3ccccc32)C1)c1[nH]c(=O)[nH]c(=O)c1O] | 5-hydroxy-2,6-dioxo-N-((1R,3R)-3-((S)-1,2,3,4-tetrahydronaphthalen-1-ylcarbamoyl)cyclopentyl)-1,2,3,6-tetrahydropyrimidine-4-carboxamide | 413.1/1.76 min (Method B) | RT = 6.92 min, 89.9% (Method A) R= 6.90 min, 97.8% (Method B) |

What is claimed is:

1. A compound of Formula (I):

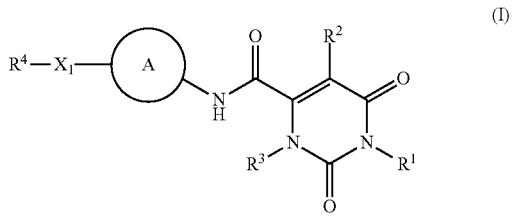

or a stereoisomer, a tautomer, or a pharmaceutically acceptable salt thereof, wherein:

ring A is independently selected from the group consisting of:

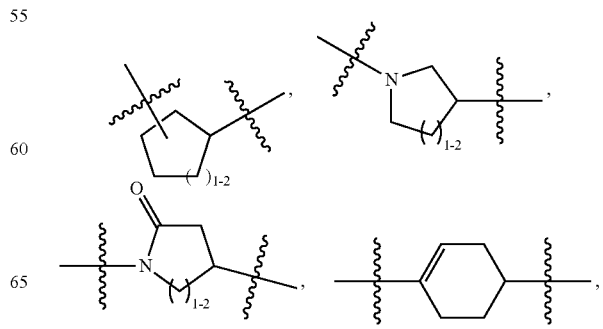

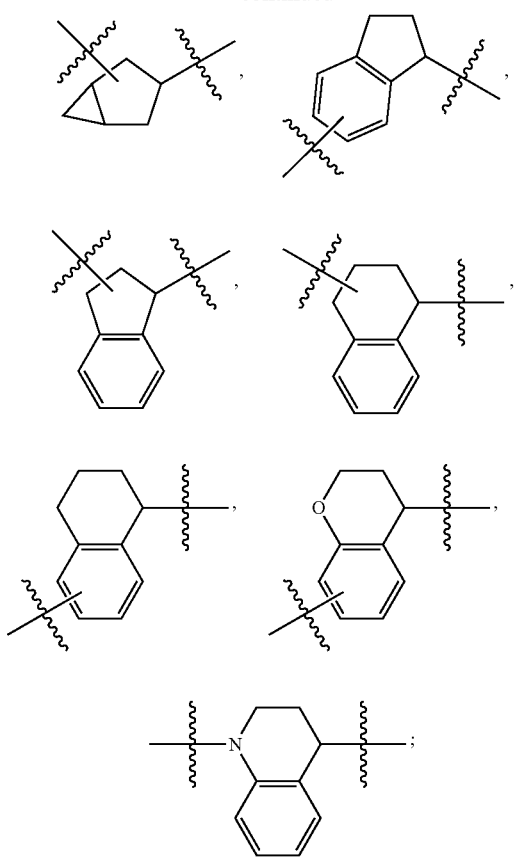

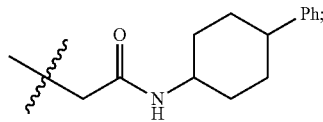 [SMILES: *CC(=O)NC1CCC(c2ccccc2)CC1]

wherein each moiety is substituted with 0-2 $R^5$;

$X_1$ is independently selected from the group consisting of: a bond, O, CO, straight or branched $C_{1-3}$ alkylene, —O—$C_{1-3}$ alkylene-, —$C_{1-3}$ alkylene-O—, NH, —SO$_2$—, —$C_{1-3}$ alkylene-NH—, —NHCO—, —CONH—, —CH$_2$NHCO—, —CH$_2$CONH—, —OCONH—, —CH$_2$OCONH—, —NHCONH—, and —SO$_2$NH—;

alternatively,

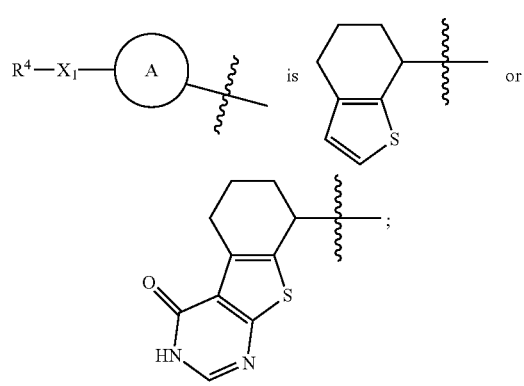

$R^1$ and $R^3$ are each independently selected from the group consisting of: H, $C_{1-6}$ alkyl, $C_{1-6}$ haloalkyl, —(CH$_2$)$_2$ OH, —CH$_2$CO$_2$H, —CH$_2$CO$_2$($C_{1-4}$ alkyl), —(CH$_2$)$_{1-3}$ Ph, 3-halo-4-halo-phenyl, 3-halo-5-CF$_3$-phenyl, and $R^2$ is independently selected from the group consisting of: OH and NHR$^7$;

$R^4$ is independently selected from the group consisting of: H, $C_{1-4}$ alkyl, $C_{1-4}$ alkoxy, halogen, $C_{1-4}$ haloalkyl, $C_{1-4}$ haloalkoxy, and a ring moiety substituted with 0-2 $R^h$ and selected from: $C_{3-10}$ carbocycle and a 5- to 10-membered heterocycle comprising: carbon atoms and 1-4 heteroatoms selected from N, NR$^e$, O, and S(O)$_p$;

$R^5$ is, independently at each occurrence, selected from the group consisting of: halogen, $C_{1-4}$ alkyl, $C_{1-4}$ alkoxy, $C_{1-4}$ haloalkyl, $C_{1-4}$ haloalkoxy, CN, NO$_2$, CO$_2$($C_{1-4}$ alkyl), —CH$_2$CO$_2$($C_{1-4}$ alkyl), NH$_2$, NH($C_{1-4}$ alkyl), and N($C_{1-4}$ alkyl)$_2$;

$R^6$ is independently selected from the group consisting of: H and $C_{1-4}$ alkyl substitute with 0-1 CO$_2$H, $R^7$ is independently selected from the group consisting of: H, $C_{1-6}$ haloalkyl, COCF$_3$, —(CH$_2$)$_2$O($C_{1-4}$ alkyl), $C_{1-6}$ alkyl substituted with 0-1 OH, —(CHR$^f$)$_n$—($C_{3-6}$ cycloalkyl substituted with 0-1 OH), —(CHR$^f$)$_n$-(phenyl substituted with 0-2 R$^b$), 1-tetralinyl, 1-indanyl, tetrahydronaphthalenyl, 1-Bn-pyrrolidin-3-yl, —(CH$_2$)$_n$-(piperidin-1-yl), 1-$C_{1-4}$ alkyl-piperidiny-4-yl, 1-CO$_2$ ($C_{1-4}$ alkyl)-piperidiny-4-yl, 1-(4-halo-phenyl)-piperidiny-4-yl, —(CH$_2$)$_n$(morpholin-4-yl), —(CH$_2$)$_n$-imidazolyl, —(CH$_2$)$_n$-pyridyl,

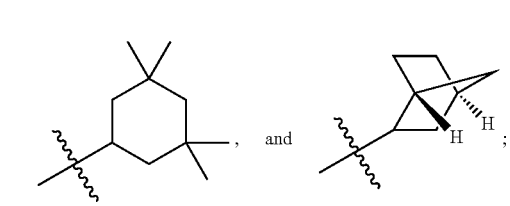 [SMILES: *C1CC(C)(C)CC(C)(C)C1 ; *C1C[C@H]2CC[C@@H]1C2]

$R^8$ is independently selected from the group consisting of: CO$_2$H and OH;

$R^a$ is, independently at each occurrence, selected from the group consisting of: halogen, OH, $C_{1-4}$ alkyl, $C_{1-4}$ alkoxy, $C_{1-4}$ haloalkyl, $C_{1-4}$ haloalkoxy, CN, NH$_2$, NO$_2$, NH($C_{1-4}$ alkyl), N($C_{1-4}$ alkyl)$_2$, CO$_2$H, CO$_2$($C_{1-4}$ alkyl), NHCO($C_{1-4}$ alkyl substituted with 0-1 NH$_2$), N($C_{1-4}$ alkyl)CO($C_{1-4}$ alkyl), NHCO$_2$($C_{1-4}$ alkyl), CONHSO$_2$ ($C_{1-4}$ alkyl), SO$_2$($C_{1-4}$ alkyl), CONH$_2$, CONH($C_{1-4}$ alkyl), NHSO$_2$($C_{1-4}$ alkyl), N($C_{1-4}$ alkyl)SO$_2$($C_{1-4}$ alkyl), phenoxy, and —CONH(phenylcyclohexyl);

$R^b$ is, independently at each occurrence, selected from the group consisting of: halogen, OH, $C_{1-4}$ alkyl substituted with 0-1 OH, $C_{1-4}$ alkoxy, $C_{1-4}$ haloalkyl, $C_{1-4}$ haloalkoxy, CN, NH$_2$, NO$_2$, NH($C_{1-4}$ alkyl), N($C_{1-4}$ alkyl)$_2$, CO$_2$H, CO$_2$($C_{1-4}$ alkyl), CONH$_2$, CONH($C_{1-4}$ alkyl), CON($C_{1-4}$ alkyl)$_2$, NHCO$_2$($C_{1-4}$ alkyl), SO$_2$($C_{1-4}$ alkyl), and SO$_2$NH$_2$;

$R^c$ is, independently at each occurrence, selected from the group consisting of: =O and R$^b$;

$R^d$ is, independently at each occurrence, selected from the group consisting of: CONH$_2$, $C_{1-4}$ alkyl, —(CH$_2$)$_2$O (CH$_2$)$_2$O($C_{1-4}$ alkyl), $C_{3-6}$ carbocycle substituted with 0-2 $R^h$, morpholin-1-yl, 1-$C_{1-4}$ alkyl-piperazin-4-yl, 1-CBz-piperazin-4-yl, pyridyl, indol-3-yl, and benzothiazol-2-yl;

$R^e$ is, independently at each occurrence, selected from the group consisting of: H, $C_{1-4}$ alkyl, CO($C_{1-4}$ alkyl), $CO_2$($C_{1-4}$ alkyl), $CO_2$(benzyl), CONH($C_{1-4}$ alkyl), CONH (phenyl substituted with 0-2 halogens), $SO_2$($C_{1-4}$ alkyl), and —$(CH_2)_n R^d$;

$R^f$ is, independently at each occurrence, selected from the group consisting of: H and methyl;

$R^g$ is, independently at each occurrence, selected from the group consisting of: halogen, OH, $C_{1-4}$ alkyl, $C_{2-4}$ alkenyl, $C_{1-4}$ haloalkyl, $C_{1-4}$ alkoxy, $CO_2$($C_{1-4}$ alkyl), $C_{3-6}$ cycloalkyl, and phenyl;

$R^h$ is, independently at each occurrence, selected from the group consisting of: H, halogen, $C_{1-6}$ alkyl, $C_{1-6}$ alkoxy, $C_{1-4}$ haloalkyl, $C_{1-4}$ haloalkoxy, —$(CH_2)_2O(C_{1-4}$ alkyl), $CF_3$, $NO_2$, $CONH_2$, OBn, quinolinyl, 1-$C_{1-4}$ alkyl-pyrazolyl, 1-($CH_2CO_2(C_{1-4}$ alkyl))pyrazolyl, 1-$C_{1-4}$ alkyl-3-$CF_3$-pyrazolyl, 1-(($CH_2)_2$(morpholin-4-yl))-pyrazolyl, 1-(tetrahydro-2H-pyran-2-yl)-pyrazolyl, 1,2,5-tri$C_{1-4}$ alkyl-pyrazolyl, 2-Ph-4-$C_{1-4}$ alkyl-thiazolyl, $NHSO_2$ (phenyl substituted with $C_{1-4}$ alkyl), and —$(CH_2)_{0-2}$- (phenyl substituted with zero to three substituents independently selected from the group consisting of: halogen, $CH_2OH$, $C_{1-4}$ alkyl, $C_{1-4}$ haloalkyl, $C_{1-4}$ alkoxy, $C_{1-4}$ haloalkoxy, N($C_{1-4}$ alkyl)$_2$, $CONH_2$, and NHCO($C_{1-4}$ alkyl)); and n is, independently at each occurrence, selected from 0, 1, 2, and 3.

2. A compound according to claim 1, wherein:

ring A is independently selected from the group consisting of:

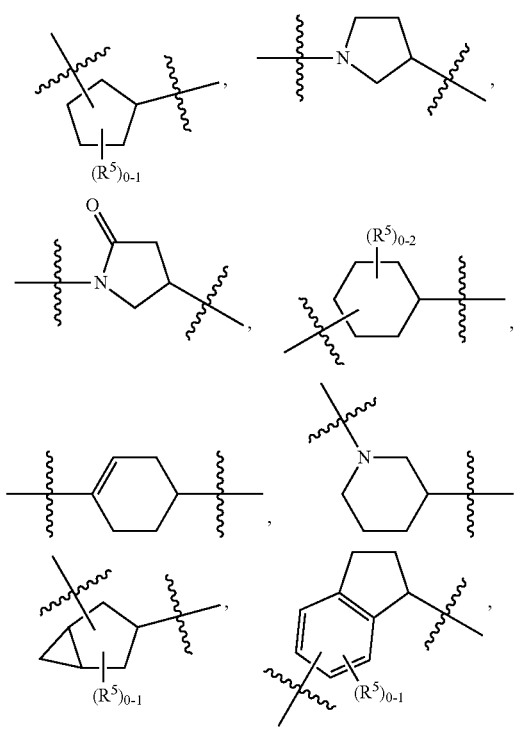

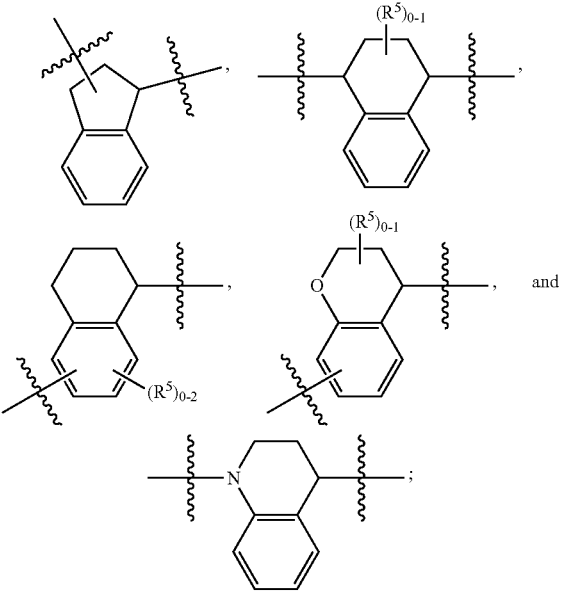

$X_1$ is independently selected from the group consisting of: a bond, O, $CH_2$, CO, —$SO_2$—, —$CH_2CH_2$—, —$CH_2O$—, —$OCH_2$—, NH, —$CH_2NH$—, —NHCO—, —CONH—, —$CH_2NHCO$—, —$CH_2CONH$—, —OCONH—, —$CH_2OCONH$—, —NHCONH—, and —$SO_2NH$—;

alternatively,

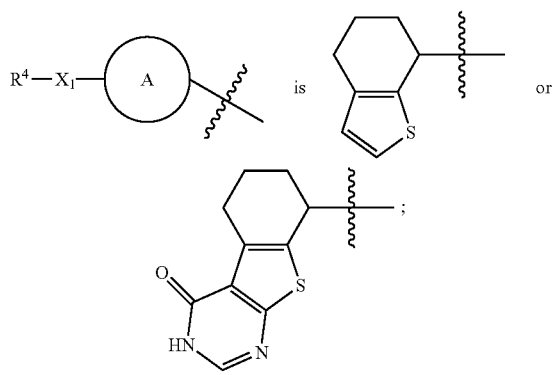

$R^1$ is independently selected from the group consisting of: H, $C_{1-4}$ alkyl, —$(CH_2)_2OH$, —$CH_2CO_2H$, $CH_2CF_3$, $CH_2CH_2CF_3$, —$(CH_2)_{1-3}Ph$, and

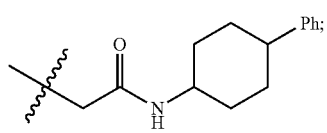 [SMILES: *CC(=O)NC1CCC(c2ccccc2)CC1]

$R^3$ is independently selected from the group consisting of: H, $C_{1-4}$ alkyl, $CH_2CF_3$, —$(CH_2)_{1-3}Ph$, 3-halo-4-halophenyl, 3-halo-5-$CF_3$-phenyl, and benzyl;

$R^4$ is independently selected from the group consisting of: H, $C_{1-4}$ alkyl, $C_{1-4}$ alkoxy, halogen, $CF_3$,

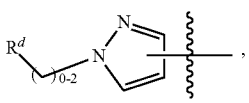

and a ring moiety substituted with 0-2 $R^h$ and selected from: $C_{3-6}$ cycloalkyl, phenyl, dihydroindenyl, tetrahydronaphthalenyl, pyrazolyl, oxadiazolyl, triazolyl, pyridyl, pyrimidinyl, benzothiazolyl, and 1H-pyrazolo[3,4-d]pyrimidinyl;

$R^5$ is, independently at each occurrence, selected from the group consisting of: halogen, $C_{1-4}$ alkyl, $C_{1-4}$ alkoxy, $CO_2(C_{1-4}$ alkyl), and $NH_2$;

$R^7$ is independently selected from the group consisting of: H, $C_{1-6}$ alkyl substituted with 0-1 OH, $C_{1-6}$ haloalkyl, —$(CH_2)_2O(C_{1-4}$ alkyl), $C_{3-6}$ cycloalkyl, —$CH(CH_3)$(cyclohexyl), —$(CH_2)_{1-3}$-(phenyl substituted with 0-2 $R^b$), tetrahydronaphthalenyl, 1-Bn-pyrrolidin-3-yl, 1-$C_{1-4}$ alkyl-piperidin-4-yl, —$(CH_2)_2$(piperidin-1-yl), —$(CH_2)_2$(morpholin-4-yl), —$(CH_2)_3$(morpholin-4-yl), —$(CH_2)_2$(1H-imidazo 4-yl), —$(CH_2)_3$(imidazol-1-yl), —$CH_2$-pyridyl, and

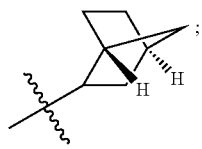 [SMILES: *C1C[C@H]2CC[C@@H]1C2]

and $R^h$ is, independently at each occurrence, selected from the group consisting of: H, halogen, $C_{1-6}$ alkyl, $C_{1-6}$ alkoxy, —$(CH_2)_2O(C_{1-4}$ alkyl), $CF_3$, $NO_2$, $CONH_2$, OBn, quinolinyl, 1-$C_{1-4}$ alkyl-pyrazolyl, 1-$(CH_2CO_2(C_{1-4}$ alkyl))-pyrazolyl, 1-$C_{1-4}$ alkyl-3-$CF_3$-pyrazolyl, 1-Ph-5-$C_{1-4}$ alkyl-pyrazolyl, 1-$((CH_2)_2$(morpholin-4-yl))-pyrazolyl, 1-(tetrahydro-2H-pyran-2-yl)-pyrazolyl, 1,2,5-tri$C_{1-4}$ alkyl-pyrazolyl, 2-Ph-4-$C_{1-4}$ alkyl-thiazolyl, —$NHSO_2$(phenyl substituted with $C_{1-4}$ alkyl), and —$(CH_2)_{0-2}$-(phenyl substituted with zero to three substituents independently selected from the group consisting of: halogen, $CH_2OH$, $C_{1-4}$ alkyl, $C_{1-4}$ haloalkyl, $C_{1-4}$ alkoxy, $N(C_{1-4}$ alkyl$)_2$, $CONH_2$, and $NHCO(C_{1-4}$ alkyl)).

3. A compound according to claim 2, wherein the compound is of Formula (II):

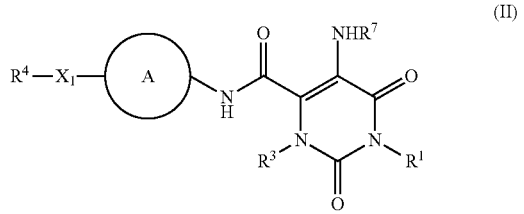

(II)

or as stereoisomer, a tautomer, or a pharmaceutically acceptable salt thereof.

4. A compound according to claim 3, wherein:
ring A is independently selected from the group consisting of:

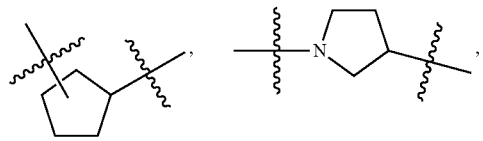

-continued

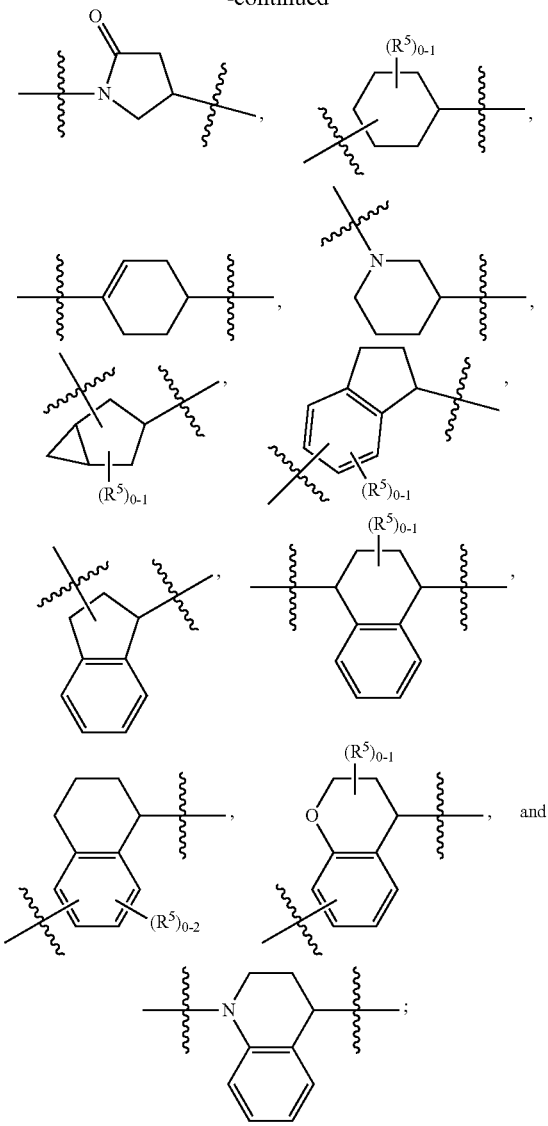

$X_1$ is independently selected from the group consisting of: a bond, O, $CH_2$, CO, $SO_2$, —$CH_2CH_2$—, —$CH_2O$—, —$OCH_2$—, NH, —$CH_2NH$—, —NHCO—, —$CH_2NHCO$—, —$CH_2CONH$—, —$CH_2OCONH$—, and —$SO_2NH$—;

alternatively,

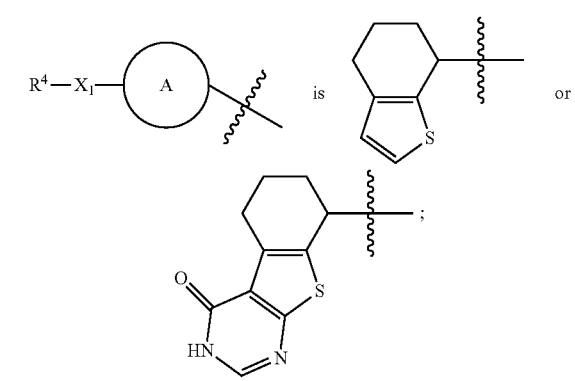

$R^1$ and $R^3$ are each independently selected from the group consisting of: H, $C_{1-4}$ alkyl, $CH_2CF_3$, and benzyl;

$R^4$ is independently selected from the group consisting of: H, $C_{1-4}$ alkyl, $C_{1-4}$ alkoxy, halogen, $CF_3$,

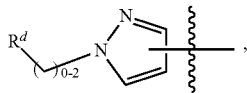

and a ring moiety substituted with 0-2 $R^h$ and selected from: $C_{3-6}$ cycloalkyl, phenyl, dihydroindenyl, tetrahydronaphthalenyl, pyrazolyl, oxadiazolyl, triazolyl, pyridyl, benzothiazolyl, and 1H-pyrazolo[3,4-d]pyrimidinyl;

$R^5$ is, independently at each occurrence, selected from the group consisting of: halogen, $C_{1-4}$ alkyl, $C_{1-4}$ alkoxy, and $CO_2(C_{1-4}$ alkyl);

$R^7$ is independently selected from the group consisting of: H, $C_{1-6}$ alkyl, $CH_2CF_3$, —$(CH_2)_2O(C_{1-4}$ alkyl), —$(CH_2)_2$ OH, —$CH(CH_3)CH_2OH$, —$CH_2C(CH_3)_2$ OH, $C_{3-6}$ cycloalkyl, —$CH(CH_3)$(cyclohexyl), —$(CH_2)_{1-3}$-(phenyl substituted with 0-2 $R^b$), tetrahydronaphthalenyl, 1-Bn-pyrrolidin-3-yl, 1-$C_{1-4}$ alkyl-piperidin-4-yl, —$(CH_2)_2$(piperidin-1-yl), —$(CH_2)_2$(morpholin-4-yl), —$(CH_2)_3$(morpholin-4-yl), —$(CH_2)_2$(1H-imidazol-4-yl), —$(CH_2)_3$(imidazol-1-yl), —$CH_2$(pyrid-3-yl), —$CH_2$(pyrid-4-yl), and

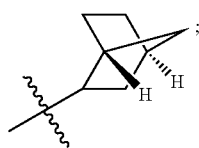 [SMILES: *C1C[C@H]2CC[C@@H]1C2]

$R^b$ is, independently at each occurrence, selected from the group consisting of: halogen, $CH_2OH$, $CF_3$, and $SO_2NH_2$;

$R^d$ is, independently at each occurrence, selected from the group consisting of: $C_{1-4}$ alkyl and phenyl substituted with 0-2 $R^h$; and $R^h$ is, independently at each occurrence, selected from the group consisting of: H, halogen, $C_{1-6}$ alkyl, $C_{1-6}$ alkoxy, $CF_3$, $NO_2$, $CONH_2$, OBn, quinolinyl, 1-$C_{1-4}$ alkyl-pyrazolyl, 1-($CH_2CO_2(C_{1-4}$ alkyl))-pyrazolyl, 1-$C_{1-4}$ alkyl-3-$CF_3$-pyrazolyl, 1-Ph-5-$C_{1-4}$ alkyl-pyrazolyl, 1-(($CH_2)_2$(morpholin-4-yl))-pyrazolyl, 1-(tetrahydro-2H-pyran-2-yl)-pyrazolyl, 1,2,5-tri$C_{1-4}$ alkyl-pyrazolyl, 2-Ph-4-$C_{1-4}$ alkyl-thiazolyl, —$NHSO_2$(phenyl substituted with $C_{1-4}$ alkyl), and —$(CH_2)_{0-2}$-(phenyl substituted with zero to three substituents independently selected from the group consisting of: halogen, $CH_2OH$, $C_{1-4}$ alkyl, $C_{1-4}$ haloalkyl, $C_{1-4}$ alkoxy, $N(C_{1-4}$ alkyl)$_2$, $CONH_2$, and $NHCO(C_{1-4}$ alkyl)).

5. A compound according to claim 4, wherein:
ring A is independently selected from the group consisting of:

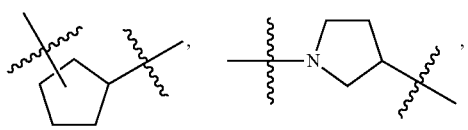

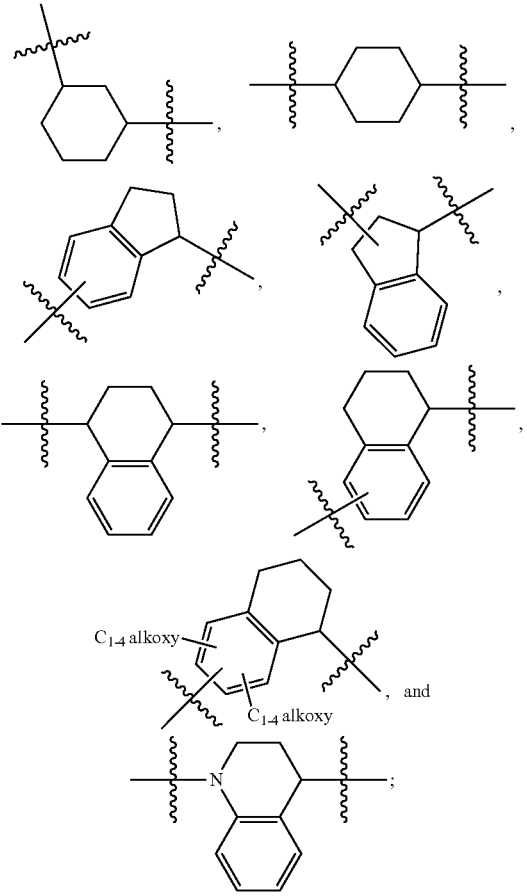

$X_1$ is independently selected from the group consisting of: a bond, O, $CH_2$, CO, $SO_2$, —$CH_2CH_2$—, —$CH_2O$—, —$OCH_2$—, NH, —$CH_2NH$—, —$NHCO$—, —$CONH$—, —$CH_2OCONH$—, and —$SO_2NH$—;

$R^4$ is independently selected from the group consisting of: H, $C_{1-4}$ alkyl, $C_{1-4}$ alkoxy, halogen, $CF_3$,

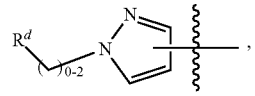

and a ring moiety substituted with 0-2 $R^h$ and selected from: $C_{3-6}$ cycloalkyl, phenyl, tetrahydronaphthalenyl, pyrazolyl, oxadiazolyl, triazolyl, pyridyl, benzothiazolyl, and 1H-pyrazolo[3,4-d]pyrimidinyl;

$R^7$ is independently selected from the group consisting of: H, —$(CH_2)_2O(C_{1-4}$ alkyl), —$CH_2C(CH_3)_2OH$, cyclopentyl, 4-halo-benzyl, 2-$CH_2OH$-benzyl, 3-$CF_3$-benzyl, 2-halo-phenethyl, 4-halo-phenethyl, —$(CH_2)_3$Ph, 1-Bn-pyrrolidin-3-yl, —$(CH_2)_2$(piperidin-1-yl), —$(CH_2)_2$(morpholin-4-yl), —$(CH_2)_3$(morpholin-4-yl), $(CH_2)_2$(1H-imidazol-4-yl), and —$CH_2$(pyrid-3-yl); and $R^h$ is, independently at each occurrence, selected from the group consisting of: H, halogen, $C_{1-6}$ alkyl, $C_{1-6}$ alkoxy, $CF_3$, OBn, quinolinyl, 1-$C_{1-4}$ alkyl-pyrazolyl, 1-($CH_2CO_2(C_{1-4}$ alkyl))-pyrazolyl, 1-Ph-pyrazolyl, 1-$C_{1-4}$ alkyl-3-$CF_3$-pyrazolyl, 1-Ph-5-$C_{1-4}$ alkyl-pyrazolyl, 1-(($CH_2)_2$(morpholin-4-yl))-pyrazolyl, 1,2,5-tri$C_{1-4}$ alkyl-pyrazolyl, —$NHSO_2$(phenyl substituted with $C_{1-4}$ alkyl), and —$(CH_2)_{0-1}$-(phenyl substituted with zero to three substituents independently selected from the group consisting of: halogen, $CH_2OH$, $CONH_2$, $C_{1-4}$ alkyl, $C_{1-4}$ haloalkyl, $C_{1-4}$ alkoxy, and $N(C_{1-4}$ alkyl)$_2$).

6. A compound according to claim 5, wherein:

$R^1$ and $R^3$ are each independently selected from the group consisting of: H, $C_{1-4}$ alkyl and benzyl;

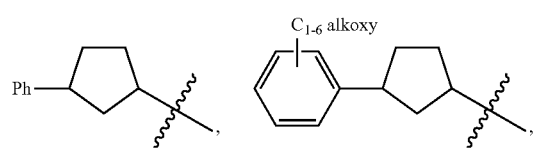

is independently selected from the group consisting of:

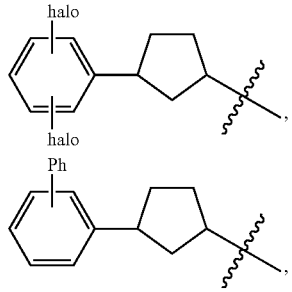

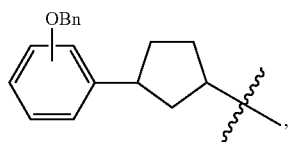

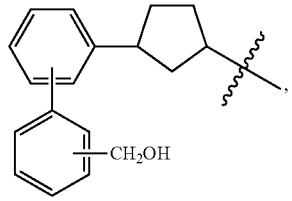

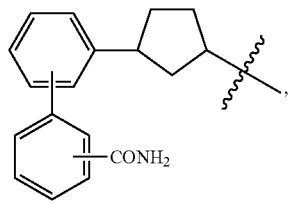

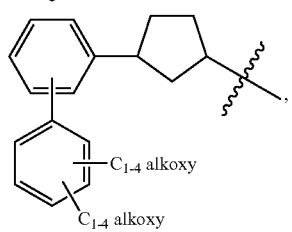

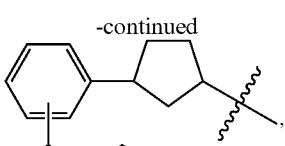

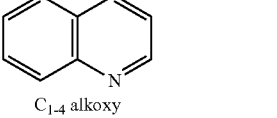

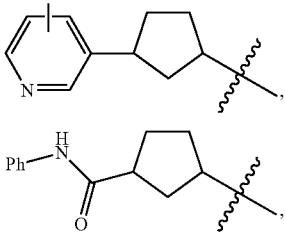

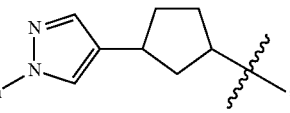

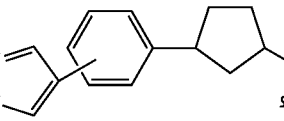

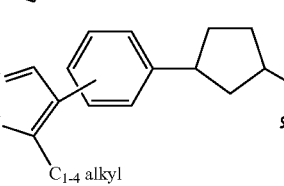

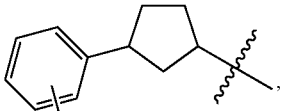

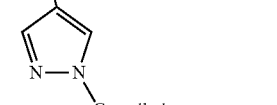

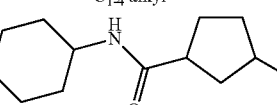

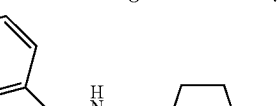

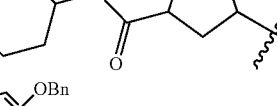

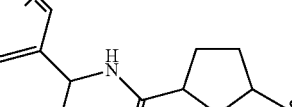

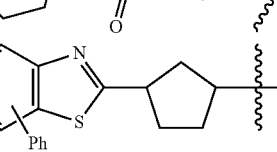

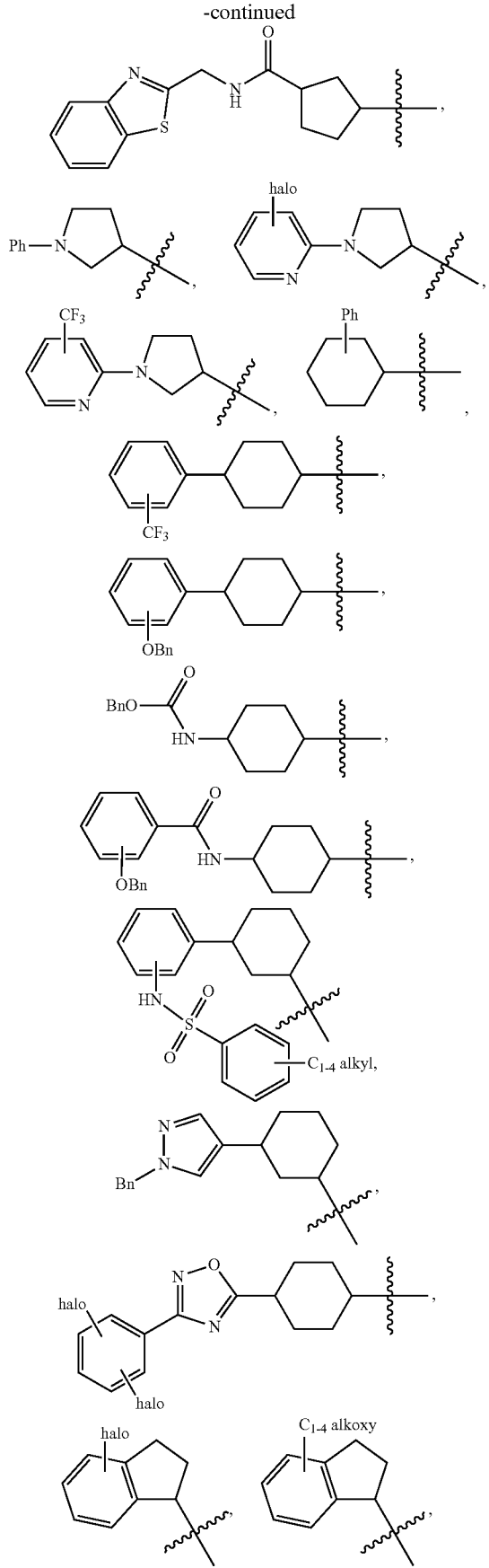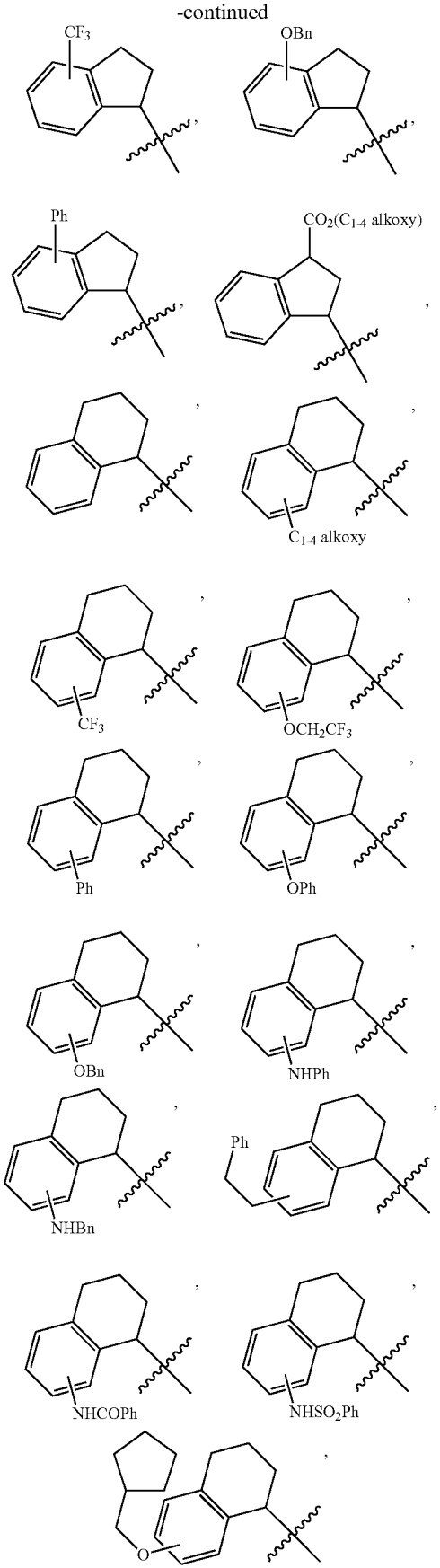

-continued

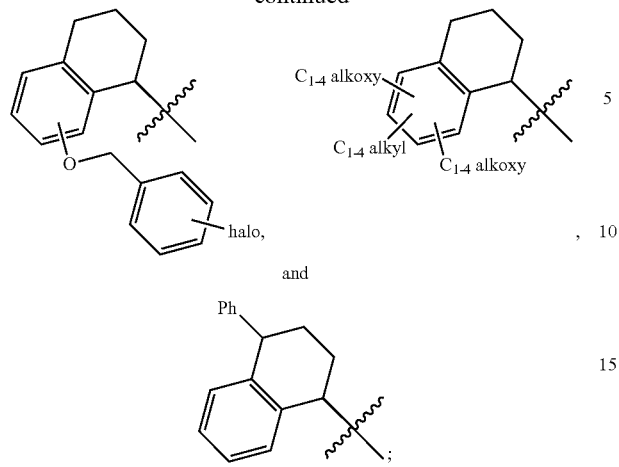

and

R[7] is independently selected from the group consisting of: H, —(CH$_2$)$_2$O(C$_{1-4}$ alkyl), —CH$_2$C(CH$_3$)$_2$OH, 4-halo-benzyl, 4-halo-phenethyl, —(CH$_2$)$_2$(morpholin-4-yl), and —(CH$_2$)$_3$(morpholin-4-yl).

7. A compound according to claim 2, wherein the compound is of Formula (III):

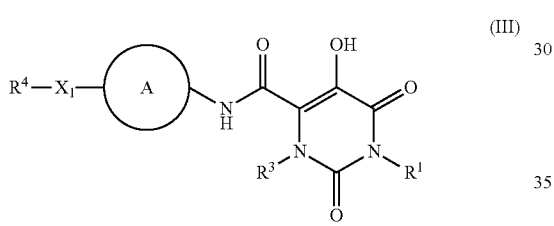

(III)

or a stereoisomer, a tautomer, or a pharmaceutically acceptable salt thereof.

8. A compound according to claim 7, wherein:

R[1] is independently selected from the group consisting of: H, C$_{1-4}$ alkyl, —(CH$_2$)$_2$OH, —CH$_2$CO$_2$H, CH$_2$CF$_3$, CH$_2$CH$_2$CF$_3$, —(CH$_2$)$_{1-3}$-Ph,

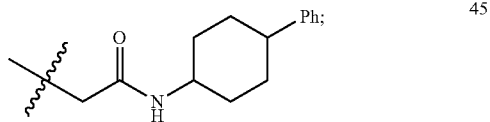

R[3] is independently selected from the group consisting of: H, C$_{1-4}$ alkyl and benzyl and

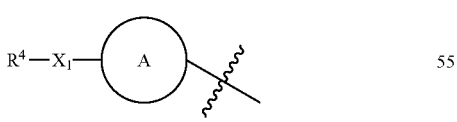

is independently selected from the group consisting of:

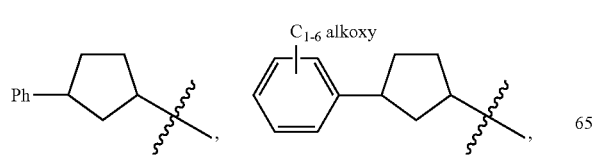

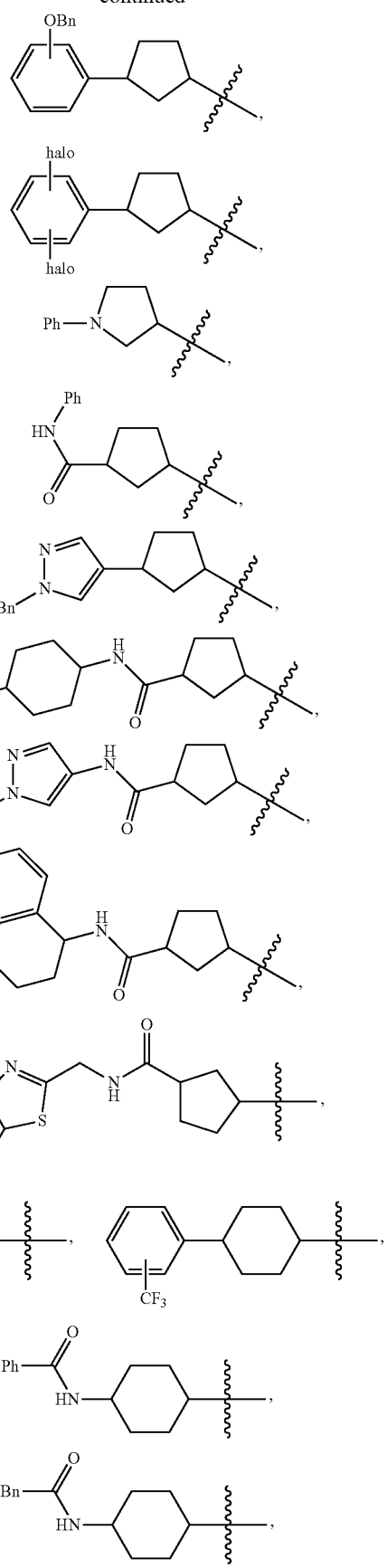

213
-continued
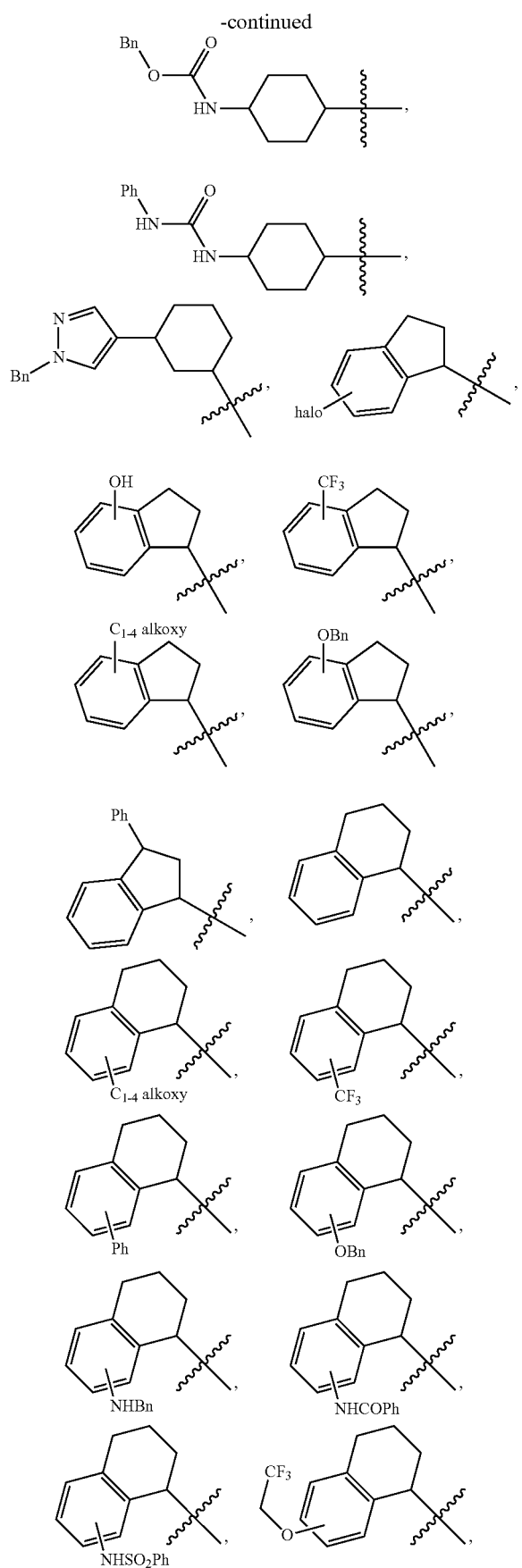
214
-continued
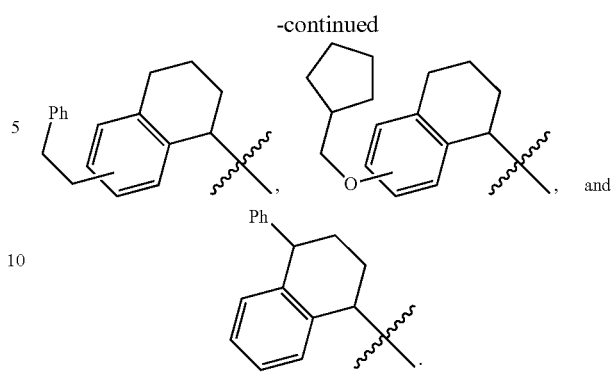
9. A compound according to claim 1, wherein the compound is selected from the following:
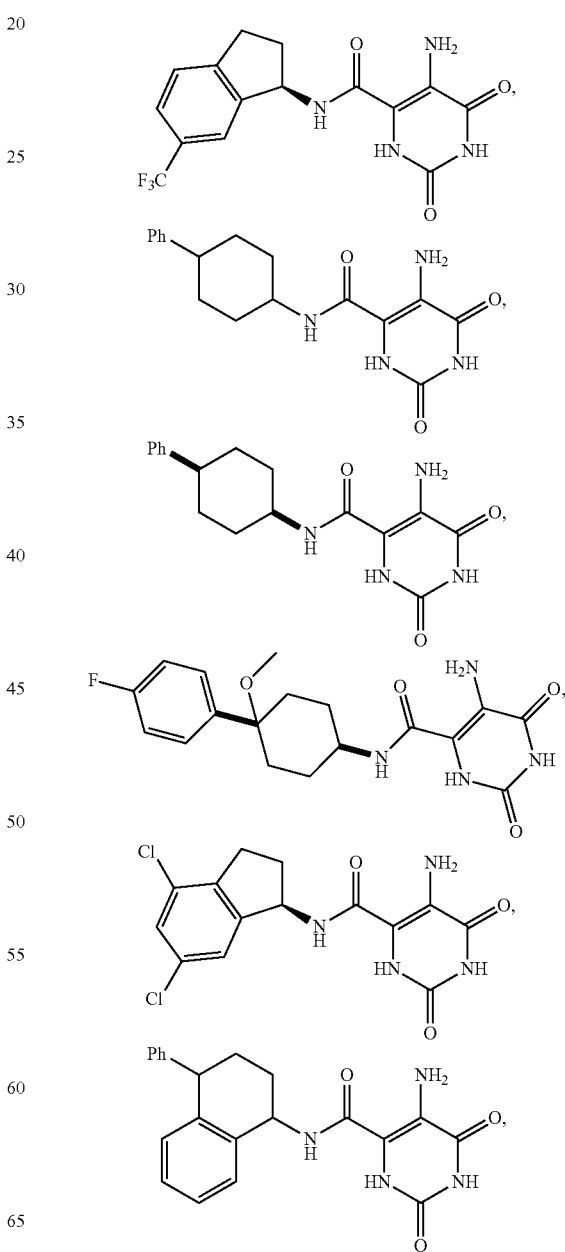

215
-continued
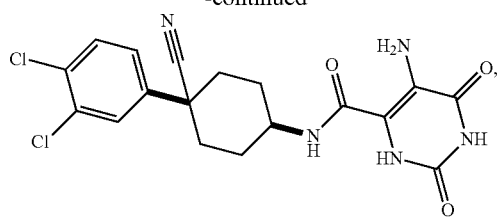
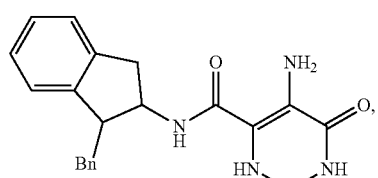
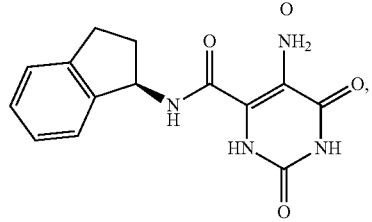
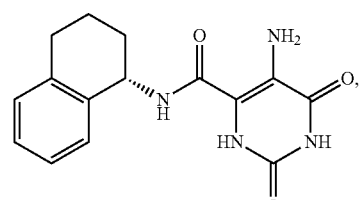
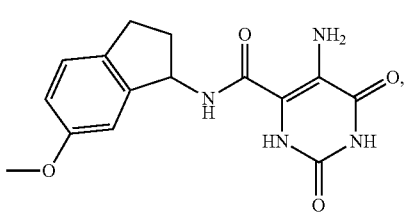
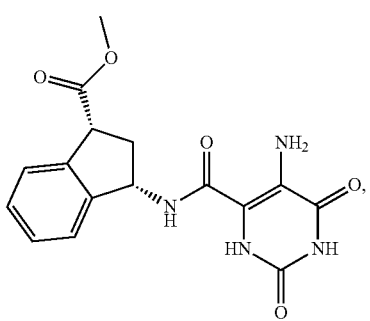
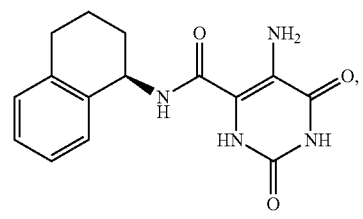
216
-continued
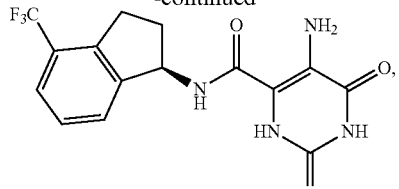
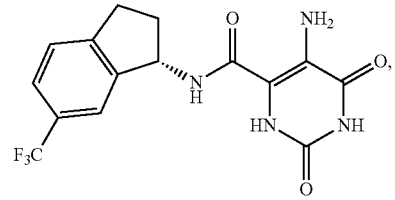
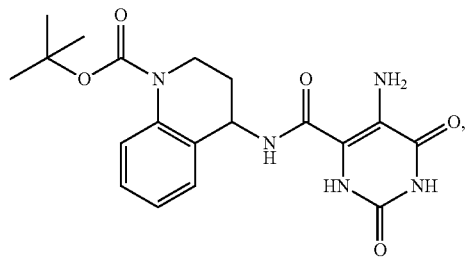
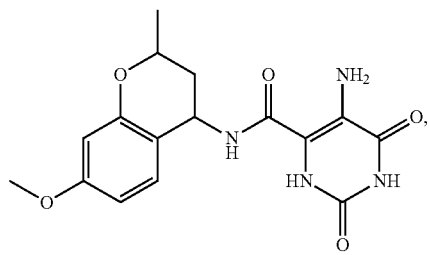
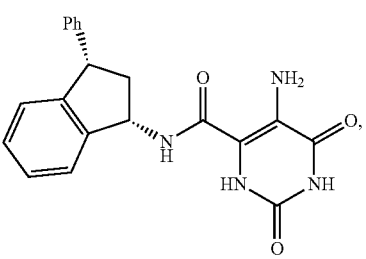
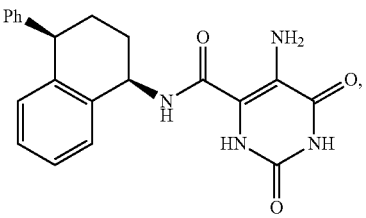
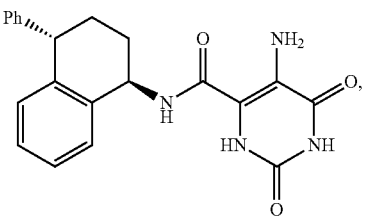

217
-continued
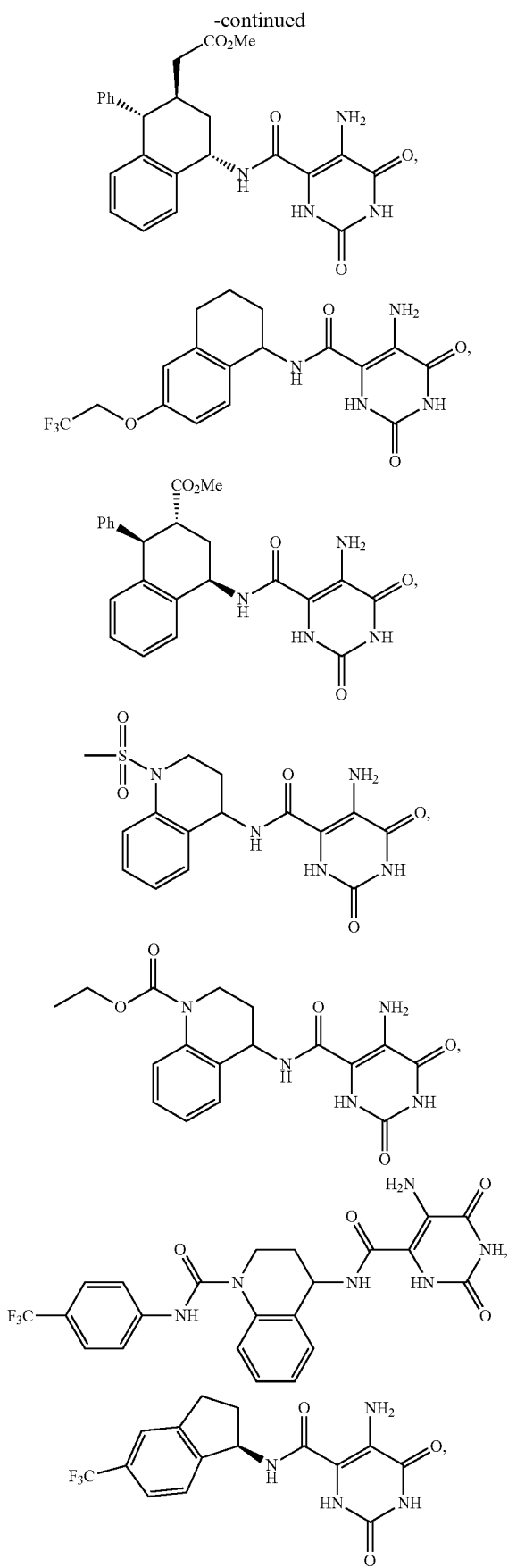
218
-continued
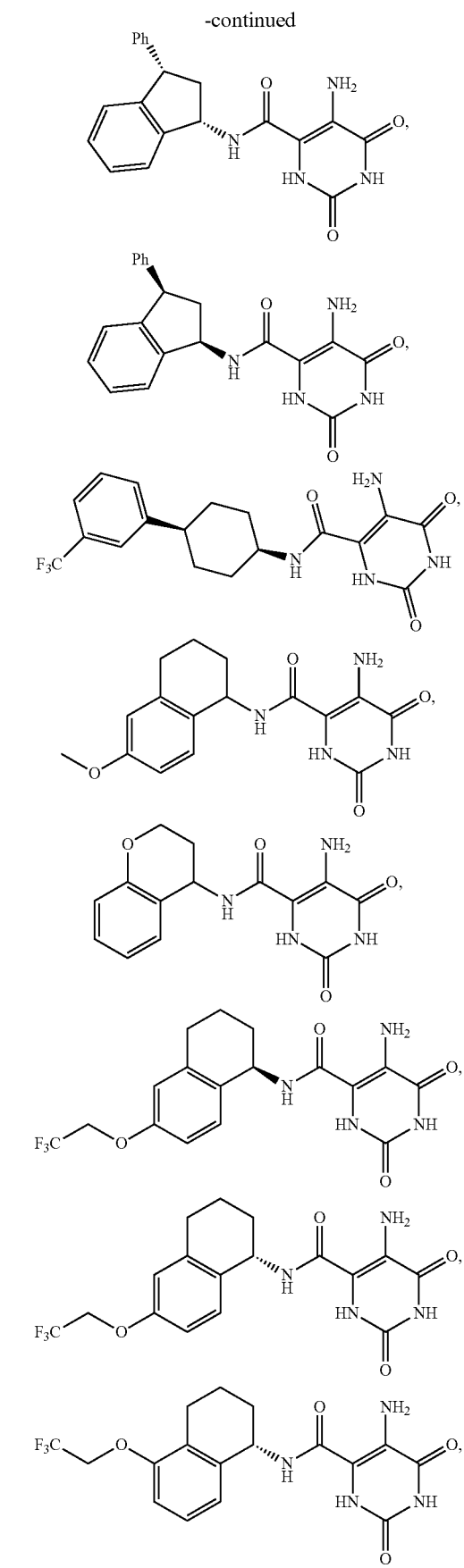

219
-continued
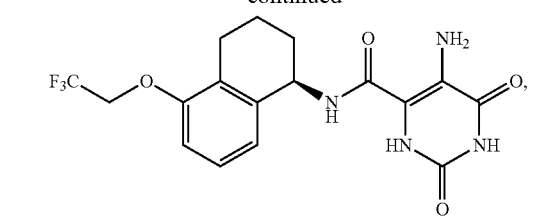
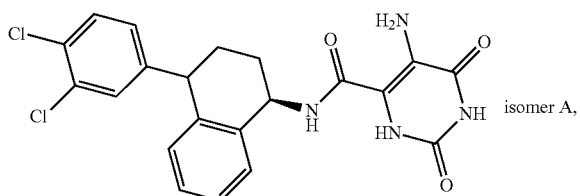
isomer A,
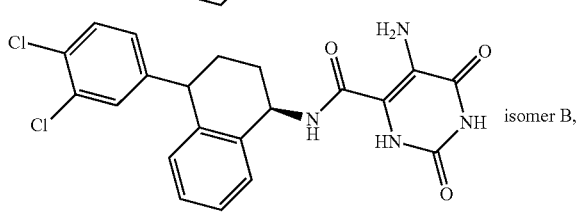
isomer B,
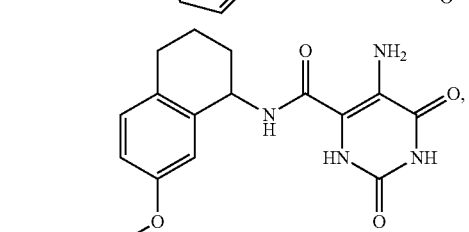
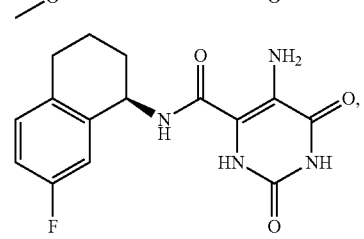
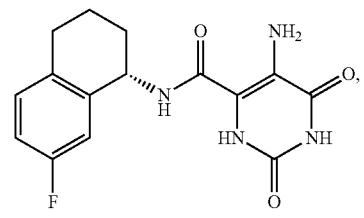
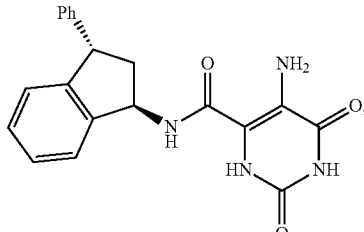
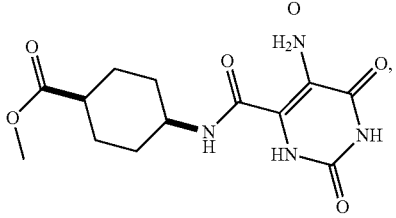
220
-continued
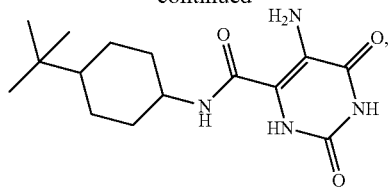
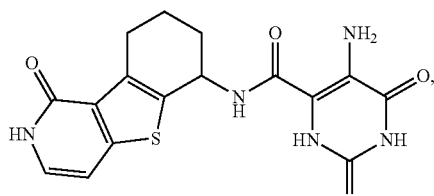
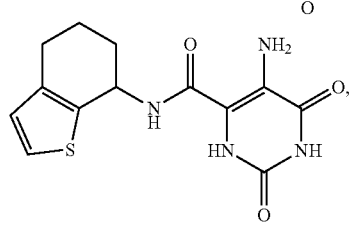
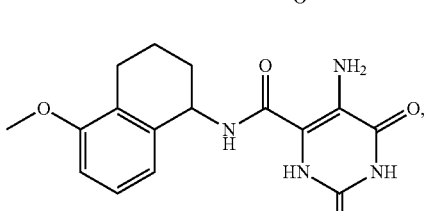
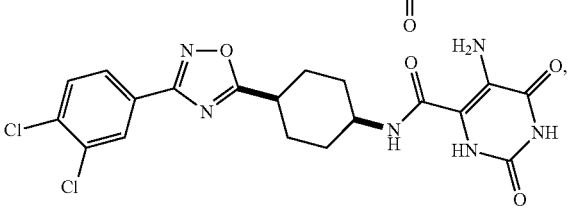
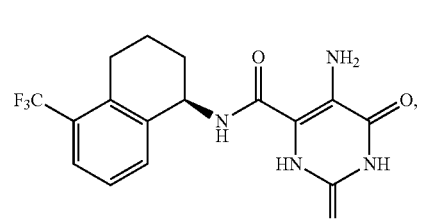
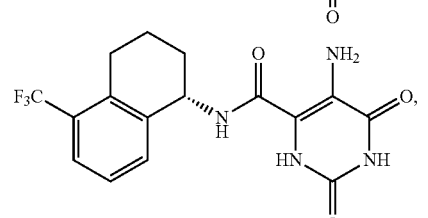
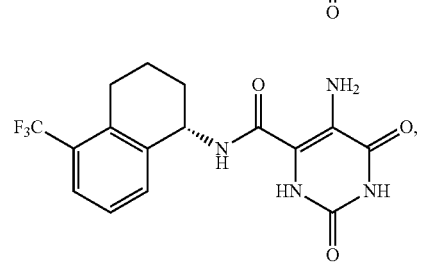

221
-continued
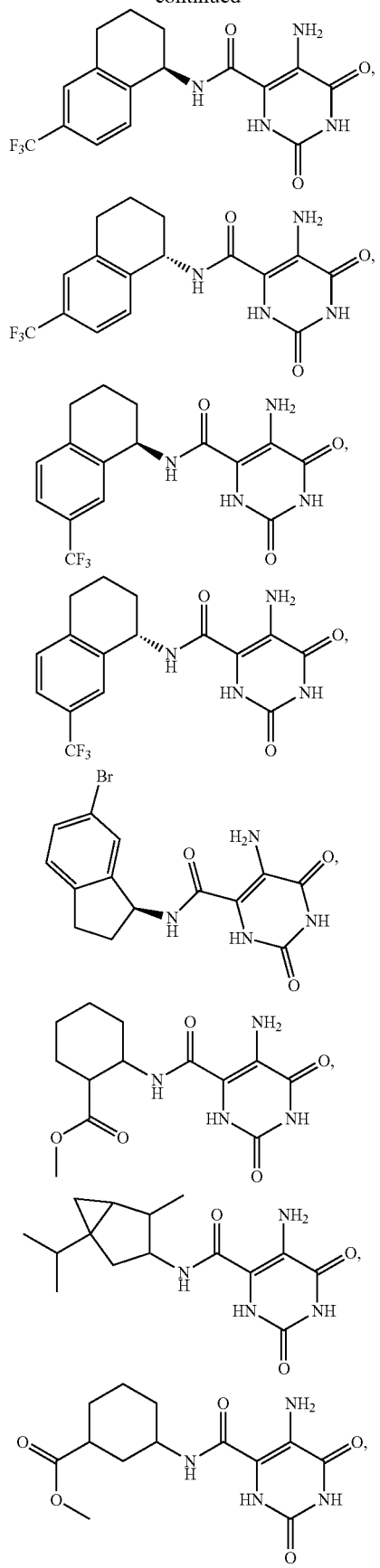
222
-continued
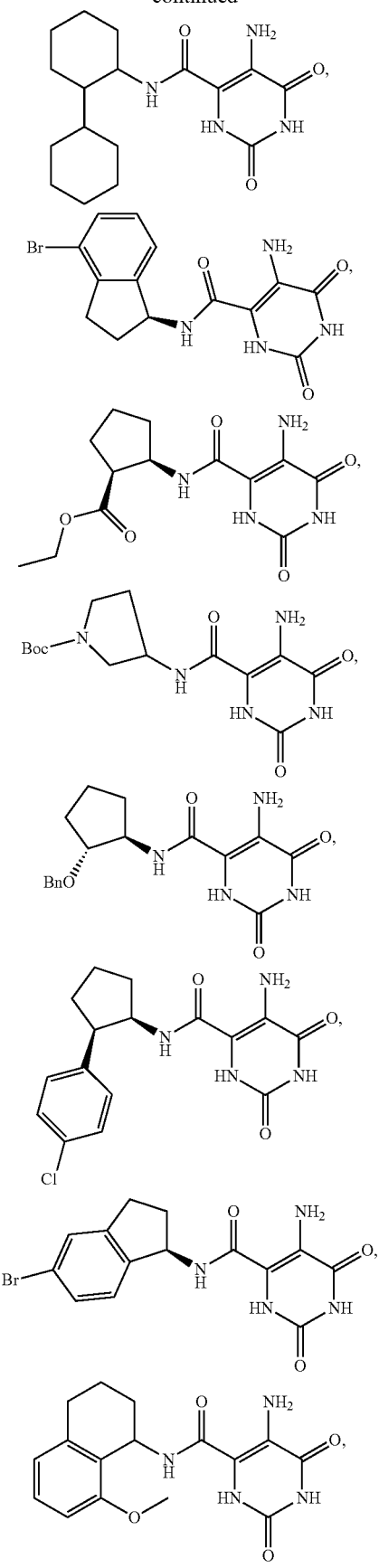

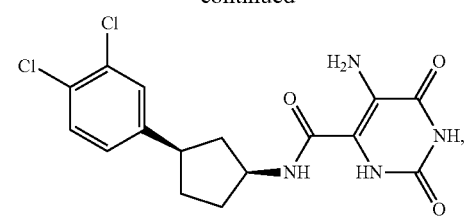
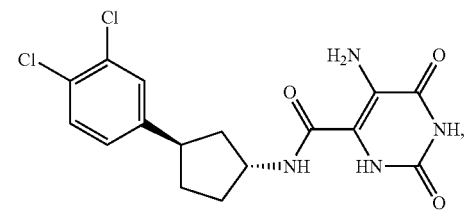
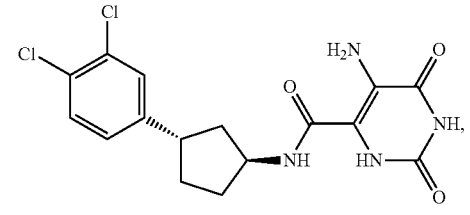
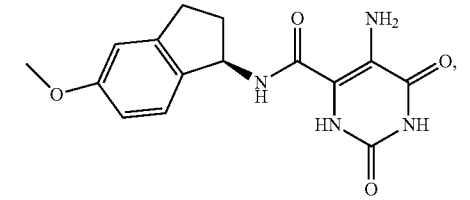
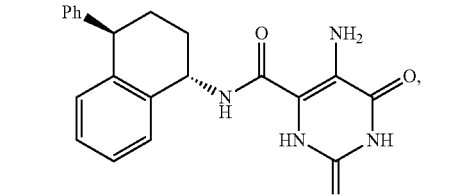
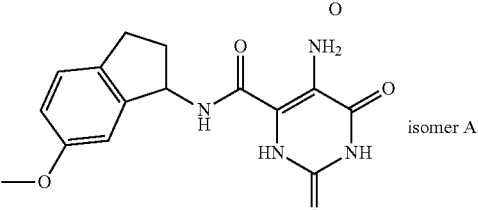 isomer A,
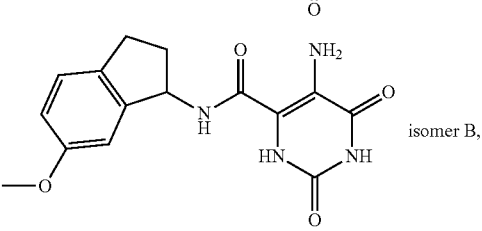 isomer B,
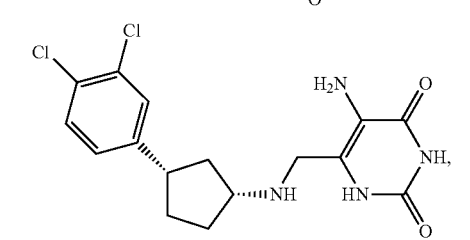
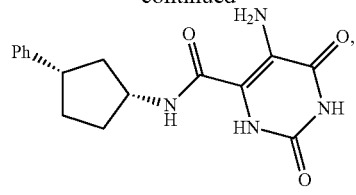
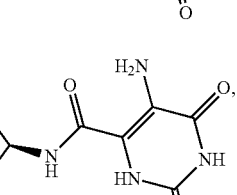
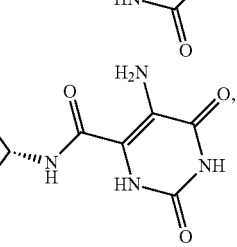
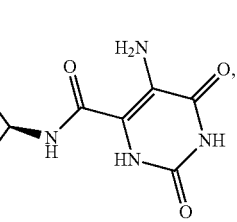
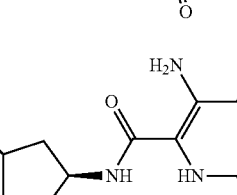
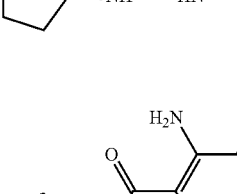
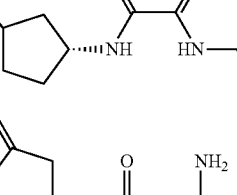
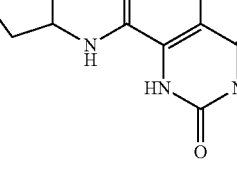

225
-continued
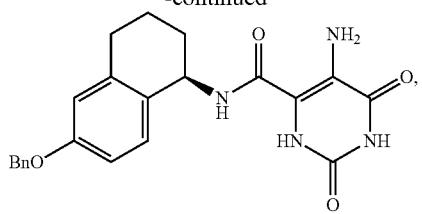
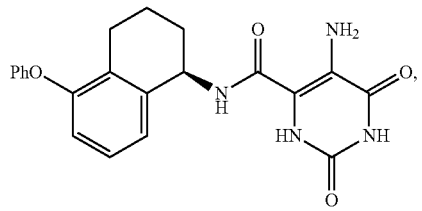
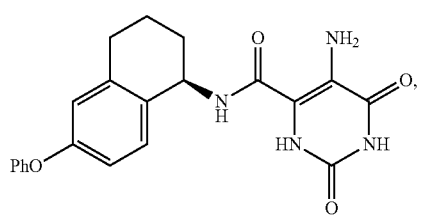
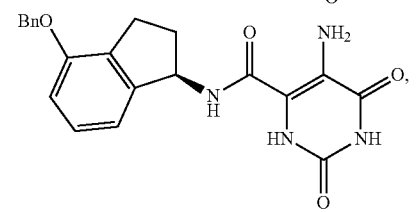
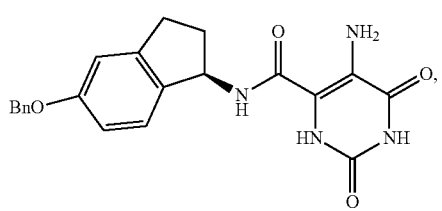
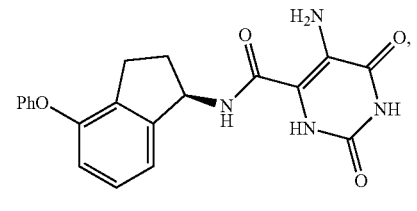
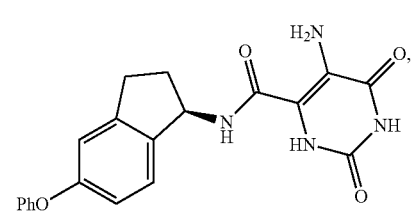
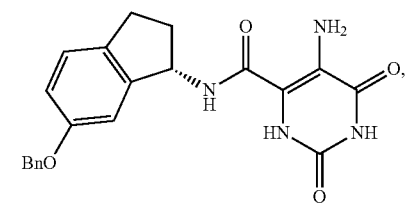
226
-continued
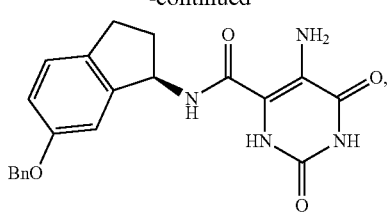
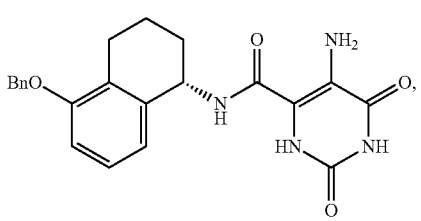
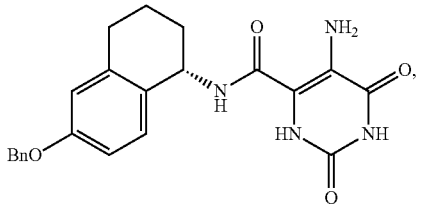
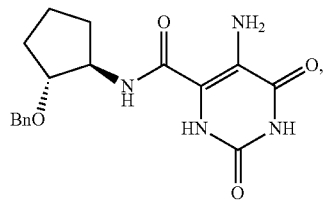
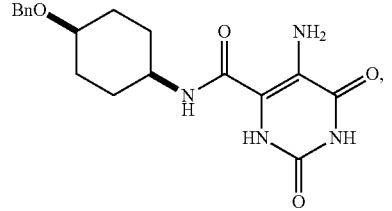
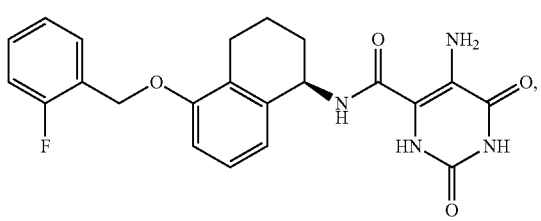
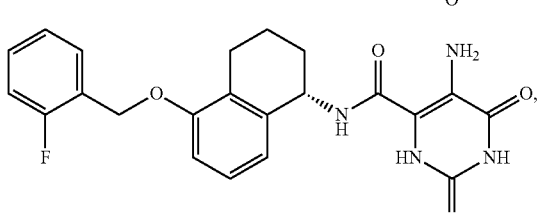
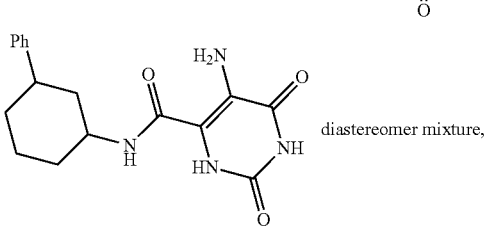
diastereomer mixture, 227
-continued
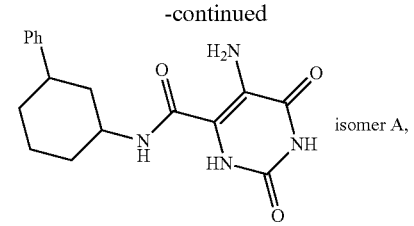
isomer A,
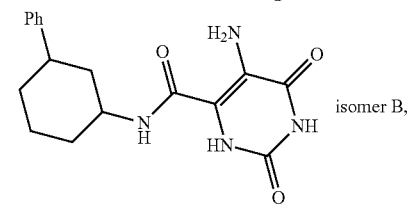
isomer B,
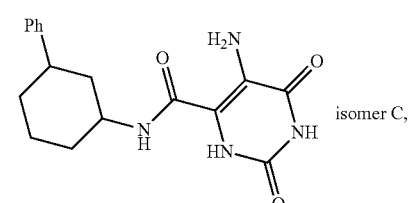
isomer C,
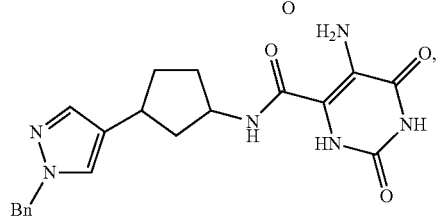
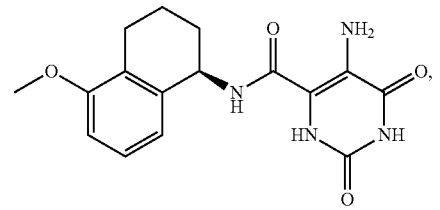
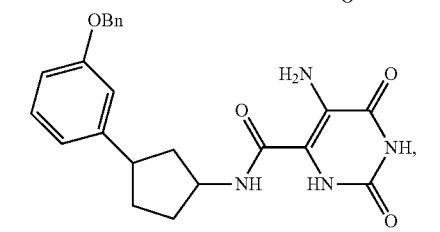
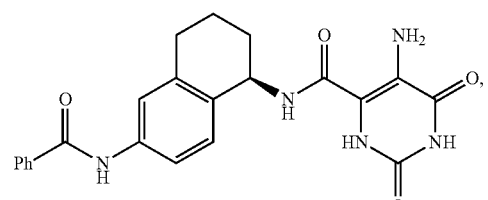
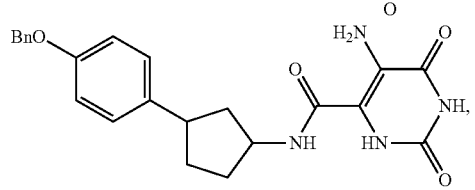
228
-continued
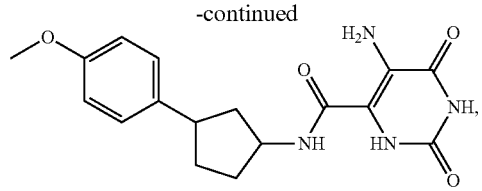
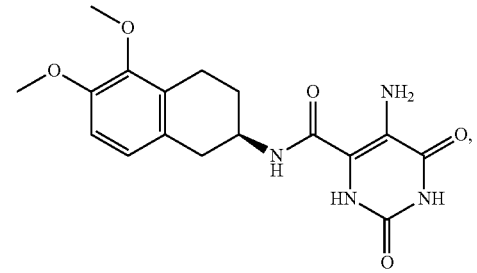
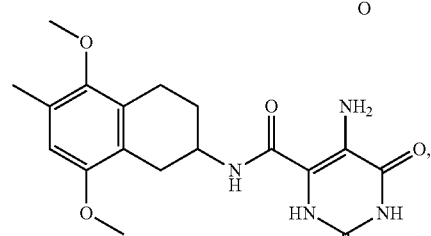
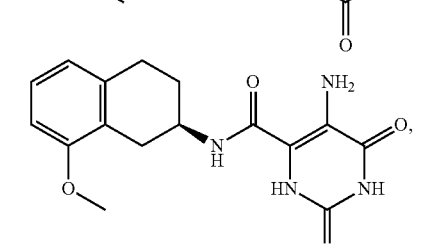
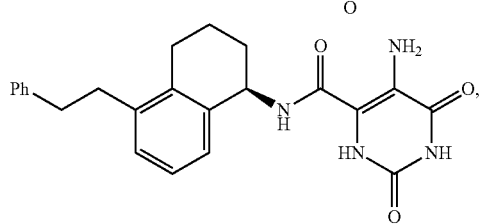
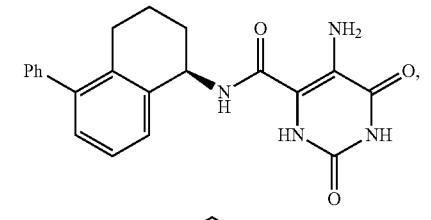
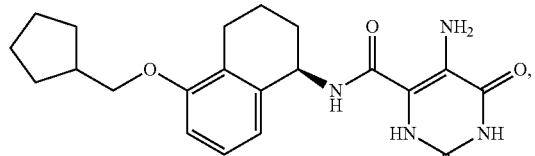
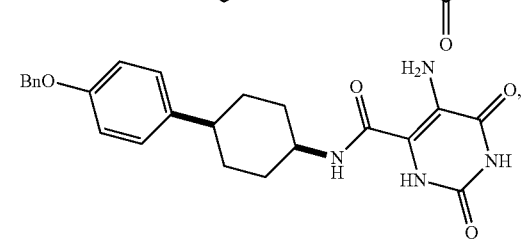

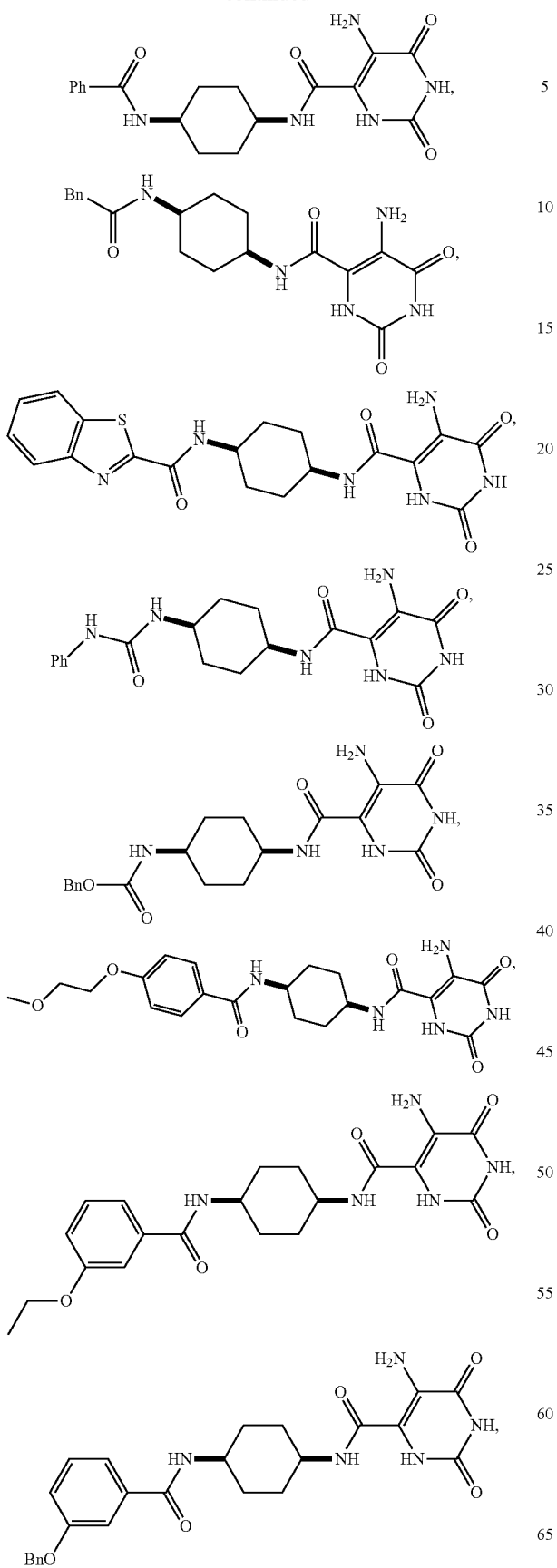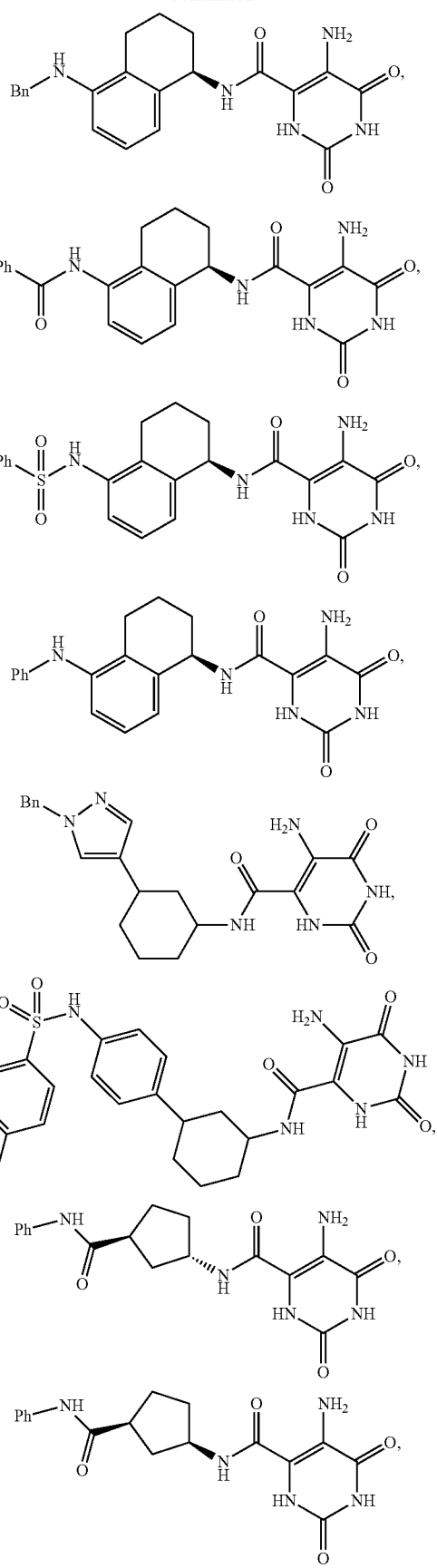

231
-continued
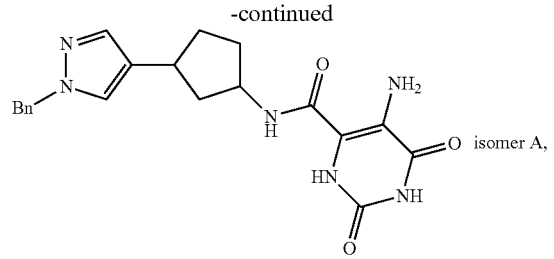 isomer A,
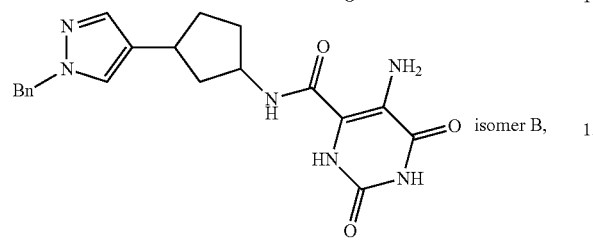 isomer B,
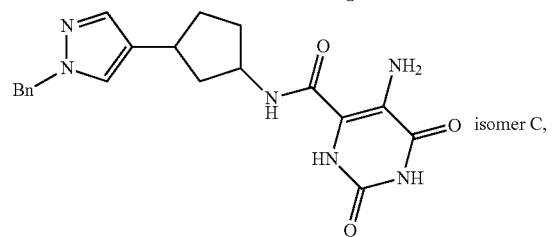 isomer C,
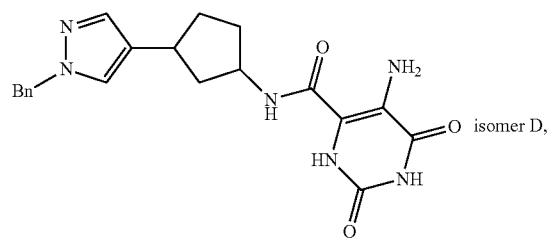 isomer D,
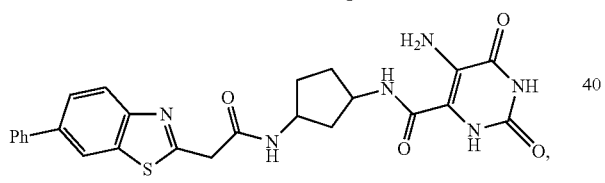
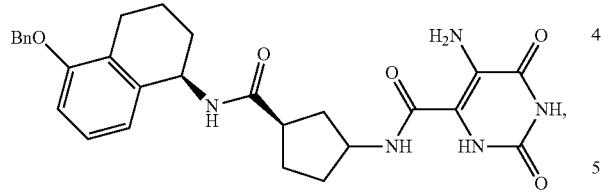
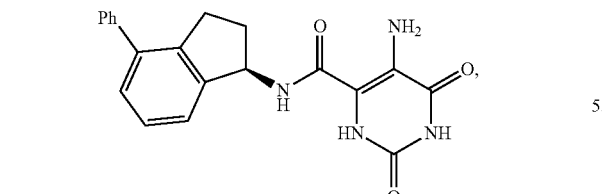
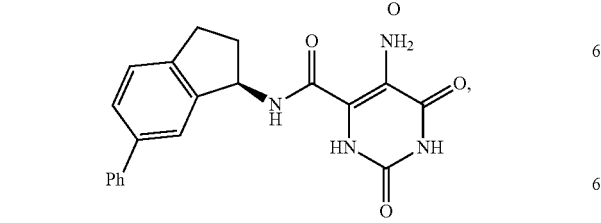
232
-continued
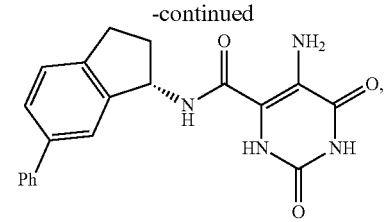
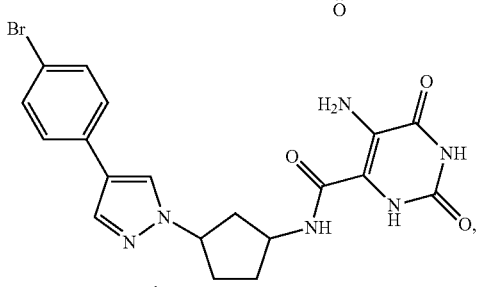
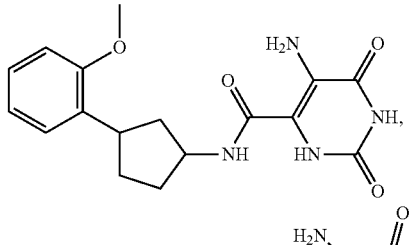
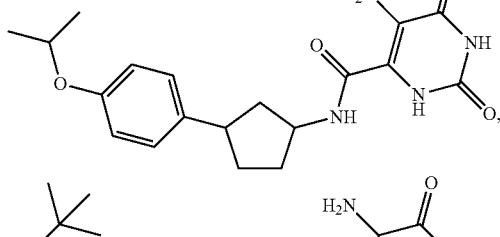
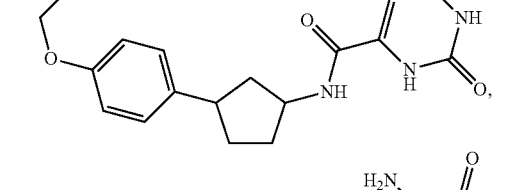
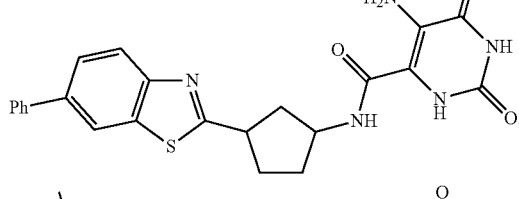
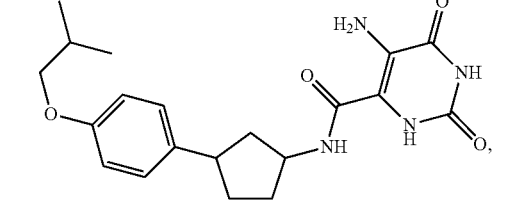
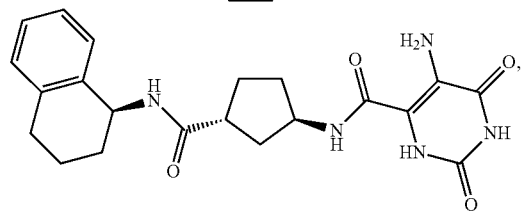

233
-continued
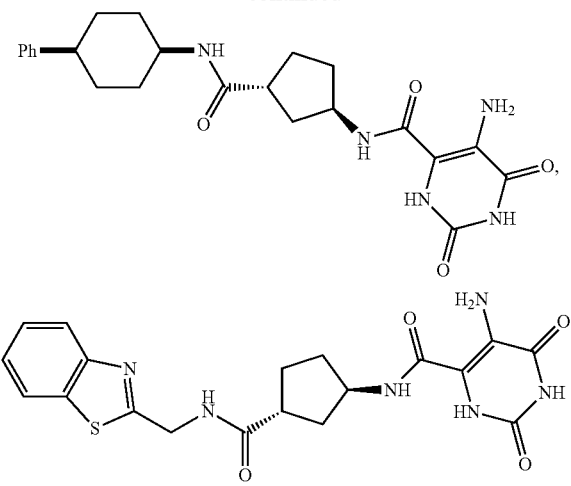
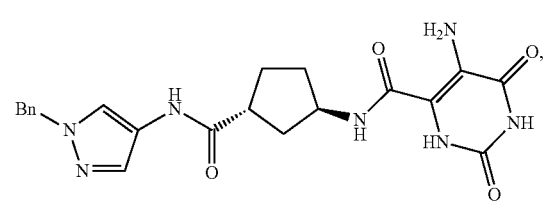
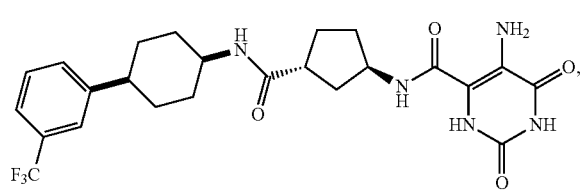
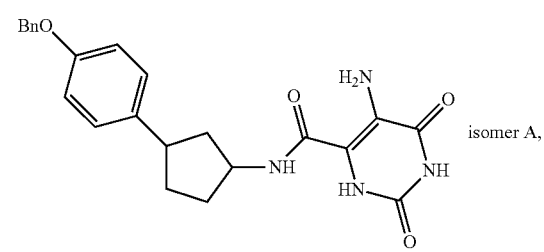
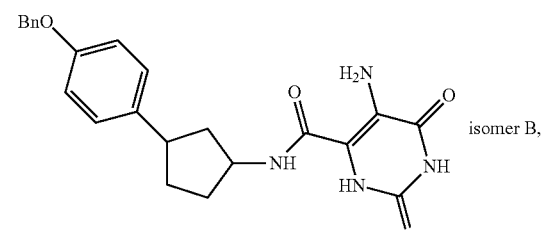
isomer A,
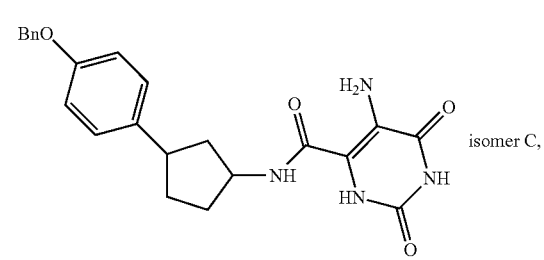
isomer B,
isomer C,
234
-continued
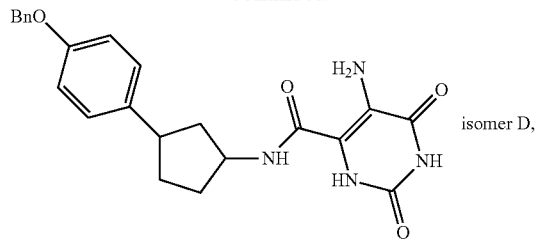
isomer D,
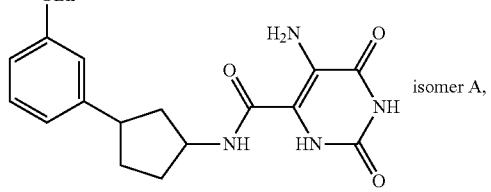
isomer A,
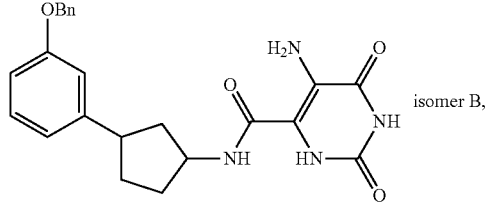
isomer B,
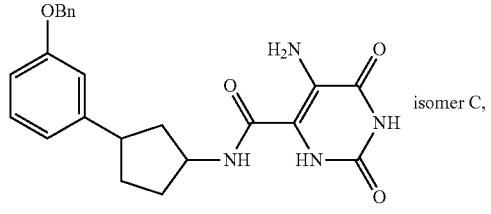
isomer C,
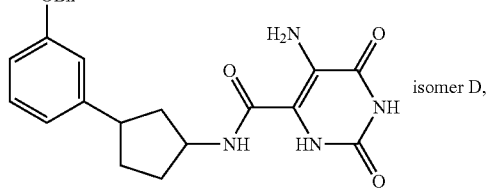
isomer D,
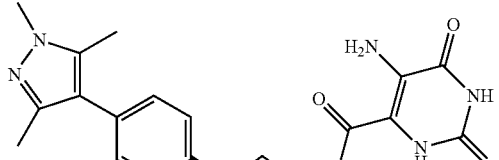
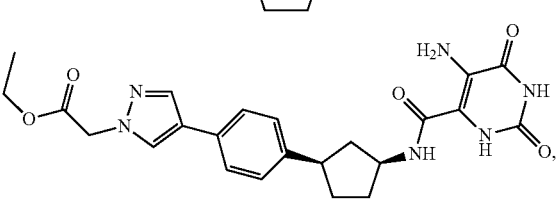
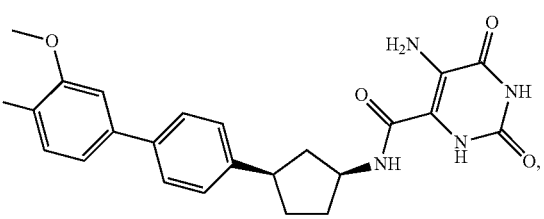

235
-continued
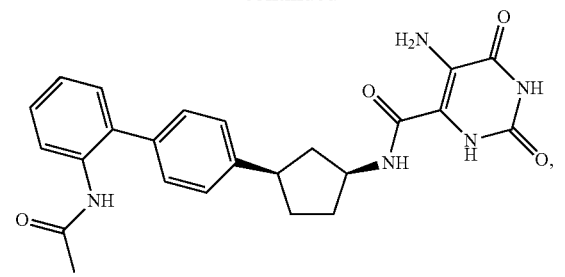
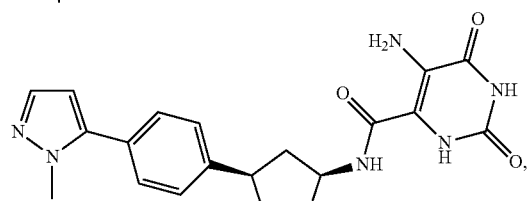
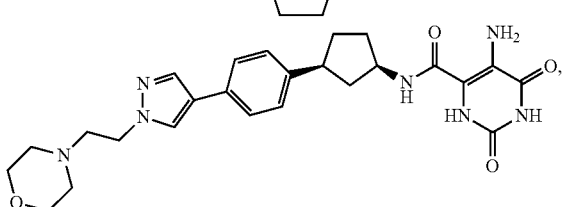
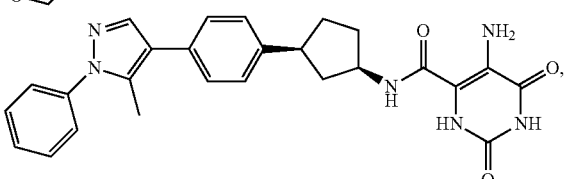
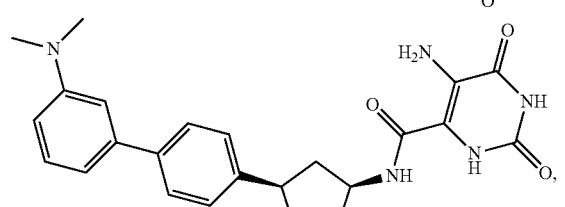
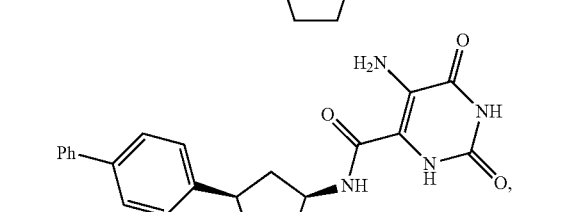
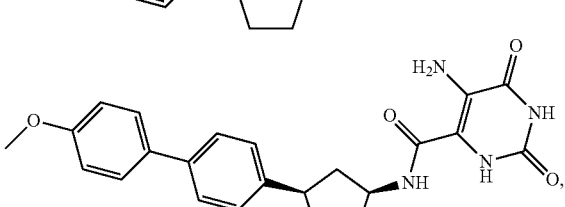
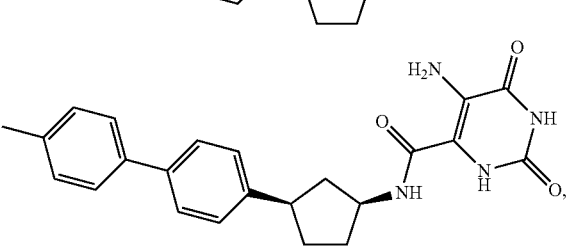
236
-continued
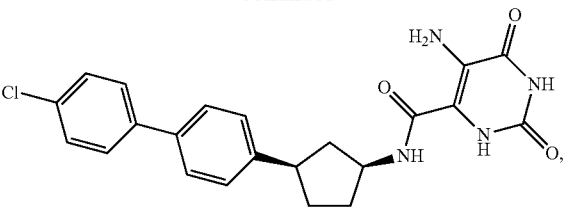
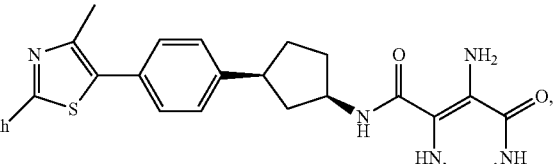
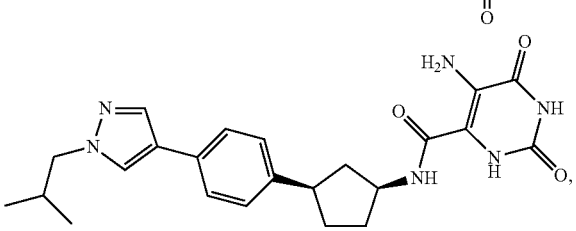
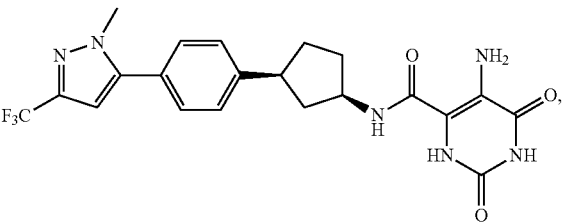
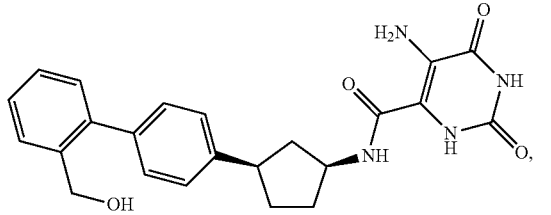
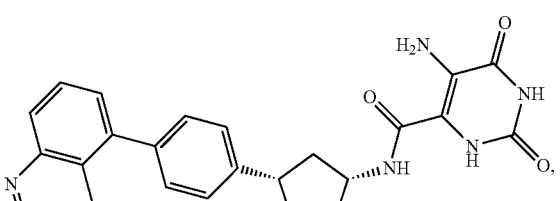
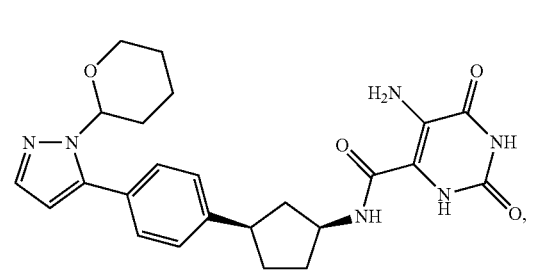

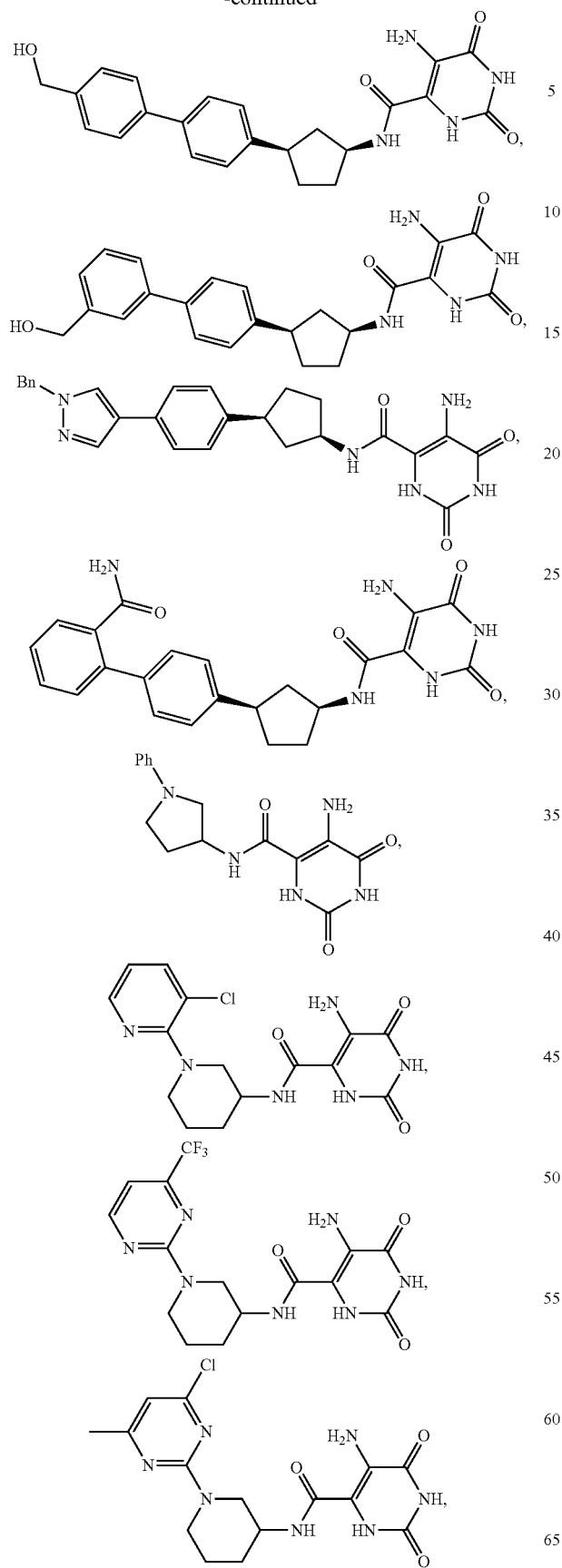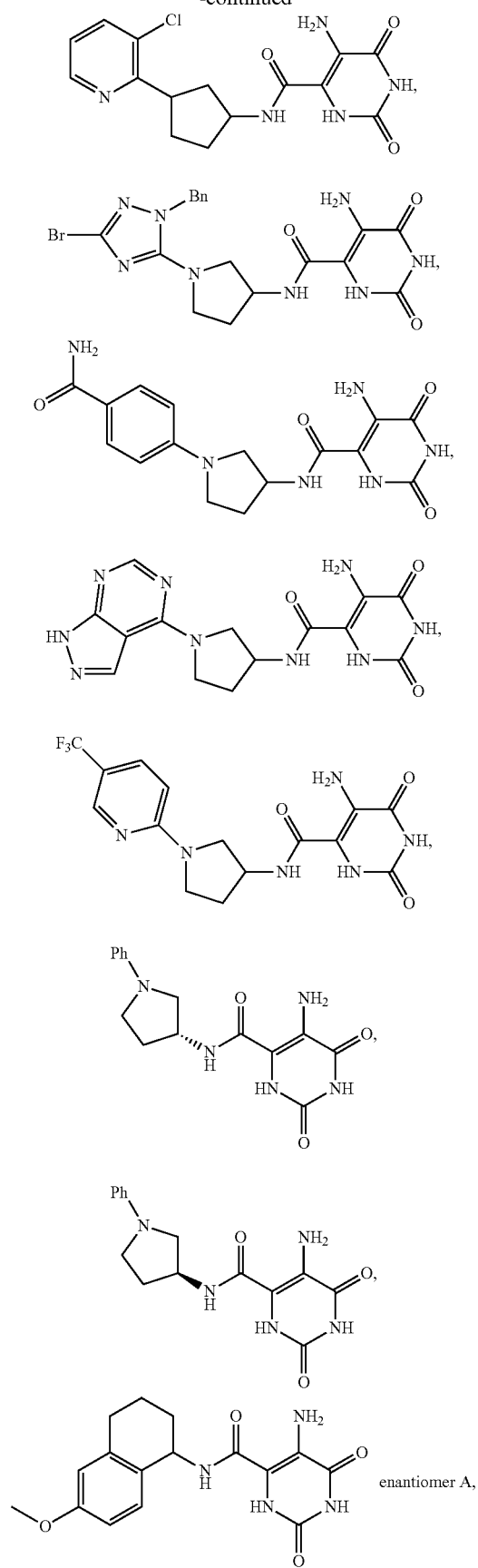
enantiomer A,

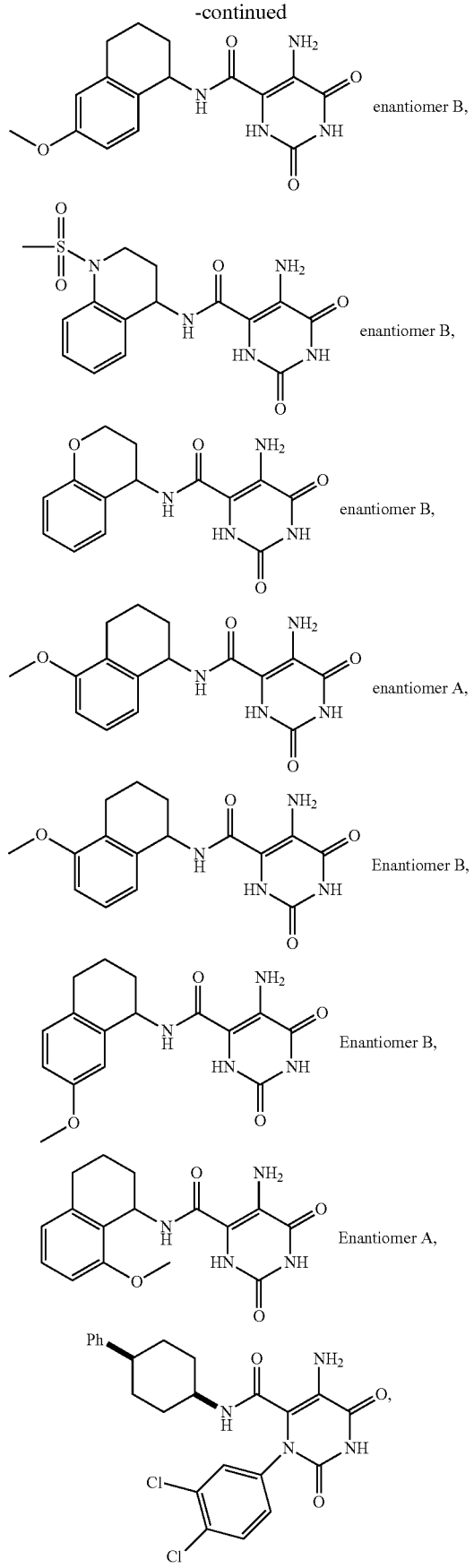
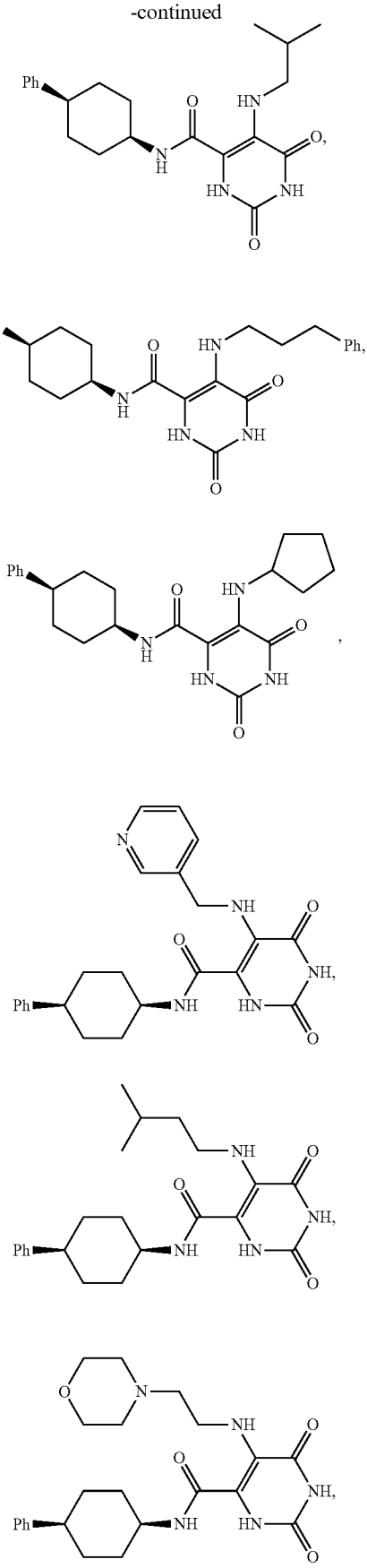

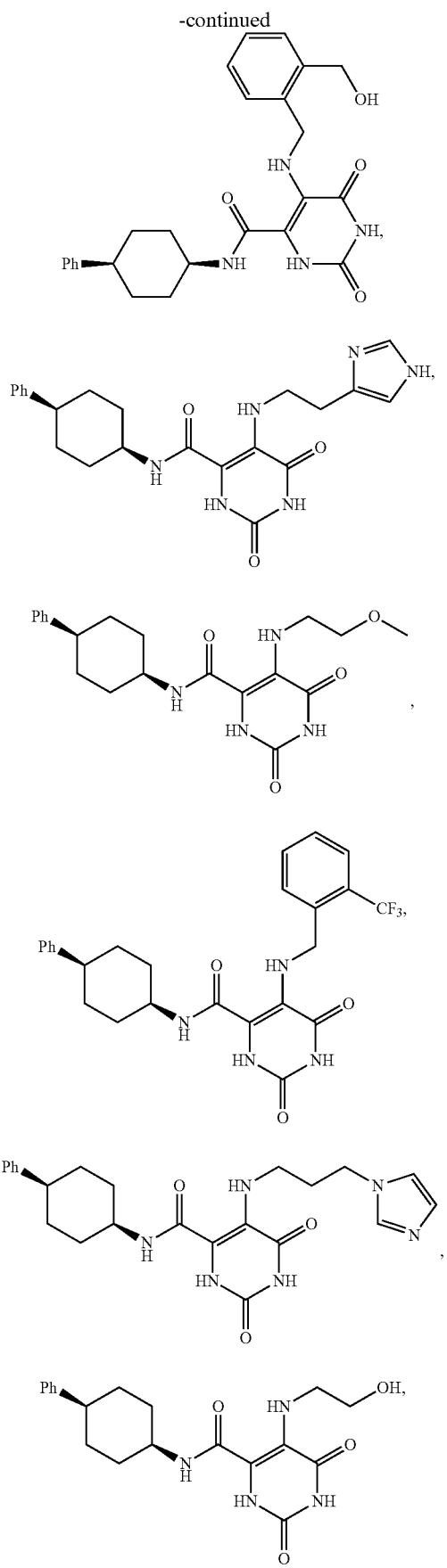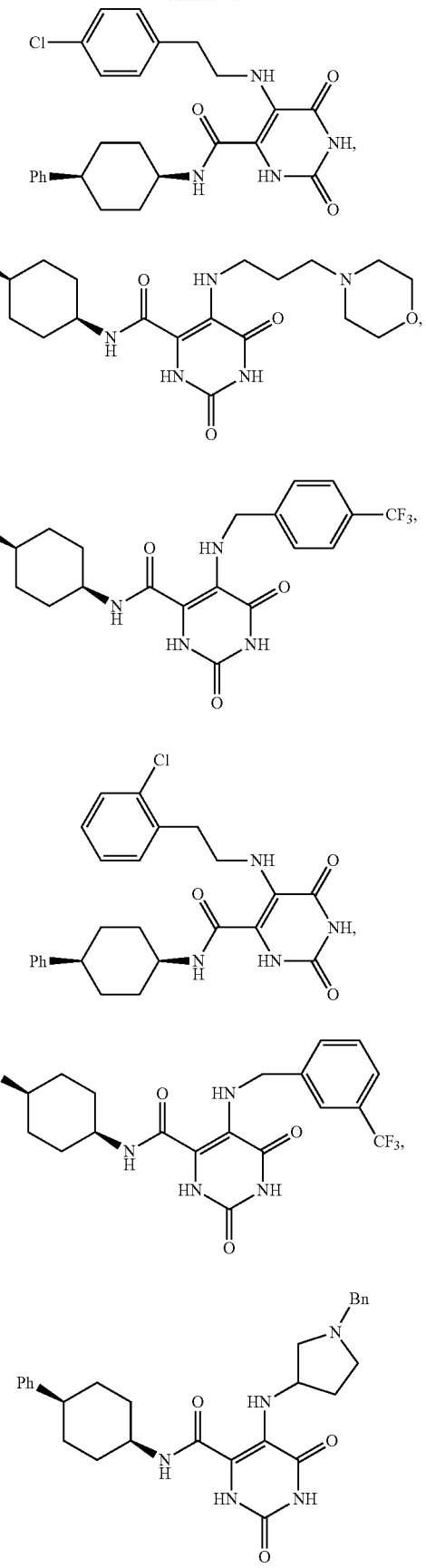

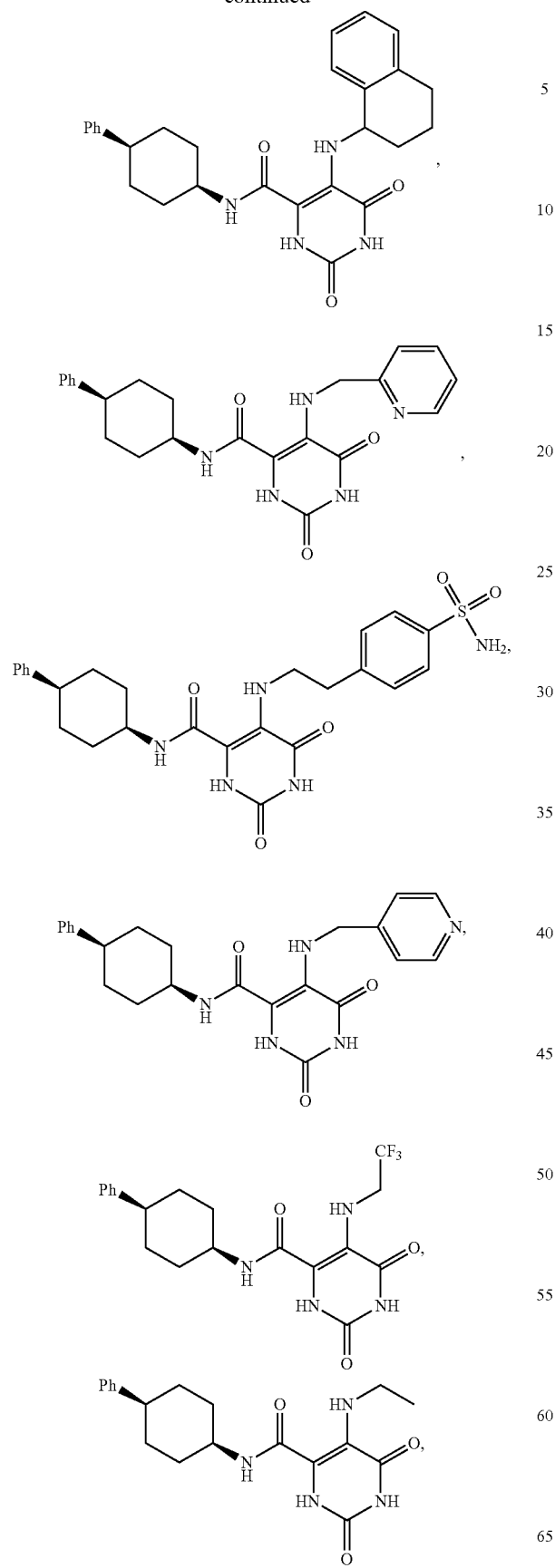
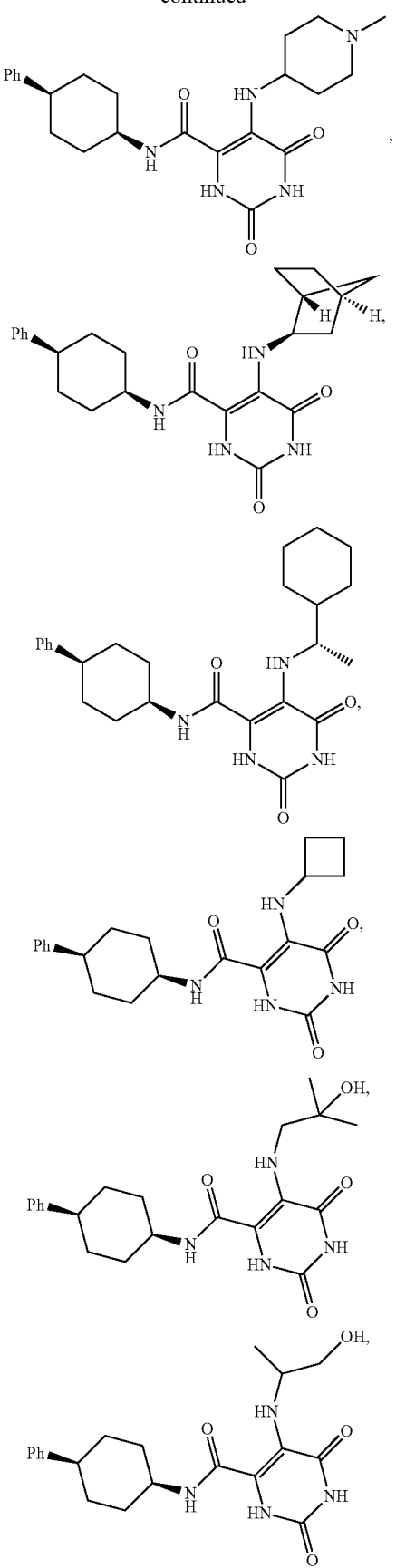

-continued
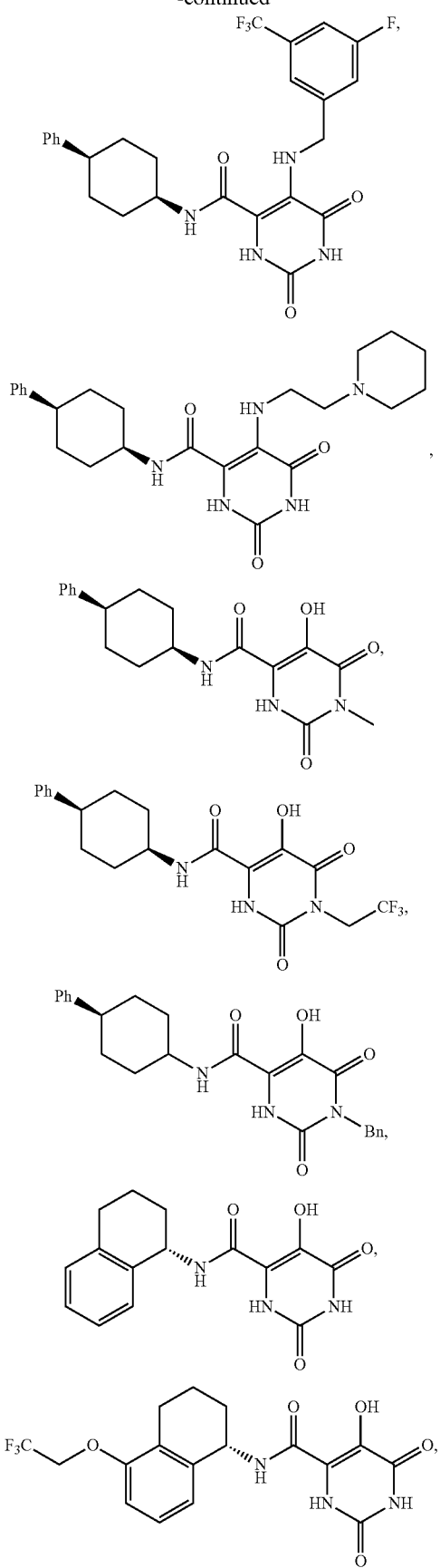
-continued
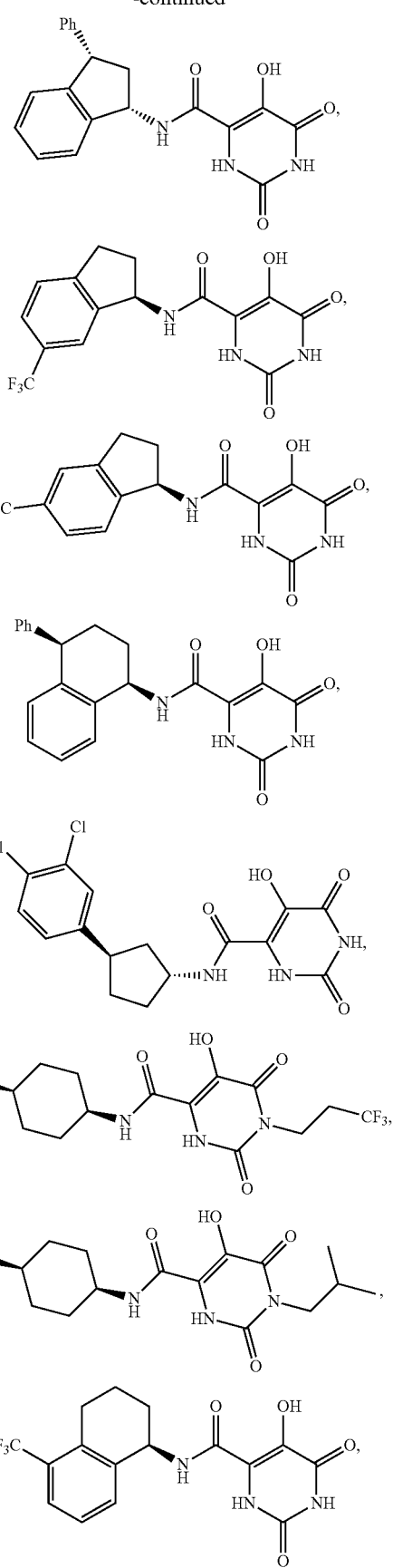

247
-continued
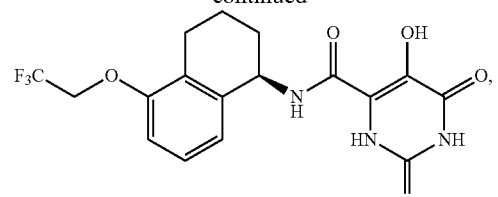
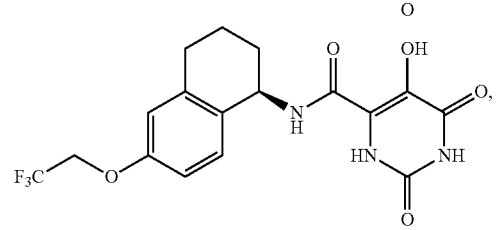
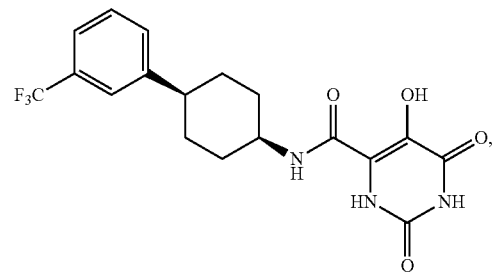
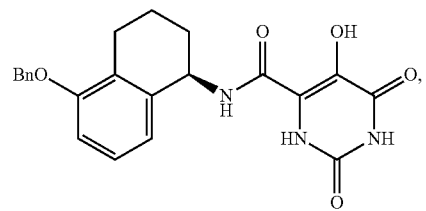
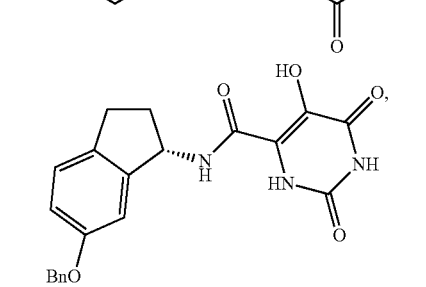
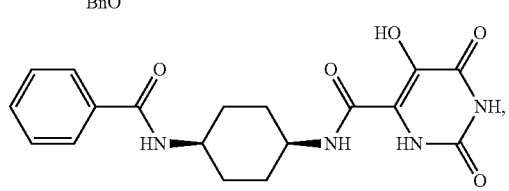
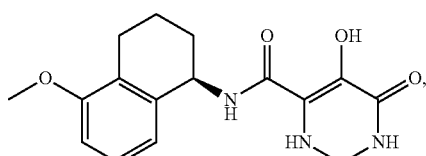
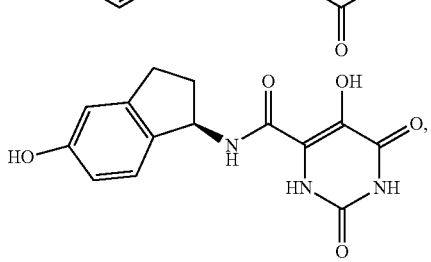
248
-continued
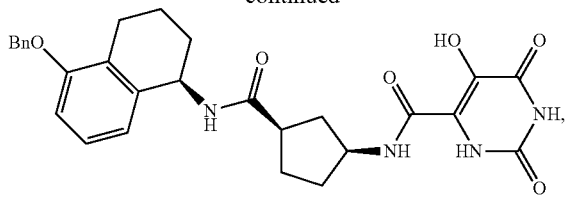
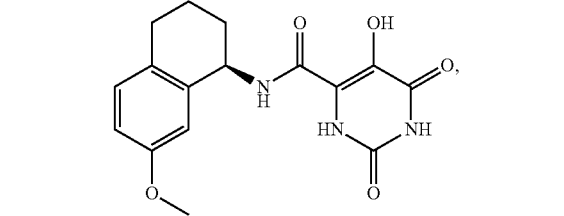
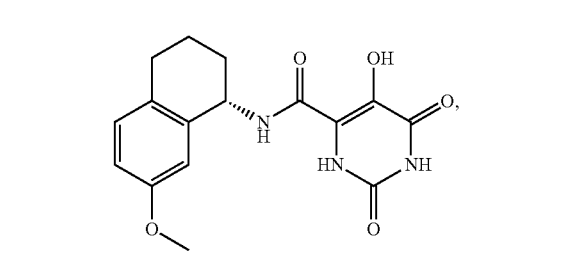
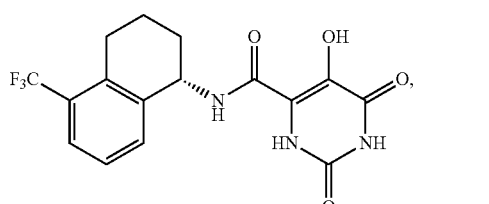
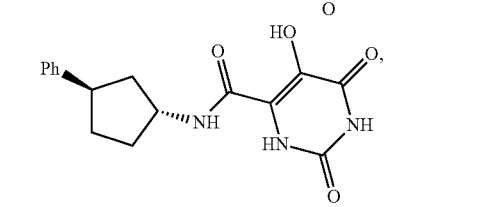
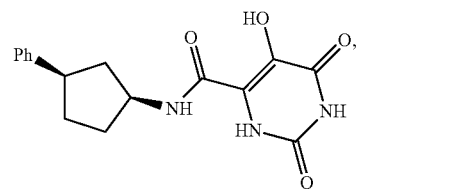
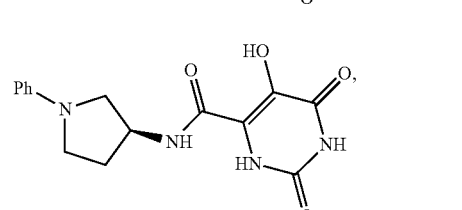
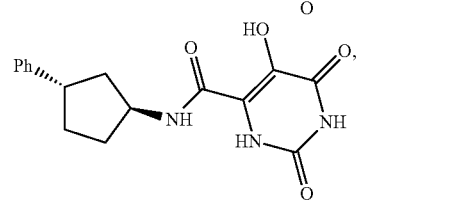

249
-continued
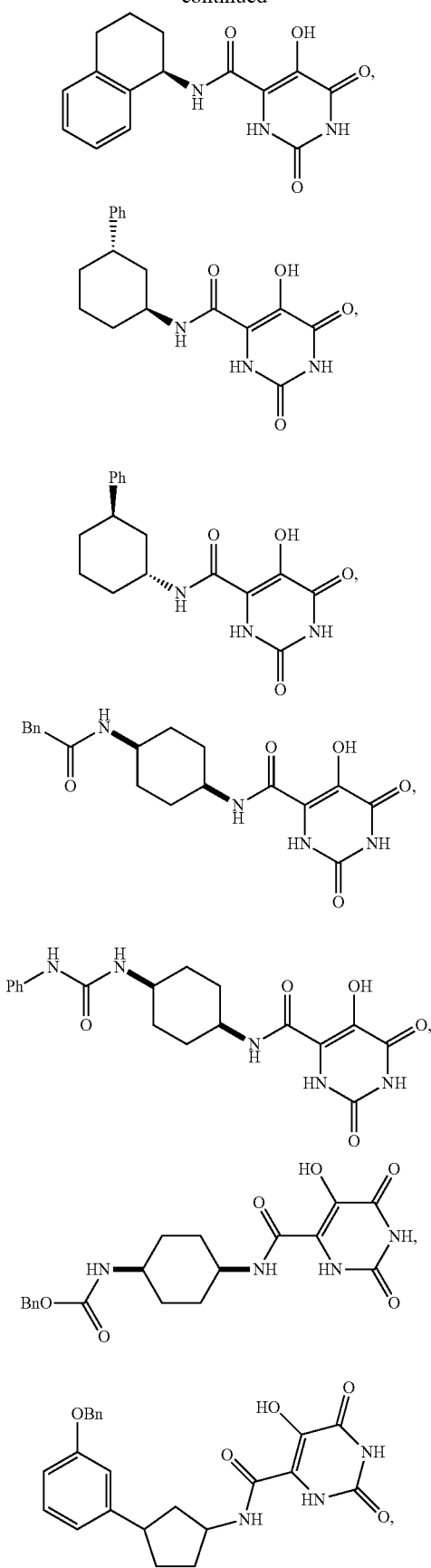
250
-continued
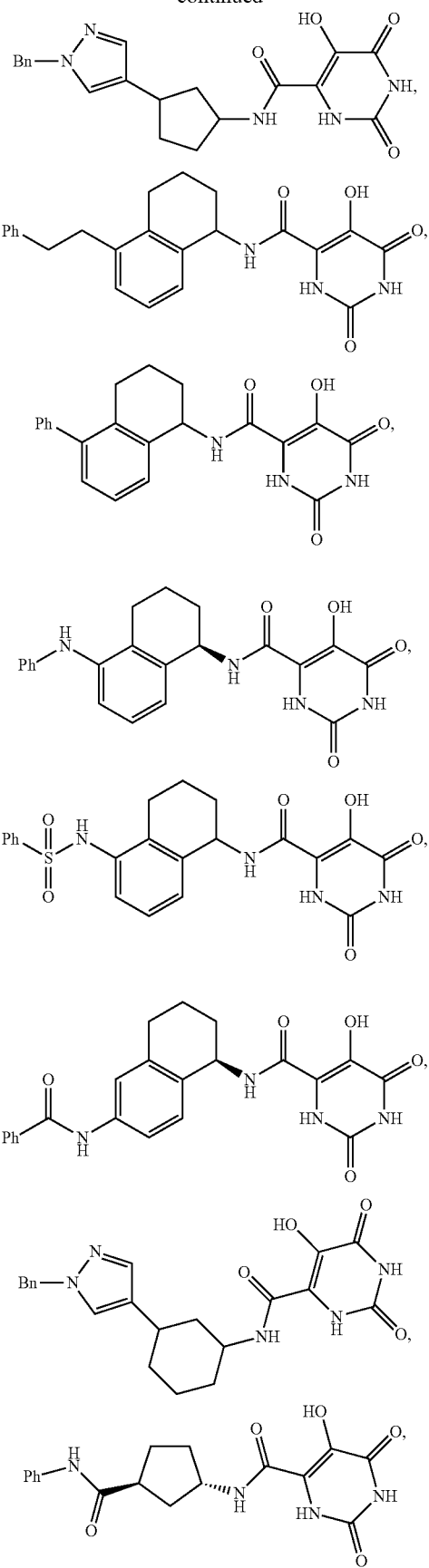

251
-continued
252
-continued
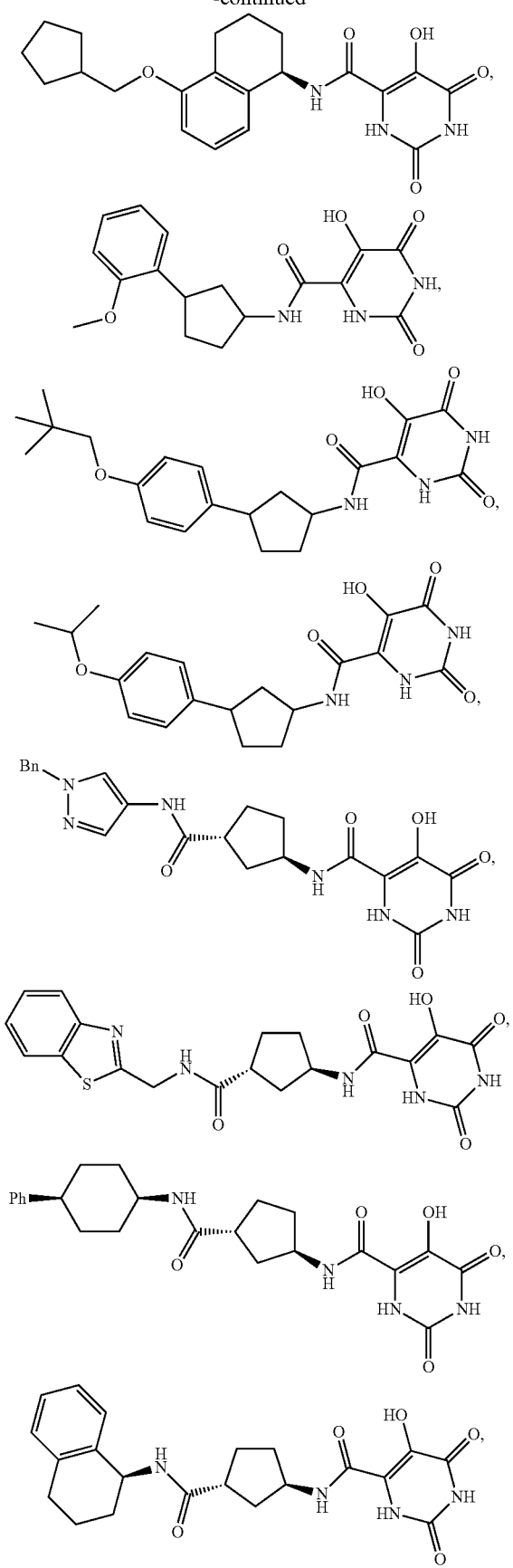
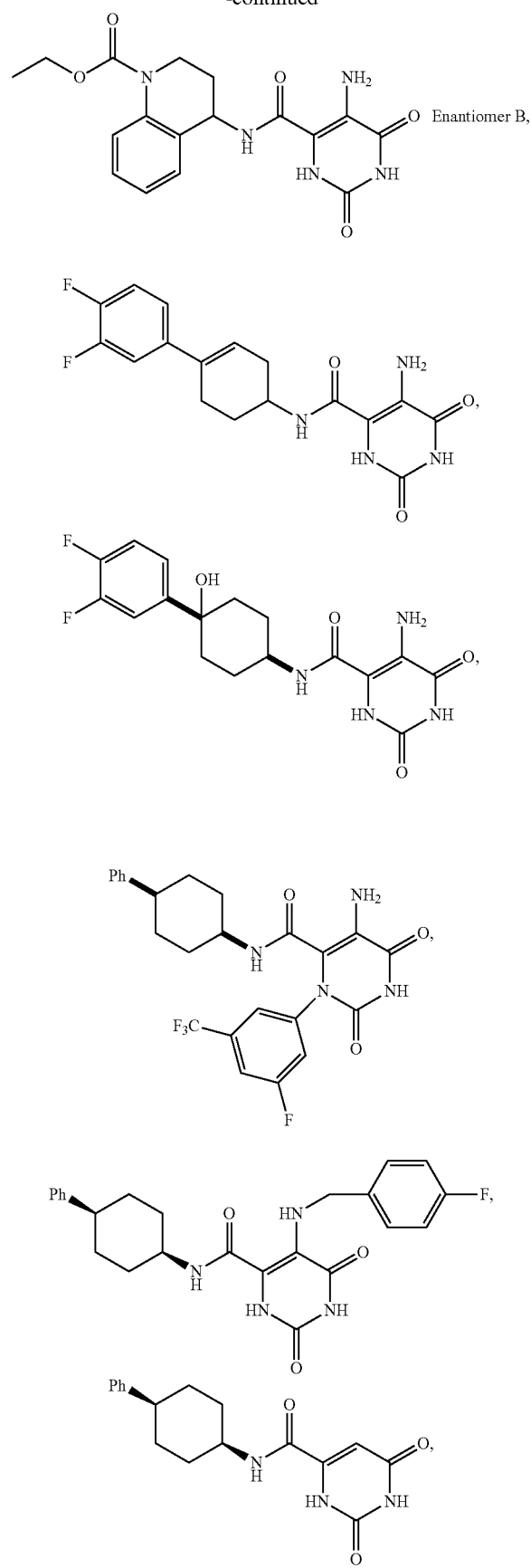

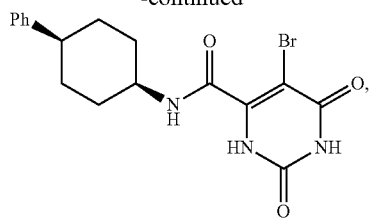
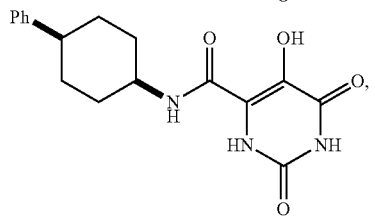
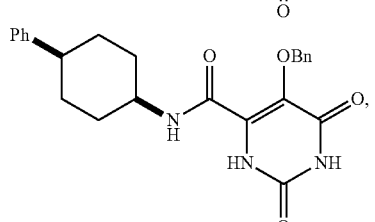
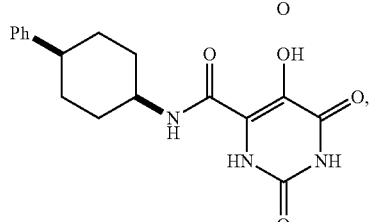
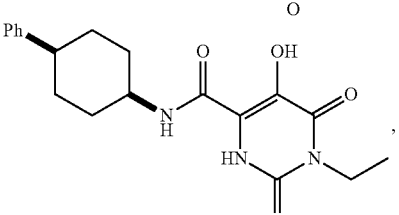
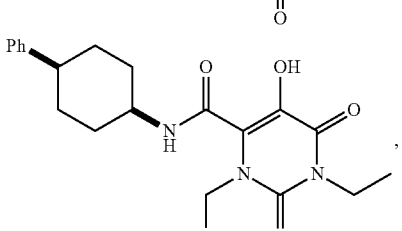
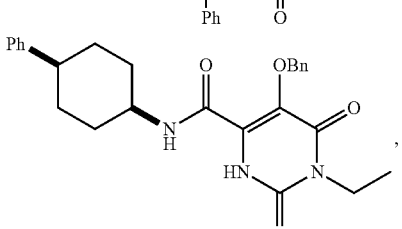
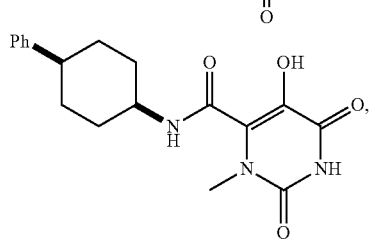
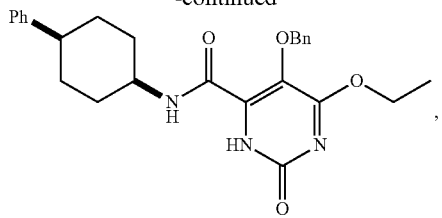
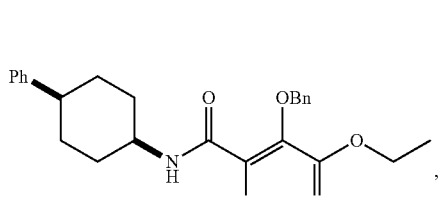
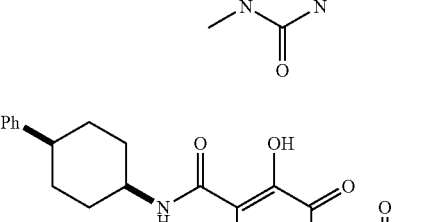
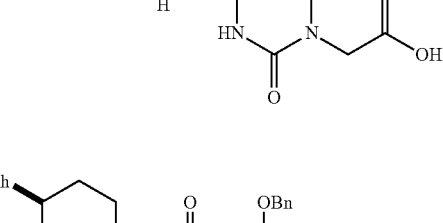
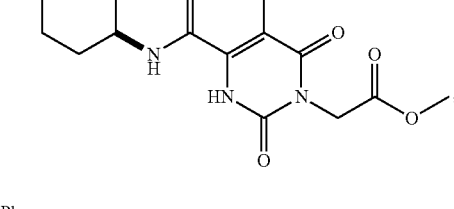
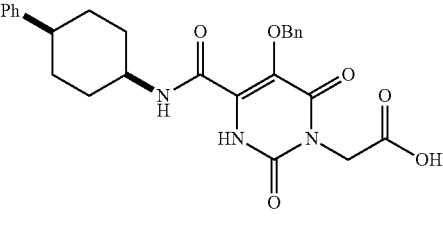
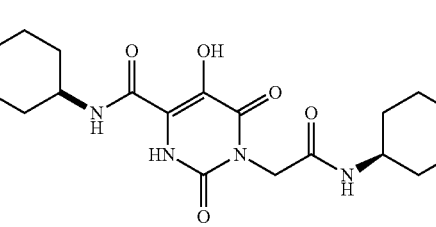
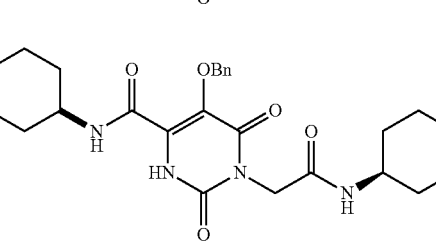

-continued
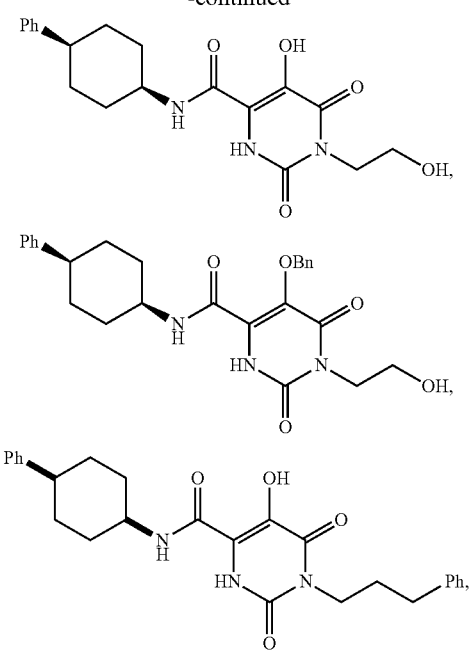
-continued
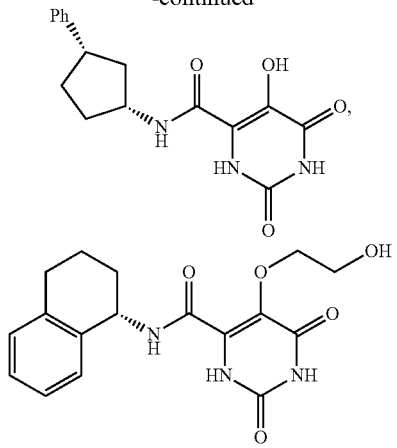
or a stereoisomer, a tautomer, or a pharmaceutically acceptable salt thereof.
10. A pharmaceutical composition, comprising: a pharmaceutically acceptable carrier and a compound of claim 1, or a stereoisomer, a tautomer, or a pharmaceutically acceptable salt thereof.
* * * * *